US007294507B2

(12) United States Patent
Harvey et al.

(10) Patent No.: US 7,294,507 B2
(45) Date of Patent: Nov. 13, 2007

(54) OVOMUCOID PROMOTERS AND METHODS OF USE

(75) Inventors: Alex J. Harvey, Athens, GA (US); Markley C. Leavitt, Watkinsville, GA (US); Youliang Wang, Monroe, GA (US)

(73) Assignee: AviGenics, Inc., Athens, GA (US)

( * ) Notice: Subject to any disclaimer, the term of this patent is extended or adjusted under 35 U.S.C. 154(b) by 239 days.

(21) Appl. No.: 10/856,218

(22) Filed: May 28, 2004

(65) Prior Publication Data

US 2005/0003414 A1 Jan. 6, 2005

Related U.S. Application Data

(63) Continuation-in-part of application No. 10/496,731, filed as application No. PCT/US02/38413 on Dec. 2, 2002, which is a continuation-in-part of application No. 09/998,716, filed on Nov. 30, 2001, now Pat. No. 6,875,588, application No. 10/856,218, which is a continuation-in-part of application No. 10/790,455, filed on Mar. 1, 2004, now abandoned.

(60) Provisional application No. 60/509,122, filed on Oct. 6, 2003, provisional application No. 60/505,562, filed on Sep. 24, 2003, provisional application No. 60/476, 596, filed on Jun. 6, 2003.

(51) Int. Cl.
*C12N 15/00* (2006.01)

(52) U.S. Cl. .................................................. 435/320.1

(58) Field of Classification Search ............ 435/320.1, 435/23.1; 536/23.1
See application file for complete search history.

(56) References Cited

U.S. PATENT DOCUMENTS

| | | | |
|---|---|---|---|
| 4,237,224 A | 12/1980 | Cohen et al. | |
| 4,603,112 A | 7/1986 | Paoletti et al. | |
| 4,722,848 A | 2/1988 | Paoletti et al. | |
| 4,769,330 A | 9/1988 | Paoletti et al. | |
| 5,174,993 A | 12/1992 | Paoletti et al. | |
| 5,175,384 A | 12/1992 | Krimpenfort et al. | |
| 5,338,683 A | 8/1994 | Paoletti et al. | |
| 5,494,807 A | 2/1996 | Paoletti et al. | |
| 5,505,941 A | 4/1996 | Paoletti et al. | |
| 5,580,859 A | 12/1996 | Felgner et al. | |
| 5,589,466 A | 12/1996 | Felgner et al. | |
| 5,591,639 A | 1/1997 | Bebbington | |
| 6,808,925 B2 * | 10/2004 | Calos | 435/462 |
| 6,875,588 B2 * | 4/2005 | Harvey et al. | 435/69.51 |
| 2003/0126629 A1 * | 7/2003 | Rapp et al. | 800/19 |

FOREIGN PATENT DOCUMENTS

| | | |
|---|---|---|
| WO | WO 92/06180 | 10/1990 |
| WO | WO 92/19749 | 5/1991 |
| WO | WO 92/20316 | 5/1991 |
| WO | WO 92/22635 | 6/1991 |
| WO | WO 93/04701 | 9/1991 |
| WO | WO 93/25234 | 6/1992 |
| WO | WO 94/06920 | 9/1992 |
| WO | WO 94/11524 | 11/1992 |
| WO | WO 97/47739 | 6/1996 |
| WO | WO 99/19472 | 10/1997 |
| WO | WO 97/47739 | * 12/1997 |
| WO | WO 03/048364 | 6/2003 |

OTHER PUBLICATIONS

Davis (Bio/Technology, Feb. 1991, vol. 9, p. 165-169).*

GenBank Accession No. J00894.*

(Lai, Nucleic Acids Res., 1982, vol. 10, No. 18, p. 5553-5567.*

Molecular Structure and Flanking Nucleotide Sequences of the Natural Chicken Ovomucoid Gene, Lai et al; Cell 18:829-842 (Nov. 1979).

DNA methylation: organ specific variations in the methylation pattern within and around ovalbumin and other chicken genes, Mandel et al; Nucleic Acids Research 7:2081-2103(1979).

Ovoinhibitor Introns Specify Functional Domains as in the Related and Linked Ovomucoid Gene, Scott et al; Journal of Biol. Chemistry, 262:5899-5907(1987).

Deoxyribonuclease I Sensitivity of the Ovomucoid-Ovoinhibitor Gene Complex in Oviduct Nuclei and Relative Location of CR1 Repetitive Sequences, Scott et al; Biochemistry 26:6831-6840 (1987).

Isolation and characterization of the chicken ovomucoid gene, Lindenmaier et al; Nucleic Acids Research, 7:1221-1232 (1979).

The chick ovomucoid gene contains at least six intervening sequences, Catterall et al; Nature 278:323-327 (Mar. 1979).

Effect of Estrogen on Gene Expression In the Chick Oviduct. Regulation of the Ovomucoid Gene, Tsai et al; Biochemistry 17:5773-5780 (1978).

Identification of potential ovomucoid mRNA precursors in chick oviduct nuclei, Nordstrom et al; Nature 278:328-331 (Mar. 1979).

mRNA Complexity and Egg White Protein mRNA Content in Mature and Hormone-Withdrawn Oviduct, Hynes et al; Cell 11:923-932 (Aug. 1977).

Multiple Initiation and Polyadenylation Sites for the Chicken Ovomucoid Transcription Unit, Gerlinger et al; J. Mol. Biol. vol. 162, p. 345-364 (1982).

Identification and fine mapping of IgG and IgE Epitopes in Ovomucoid, Mine et al; Biochem Biophys Res Comm, vol. 292 p. 1070-1074 (2002).

(Continued)

*Primary Examiner*—Michael C. Wilson
(74) *Attorney, Agent, or Firm*—Kyle D. Yesland

(57) ABSTRACT

The present invention includes nucleic acid molecules comprising an artificial chromosome and an avian ovomucoid gene expression controlling region operably linked to the coding sequence of a useful polypeptide.

42 Claims, 17 Drawing Sheets

OTHER PUBLICATIONS

Heterogenous Initiation Sites for Transcription of the Chicken Ovomucoid Gene, Lai EC et al, J. of Supramolecular Structure and Cellular Biochemistry, No. 1157 p. 429 (abstract).
Chicken Ovomucoid Gene, 5' End Region, Gerlinger p. et al; Lai etal; Database Accession No. J00894 (1986).
Gallus Gallus Isolate No. 26 Ovomucoid Gene, Promoter Region and Partial cds, Wang et al, Database Accession No. AF453747.
Expression of Exogenous Protein in the Egg White of Transgenic Chicken, Harvey et al Nature Biotechnology vol. 19 p. 396-399 (2002).

* cited by examiner

| | | |
|---|---|---|
| OVINs1: | GGGAAACAATCTGCCTTGCA | SEQ ID NO: 3 |
| OVINs2: | TAGGCAGAGCAATAGGACTCTCAACCTCGT | SEQ ID NO: 1 |
| OVINs4: | AGATGAGGTGGATGGTTTAC | SEQ ID NO: 7 |
| OVINs5: | CAGCTTCTGCTAGCGTAGGT | SEQ ID NO: 8 |
| OVINs6: | ACGTGAACTCAAAGAGGCAC | SEQ ID NO: 9 |
| OVINs7: | ATCTCCTGAGCTCGGTGCTT | SEQ ID NO: 10 |
| OVINs8: | ACGAGGTTCCATGTCTTTCA | SEQ ID NO: 11 |
| OVMUa1: | AAGCCACAAAGCACGAAAGAG | SEQ ID NO: 4 |
| OVMUa2: | AAGCTTCTGCAGCACTCTGGGAGTTACTCA | SEQ ID NO: 2 |
| OVMUa3: | TAAATAGCACAGAACGCTGAGGGGAGTAAGG | SEQ ID NO: 12 |
| OVMUa4: | GAAGAGCTTGGTAGAAGACT | SEQ ID NO: 13 |
| OVMUa5: | ATGGAAATATGGGTTTCCTTC | SEQ ID NO: 14 |
| OVMUa6: | GCAGCTTATGGCTAATCGCT | SEQ ID NO: 15 |
| OVMUa7: | AGTGACCACTATCTGACCTG | SEQ ID NO: 16 |
| OVMUa8: | TAATCAGGAAGGCACACAGC | SEQ ID NO: 17 |
| OVMUP4.7.1: | AGATCTGGAGCAGCACTTGT | SEQ ID NO: 18 |
| OVMUP4.7.2: | AGCATGAAGTTCCTCACCCA | SEQ ID NO: 19 |
| OVMUP4.7.3: | ATGGAGAGGAATATTCCCTT | SEQ ID NO: 20 |
| OVMUP4.7.4: | ATTTCTCCAGGCGTGTGG | SEQ ID NO: 21 |
| OVMUP5.5.1: | ATTTCTCCAGGCGTGTGG | SEQ ID NO: 22 |
| OVMUP5.5.2: | ATGCGAGTGAAGGAGAGTTC | SEQ ID NO: 23 |
| OVMUP5.5.3: | GCAGCACGTGTAAGCTTGTA | SEQ ID NO: 24 |
| OVMUP5.5.4: | CAAGGCAAATTATCAGCAGA | SEQ ID NO: 25 |
| OVMUa9: | AAATGAAGCCGGCTGTTTTC | SEQ ID NO: 27 |
| OVINs9 | CTCTCAGCCACTCTGAACAA | SEQ ID NO: 28 |

FIG.3

TAGGCAGAGCAATAGGACTCTCAACCTCGTGAGTATGGCAGCATGTTAACTCTGCACTGG 60
OVOINHIBITOR 3' UNTRANSLATED REGION
AGTCCAGCGTGGGAAACAATCTGCCTTGCACATGAGTCTTCGTGGGCCAATATTCCCCAA
OVOINHIBITOR 3' UNTRANSLATED REGION
CGGTTTTCCTTCAGCTTGTCTTGTCTCCTAAGCTCTCAAAACACCTTTTTGGTGAATAAA
OVOINHIBITOR 3' UNTRANSLATED REGION
CTCACTTGGCAACGTTTATCTGTCTTACCTTAGTGTCACGTTTCATCCCTATTCCCCTTT

CTCCTCCTCCGTGTGGTACACAGTGGTGCACACTGGTTCTTCTGTTGATGTTCTGCTCTG..300
ACAGCCAATGTGGGTAAAGTTCTTCCTGCCACGTGTCTGTGTTGTTTTCACTTCAAAAAG
GGCCCTGGGCTCCCCTTGGAGCTCTCAGGCATTTCCTTAATCATCACAGTCACGCTGGCA
GGATTAGTCCCTCCTAAACCTTAGAATGACCTGAACGTGTGCTCCCTCTTTGTAGTCAGT
GCAGGGAGACGTTTGCCTCAAGATCAGGGTCCATCTCACCCACAGGGCCATTCCCAAGAT
GAGGTGGATGGTTTACTCTCACAAAAAGTTTTCTTATGTTTGGCTAGAAAGGAGAACTCA 600
CTGCCTACCTGTGAATTCCCCTAGTCCTGGTTCTGCTGCCACTGCTGCCTGTGCAGCCTG
TCCCATGGAGGGGGCAGCAACTGCTGTCACAAAGGTGATCCCACCCTGTCTCCACTGAAA
TGACCTCAGTGCCACGTGTTGTATAGGGTATAAAGTACGGGAGGGGGATGCCCGGCTCCC
TTCAGGGTTGCAGAGCAGAAGTGTCTGTGTATAGAGTGTGTCTTAATCTATTAATGTAAC
AGAACAACTTCAGTCCTAGTGTTTTGTGGGCTGGAATTGCCCATGTGGTAGGGACAGGCC 900
TGCTAAATCACTGCAATCGCCTATGTTCTGAAGGTATTTGGGAAAGAAAGGGATTTGGGG
GATTGCCTGTGATTGGCTTTAATTGAATGGCAAATCACAGGAAAGCAGTTCTGCTCAACA
GTTGGTTGTTTCAGCCAATTCTTGCAGCCAAAGAGCCGGGTGCCCAGCGATATAATAGTT
GTCACTTGTGTCTGTATGGATGACAGGGAGGTAGGGTGACCTGAGGACCACCCTCCAGCT
TCTGCTAGCGTAGGTACAGTCACCACCTCCAGCTCCACACGAGTCCCATCGTGGTTTACC 1200
AAAGAAACACAATTATTTGGACCAGTTTGGAAAGTCACCCGCTGAATTGTGAGGCTAGAT
TAATAGAGCTGAAGAGCAAATGTTCCCAACTTGGAGATACTAGTTGGTATTAGTATCAGA
GGAACAGGGCCATAGCACCTCCATGCTATTAGATTCCGGCTGGCATGTACTTTTCAAGAT
GATTTGTAACTAACAATGGCTTATTGTGCTTGTCTTAAGTCTGTGTCCTAATGTAAATGT
TCCTTTGGTTTATATAACCTTCTTGCCATTTGCTCTTCAGGTGTTCTTGCAGAACACTGG 1500
CTGCTTTAATCTAGTTTAACTGTTGCTTGATTATTCTTAGGGATAAGATCTGAATAAACT
TTTTGTGGCTTTGGCAGACTTTAGCTTGGGCTTAGCTCCCACATTAGCTTTTGCTGCCTT
TTCTGTGAAGCTATCAAGATCCTACTCAATGACATTAGCTGGGTGCAGGTGTACCAAATC
CTGCTCTGTGGAACACATTGTCTGATGATACCGAAGGCAAACGTGAACTCAAAGAGGCAC
AGAGTTAAGAAGAAGTCTGTGCAATTCAGAGGAAAAGCCAAAGTGGCCATTAGACACACT 1800
TTCCATGCAGCATTTGCCAGTAGGTTTCATATAAAACTACAAAATGGAATAAACCACTAC
AAATGGGAAAAGCCTGATACTAGAATTTAAATATTCACCCAGGCTCAAGGGGTGTTTCAT
GGAGTAATATCACTCTATAAAAGTAGGGCAGCCAATTATTCACAGACAAAGCTTTTTTTT
TTCTGTGCTGCAGTGCTGTTTTTCGGCTGATCCAGGGTTACTTATTGTGGGTCTGAGAGC
TGAATGATTTCTCCTTGTGTCATGTTGGTGAAGGAGATATGGCCAGGGGGAGATGAGCAT 2100
GTTCAAGAGGAAACGTTGCATTTTGGTGGCTTGGGAGAAAGGTAGAACGATATCAGGTCC
ATAGTGTCACTAAGAGATCTGAAGGATGGTTTTACAGAACAGTTGACTTGGCTGGGTGCA
GGCTTGGCTGTAAATGGATGGAAGGATGGACAGATGGGTGGACAGAGATTTCTGTGCAGG
AGATCATCTCCTGAGCTCGGTGCTTGACAGACTGCAGATCCATCCCATAACCTTCTCCAG
CATGAGAGCGCGGGGAGCTTTGGTACTGTTCAGTCTGCTGCTTGTTGCTTCCTGGGTGCA 2400
CAGTGGTGATTTTCTTACTCACACAGGGCAAAAACCTGAGCAGCTTCAAAGTGAACAGGT
TGCTCTCATAGGCCATTCAGTTGTCAAGATGAGGTTTTTGGTTTCTTGTTTTGTAAGGTG
GGAAGAAGCACTGAAGGATCAGTTGCGAGGGCAGGGGTTTAGCACTGTTCAGAGAAGTCT
TATTTTAACTCCTCTCATGAACAAAAAGAGATGCAGGTGCAGATTCTGGCAAGCATGCAG
TGAAGGAGAAAGCCCTGAATTTCTGATATATGTGCAATGTTGGGCACCTAACATTCCCCG 2700
CTGAAGCACAGCAGCTCCAGCTCCATGCAGTACTCACAGCTGGTGCAGCCCTCGGCTCCA

FIG.4A

GGGTCTGAGCAGTGCTGGGACTCACGAGGTTCCATGTCTTTCACACTGATAATGGTCCAA
CR1
TTTCTGGAATGGGTGCCCATCCTTGGAGGTCCCCAAGGCCAGGCTGGCTGCGTCTCCGAG
CR1
CAGCCCGATCTGGTGGTGAGTAGCCAGCCCATGGCAGGAGTTAGAGCCTGATGGTCTTTA
CR1
AGGTCCCTTCCAACCTAAGCCATCCTACGATTCTAGGAATCATGACTTGTGAGTGTGTAT 3000
CR1
TGCAGAGGCAATATTTTAAAGTTATAAATGTTTTCTCCCCTTCCTTGTTTGTCAAAGTTA
CR1
TCTTGATCGCCTTATCAATGCTTTTGGAGTCTCCAGTCATTTTTCTTACAMCAAAAAGAG
GAGGAAGAATGAAGAGAATCATTTAATTTCTTGATTGAATAGTAGGATTCAGAAAGCTGT
ACGTAATGCCGTCTCTTTGTATCGAGCTGTAAGGTTTCTCATCATTTATCAGCGTGGTAC
ATATCAGCACTTTTCCATCTGATGTGGAAAAAAAAATCCTTATCATCTACAGTCTCTGTA 3300
CCTAAACATCGCTCAGACTCTTTACCAAAAAAGCTATAGGTTTTAAAACTACATCTGCTG
ATAATTTGCCTTGTTTTAGCTCTTCTTCCATATGCTGCGTTTGTGAGAGGTGCGTGGATG
GGCCTAAACTCTCAGCTGCTGAGCTTGATGGGTGCTTAAGAATGAAGCACTCACTGCTGA
AACTGTTTTCATTTCACAGGAATGTTTTAGTGGCATTGTTTTTATAACTACATATTCCTC
AGATAAATGAAATCCAGAAATAATTATGCAAACTCACTGCATCCGTTGCACAGGTCTTTA 3600
TCTGCTAGCAAAGGAAATAATTTGGGGATGGCAAAAACATTCCTTCAGACATCTATATTT
AAAGGAATATAATCCTGGTACCCACCCACTTCATCCCTCATTATGTTCACACTCAGAGAT
ACTCATTCTCTTGTTGTTATCATTTGATAGCGTTTTCTTTGGTTCTTTGCCACGCTCTGG
GCTATGGCTGCACGCTCTGCACTGATCAGCAAGTAGATGCGAGGGAAGCAGCAGTGAGAG
GGGCTGCCCTCAGCTGGCACCCAGCCGCTCAGCCTAGGAGGGGACCTTGCCTTTCCACCA 3900
GCTGAGGTGCAGCCCTACAAGCTTACACGTGCTGCGAGCAGGTGAGCAAAGGGAGTCTTC
ATGGTGTGTTTCTTGCTGCCCGGAAGCAAAACTTTACTTTCATTCATTCCCCTTGAAGAA
TGAGGAATGTTTGGAAACGGACTGCTTTACGTTCAATTTCTCTCTTCCCTTTAAGGCTCA
GCCAGGGGCCATTGCTGAGGACGGCATCGGGGCCCCCTGGACCAAATCTGTGGCACAGAT
GGTTTCACTTACATCAGTGGATGTGGGATCTGCGCCTGTAATGTGTCCTTCTGAAGGAAG 4200
GAACGTGCCTTCCAAGTGCCAGCCCCACAGCCCCCAGCCCCTCCCTGTGCTGCTCCAATT
CATCTCCTCTTCCTCCTTCTCCCTTTGCTGTTTGTGCTCGGGTAGAAATCATGAAGATTT
AGAAGAGAAAACAAAATAACTGGAGTGGAAACCCAGGTGATGCAGTTCATTCAGCTGTCA
TAGGTTTGTCGTTGCTATAGGTCTGTATCAGAGATGCTARCACCACTTTGCTGTCGGTGC
TTAACTCGGGTGAACTCTCCTTCACTCGCATCATTTGCGGGCCTTATTTACATCCCCAGC 4500
ATCCATCACCCTCTGGGAAAATGGGCGCACTGGATCTCTAATGGAAGACTTTCCCTCTTT
CAGAGCCTGTGGGATGTGCAGTGACAAGAAACGTGGAGGGGCTGAGCAGCAGCACTGCCC
CCAGGGAGCAGGAGCGGATGCCATCGGTGGCAGCATCCCAAATGATGTCAGCGGATGCTG
AGCAGGCAGCGGACGAACGGACAGAAGCGATGCGTACACCTTCTGTTGACATGGTATTTG
GCAGCGATTTAACACTCGCTTCCTAGTCCTGCTATTCTCCACAGGCTGCATTCAAATGAA 4800
CGAAGGGAAGGGAGGCAAAAAGATGCAAAATCCGAGACAAGCAGCAGAAATATTTCTTCG
CTACGGAAGCGTGCGCAAACAACCTTCTCCAACAGCACCAGAAGAGCACAGCGTAACCTT
TTTCAAGACCAGAAAAGGAAATTCACAAAGCCTCTGTGGATACCAGCGCGTTCAGCTCTC
CTGATAGCAGATTTCTTGTCAGGTTGCGAATGGGGTATGGTGCCAGGAGGTGCAGGGACC
ATATGATCATATACAGCACAGCAGTCATTGTGCATGTATTAATATATATTGAGTAGCAGT 5100
GTTACTTTGCCAAAGCAATAGTTCAGAGATGAGTCCTGCTGCATACCTCTATCTTAAAAC
TAACTTATAAATAGTAAAACCTTCTCAGTTCAGCCACGTGCTCCTCTCTGTCAGCACCAA
TGGTGCTTCGCCTGCACCCAGCTGCAAGGAATCAGCCCGTGATCTCATTAACACTCAGCT
CTGCAGGATAAATTAGATTGTTCCACTCTCTTTTGTTGTTAATTACGACGGAACAATTGT
TCAGTGCTGATGGTCCTAATTGTCAGCTACAGAAAACGTCTCCATGCAGTTCCTTCTGCG 5400
CCAGCAAACTGTCCAGGCTATAGCACCGTGATGCATGCTACCTCTCACTCCATCCTTCTT

FIG.4B

CTCTTTCCCACCAGGGAGAGCTGTGTGTTTTCACTCTCAGCCACTCTGAACAATACCAAA
CTGCTACGCACTGCCTCCCTCGGAAAGAGAATCCCCTTGTTGCTTTTTTATTTACAGGAT
CCTTCTTAAAAAGCAGACCATCATTCACTGCAAACCCAGAGCTTCATGCCTCTCCTTCCA
CAACCGAAAACAGCCGGCTTCATTTGTCTTTTTTAAATGCTGTTTTCCAGGTGAATTTTG 5700
GCCAGCGTGTTGGCTGAGATCCAGGAGCACGTGTCAGCTTTCTGCTCTCATTGCTCCTGT
TCTGCATTGCCTCTTTCTGGGGTTTCCAAGAGGGGGGAGACTTTGCGCGGGGATGAGAT
AATGCCCCTTTTCTTAGGGTGGCTGCTGGGCAGCAGAGTGGCTCTGGGTCACTGTGGCAC
CAATGGGAGGCACCAGTGGGGGTGTGTTTTGTGCAGGGGGGAAGCATTCACAGAATGGGG
CTGATCCTGAAGCTTGCAGTCCAAGGCTTTGTCTGTGTACCCAGTGAAATCCTTCCTCTG 6000
TTACATAAAGCCCAGATAGGACTCAGAAATGTAGTCATTCCAGCCCCCCTCTTCCTCAGA
TCTGGAGCAGCACTTGTTTGCAGCCAGTCCTCCCCAAAATGCACAGACCTCGCCGAGTGG
AGGGAGATGTAAACAGCGAAGGTTAATTACCTCCTTGTCAAAAACACTTTGTGGTCCATA
GATGTTTCTGTCAATCTTACAAAACAGAACCGAGAGGCAGCGAGCACTGAAGAGCGTGTT
CCCATGCTGAGTTAATGAGACTTGGCAGCTCGCTGTGCAGAGATGATCCCTGTGCTTCAT 6300
GGGAGGCTGTAACCTGTCTCCCCATCGCCTTCACACCGCAGTGCTGTCCTGGACACCTCA
CCCTCCATAAGCTGTAGGATGCAGCTGCCCAGGGATCAAGAGACTTTTCCTAAGGCTCTT
AGGACTCATCTTTGCCGCTCAGTAGCGTGCAGCAATTACTCATCCCAACTATACTGAATG
GGTTTCTGCCAGCTCTGCTTGTTTGTCAATAAGCATTTCTTCATTTTGCCTCTAAGTTTC
TCTCAGCAGCACCGCTCTGGGTGACCTGAGTGGCCACCTGGAACCCGAGGGGCACAGCCA 6600
CCACCTCCCTGTTGCTGCTGCTCCAGGGACTCATGTGCTGCTGGATGGGGGGAAGCATGA
AGTTCCTCACCCAGACACCTGGGTTGCAATGGCTGCAGCGTGCTCTTCTTGGTATGCAGA
TTGTTTCCAGCCATTACTTGTAGAAATGTGCTGTGGAAGCCCTTTGTATCTCTTTCTGTG
GCCCTTCAGCAAAAGCTGTGGGAAAGCTCTGAGGCTGCTTTCTTGGGTCGTGGAGGAATT
GTATGTTCCTTCTTTAACAAAAATTATCCTTAGGAGAGAGCACTGTGCAAGCATTGTGCA 6900
CATAAAACAATTCAGGTTGAAAGGGCTCTCTGGAGGTTTCCAGCCTGACTACTGCTCGAA
GCAAGGCCAGGTTCAAAGATGGCTCAGGATGCTGTGTGCCTTCCTGATTATCTGTGCCAC
CAATGGAGGAGATTCACAGCCACTCTGCTTCCCGTGCCACTCATGGAGAGGAATATTCCC
TTATATTCAGATAGAATGTTATCCTTTAGCTCAGCCTTCCCTATAACCCCATGAGGGAGC
TGCAGATCCCCATACTCTCCCCTTCTCTGGGGTGAAGGCCGTGTCCCCCAGCCCCCCTTC 7200
CCACCCTGTGCCCTAAGCAGCCCGCTGGCCTCTGCTGGATGTGTGCCTATATGTCAATGC
CTGTCCTTGCAGTCCAGCCTGGGACATTTAATTCATCACCAGGGTAATGTGGAACTGTGT
CATCTTCCCCTGCAGGGTACAAAGTTCTGCACGGGGTCCTTTCGGTTCAGGAAAACCTTC
ACTGGTGCTACCTGAATCAAGCTCTATTTAATAAGTTCATAAGCACATGGATGTGTTTTC
CTAGAGATACGTTTTAATGGTATCAGTGATTTTTATTTGCTTTGTTGCTTACTTCAAACA 7500
GTGCCTTTGGGCAGGAGGTGAGGGACGGGTCTGCCGTTGGCTCTGCAGTGATTTCTCCAG
GCGTGTGGCTCAGGTCAGATAGTGGTCACTCTGTGGCCAGAAGAAGGACAAAGATGGAAA
TTGCAGATTGAGTCACGTTAAGCAGGCATCTTGGAGTGATTTGAGGCAGTTTCATGAAAG
AGCTACGACCACTTATTGTTGTTTTCCCCTTTTACAACAGAAGTTTTCATCAAAATAACG
TGGCAAAGCCCAGGAATGTTTGGGAAAAGTGTAGTTAAATGTTTTGTAATTCATTTGTCG 7800
GAGTGCTACCAGCTAAGAAAAAAGTCCTACCTTTGGTATGGTAGTCCTGCAGAGAATACA
ACATCAATATTAGTTTGGAAAAAAACACCACCACCACCAGAAACTGTAATGGAAAATGTA
AACCAAGAAATTCCTTGGGTAAGAGAGAAAGGATGTCGTATACTGGCCAAGTCCTGCCCA
GCTGTCAGCCTGCTGACCCTCTGCAGTTCAGGACCATGAAACGTGGCACTGTAAGACGTG
TCCCCTGCCTTTGCTTGCCCACAGATCTCTGCCCTTGTGCTGACTCCTGCACACAAGAGC 8100
ATTTCCCTGTAGCCAAACAGCGATTAGCCATAAGCTGCACCTGACTTTGAGGATTAAGAG
TTTGCAATTAAGTGGATTGCAGCAGGAGATCAGTGGCAGGGTTGCAGATGAAATCCTTTT
CTAGGGGTAGCTAAGGGCTGAGCAACCTGTCCTACAGCACAAGCCAAACCAGCCAAGGGT
TTTCCTGTGCTGTTCACAGAGGCAGGGCCAGCTGGAGCTGGAGGAGGTTGTGCTGGGACC
CTTCTCCCTGTGCTGAGAATGGAGTGATTTCTGGGTGCTGTTCCTGTGGCTTGCACTGAG 8400
CAGCTCAAGGGAGATCGGTGCTCCTCATGCAGTGCCAAAACTCGTGTTTGATGCAGAAAG

FIG.4C

ATGGATGTGCACCTCCCTCCTGCTAATGCAGCCGTGAGCTTATGAAGGCAATGAGCCCTC
AGTGCAGCAGGAGCTGTAGTGCACTCCTGTAGGTGCTAGGGAAAATCTCTGGTTCCCAGG
GATGCATTCATAAGGGCAATATATCTTGAGGCTGCGCCAAATCTTTCTGAAATATTCATG
CGTGTTCCCTTAATTTATAGAAACAAACACAGCAGAATAATTATTCCAATGCCTCCCCTC 8700
GAAGGAAACCCATATTTCCATGTAGAAATGTAACCTATATACACACAGCCATGCTGCATC
CTTCAGAACGTGCCAGTGCTCATCTCCCATGGCAAAATACTACAGGTATTCTCACTATGT
TGGACCTGTGAAAGGAACCATGGTAAGAAACTTCGGTTAAAGGTATGGCTGCAAAACTAC
TCATACCAAAACAGCAGAGCTCCAGACCTCCTCTTAGGAAAGAGCCACTTGGAGAGGGAT
GGTGTGAAGGCTGGAGGTGAGAGACAGAGCCTGTCCCAGTTTTCCTGTCTCTATTTTCTG 9000
AAACGTTTGCAGGAGGAAAGGACAACTGTACTTTCAGGCATAGCTGGTGCCCTCACGTAA
ATAAGTTCCCCGAACTTCTGTGTCATTTGTTCTTAAGATGCTTTGGCAGAACACTTTGAG
TCAATTCGCTTAACTGTGACTAGGTCTGTAAATAAGTGCTCCCTGCTGATAAGGTTCAAG
TGACATTTTTAGTGGTATTTGACAGCATTTACCTTGCTTTCAAGTCTTCTACCAAGCTCT
TCTATACTTAAGCAGTGAAACCGCCAAGAAACCCTTCCTTTTATCAAGCTAGTGCTAAAT 9300
ACCATTAACTTCATAGGTTAGATACGGTGCTGCCAGCTTCACCTGGCAGTGGTTGGTCAG
TTCTGCTGGTGACAAAGCCTCCCTGGCCTGTGCTTTTACCTAGAGGTGAATATCCAAGAA
TGCAGAACTGCATGGAAAGCAGAGCTGCAGGCACGATGGTGCTGAGCCTTAGCTGCTTCC
TGCTGGGAGATGTGGATGCAGAGACGAATGAAGGACCTGTCCCTTACTCCCCTCAGCATT
CTGTGCTATTTAGGGTTCTACCAGAGTCCTTAAGAGGTTTTTTTTTTTTTTGGTCCAAAA 9600
GTCTGTTTGTTTGGTTTTGACCACTGAGAGCATGTGACACTTGTCTCAAGCTATTAACCA
AGTGTCCAGCCAAAATCAATTGCCTGGGAGACGCAGACCATTACCTGGAGGTCAGGACCT
CAATAAATATTACCAGCCTCATTGTGCCGCTGACAGATTCAGCTGGCTGCTCCGTGTTCC
AGTCCAACAGTTCGGACGCCACGTTTGTATATATTTGCAGGCAGCCTCGGGGGGACCATC

TCAGGAGCAGAGCACCGGCAGCCGCCTGCAGAGCCGGGCAGTACTCTCACCATGGCCATG 9900
OVOMUCOID 5' UNTRANSLATED REGION
GCAGGTGTCTTCGTGCTGTTCTCTTTCGTGCTTTGTGGCTTCCTCCCAGGTGAGTAACTC
OVOMUCOID 5' UNTRANSLATED REGION
CCAGAGTGCTGCAGAAGCTT 9920

FIG.4D

OVOMUCOID PROMOTERS AND METHODS OF USE

RELATED APPLICATION INFORMATION

This application is a continuation-in-part of U.S. patent application Ser. No. 10/496,731, filed May 21, 2004, which is the National Stage of International Application No. PCT/US02/38413, filed Dec. 2, 2002, which is a continuation-in-part of U.S. patent application Ser. No. 09/998,716 filed Nov. 30, 2001, now U.S. Pat. No. 6,875,588 issued Apr. 5, 2005. This application is also a continuation-in-part of U.S. patent application Ser. No. 10/790,455, filed Mar. 1, 2004, now abandoned, and claims the benefit of U.S. Provisional Patent Application No. 60/476,596, filed Jun. 6, 2003, U.S. Provisional Patent Application No. 60/505,562, filed Sep. 24, 2003 and U.S. Provisional Patent Application No. 60/509,122, filed Oct. 6, 2003. The disclosures of each of these two U.S. Patent Applications, one issued patent and the International Application are incorporated by reference herein in their entirety.

GOVERNMENT RIGHTS STATEMENT

This invention was made with government support under a grant from to National Institute of Standards and Technology. Therefore, the U.S. Government may have certain rights in this invention.

FIELD OF THE INVENTION

The present invention relates generally to an avian ovomucoid gene expression control region, for example, from the chicken. More specifically, the invention relates to recombinant nucleic acids and expression vectors, transfected cells and transgenic animals that comprise the avian ovomucoid gene expression controlling region operably linked to a heterologous polypeptide-encoding nucleic acid.

BACKGROUND

The field of transgenics was initially developed to understand the action of a single gene in the context of the whole animal and the phenomena of gene activation, expression, and interaction. This technology has also been used to produce models for various diseases in humans and other animals and is amongst the most powerful tools available for the study of genetics, and the understanding of genetic mechanisms and function. From an economic perspective, the use of transgenic technology for the production of specific proteins or other substances of pharmaceutical interest (Gordon et al., (1987) Biotechnology 5: 1183-1187; Wilmut et al., (1990) Theriogenology 33: 113-123) offers significant advantages over more conventional methods of protein production by gene expression.

Heterologous nucleic acids have been engineered so that an expressed protein may be joined to a protein or peptide that will allow secretion of the transgenic expression product into milk or urine, from which the protein may then be recovered. These procedures have had limited success and may require lactating animals, with the attendant costs of maintaining individual animals or herds of large species, including cows, sheep, or goats.

Historically, transgenic animals have been produced almost exclusively by microinjection of the fertilized egg. The pronuclei of fertilized eggs are microinjected in vitro with foreign, i.e., xenogeneic or allogeneic, heterologous DNA or hybrid DNA molecules. The microinjected fertilized eggs are then transferred to the genital tract of a pseudopregnant female (See e.g., Krimpenfort et al., in U.S. Pat. No. 5,175,384).

One system that holds potential is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct which is lined with tubular gland cells. These cells secrete the egg-white proteins, including ovalbumin, ovomucoid, ovoinhibitor, conalbumin, ovomucin and lysozyme, into the lumen of the magnum where they are deposited onto the avian embryo and yolk.

The hen oviduct offers outstanding potential as a protein bioreactor because of the high levels of protein production, the promise of proper folding and post-translation modification of the target protein, the ease of product recovery, and the shorter developmental period of chickens compared to other potential animal species. As a result, efforts have been made to create transgenic chickens expressing heterologous proteins in the oviduct.

Chicken oviduct cells, when stimulated by steroid hormones during egg-laying, secrete three principal polypeptides, ovalbumin, ovomucoid and lysozyme (Tsai et al., (1978) Biochemistry 17: 5773-5779). The mRNA transcript encoding ovalbumin constitutes about 50% of the total mRNA of these cells. Ovomucoid and lysozyme mRNAs contribute about 6.6% and 3.4% respectively of the total mRNA of the steroid stimulated cells. (Hynes et al. (1977) pp 932).

Detailed restriction enzyme analysis of fragments of chicken genomic DNA have shown that the ovomucoid-encoding sequence includes seven intronic sequences (Lindenmaier et al. (1979) Nuc. Acid Res. 7;1221-1232; Catterall et al. (1979) Nature 278: 323-327; Lai et al. (1979) Cell 18:829-842). Short stretches of the 5' flanking region of the ovomucoid gene have been sequenced (Lai et al. (1979) Cell 18: 829-842; Genbank Accession No. J00897), but extending only 579 bases upstream of the recognized transcription start site. The 5' flanking region of the ovomucoid gene has been isolated (Catterall et al. (1979) Nature 278: 323-327; Lai et al. (1979) Cell 18: 829-842), but not generally characterized beyond low-resolution restriction site mapping. Scott et al. (1987) Biochemistry 26: 6831-6840, identified a CR1-like region within the 10 kb chicken genomic DNA located between the ovoinhibitor-encoding region and the downstream ovomucoid gene. The ovoinhibitor-encoding cDNA and the attached 3'-untranslated region, which extends into the 10 kb ovoinhibitor-ovomucoid region, were also sequenced (Scott et al. (1987) J. Biol. Chem. 262: 5899-5907).

The chicken ovomucoid gene, therefore, is highly expressed in the tubular glands of the mature hen oviduct and represents a suitable candidate for an efficient promoter for heterologous protein production in transgenic animals, especially animals. The regulatory region of the ovomucoid locus may extend over a nucleic acid region of about 10 kb of DNA 5' upstream of the transcription start site and includes at least one recognized element, CR1.

SUMMARY OF THE INVENTION

The present invention relates to nucleic acids comprising an avian ovomucoid gene expression control region, which is useful for the expression of nucleotide sequences encoding a polypeptide of interest in a transfected avian cell such as, for example, an oviduct cell. In one embodiment, the polypeptide is heterologous, i.e., not the ovomucoid protein product, and may be a mammalian, for example, a human polypeptide. One aspect of the present invention provides a nucleic acid isolated from a region immediately 5' upstream of a transcription start site of the chicken (or other avian) ovomucoid gene locus. The nucleic acid comprises an avian nucleic acid sequence comprising an ovomucoid gene expression control region comprising at least one avian CR1 repeat element, and a proximal ovomucoid promoter. Interspersed between these constituent elements may be stretches of nucleic acid that may serve at least to organize the gene regulatory elements in an ordered array relative to a polypeptide-encoding region. In one embodiment of the present invention, the ovomucoid gene expression control region is isolated from a chicken. In a specific embodiment, the ovomucoid gene expression control region has a nucleotide sequence of SEQ ID NO: 26. In other embodiments, the ovomucoid gene expression control region is at least 60%, at least 75%, at least 95%, or at least 99% identical or homologous to SEQ ID NO:26 and directs expression of a polypeptide encoding nucleotide sequence in an avian oviduct cell.

The avian ovomucoid gene expression control region of the present invention is useful for directing tissue-specific expression of a polypeptide-encoding nucleic acid. The avian ovomucoid gene expression control region may be operably linked with a selected nucleic acid insert, wherein the nucleic acid insert encodes a polypeptide, preferably heterologous, desired to be expressed in a transfected cell. The nucleic acid insert may be placed in frame with a nucleotide sequence encoding a signal peptide. Translation initiation may start with the signal peptide and continue through the nucleic acid insert, thereby producing an expressed polypeptide having the desired amino acid sequence.

The recombinant DNA of the present invention may further comprise a polyadenylation signal sequence that will allow the transcript directed by the ovomucoid gene expression control region of the invention to proceed beyond the nucleic acid insert encoding a heterologous polypeptide (i.e., not the ovomucoid protein that is expressed from the endogenous gene containing the ovomucoid gene expression control region) and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like. There are many know useful signal sequences including those disclosed in U.S. Pat. No. 5,856,187, the disclosure of which is incorporated in its entirety herein by reference.

Optionally, the nucleic acid of the invention may comprise gene expression control elements, e.g. promoters, enhancers, IRES's, from other than an ovomucoid gene and may even be from a non-avian gene.

The sequence of the expressed nucleic acid insert may be optimized for codon usage by a host cell. This may be determined from the codon usage of at least one, and preferably more than one, protein expressed in a chicken cell. For example, the codon usage may be determined from the nucleic acid sequences encoding the proteins ovalbumin, ovomucoid, ovomucin and ovotransferrin of chicken.

Yet another aspect of the present invention is expression vectors suitable for delivery to a recipient cell for expression of heterologous protein coding sequences in the vector therein. The expression vector of the present invention may comprise an avian ovomucoid gene expression control region operably linked to a nucleic acid insert encoding a non-ovomucoid polypeptide, and optionally, a polyadenylation signal sequence. The expression vector may further comprise a bacterial plasmid sequence, a viral nucleic acid sequence, or fragments or variants thereof that may allow for replication of the vector in a suitable host. As also contemplated in the present invention the nucleic acid may be a YAC, BAC, HAC, MAC, bacteriophage-derived artificial chromosome (BBPAC), cosmid or P1 derived artificial chromosome (PAC).

The present invention further relates to nucleic acid vectors and transgenes inserted therein that incorporate multiple polypeptide-encoding regions, wherein a first polypeptide-encoding region is operatively linked to a transcription promoter and a second polypeptide-encoding region is operatively linked to an Internal Ribosome Entry Sequence (IRES). For example, the vector may contain coding sequences for two different heterologous proteins (e.g., the heavy and light chains of an immunoglobulin).

Such nucleic acid constructs, when inserted into the genome of a bird and expressed therein, will generate individual polypeptides that may be post-translationally modified, for example, glycosylated or, in certain embodiments, be present as complexes, such as heterodimers with each other.

Another aspect of the present invention is a method of expressing a heterologous polypeptide in a eukaryotic cell by transfecting the cell with a recombinant DNA comprising an avian ovomucoid gene expression controlling region operably linked to a nucleic acid insert encoding the heterologous polypeptide and, optionally, a polyadenylation signal sequence, and culturing the transfected cell in a medium suitable for expression of the heterologous polypeptide under the control of the avian ovomucoid gene expression control region. In certain embodiments, the polypeptide is a cytokine, growth factor, enzyme, structural protein, and more preferably, an immunoglobulin, or subunit thereof. In other embodiments, the polypeptide is a mammalian, preferably a human polypeptide or derived from a human or mammalian polypeptide.

Also within the scope of the present invention are recombinant cells, tissues and animals, in for example avians, such as chickens, containing recombinant nucleic acid molecules according to the present invention and described above. In certain embodiments, the level of expression of the heterologous protein is greater than 5 μg, 10 μg, 50 μg, 100 μg, 250 μg, 500 μg, or 750 μg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams in an egg (preferably the egg white) produced by the transgenic avian of the invention. In one embodiment of the present invention, the transformed cell is a chicken oviduct cell and the nucleic acid comprises the chicken ovomucoid gene expression control region, a nucleic acid insert encoding a heterologous polypeptide of interest, e.g. human interferon a2, which optionally is codon optimized for expression in an avian cell, and an SV40 polyadenylation sequence.

The present invention includes nucleic acid molecules, e.g., DNA, which comprise an artificial chromosome and an ovomucoid gene expression controlling region and methods of using the nucleic acid molecules.

In one embodiment, the gene expression controlling region of the present invention is a nucleotide sequence that hybridizes to the nucleotide sequence of SEQ ID NO: 26 or a nucleotide sequence that hybridizes to the complement of the nucleotide sequence of SEQ ID NO: 26. In one embodiment, the hybridizations are under stringent conditions. High stringency conditions, when used in reference to nucleic acid hybridization, may comprise conditions equivalent to binding or hybridization at 65° C. in a solution consisting of 6×SSPE, 1% SDS, 5× Denhardt's reagent and 100 μg/ml denatured salmon sperm DNA followed by washing in a solution comprising 0.1×SSPE, and 0.1% SDS at 65° C. for about 15 to about 20 minutes. In certain embodiments, the wash conditions may include 50% formamide at 42° C. instead of 65° C. High stringency washes may include 0.1×SSC. to 0.2×SSC. and 1% SDS at 65° C. for about 15 to about 20 min. (see, Sambrook et al., Molecular Cloning—A Laboratory Manual (2nd ed.) Vol. 1-3, Cold Spring Harbor Laboratory, Cold Spring Harbor Press, N.Y., 1989, the disclosure of which is incorporated herein in its entirety by reference). Exemplary medium stringency conditions are as described above for high stringency except that the washes are carried out at 55° C. or at 37° C. when in the presence of 50% formamide.

In one embodiment, the ovomucoid gene expression controlling region is that of SEQ ID NO: 26 or the avian nucleic acid contained in SEQ ID NO: 36. In another embodiment, the ovomucoid gene expression controlling region comprises a functional portion of SEQ ID NO: 26 or a functional portion of the avian nucleic acid contained in SEQ ID NO: 36. The ovomucoid gene expression controlling region may also be the complement of SEQ ID NO: 26 or the complement of the avian nucleic acid contained in SEQ ID NO: 36 or a functional portion of the complement of SEQ ID NO: 26 or a functional portion of the complement of the avian nucleic acid contained in SEQ ID NO: 36.

What is meant by functional portion is a portion of a nucleotide sequence that is effective to control (i.e., facilitate or initiate in whole or in part) gene expression in a cell. Functional portions may be of any useful size. For example, functional portions may be about 20 nucleotides in length to one nucleotide less than the length of an entire nucleotide sequence, for example, the nucleotide sequence of SEQ ID NO: 26 or SEQ ID NO: 36. Functional portions may include, for example, and without limitation, one or more of a matrix attachment region, a transcription enhancer, a hormone responsive element or a CRI repeat element.

In one embodiment, a functional portion of SEQ ID NO: 26 is a fragment of SEQ ID NO: 26 which can operate to control transcription of a coding sequence operably attached to the functional portion or fragment while in a cell. For example, a functional portion of SEQ ID NO: 26 may be the portion of SEQ ID NO: 26 spanning from nucleotide 1 to about nucleotide 2000. In another example, a functional portion of SEQ ID NO: 26 may be the portion of SEQ ID NO: 26 spanning from nucleotide 1 to about nucleotide 5000. In another example, a functional portion of SEQ ID NO: 26 may be the portion of SEQ ID NO: 26 spanning from nucleotide 1 to about nucleotide 9,000. In another example, a functional portion of SEQ ID NO: 26 may be the portion of SEQ ID NO: 26 spanning from about nucleotide 10 to about nucleotide 1,000. In another example, a functional portion of SEQ ID NO: 26 may be the portion of SEQ ID NO: 26 spanning from about nucleotide 10 to about nucleotide 2,000. In another example, a functional portion of SEQ ID NO: 26 may be the portion of SEQ ID NO: 26 spanning from about nucleotide 50 to about nucleotide 1,000. In another example, a functional portion of SEQ ID NO: 26 may be the portion of SEQ ID NO: 26 spanning from about nucleotide 50 to about nucleotide 5,000. In another example, a functional portion of SEQ ID NO: 26 may be the portion of SEQ ID NO: 26 spanning from about nucleotide 100 to about nucleotide 2,000. In another example, a functional portion of SEQ ID NO: 26 may be the portion of SEQ ID NO: 26 spanning from about nucleotide 200 to about nucleotide 5000. In another example, a functional portion of SEQ ID NO: 26 may be the portion of SEQ ID NO: 26 spanning from about nucleotide 200 to about nucleotide 8,000. In another example, a functional portion of SEQ ID NO: 26 may be the portion of SEQ ID NO: 26 spanning from about nucleotide 250 to about nucleotide 5000. In another example, a functional portion of SEQ ID NO: 26 may be the portion of SEQ ID NO: 26 spanning from about nucleotide 250 to about nucleotide 6,000. In another example, a functional portion of SEQ ID NO: 26 may be the portion of SEQ ID NO: 26 spanning from about nucleotide 250 to about nucleotide 8,000. In another example, a functional portion of SEQ ID NO: 26 may be the portion of SEQ ID NO: 26 spanning from about nucleotide 300 to about nucleotide 4000. In another example, a functional portion of SEQ ID NO: 26 may be the portion of SEQ ID NO: 26 spanning from about nucleotide 300 to about nucleotide 5,000. In another example, a functional portion of SEQ ID NO: 26 may be the portion of SEQ ID NO: 26 spanning from about nucleotide 500 to about nucleotide 5000. In another example, a functional portion of SEQ ID NO: 26 may be the portion of SEQ ID NO: 26 spanning from about nucleotide 500 to about nucleotide 8,000.

In one embodiment, the gene expression controlling region comprises a nucleotide sequence that is at least 50% homologous to SEQ ID NO: 26 or to the complement of SEQ ID NO: 26. For example, the gene expression controlling region may comprise a nucleotide sequence that is at least 60% homologous to SEQ ID NO: 26 or its complement. In another example, the gene expression controlling region comprises a nucleotide sequence that is at least 70% homologous to SEQ ID NO: 26 or its complement. In another example, the gene expression controlling region comprises a nucleotide sequence that is at least 75% homologous to SEQ ID NO: 26 or its complement. In another example, the gene expression controlling region comprises a nucleotide sequence that is at least 80% homologous to SEQ ID NO: 26 or its complement. In another example, the gene expression controlling region comprises a nucleotide sequence that is at least 85% homologous to SEQ ID NO: 26 or its complement. In another example, the gene expression controlling region comprises a nucleotide sequence that is at least 90% homologous to SEQ ID NO: 26 or its complement. In another example, the gene expression controlling region comprises a nucleotide sequence that is at least 95% homologous to SEQ ID NO: 26 or its complement. In another example, the gene expression controlling region comprises a nucleotide sequence that is at least 99% homologous to SEQ ID NO: 26 or its complement.

In one embodiment, nucleic acid molecules of the invention tclude an attB site. The use of attB is disclosed in, for example, U.S. patent application Ser. No. 10/790,455, filed Mar. 1, 2004, now abandoned, the disclosure of which is incorporated in its entirety herein by reference.

The nucleic acid molecules of the present invention may also include a signal sequence coding region which may be useful for secretion of a polypeptide product from a cell. In one embodiment, the signal sequence is cleaved from the polypeptide product during the secretion process. For the purposes of the present invention, "signal sequence peptide" refers to amino acid sequences of about 15 to about 25 amino acids in length which are known in the art to be generally located at the amino terminus of proteins and which are capable of facilitating secretion of a peptide or polypeptide from a cell.

In one particularly useful embodiment, the nucleic acid molecules of the present invention include an artificial chromosome. Any useful artificial chromosomes are contemplated for use in the present invention. In one embodiment, an artificial chromosome is a DNA molecule which includes a telomere and is capable of self replication in a cell, for example, in an avian cell. In another embodiment, an artificial chromosome includes a telomere and a centromere. Artificial chromosomes include, without limitation, BACs (bacterial artificial chromosomes), YACs (yeast artificial chromosomes), HACs (human artificial chromosomes) MACs (mammalian artificial chromosomes), BBPACs (bacteriophage derived artificial chromosomes) or PACs (P1 derived artificial chromosomes) or combinations thereof.

The present invention also relates to compositions and methods for expressing certain peptides and polypeptides (e.g., proteins). The compositions can include a nucleic acid molecule comprising an artificial chromosome and an ovomucoid gene expression controlling region, as disclosed herein, which may be operably linked to a nucleotide sequence encoding a polypeptide. The nucleic acid may be inserted into a cell, for example, into a cell of an avian, where the polypeptide is expressed. In one embodiment, the nucleic acid molecule is present in an oviduct cell, for example, a tubular gland cell of a transgenic avian. The coding region may encode any useful polynucleotide including pharmaceutical compositions which comprise a polypeptide.

Certain specific examples of pharmaceutical compositions which are contemplated for production as disclosed herein include, with out limitation, Factor VIII (e.g., Recombinate®, Bioclate®, Kogenate®, Helixate® (Centeon), B-domain deleted Factor VIII (e.g., ReFacto®), Factor VIIa (e.g., NovoSeven®), Factor IX (e.g., Benefix®), anticoagulant; recombinant hirudin (e.g., Revasc®, Refludan®) Alteplase, tPA (e.g., Activase®), Reteplase, tPA, tPA—3 of 5 domains deleted, Ecokinase®, Retavase®, Rapilysin®, insulin (e.g., Humulin®, Novolin®, Insuman®) insulin lispro (e.g., Humalog®), Bio Lysprol, Liprolog®), insulin Aspart, iNovoRapid®, insulin glargine, long-acting insulin analog (e.g.,Lantus®), rhGH (e.g., Protropin®, Humatrope®, Nutropin®, BioTropin®, Genotropin®, Norditropin®, Saizen®, Serostim®, glucagons (e.g., Glucagen®), TSH (e.g., Thyrogen®, Gonal F®), Puregon®), follitropin-beta FSH (e.g., Follistim®), EPO (e.g., Epogen®, Procritt, Neorecormon®), GM-CSF (e.g., Leukine®, Neupogen®), PDGH (e.g., Regranex®), hormones such as cytokines, IFN alpa2a (e.g., Roferon A®), INF-apha (e.g., Infergen®), IFN alpa2b (e.g., Intron A®, Alfatronol®, Virtron®), ribavirin & INF-alpha 2b (e.g., Robetron®) INF-beta 1b, differs from h protein by C17 to S (e.g., Betaferon®), IFN-beta 1a (e.g., Avonex®, Rebif®), IFN-gamma1b (e.g., Actimmune®), IL-2 (e.g., Proleukin®) rIL-11 (e.g., Neumega®), rHBsAg (e.g., Recombivax®), Combination vaccine containing HBsAgn as one component (e.g., Comvax®, Tritarix®, Twinrix®, Primavax®, Procomax®g), OspA, a lipoprotein found on the surface of B burgoeri (e.g., Lymerix®), murine MAb directed against t-lymphocyte antigen CD3 (e.g., Orthoclone OKT3®), murine MAb directed against TAG-72, tumor-associated glycoprotein (e.g., OncoScint CR/OV®), FAb fragments derived from chimeric MAb, directed against platelet surface receptor GPII(b)/III(a) (e.g., ReoPro®), murine MAb fragment directed against tumor-associated antigen CA125 (e.g., Indimacis®), murine MAb fragment directed against human carcinoembryonic antigen, CEA (e.g., CEA-scan®), murine MAb fragment directed against human cardiac myosin (e.g., MyoScint®), murine MAb fragment directed against tumor surface antigen PSMA (e.g., ProstaScint®), murine MAb fragments (FAb/FAb2 mix) directed against HMW-MAA (e.g., Tacnemab®), murine MAb fragment (FAb) directed against carcinoma-associated antigen (e.g., Verluma®), MAb fragments (FAb) directed against NCA 90, a surface granulocyte nonspecific cross reacting antigen (e.g., LeukoScan®), chimeric MAb directed against CD20 antigen found on surface of B lymphocytes (e.g., Rituxan®), humanized MAb directed against the alpha chain of the IL2 receptor (e.g., Zenapax®), chimeric MAb directed against the alpha chain of the IL2 receptor (e.g., Simulect®), chimeric MAb directed against TNF-alpha (e.g., Remicade®), humanized MAb directed against an epitope on the surface of respiratory synctial virus (e.g., Synagis®), humanized MAb directed against HER 2, i.e., human epidermal growth factor receptor 2 (e.g., Herceptin®), human MAb directed against cytokeratin tumor-associated antigen (e.g., Humaspect®), anti-CTLA4, chimeric MAb directed against CD 20 surface antigen of B lymphocytes (e.g., Mabthera®), dornase-alpha DNAse (e.g., Pulmozyme®), beta glucocerebrosidase (e.g., Cerezyme®), TNF-alpha (e.g., Beromun®), IL-2-diptheria toxin fusion protein that targets cells displaying a surface IL-2 receptor (e.g., Ontak®), TNFR-lgG fragment fusion protein (e.g., Enbrel®), Laronidase, Recombinant DNA enzyme, (e.g., Aldurazyme®), Alefacept, Amevive®, Darbepoetin alfa (Colony stimulating factor) (e.g., Aranesp®), Tositumomab and iodine 1 131 tositumomab, murine MAb, Bexxar®, Alemtuzumab, Campath®, Rasburicase, Elitek®), Agalsidase beta, Fabrazyme®, FluMist®, Teriparatide, Parathyroid hormone derivative (e.g., Forteo®), Enfuvirtide Fuzeon®, Adalimumab (lgG1) (e.g., Humira®), Anakinra, Biological modifier (e.g., Kineret®), nesiritide, Human B-type natriuretic peptide (hBNP) (e.g., Natrecor®), Pegfilgrastim, Colony stimulating factor (e.g., Neulasta®), ribavarin and peg Intron A (e.g., Rebetron®), Pegvisomant, PEGylated human growth hormone receptor antagonist, (e.g., Somavert®), recombinant activated protein C. (e.g., Xigris®), Omalizumab, Immunoglobulin E (lgE) blocker (e.g., Xolair®) and lbritumomab tiuxetan (murine MAb) (e.g., Zevalin®).

In one particularly useful embodiment, the polypeptide (e.g., pharmaceutical composition) encoded by the nucleotide sequence operably linked to the ovomucoid gene expression controlling region is present in egg white produced by a transgenic avian of the present invention (i.e., an avian comprising a cell which includes a nucleic acid molecule of the present invention)

In one aspect of the invention, the nucleic acid molecule includes a nucleotide sequence encoding a light chain and/or a heavy chain of an antibody or a portion of a light chain and/or a heavy chain of an antibody which is operably linked to the ovomucoid gene expression controlling region. The antibody may be IgG (e.g., IgG1, IgG2, IgG3 or IgG4), IgA (e.g., IgA1 or IgA2), IgD, IgM or IgE. In addition, the light chain of the antibody may be a kappa light chain or a lambda light chain.

The present invention also contemplates the production of useful fusion proteins. For example, an antibody or a portion of an antibody may be produced as a fusion protein with another useful polypeptide.

The nucleic acid molecules of the present invention may be introduced into a cell, for example, into the cell of an avian, by any useful method. Such methods include, without limitation, microinjecting, transfection, electroporation and lipofection. The nucleic acid molecules may be introduced into a germinal disc or an avian embryo cell such as an early stage avian embryo. In one embodiment, the nucleic acid molecules of the present invention are introduced into an avian embryo cell such as a stage I avian embryo, stage II avian embryo, stage III avian embryo, stage IV avian embryo, stage V avian embryo, stage VI avian embryo, stage VII avian embryo, stage VIII avian embryo, stage IX avian embryo, stage X avian embryo, stage XI avian embryo or stage XII avian embryo.

Any combination of features described herein is included within the scope of the present invention provided that the features included in any such combination are not mutually inconsistent. Such combinations will be apparent based on this specification and on the knowledge of one of ordinary skill in the art.

Definitions

The term "animal" is used herein to include all vertebrate animals, including humans. It also includes an individual animal in all stages of development, including embryonic and fetal stages.

The term "avian" as used herein refers to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, e.g., plasmids and cosmids, artificial chromosomes, such as but not limited to, Yeast Artificial Chromosomes (YACs) and Bacterial Artificial Chromosomes (BACs), and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid that has been removed from other components of the cell containing the nucleic acid or from other components of chemical/synthetic reaction used to generate the nucleic acid. In specific embodiments, the nucleic acid is 50%, 60%, 70%, 80%, 90%, 95%, 99% or 100% pure. The "isolated nucleic acid" does not include nucleic acids that are members of a library, e.g. cDNA or genomic library, unless identified and separated from the other members of the library. The techniques used to isolate and characterize the nucleic acids and proteins of the present invention are well known to those of skill in the art and standard molecular biology and biochemical manuals may be consulted to select suitable protocols without undue experimentation. See, for example, Sambrook et al, 2001, Molecular Cloning: A Laboratory Manual, 3rd ed., Cold Spring Harbor Press; the content of which is herein incorporated by reference in its entirety.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased, for example, by 1 fold, 2 fold, 5 fold, 10 fold, 50 fold, 100 fold, 500 fold, 1000 fold, 10,000 fold, 100,000 fold, or 1,000,000 fold. The other DNA may, for example, be derived from a yeast or bacterial genome, or a cloning vector, such as a plasmid or a viral vector.

It is advantageous for some purposes that a nucleotide sequence is in purified form. The term "purified" in reference to nucleic acid represents that the sequence has increased purity relative to the natural environment, preferably, 50%, 60%, 70%, 80%, 90%, 95%, or 99% pure.

The terms "polynucleotide" and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term polypeptide as used herein can also refer to a peptide. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or noncovalently linked to labeling ligands.

The term "fragment" as used herein to refers to an at least about 10, 20, 50, 75, 100, 150, 200, 250, 300, 500, 1000, 2000, 5000, 6,000, 8,000, or 10,000 nucleotide long portion of a nucleic acid (e.g., cDNA) that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein may also refer to an at least about 5, 10, 20, 30, 40, 50, 75, 100, 150, 200, 250, 300, 400, 500, 1000, 2000, 5000, 6,000, 8,000, or 10,000 amino acid portion of a polypeptide, which portion is cleaved from a naturally occurring polypeptide by proteolytic cleavage by at least one protease, or is a portion of the naturally occurring polypeptide synthesized by chemical methods or using recombinant DNA technology (e.g., expressed from a portion of the nucleotide sequence encoding the naturally occurring polypeptide) known to one of skill in the art. "Fragment" may also refer to a portion of about 5%, about 10%, about 20%, about 30%, about 40%, about 50%, about 60%, about 70%, about 80% about 90 or about 95% of a particular nucleotide or amino acid sequence.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide or a portion thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The terms "operably linked" or "operatively linked" refer to the configuration of the coding and control sequences so as to perform the desired function. Thus, control sequences operably linked to a coding sequence are capable of effecting the expression of the coding sequence and regulating in which tissues, at what developmental time points, or in response to which signals, etc., a gene is expressed. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence. Such intervening sequences include but are not limited to enhancer sequences which are not transcribed or are not bound by polymerase.

The terms "gene expression control regions" or "gene expression controlling regions" as used herein refer to nucleotide sequences that are associated with a nucleic acid sequence and which regulate, in whole or in part, the expression of the nucleic acid sequence, for example, regulate in whole or in part the transcription of a nucleotide sequence. Exemplary transcription regulatory sequences include enhancer elements, hormone response elements, steroid response elements, negative regulatory elements, and the like. The "transcription regulatory sequences" may be isolated and incorporated into a nucleic acid vector to enable regulated transcription in appropriate cells of portions of the vector DNA. The "transcription regulatory sequence" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter' as used herein refers to the DNA sequence that determines the site of transcription initiation by an RNA polymerase. A "promoter-proximal element" may be a regulatory sequence within about 200 base pairs of the transcription start site. A "magnum-specific" promoter, as used herein, is a promoter that is primarily or exclusively active in the tubular gland cells of the avian magnum. Useful promoters also include exogenously inducible promoters. These are promoters that can be "turned on" in response to an exogenously supplied agent or stimulus, which is generally not an endogenous metabolite or cytokine. Examples include an antibiotic-inducible promoter, such as a tetracycline-inducible promoter, a heat-inducible promoter, a light-inducible promoter, or a laser inducible promoter. (e.g., Halloran et al. (2000) Development 127: 1953-1960; Gemer et al. (2000) Int. J. Hyperthermia 16: 171-81; Rang and Will, 2000, Nucleic Acids Res. 28: 1120-5; Hagihara et al. (1999) Cell Transplant 8: 4314; Huang et al. (1999) Mol. Med. 5: 129-37; Forster et al. (1999) Nucleic Acids Res. 27: 708-10; Liu et al. (1998) Biotechniques 24: 624-8, 630-2; the contents of which have been incorporated herein by reference in their entireties).

The term "coding region" as used herein refers to a continuous linear arrangement of nucleotides which may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, and the like that are well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of an ovomucoid gene expression control region or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC. (wherein 1×SSC. comprises 0.015 M sodium citrate and 0.15 M sodium chloride), at 65° C. in an aqueous solution, followed by washing with 1×SSC. at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

1 to 1.0 M Na ion concentration (or other salts) from about pH 7.0 to about pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1× to 2×SSC at 50 to 55° Celsius. Exemplary moderate stringency conditions include hybridization in 40 to 45% formamide, 1 M NaCl, 1% SDS at 37° Celsius, and a wash in 0.5× to 1×SSC at 55 to 60° Celsius. Exemplary high stringency conditions include hybridization in 50% formamide, 1 M NaCl, 1% SDS at 37° Celsius, and a wash in 0.1×SSC. at 60 to 65° Celsius.

The terms "unique nucleic acid region" and "unique protein (polypeptide) region" as used herein refer to sequences present in a nucleic acid or protein (polypeptide) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The terms "percent sequence identity" or "percent sequence similarity" as used herein refer to the degree of sequence identity between two nucleic acid sequences or two amino acid sequences as determined using the algorithm of Karlin & Attschul (1990) Proc. Natl. Acad. Sci. 87: 2264-2268, modified as in Karlin & Attschul (1993) Proc. Natl. Acad. Sci. 90: 5873-5877. Such an algorithm is incorporated into the NBLAST and XBLAST programs of Attschul et al. (1990) T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al. (1997) Nucl. Acids Res. 25: 3389-3402. When utilizing BLAST and Gapped BLAST programs, the default parameters of the respective programs (e.g. XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "sense strand" as used herein refers to a single stranded DNA molecule from a genomic DNA that may be transcribed into RNA and translated into the natural polypeptide product of the gene. The term "antisense strand" as used herein refers to the single strand DNA molecule of a genomic DNA that is complementary with the sense strand of the gene.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; the antisense transcripts may inhibit transport of the "target RNA", or, the antisense transcripts may inhibit translation of "target RNA".

The term "nucleic acid vector" or "vector" as used herein refers to a natural or synthetic single or double stranded plasmid or viral nucleic acid molecule, or any other nucleic acid molecule, such as but not limited to YACs, BACs, bacteriophage-derived artificial chromosome (BBPAC), cosmid or P1 derived artificial chromosome (PAC), that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that comprises the ovomucoid gene expression control region operably linked to a nucleotide sequence coding at least one polypeptide. As used herein, the term "regulatory sequences" includes promoters, enhancers, and other elements that may control gene expression. Standard molecular biology textbooks such as Sambrook et al. eds "Molecular Cloning: A Laboratory Manual" 3rd ed., Cold Spring Harbor Press (2001) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration.

The term "transfecting agent" as used herein refers to a composition of matter added to the genetic material for enhancing the uptake of heterologous DNA segment(s) into a eukaryotic cell, preferably an avian cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes can be targeted to, e.g., the male germ cells using specific ligands that are recognized by receptors on the cell surface of the germ cell, such as the c-kit ligand or modifications thereof.

Other transfecting agents include but are not limited to lipofectin, lipfectamine, DIMRIE C, Supeffect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecytammonium bromide), DHDEAB (N,N-di-n-hexadecyl-N,N-dihydroxyethyl ammonium bromide), HDEAB (N-n-hexadecylN,N-dihydroxyethylammonium bromide), polybrene, or poly(ethylenimine) (PEI). These non-viral agents have the advantage that they can facilitate stable integration of xenogeneic DNA sequences into the vertebrate genome, without size restrictions commonly associated with virus-derived transfecting agents.

A "pharmaceutical composition" is a substance that, in whole or in part, makes up a drug.

The term "recombinant cell" refers to a cell that has a new combination of nucleic acid segments that are not covalently linked to each other in nature in that particular configuration. A new configuration of nucleic acid segments can be introduced into an organism using a wide array of nucleic acid manipulation techniques available to those skilled in the art. A recombinant cell can be a single eukaryotic cell, such as a mammalian or avian cell (including within a transgenic mammal or avian) or a single prokaryotic cell. The recombinant cell may harbor a vector that is extragenomic. An extragenomic nucleic acid vector does not insert into the cell's genome. A recombinant cell may further harbor a vector or a portion thereof (e.g., the portion containing the regulatory sequences and the coding sequence) that is intragenomic. The term intragenomic defines a nucleic acid construct incorporated within the recombinant cell's genome.

The terms "recombinant nucleic acid" and "recombinant DNA" as used herein refer a combination of at least two nucleic acids that is not naturally found in a eukaryotic or prokaryotic cell in that particular configuration. The nucleic acids may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

Pharmaceutical comprising agents that will modulate the regulation of the expression of a polypeptide-encoding nucleic acid operably linked to a ovomucoid gene expression control region can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Pharmaceutical compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Pharmaceutical compositions may be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as Remmington's Pharmaceutical Science, 17th edition, 1985 may be consulted to prepare suitable preparations, without undue experimentation. Dosages can generally range from a few hundred milligrams to a few grams.

As used herein, a "transgenic animal" is any non-human animal, such as an avian species, including the chicken, in which one or more of the cells of the animal contain a heterologous nucleic acid introduced by way of human intervention, such as by transgenic techniques well known in the art. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject polypeptide, e.g. either agonistic or antagonistic forms, or in which the gene has been disrupted. In certain embodiments, the genome of the animal has been modified such that a heterologous gene expression element is inserted so as to be operably linked to an endogenous coding sequence. The terms "chimeric animal" or "mosaic animal" are used herein to refer to animals in which the recombinant gene is found, or in which the recombinant gene is expressed in some but not all cells of the animal. The term "tissue-specific chimeric animal" indicates that the recombinant gene is present and/or expressed in some tissues but not others.

As used herein, the term "transgene" means a nucleic acid sequence (encoding, for example, a human interferon polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location that differs from that of the natural gene or its insertion results in a knockout). A trangene also includes a regulatory sequence designed to be inserted into the genome such that it regulates the expression of an endogenous coding sequence, e.g., to increase expression and or to change the timing and or tissue specificity of expression, etc. (e.g., to effect "gene activation").

The term "cytokine" as used herein refers to any secreted polypeptide that affects the functions of cells and is a molecule that modulates interactions between cells in the immune, inflammatory or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-alpha) and Tumor Necrosis Factor beta (TNF-beta).

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and may further comprise any modified or derivatised variant thereof that retains the ability to specifically bind an epitope. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, $F(ab')_2$ fragments, disulfide-linked Fvs (sdFv) fragments, e.g., as produced by a Fab expression library, anti-idiotypic (anti-Id) antibodies, intrabodies, synthetic antibodies, and epitope-binding fragments of any of the above.

The term "immunoglobulin polypeptide" as used herein refers to a polypeptide derived from a constituent polypeptide of an immunoglobulin. An "immunoglobulin polypeptide" may be, but is not limited to, an immunoglobulin (preferably an antibody) heavy or light chain and may include a variable region, a diversity region, joining region and a constant region or any combination, variant or truncated form thereof. The term "immunoglobulin polypeptides" further includes single-chain antibodies comprised of, but not limited to, an immunoglobulin heavy chain variable region, an immunoglobulin light chain variable region and optionally a peptide linker.

The techniques used to isolate and characterize the nucleic acids and proteins of the present invention are well known to those of skill in the art and standard molecular biology and biochemical manuals may be consulted to select suitable protocols without undue experimentation. See, for example, Sambrook et al. (2001) Molecular Cloning: A Laboratory Manual, 3rd ed., Cold Spring Harbor Press, the content of which is herein incorporated by reference in its entirety.

This description uses gene nomenclature accepted by the Cucurbit Genetics Cooperative as it appears in the Cucurbit Genetics Cooperative Report 18:85 (1995), herein incorporated by reference in its entirety. Using this gene nomenclature, genes are symbolized by italicized Roman letters. If a mutant gene is recessive to the normal type, then the symbol and name of the mutant gene appear in italicized lower case letters.

Abbreviations

Abbreviations used in the present specification include the following: aa, amino acid(s); bp, base pair(s); cDNA, DNA complementary to RNA; min, miunte(s); nt, nucleotide(s); SSC, sodium chloride-sodium citrate; UTR, untranslated region; DMSO, dimethyl sulfoxide.

Additional objects and aspects of the present invention will become more apparent upon review of the detailed description set forth below when taken in conjunction with the accompanying figures, which are briefly described as follows.

BRIEF DESCRIPTION OF THE FIGURES

FIG. 3 shows the PCR primers SEQ ID NOS: 1-25 used to PCR amplify and/or sequence the approximately 10 kb nucleic acid region that is 5' upstream of the chicken ovomucoid transcription start site.

FIG. 4A-4D shows the nucleic acid sequence SEQ ID NO: 26 of the approximately 10 kb nucleic acid region that is 5' upstream of the chicken ovomucoid transciiption start site.

FIG. 8 A. The ovoinhibitor (OI) and adjacent ovomucoid (OM) regions are shown with transcriptional start sites indicated with bent arrows. The left and right sides of the BAC, relative to an EcoR1 site found in the 3' UTR, are shown with their approximate sizes in kilobase pairs (kb). FIG. 8B. The coding region of ovomucoid is shown with exons as white boxes and introns as black boxes. C. The IRES and polynucleotide coding sequence for the light chain and heavy chain of the IgG1 inserted at the EcoR1 site.

DETAILED DESCRIPTION OF THE INVENTION

Figure 1:
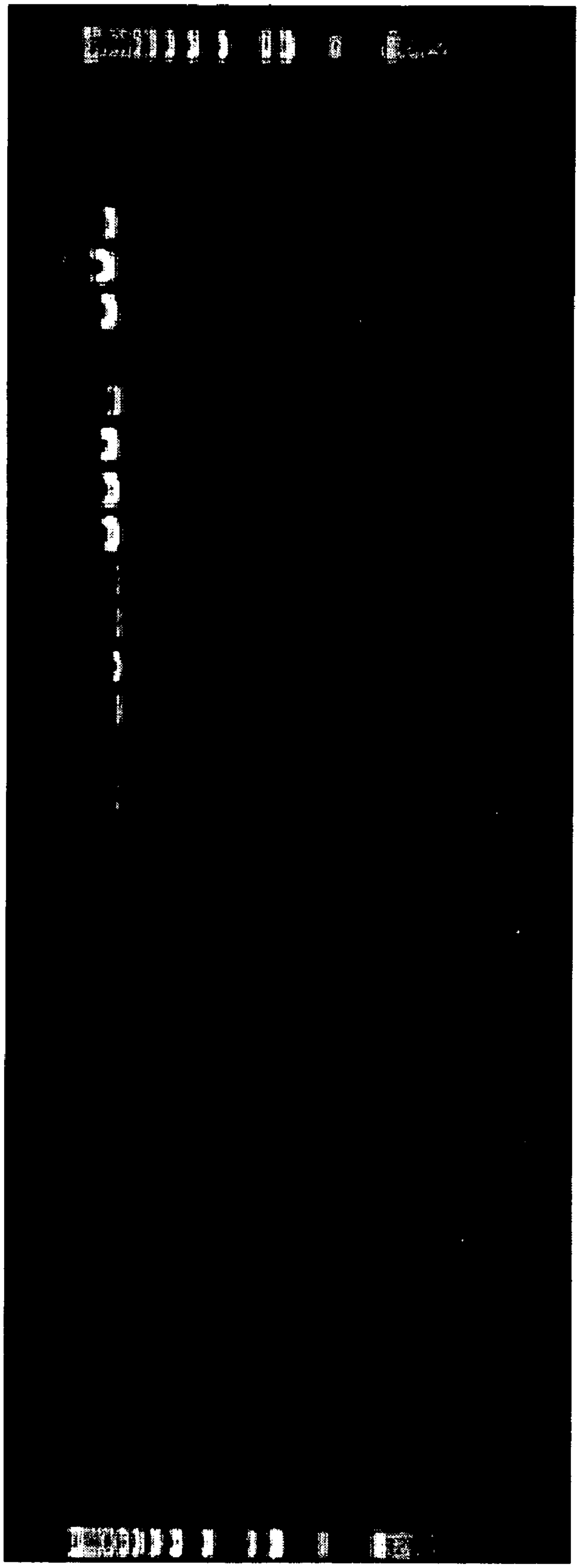
FIG. 1 illustrates an agarose gel analysis of PCR products from PCR amplification of chicken genomic DNA using the primers OVINs2 (SEQ ID NO: 1) and OVMUa2 (SEQ ID NO: 2).

The present invention relates to avian gene expression controlling regions and to methods of their use. In one embodiment, the invention relates to avian (e.g., chicken) ovomucoid promoters and to methods of using such promoters in the production of useful polypeptide compositions.

A series of PCR amplifications of template chicken genomic DNA were used to isolate the gene expression control region of the chicken ovomucoid locus. The region of the chicken genome lying between the 3' end of the ovoinhibitor gene and the 5' transcription start site of the ovomucoid gene was PCR amplified using the primers OVINs 2, 5'-TAGGCAGAGCAATAGGACTCTCAACCTCGT-3' (SEQ ID NO: 1) and OVMUa2, 5'-AAGCTTCTGCAGCACTCTGGGAGTTACTCA-3' (SEQ ID NO: 2) as described in detail in Example 1 below and FIG. 1. The approximately 10 kb fragment was blunt-ended and cleaved with the restriction endonuclease Bam HI. The resulting fragments of about 4.7 kb and 5.5 kb were subcloned into the linearized plasmid vector pBluescript KS II (+/−) (Stratagene, La Jolla, Calif.). Each insert was sequenced using the primers SEQ ID NOS: 5-25 shown in FIGS. 2 and 3 and as described in Example 3 below. The compiled nucleic acid sequence (SEQ ID NO: 26) of the approximately 10 kb nucleic acid region that is 5' upstream of the chicken ovomucoid transcription start site is shown in FIG. 4.

SEQ ID NO: 26 includes the ovoinhibitor gene 3' untranslated region described by Scott et al. (1987) J. Biol. Chem. 262: 5899-5909, from bases positions 1-255 as shown in FIG. 4. A CR1-like element (Scott et al., Biochemistry (1987) 26: 6831-6840; Genbank Accession No: M17966) is located at base positions 2761-3024 as shown in FIG. 4. The region of SEQ ID NO: 26 from base positions 9403-9920, as shown in FIG. 4, has been described in Genbank Accession No: J00897 and in Lai et al., Cell (1979) 18: 829-842 and includes a portion of the 5' untranslated region of the ovomucoid gene.

An avian ovomucoid gene region has been identified in a chicken artificial chromosome library. The library was constructed with HindIII chicken DNA inserts ligated into a BAC vector (see, Crooijmans et al. (2000) Mammalian Genome 11: 360-363, the disclosure of which is incorporated in its entirety by reference). However, the present invention contemplates the employment of any useful artificial chromosome library including, but not limited to, libraries constructed from YACs, HACs, MACs, BBPACs or PACs.

The library was screened by PCR identifying a BAC clone which included a single chicken DNA segment which extends into both the 5' untranslated region of the ovomucoid gene and the 3' ovoinhibitor gene. The nucleotide sequence of the clone, designated OMC24, is shown in SEQ ID NO: 36. The nucleotide region spanning from about nucleotide 68,296 to about nucleotide 75,815 of SEQ ID NO: 36 represents the BAC vector. The ovomucoid region spans from about nucleotide 1 to about nucleotide 68,295 of SEQ ID NO: 36. The nucleotide sequence for a functional ovomucoid gene expression controlling region disclosed in SEQ ID NO: 26 represents a fragment or a functional portion of the ovomucoid nucleotide sequence region disclosed in SEQ ID NO: 36.

The nucleotide sequence of the gene expression controlling region disclosed in SEQ ID NO: 26 is essentially encompassed in SEQ ID NO: 36 from about nucleotide 26,416 to about nucleotide 36,390. Nucleotide sequence alignment between SEQ ID NO: 26 and nucleotides 26,416 to 36,390 of SEQ ID NO: 36 show a 99.0% sequence homology. The chicken genomic DNAs which yielded SEQ ID NO: 26 and SEQ ID NO: 36 were isolated from different strains of white leghorn chickens (SEQ ID NO: 26—American Strain, SEQ ID NO: 36: Dutch Strain) thus showing the sequence diversity of the ovomucoid gene expression controlling region of the present invention. Other useful fragments or functional portions of SEQ ID NO: 36 can be easily obtained by standard techniques well known in the art. For example, a functional portion of SEQ ID NO: 36 may be the portion of SEQ ID NO: 36 spanning from about nucleotide 1 to about nucleotide 20,000. In another example, a functional portion of SEQ ID NO: 36 may be the portion of SEQ ID NO: 36 spanning from about nucleotide 1 to about nucleotide 30,000. In another example, a functional portion of SEQ ID NO: 36 may be the portion of SEQ ID NO: 36 spanning from about nucleotide 1 to about nucleotide 40,000. In another example, a functional portion of SEQ ID NO: 36 may be the portion of SEQ ID NO: 36 spanning from about nucleotide 10,000 to about nucleotide 50,000. In another example, a functional portion of SEQ ID NO: 26 may be the portion of SEQ ID NO: 36 spanning from about nucleotide 1 to about nucleotide 60,000. In another example, a functional portion of SEQ ID NO: 26 may be the portion of SEQ ID NO: 36 spanning from about nucleotide 20,000 to about nucleotide 30,000. In another example, a functional portion of SEQ ID NO: 36 may be the portion of SEQ ID NO: 36 spanning from about nucleotide 30,000 to about nucleotide 45,000. In another example, a functional portion of SEQ ID NO: 36 may be the portion of SEQ ID NO: 36 spanning from about nucleotide 20,000 to about nucleotide 50,000. In another example, a functional portion of SEQ ID NO: 26 may be the portion of SEQ ID NO: 36 spanning from about nucleotide 25,000 to about nucleotide 60,000. The invention contemplates any useful fragment or portion of nucleotide sequences disclosed herein and its use.

Fragments or portions of certain DNA sequences which function to control gene expression can be identified by techniques that are well know to practitioners of ordinary skill in the art. For example, promoter analysis by saturation mutagenesis has been describe in Biol. Proced. Online (2001) Vol 1, No.3, pp 64-69, the disclosure of which is incorporated by reference herein in its entirety. Using well known techniques a molecular biologist of ordinary skill can specify fragments or functional portions of the cloned chicken ovomucoid gene expression controlling region (e.g., promoter) disclosed herein effective to control gene expression, for example, control transcription in a cell.

In one embodiment, the gene expression controlling region comprises a nucleotide or portion of a nulceotide sequence that is at least 50% homologous to the avian nucleic acid contained in SEQ ID NO: 36 or to the complement of the avian nucleic acid contained in SEQ ID NO: 36. For example, the gene expression controlling region may comprise a nucleotide sequence or portion of a nulceotide sequence that is at least 60% homologous to the avian nucleic acid contained in SEQ ID NO: 36 or its complement. In another example, the gene expression controlling region comprises a nucleotide sequence or portion of a nulceotide sequence that is at least 70% homologous to the avian nucleic acid contained in SEQ ID NO: 36 or its complement. In another example, the gene expression controlling region comprises a nucleotide sequence or portion of a nulceotide sequence that is at least 75% homologous to the avian nucleic acid contained in SEQ ID NO: 36 or its complement. In another example, the gene expression controlling region comprises a nucleotide sequence or portion of a nulceotide sequence that is at least 80% homologous to the avian nucleic acid contained in SEQ ID NO: 36 or its complement. In another example, the gene expression controlling region comprises a nucleotide sequence or portion of a nulceotide sequence that is at least 85% homologous to the avian nucleic acid contained in SEQ ID NO: 36 or its complement. In another example, the gene expression controlling region comprises a nucleotide sequence or portion of a nulceotide sequence that is at least 90% homologous to the avian nucleic acid contained in SEQ ID NO: 36 or its complement. In another example, the gene expression controlling region comprises a nucleotide sequence or portion of a nulceotide sequence that is at least 95% homologous to the avian nucleic acid contained in SEQ ID NO: 36 or its complement. In another example, the gene expression controlling region comprises a nucleotide sequence or portion of a nulceotide sequence that is at least 99% homologous to the avian nucleic acid contained in SEQ ID NO: 36 or its complement.

Nucleotide sequences encoding the heavy chain and light chain of an IgG1 monoclonal antibody were inserted into the 3' UTR of the ovomucoid transcript encoding region in two separate ovomucoid BAC clones of SEQ ID NO: 36. The heavy chain and light chain coding sequences each included a signal sequence located at their 5' ends; however, use of a signal sequence may not be required in the present invention. The resulting mRNA transcript produced by the ovomucoid gene expression contolling region for each clone contains two coding sequences; one for the ovomucoid protein and another for the antibody light chain or heavy chain downstream of the ovomucoid coding sequence. To facilitate translation of the downstream heavy chain or light chain coding sequence, an internal ribosome entry site (IRES) was inserted immediately upstream of the heavy chain or light chain coding sequence in each clone.

In another example, a CTLA4-Fc fusion coding sequence comprising a nucleotide coding sequence for the extracellular domains of the CTLA4 (cytotoxic T lymphocyte antigen 4) receptor protein linked to a nucleotide coding sequence for an immunoglobulin constant region (IgG1 Fc) was cloned into an ovomucoid BAC clone of SEQ ID NO: 36. In addition, an attB site was included in the construct. To produce this clone, the IRES-LC portion of the ovomucoid-IRES-antibody light chain clone was deleted and was replaced with an IRES-CTLA4-Fc cassette.

Disclosed above are examples of expression constructs that can be produced in accordance with the present invention. However, these are merely examples and it is contemplated that any nucleic acid sequence encoding a useful polypeptide can be operably linked to an avian ovomucoid gene expression controlling region of the present invention so as to be expressed in an avian cell, for example, in cells of a transgenic avian such as a chicken, turkey, duck, goose, quail, pheasant, parrot, finch, ratites including ostrich, emu or cassowary.

The present invention can be used to express, in large yields and at low cost, a wide range of desired proteins including those used as human and animal pharmaceuticals, diagnostics, and livestock feed additives. Proteins such as growth hormones, cytokines, structural proteins and enzymes, including human growth hormone, interferon, lysozyme, and β-casein, are examples of proteins that are desirably expressed in the oviduct and deposited in eggs according to the invention. Other possible proteins to be produced include, but are not limited to, albumin, α-1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin Immunoglobulins and genetically engineered antibodies, including immunotoxins that bind to surface antigens on human tumor cells and destroy them, can also be expressed for use as pharmaceuticals or diagnostics. It is contemplated that immunoglobulin polypeptides expressed in avian cells following transfection by the methods of the present invention may include monomeric heavy and light chains, single-chain antibodies or multimeric immunoglobulins comprising variable heavy and light chain regions, i.e., antigen-binding domains, or intact heavy and light immunoglobulin chains.

The chicken ovomucoid gene expression control region of the present invention may include the nucleotide elements that are positioned 5' upstream of the transcription start site of the native chicken ovomucoid locus and which are necessary for the regulated expression of a downstream polypeptide-encoding nucleic acid. It is contemplated that this region may include transcription control regions which are regulated by certain hormones including, for example, steroid hormones and the like.

One aspect of the present invention, therefore, provides a novel isolated nucleic acid that comprises the nucleotide sequence SEQ ID NO: 26, shown in FIG. 4, (Genbank Accession No: AF 453747) and derivatives and variants thereof, that is located immediately 5' upstream of the transcription start site of the chicken ovomucoid gene locus.

In one embodiment of the present invention, the isolated nucleic acid may be isolated from an avian selected from the group consisting of a chicken, a turkey, a duck, a goose, a quail, a pheasant, a ratite, an ornamental bird or a feral bird.

In another embodiment of the present invention, the isolated nucleic acid is obtained from a chicken. In this embodiment, the isolated nucleic acid has the sequence of SEQ ID NO: 26, as shown in FIG. 4, or a variant thereof. SEQ ID NO: 26 was cloned into pBluescript KS II (+/−) vector, as described in Example 2, and named pBS-OVMUP-10. pBS-OVMUP-10 was deposited with American Type Culture Collection (ATCC), 10801 University Blvd., Manassas, Va. 20110, as ATCC. No. PTA-4821 on Nov. 26, 2002 under the conditions set forth in the Budapest Treaty.

Another aspect of the invention provides nucleic acids that can hybridize under high, medium or low stringency conditions to an isolated nucleic acid comprising a chicken ovomucoid gene expression control region having all, a derivative of, or a portion of the nucleic acid sequence SEQ ID NO: 26 shown in FIG. 4 and direct expression of a polypeptide coding sequence in an avian oviduct cell. The nucleotide sequence determined from the isolation of the ovomucoid gene expression control region from a chicken (SEQ ID NO: 26) will allow for the generation of probes designed for use in identifying ovomucoid gene expression control regions, or homologs thereof in other avian species.

Fragments of a nucleic acid comprising a portion of the subject ovomucoid gene expression control region are also within the scope of the invention. As used herein, a fragment of the nucleic acid comprising an active portion of a ovomucoid gene expression control region refers to a nucleotide sequence having fewer nucleotides than the nucleotide sequence comprising the entire nucleic acid sequence of the ovomucoid gene expression control region.

A fragment of the ovomucoid gene expression control region may contain one or more of the following elements: the ovoinhibitor gene 3' untranslated region from bases positions 1-255 as shown in FIG. 4, a CR1-like element located at base positions 2761-3024 as shown in FIG. 4, the region from base positions 9403-9920, as shown in FIG. 4 which includes a portion of the 5' untranslated region of the ovomucoid gene. Alternatively, the fragment may be about 10, 20, 50, 75, 100, 150, 200, 250, 300, 500, 1000, 2000, 4000, 5000, 6000, 7000, 8000 or 9000 nucleotides in length and be capable of directing expression of an operably linked heterologous gene sequence, particularly in an avian cell, for example, an avian oviduct cell.

In one embodiment of the present invention, the nucleotide sequence of the isolated DNA molecule of the present invention may be used as a probe in nucleic acid hybridization assays for the detection of the ovomucoid gene expression control region. The nucleotide sequence of the present invention may be used in any nucleic acid hybridization assay system known in the art, including, but not limited to, Southern blots (Southern, E.M. J. Mol. Biol. 98: 508 (1975)), Northern blots (Thomas et al. (1980) Proc. Natl. Acad. Sci. 77: 5201-05), and Colony blots (Grunstein et al. (1975) Proc. Natl. Acad. Sci. 72: 3961-65), which are hereby incorporated by reference in their entireties. Alternatively, the isolated DNA molecules of the present invention can be used in a gene amplification detection procedure such as a polymerase chain reaction (Erlich et al. (1991) Science 252: 1643-51, which is hereby incorporated by reference in its entirety) or in restriction fragment length polymorphism (RFLP) diagnostic techniques, as described in Watson et al., (2d ed. 1992), Recombinant DNA, Scientific American Books, 519-522, 545-547, which is hereby incorporated by reference.

Nucleic acids constructed in accordance with the present invention can be labeled to provide a signal as a means of detection. For example, radioactive elements such as $^{32}P$, $^{3}H$, and $^{35}S$ or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals such as *Promega: Protocol and Applications Guide,* 2nd Edition, 1991 (Promega Corp., Madison, Wis., the disclosure of which is incorporated herein in its entirety) may be consulted to select an appropriate labeling protocol without undue experimentation.

In another embodiment of the present invention, an isolated nucleic acid molecule of the present invention includes a nucleic acid that is at least about 75%, preferably at least about 80%, more preferably at least about 85%, even more preferably at least about 90%, still more preferably at least about 95%, and even more preferably at least about 99%, identical to a chicken-derived ovomucoid gene expression control region-comprising nucleic acid molecule as depicted in SEQ ID NO: 26 and directs expression of a polypeptide encoding sequence in an avian oviduct cell, when operably linked to the polypeptide encoding sequence.

In another embodiment of the present invention, an isolated nucleic acid molecule of the present invention includes a nucleic acid that hybridizes to SEQ ID NO: 26 or the complement thereof, or the insert in pBS-OVMUP-10, under high, moderate or low stringency hybridization conditions.

In another embodiment of the present invention, an avian ovomucoid gene expression control region gene or nucleic acid molecule can be an allelic variant of SEQ ID NO: 26 or a homolog from a different avian, e.g., quail, duck, etc.

The present invention also contemplates the use of antisense nucleic acid molecules that are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized oligonucleotides can be produced in variable lengths. The number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine substituted nucleotides can be synthesized. Protocols for designing isolated nucleotides, nucleotide probes, and/or nucleotide primers are well-known to those of ordinary skill, and can be purchased commercially from a variety of sources (e.g., Sigma Genosys, The Woodlands, Tex. or The Great American Gene Co., Ramona, Calif.).

The nucleic acid sequence of a chicken ovomucoid gene expression control region nucleic acid molecule (SEQ ID NO: 26) of the present invention allows one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain ovomucoid gene expression control region nucleic acid homologs in other avian species such as, but not limited to, turkey, duck, goose, quail, pheasant, parrot, finch, ratites including ostrich, emu and cassowary and, (d) to obtain isolated nucleic acids capable of hybridizing to an avian ovomucoid gene expression control region nucleic acid and be used to detect the presence of nucleic acid-related sequences by complementation between the probe and the target nucleic acid.

Such nucleic acid homologs can be obtained in a variety of ways including by screening appropriate expression libraries with antibodies of the present invention, using traditional cloning techniques to screen appropriate libraries, amplifying appropriate libraries or DNA using oligonucleotide primers of the present invention in a polymerase chain reaction or other amplification method, and screening public and/or private databases containing genetic sequences using nucleic acid molecules of the present invention to identify targets. Examples of libraries to screen, or from which to amplify nucleic acid molecules, include but are not limited to mammalian BAC libraries, genomic DNA libraries, and cDNA libraries. Similarly, sequence databases useful for screening to identify sequences in other species homologous to chicken ovomucoid gene expression control region include, but are not limited to, GenBank and the mammalian Gene Index database of The Institute of Genomics Research (TIGR).

Another aspect of the present invention is a recombinant DNA molecule comprising the novel isolated avian ovomucoid gene expression control region of the present invention operably linked to a selected polypeptide-encoding nucleic acid insert, and which may express the nucleic acid insert when transfected to a suitable host cell, preferably an avian cell. The nucleic acid insert may be placed in frame with a signal peptide sequence, whereby translation initiation from the transcript may start with the signal peptide and continue through the nucleic acid insert, thereby producing an expressed polypeptide having the desired amino acid sequence.

It is anticipated that the recombinant DNA may further comprise a polyadenylation signal sequence that will allow the transcript directed by the novel ovomucoid gene expression control region to proceed beyond the nucleic acid insert encoding a polypeptide and allow the transcript to further comprise a 3' untranslated region and a polyadenylated tail. Any functional polyadenylation signal sequence may be linked to the 3' end of the nucleic acid insert including the SV40 polyadenylation signal sequence, bovine growth hormone adenylation sequence or the like, or derivatives thereof. One embodiment of the present invention is a recombinant DNA molecule comprising the isolated avian ovomucoid gene expression controlling region of the present invention, operably linked to a nucleic acid insert encoding a polypeptide which may include a polyadenylation signal sequence. In certain embodiments, the recombinant DNA molecule which includes include a polyadenylation signal sequence is an artificial chromosome.

Another aspect of the present invention is to provide nucleic acid sequences of a protein optimized for expression in avian cells, and derivatives and fragments thereof. For example, it is contemplated that when the recombinant DNA is to be delivered to a recipient cell for expression therein, the sequence of the nucleic acid sequence may be modified so that the codons are optimized for the codon usage of the recipient species. When a heterologous nucleic acid is to be delivered to a recipient cell for expression therein, the sequence of the nucleic acid sequence may be modified so that the codons are optimized for the codon usage of the recipient species. For example, if the heterologous nucleic acid is transfected into a recipient chicken cell, the sequence of the expressed nucleic acid insert is optimized for chicken codon usage. This may be determined from the codon usage of at least one, and preferably more than one, protein expressed in a chicken cell. For example, the codon usage may be determined from the nucleic acid sequences encoding the proteins ovalbumin, lysozyme, ovomucin and ovotransferrin of chicken. Briefly, the DNA sequence for the target protein may be optimized using the BACKTRANSLATE® program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins. The template and primer oligonucleotides are then amplified, by any means known in the art, including but not limited to PCR with Pfu polymerase (STRATAGENE®, La Jolla Calif.).

In one exemplary embodiment of a heterologous nucleic acid for use by the methods of the present invention, a nucleic acid insert encoding the human interferon α2b polypeptide optimized for codon-usage by the chicken is used. Optimization of the sequence for codon usage is useful in elevating the level of translation in avian eggs.

It is contemplated to be within the scope of the present invention for any nucleic acid encoding a polypeptide to be optimized for expression in avian cells. It is further contemplated that the codon usage may be optimized for a particular avian species used as a source of the host cells. In one embodiment of the present invention, the heterologous polypeptide is encoded using the codon-usage of a chicken.

In yet another embodiment of the present invention, the recombinant DNA comprises the isolated avian ovomucoid gene expression control region operably linked to a nucleic acid encoding a human interferon a2b and the SV40 polyadenylation sequence.

The protein of the present invention may be purified by any known conventional technique. In a one embodiment, the protein is purified from chicken eggs, preferably egg whites. For example, chicken cells may be homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

The invention provides methods for producing multimeric proteins, preferably immunoglobulins, such as antibodies, and antigen binding fragments thereof.

In one embodiment of the present invention, the multimeric protein is an immunoglobulin, wherein the first and second heterologous polypeptides are an immunoglobulin heavy and light chains respectively. Illustrative examples of this and other aspects and embodiments of the present invention for the production of heterologous multimeric polypeptides in avian cells are fully disclosed in U.S. patent application Ser. No. 09/877,374, filed Jun. 8, 2001, published as US-2002-0108132-A1 on Aug. 8, 2002, and U.S. patent application Ser. No. 10/251,364, filed Sep. 18, 2002, each of which are incorporated herein by reference in their entirety. In one embodiment of the present invention, therefore, the multimeric protein is an immunoglobulin wherein the first and second heterologous polypeptides are an immunoglobulin heavy and light chain respectively. Accordingly, the invention provides immunoglobulin and other multimeric proteins that have been produced by transgenic avians of the invention.

In the various embodiments of this aspect of the present invention, an immunoglobulin polypeptide encoded by the transcriptional unit of at least one expression vector may be an immunoglobulin heavy chain polypeptide comprising a variable region or a variant thereof, and may further comprise a D region, a J region, a C. region, or a combination thereof. An immunoglobulin polypeptide encoded by the transcriptional unit of an expression vector may also be an immunoglobulin light chain polypeptide comprising a variable region or a variant thereof, and may further comprise a J region and a C. region. It is also contemplated to be within the scope of the present invention for the immunoglobulin regions to be derived from the same animal species, or a mixture of species including, but not only, human, mouse, rat, rabbit and chicken. In certain embodiments, the antibodies are human or humanized.

In other embodiments of the present invention, the immunoglobulin polypeptide encoded by the transcriptional unit of at least one expression vector comprises an immunoglobulin heavy chain variable region, an immunoglobulin light chain variable region, and a linker peptide thereby forming a single-chain antibody capable of selectively binding an antigen.

Another aspect of the present invention provides a method for the production in an avian of an heterologous protein capable of forming an antibody suitable for selectively binding an antigen comprising the step of producing a transgenic avian incorporating at least one transgene, wherein the transgene encodes at least one heterologous polypeptide selected from an immunoglobulin heavy chain variable region, an immunoglobulin heavy chain comprising a variable region and a constant region, an immunoglobulin light chain variable region, an immunoglobulin light chain comprising a variable region and a constant region, and a single-chain antibody comprising two peptide-linked immunoglobulin variable regions.

In an embodiment of this method of the present invention, the isolated heterologous protein is an antibody capable of selectively binding to an antigen. In one embodiment, the antibody may be generated by combining at least one immunoglobulin heavy chain variable region and at least one immunoglobulin light chain variable region, preferably cross-linked by at least one di-sulfide bridge. The combination of the two variable regions will generate a binding site capable of binding an antigen using methods for antibody reconstitution that are well known in the art.

It is, however, contemplated to be within the scope of the present invention for immunoglobulin heavy and light chains, or variants or derivatives thereof, to be expressed in separate transgenic avians, and therefore isolated from separate media including serum or eggs, each isolate comprising a single species of immunoglobulin polypeptide. The method may include combining certain isolated heterologous immunoglobulin polypeptides, thereby producing an antibody capable of selectively binding to an antigen. In this embodiment, two individual transgenic avians may be generated wherein one transgenic produces serum or eggs having an immunoglobulin heavy chain variable region, or a polypeptide comprising such, expressed therein. A second transgenic animal, having a second transgene, produces serum or eggs having an immunoglobulin light chain variable region, or a polypeptide comprising such, expressed therein. The polypeptides may be isolated from their respective sera and eggs and combined in vitro to generate a binding site capable of binding an antigen.

The present invention is useful for the production of many biological products such as, pharmaceutical compositions. For example, the present invention can be useful for the production of biological molecules such as hormones including cytokines (i.e., secreted polypeptides that affect a function of cells and modulates an interaction between cells in an immune, inflammatory or hematopoietic response), antibodies and other useful pharmaceutical molecules which include polypeptides. Cytokines includes, but are not limited to, monokines and lymphokines. Examples of cytokines include, but are not limited to, interferon α2b, Interleukin-1 (IL-1), Interleukin-6 (IL-6), Interleukin-8 (IL-8), Tumor Necrosis Factor-α (TNF-α.) and Tumor Necrosis Factor β (TNF-β), antibodies such as polyclonal and monoclonal antibodies and fragments thereof, and immunologic binding equivalents thereof. Antibodies may include, but are not limited to polyclonal antibodies, monoclonal antibodies (MAbs), humanized or chimeric antibodies, single chain antibodies, FAb fragments, $F(Ab')_2$ fragments, fragments produced by a FAb expression library, anti-idiotypic (anti-ID) antibodies, and epitope-binding fragments thereof. Also contemplated is the production of antibody fusion proteins, for example, Fc fusion proteins in accordance with the present methods. The methods of the present invention can also be useful for producing immunoglobulin polypeptides which are constituent polypeptides of an antibody or a polypeptide derived therefrom. An "immunological polypeptide" may be, but is not limited to, an immunological heavy or light chain and may include a variable region, a diversity region, joining region and a constant region or any combination, variant or truncated form thereof. Immunological polypeptides also include single-chain antibodies comprised of, but not limited to, an immunoglobulin heavy chain variable region, an immunoglobulin light chain variable region and optionally a peptide linker.

Examples of certain antibodies that can be produced in methods of the invention may include but are not limited to HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-$\alpha V\beta 3$ integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-$\alpha$ antibody (CAT/BASF); CDP870 is a humanized anti-TNF-$\alpha$ Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-$\alpha$ IgG4 antibody (Celltech); LDP-02 is a humanized anti-$\alpha 4\beta 7$ antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$\beta_2$ antibody (Cambridge Ab Tech).

Another potentially useful application of the novel isolated ovomucoid gene expression control region of the present invention is the possibility of increasing the amount of a heterologous protein present in a bird, (especially the chicken) by gene transfer. In most instances, a heterologous polypeptide-encoding nucleic acid insert transferred into the recipient animal host will be operably linked with the ovomucoid gene expression control region to allow the cell to initiate and continue production of the genetic product protein. A recombinant DNA molecule of the present invention can be transferred into the extra-chromosomal or genomic DNA of the host.

The recombinant ovomucoid gene expression controlling region of the present invention and polypeptide coding sequence, which may include an artificial chromosome and/or a polyadenylation coding sequence, may be introduced into cells by any useful method. The recombinant molecules may be inserted into a cell to which the polypeptide-encoding nucleic acid is heterologous (i.e. not normally present). Alternatively, as described more fully below, the recombinant DNA molecule may be introduced into cells which normally contain the polypeptide-encoding nucleic acid insert of the recombinant DNA molecule, for example, to correct a deficiency in the expression of a polypeptide, or where over-expression of the polypeptide is desired.

For expression in heterologous systems, the heterologous DNA molecule is inserted into the expression system or vector of the present invention in proper sense orientation and correct reading frame. The vector contains the necessary elements for the transcription and translation of the inserted protein-coding sequences, including the novel isolated ovomucoid gene expression control region.

U.S. Pat. No. 4,237,224 to Cohen & Boyer, which is hereby incorporated by reference in its entirety, describes the production of expression systems in the form of recombinant plasmids using restriction enzyme cleavage and ligation with DNA ligase. These recombinant plasmids are then introduced to a cell by means of transformation and replicated in cultures, including eukaryotic cells grown in tissue culture.

One aspect of the present invention, therefore, is an expression vector suitable for delivery to a recipient cell for replication OR expression of a polypeptide-encoding nucleic acid of the vector therein. It is contemplated to be within the scope of the present invention for the expression vector to comprise an isolated avian ovomucoid gene expression control region operably linked to a nucleic acid insert encoding a polypeptide, and optionally a polyadenylation signal sequence. The expression vector of the present invention may further comprise a bacterial plasmid sequence, a viral nucleic acid sequence, or fragments or variants thereof that may allow for replication of the vector in a suitable host.

The recombinant nucleic acid molecules of the present invention can be delivered to cells using viruses such as vaccinia virus. Methods for making a viral recombinant vector useful for expressing a protein under the control of the ovomucoid promoter are analogous to the methods disclosed in U.S. Pat. Nos. 4,603,112; 4,769,330; 5,174,993; 5,505,941; 5,338,683; 5,494,807; 4,722,848; Paoletti, E. Proc. Natl. Acad. Sci. 93: 11349-11353 (1996); Moss Proc. Natl. Acad. Sci. 93: 11341-11348 (1996); Roizman Proc. Natl. Acad. Sci. 93: 11307-11302 (1996); Frolov et al. Proc. Natl. Acad. Sci. 93: 11371-11377 (1996); Grunhaus et al. Seminars in Virology 3: 237-252 (1993) and U.S. Pat. Nos. 5,591,639; 5,589,466; and 5,580,859 relating to DNA expression vectors, inter alia; the disclosure of which is incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK ± or KS ± (see "Stratagene Cloning Systems" Catalog (1993) from Stratagene, La Jolla, Calif., which is hereby incorporated by reference), pQE, pIH821, pGEX, pET series (see Studier, F. W. et. al. (1990) "Use of T7 RNA Polymerase to Direct Expression of Cloned Genes" Gene Expression Technology, vol. 185, which is hereby incorporated by reference in its entirety) and any derivatives thereof, cosmid vectors and, in certain embodiments, artificial chromosomes, such as, but not limited to, YACs, BACs, BBPACs or PACs. Such artificial chromosomes are useful in that a large nucleic acid insert can be propagated and introduced into the avian cell.

Recombinant molecules can be introduced into cells via transformation, particularly transduction, conjugation, mobilization, or electroporation. The DNA sequences are cloned into the vector using standard cloning procedures in the art, as described by Sambrook et al. Molecular Cloning: A Laboratory Manual, 3rd ed., Cold Spring Harbor Laboratory, Cold Springs Harbor, N.Y. (2001), which is hereby incorporated by reference in its entirety.

The vectors of the invention comprise one or more nucleotide sequences encoding a heterologous protein desired to be expressed in the transgenic avian, as well as regulatory elements such as promoters, enhancers, Matrix Attachment Regions, IRES's and other translation control elements, transcriptional termination elements, polyadenylation sequences, etc. In particular embodiments, the vector of the invention contains at least two nucleotide sequences coding for heterologous proteins, for example, but not limited to, the heavy and light chains of an immunoglobulin.

The present invention further relates to nucleic acid vectors and transgenes inserted therein, having the avian ovomucoid gene expression control region of the invention, that incorporate multiple polypeptide-encoding regions, wherein a first polypeptide-encoding region is operatively linked to a transcription promoter and a second polypeptide-encoding region is operatively linked to an IRES. For example, the vector may contain coding sequences for two different heterologous proteins (e.g., the heavy and light chains of an immunoglobulin).

Such nucleic acid constructs, when inserted into the genome of a bird and expressed therein, will generate individual polypeptides that may be post-translationally modified, for example, glycosylated or, in certain embodiments, form complexes, such as heterodimers with each other in the white of the avian egg. Alternatively, the expressed polypeptides may be isolated from an avian egg and combined in vitro, or expressed in a non-reproductive tissue such as serum. In other embodiments, for example, but not limited to, when expression of both heavy and light chains of an antibody is desired, two separate constructs, each containing a coding sequence for one of the heterologous proteins operably linked to the ovomucoid gene expression control region of the invention are introduced into the avian cell. Alternatively, two transgenic avians each containing one of the two heterologous proteins (e.g., one transgenic avian having a transgene encoding the light chain of an antibody and a second transgenic avian having a transgene encoding the heavy chain of the antibody) can be bred to obtain an avian containing both transgenes in its germline and expressing both transgene encoded proteins, preferably in eggs.

Once the ovomucoid gene expression control region of the present invention has been cloned into a vector system, it is ready to be incorporated into a host cell. Such incorporation can be carried out by the various forms of transformation noted above, depending upon the vector/host cell system. Suitable host cells include, but are not limited to, bacteria, virus, yeast, mammalian or avian cells, and the like. Alternatively, it is contemplated that the incorporation of the DNA of the present invention into a recipient cell may be by any suitable method such as, but not limited to, viral transfer, electroporation, gene gun insertion, sperm mediated transfer to an ovum, microinjection, cytoplasmic injection, pronuclear injection and the like.

Another aspect of the present invention, therefore, is a method of expressing a heterologous polypeptide in a eukaryotic cell by transfecting the cell with a recombinant DNA comprising an avian ovomucoid gene expression control region operably linked to a nucleic acid insert encoding a polypeptide and, optionally, a polyadenylation signal sequence, and culturing the transfected cell in a medium suitable for expression of the heterologous polypeptide under the control of the avian ovomucoid gene expression control region.

In certain embodiments, the ovomucoid gene expression control region directs a level of expression of the heterologous protein in avian eggs that is greater than 5 μg, 10 μg, 50 μg, 100 μg, 250 μg, 500 μg, or 750 μg, more preferably greater than 1 mg, 2 mg, 5 mg, 10 mg, 20 mg, 50 mg, 100 mg, 200 mg, 500 mg, 700 mg, 1 gram, 2 grams, 3 grams, 4 grams or 5 grams per egg. Such levels of expression can be obtained using the expression control regions of the invention.

In one embodiment of the method of the present invention, the recipient eukaryotic cell is derived from an avian. In one embodiment, the avian is a chicken.

Yet another aspect of the present invention is a eukaryotic cell transformed with an expression vector according to the present invention and described above. In one embodiment of the present invention, the transformed cell is a chicken oviduct cell and the nucleic acid insert comprises the chicken ovomucoid gene expression control region, a nucleic acid insert encoding a human interferon a2d with codons optimized for expression in an avian cell, and an SV40 polyadenylation sequence.

It is contemplated that the transfected cell according to the present invention may be transiently transfected, whereby the transfected recombinant DNA or expression vector may not be integrated into the genomic nucleic acid. It is further contemplated that the transfected recombinant DNA or expression vector may be stably integrated into the genomic DNA of the recipient cell, thereby replicating with the cell so that each daughter cell receives a copy of the transfected nucleic acid. It is still further contemplated for the scope of the present invention to include a transgenic animal producing a heterologous protein expressed from a transfected nucleic acid according to the present invention.

In one embodiment of the present invention, the transgenic animal is an avian selected from a turkey, duck, goose, quail, pheasant, ratite, an ornamental bird or a feral bird. In another embodiment, the avian is a chicken and the heterologous protein produced under the transcriptional control of the isolated avian ovomucoid gene expression control region according to the present invention is produced in the white of an egg.

An exemplary approach for the in vivo introduction of a polypeptide-encoding nucleic acid operably linked to the subject novel isolated ovomucoid gene expression control region into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors provide efficient delivery of genes into cells, and the transferred nucleic acids are stably integrated into the chromosomal DNA of the host. Recombinant retrovirus can be constructed in the part of the retroviral coding sequence (gag, pol, env) that has been replaced by nucleic acid comprising a ovomucoid gene expression control region, thereby rendering the retrovirus replication defective. Protocols for producing recombinant retroviruses and for infecting cells in vitro or in vivo with such viruses can be found in Current Protocols in Molecular Biology, Ausubel et al. (1989) (eds.) Greene Publishing Associates, Sections 9.10-9.14 and other standard laboratory manuals. Examples of suitable retroviruses include pLJ, pZIP, pWE and pEM which are all well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include coupling antibodies specific for cell surface antigens to the viral env protein (Roux et al., Proc. Natl. Acad. Sci. 86: 9079-9083 (1989); Julan et al., J. Gen. Virol. 73: 3251-3255 (1992); and Goud et al., Virology 163: 251-254 (1983)) or coupling cell surface ligands to the viral env proteins (Neda et al., J. Biol. Chem. 266: 14143-14146 (1991)), all of which are incorporated herein by reference in their entireties. Coupling can be in the form of the chemical cross-linking with a protein or other moiety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al., BioTechniques 6: 616 (1988); Rosenfeld et al., Science 252: 43 1434 (1991); and Rosenfeld et al., Cell 68: 143-155 (1992)), all of which are incorporated herein by reference in their entireties. Suitable adenoviral vectors derived from the adenovirus strain Ad type 5 d1324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, e.g., Jones et al., Cell 16:683 (1979); Berkner et al., supra; and Graham et al., in Methods in Molecular Biology, E. J. Murray, (1991) Ed. (Humana, Clifton, N.J.) vol. 7. pp. 109-127), all of which are incorporated herein by reference in their entireties. Expression of an inserted gene such as, for example, encoding the human interferon α2b, can be under control of the exogenously added ovomucoid gene expression control region sequences.

Yet another viral vector system useful for delivery of, for example, the subject avian ovomucoid gene expression control region operably linked to a nucleic acid encoding a polypeptide, is the adeno-associated virus (AAV). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268: 3781-3790 (1993)), all of which are incorporated herein by reference in their entireties.

Most non-viral methods of gene transfer rely on normal mechanisms used by eukaryotic cells for the uptake and intracellular transport of macromolecules. In one embodiment, non-viral gene delivery systems of the present invention rely on endocytic pathways for the uptake of the subject ovomucoid gene expression control region and operably linked polypeptide-encoding nucleic acid by the targeted cell. Exemplary gene delivery systems of this type include liposomal derived systems, poly-lysine conjugates, and artificial viral envelopes.

In a representative embodiment, a nucleic acid comprising the novel isolated ovomucoid gene expression control region of the present invention can be entrapped in liposomes bearing positive charges on their surface (e.g., lipofectins) and (optionally) which are tagged with antibodies against cell surface antigens of the target tissue (Mizuno et al., NO Shinkei Geka 20:547-551 (1992); PCT publication WO91/06309; Japanese patent application 1047381; and European patent publication EP-A-43075), all of which are incorporated herein by reference in their entireties.

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180), all of which are incorporated herein by reference in their entireties. It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al., Science 260: 926 (1993); Wagner et al., Proc. Natl. Acad. Sci. 89:7934 (1992); and Christiano et al., Proc. Natl. Acad. Sci. 90:2122 (1993)), all of which are incorporated herein by reference in their entireties. It is further contemplated that a recombinant DNA molecule comprising the novel isolated ovomucoid gene expression control region of the present invention may be delivered to a recipient host cell by other non-viral methods including by gene gun, microinjection, sperm-mediated transfer as described in PCT/US02/30156, filed Sep. 23, 2002 and incorporated herein by reference in its entirety, nuclear transfer, or the like.

Another aspect of the present invention relates to transgenic animals including avians and methods of producing them. Transgenicc animals of the presnt invention contain a transgene which includes an isolated ovomucoid gene expression controlling region of the present invention and which preferably (though optionally) expresses a heterologous gene in one or more cells in the animal. Transgenic avians can be produced by introduction of nucleic acid molecules disclosed herein into the cells of avians including, but not limited to chicken, turkey, duck, goose, quail, pheasants, parrots, finches, hawks, crows and ratites including ostrich, emu and cassowary. Any useful method for introducing nucleic acid into the cells of an animal may be employed in the present invention.

Suitable methods for the generation of transgenic avians having heterologous DNA incorporated therein, for example, cytoplasmic injection and pronuclear injection, are described, for example, in U.S. patent application Ser. No. 10/251,364 filed Sep. 18, 2002 and U.S. patent application Ser. No. 10/679,034, file Oct. 2, 2003, the disclosure of both of these patent applications is incorporated herein by reference in its entirety. Other methods for the introduction of nucleic acids of the present invention include those disclosed in U.S. patent application Ser. No. 10/842,606 filed May 10, 2004, the disclosure of which is incorporated herein by reference in its entirety, and other methods disclosed herein.

In various embodiments of the present invention, the expression of the transgene may be restricted to specific subsets of cells, tissues or developmental stages utilizing, for example, cis-acting sequences acting on the ovomucoid gene expression control region of the present invention and which control gene expression in the desired pattern. Tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

One embodiment of the present invention, therefore, is a transgenic avian having a heterologous polynucleotide sequence comprising a nucleic acid insert encoding the heterologous polypeptide and operably linked to the novel isolated avian ovomucoid gene expression control region. In an embodiment of the present invention, the transgenic avian is selected from a chicken, a turkey, a duck, a goose, a quail, a pheasant, a ratite, an ornamental bird or a feral bird. In another embodiment of the present invention, the transgenic avian is a chicken.

In still another embodiment of the transgenic avian of the present invention, the transgenic avian includes an avian ovomucoid gene expression control region comprising the nucleic acid sequence in SEQ ID NO: 26, or a degenerate variant thereof.

In yet another embodiment of the transgenic avian of the present invention, the transgenic avian further comprises a polyadenylation signal sequence.

In still yet another embodiment of the transgenic avian of the present invention, the polyadenylation signal sequence is derived from the SV40 virus.

In another embodiment of the transgenic avian of the present invention, the nucleic acid insert encoding a polypeptide has a codon complement optimized for protein expression in an avian.

In another embodiment of the transgenic avian of the present invention, the transgenic avian produces the heterologous polypeptide in the serum or an egg white. In another embodiment of the transgenic avian of the present invention, the transgenic avian produces the heterologous polypeptide in an egg white.

The present invention is further illustrated by the following examples, which are provided by way of illustration and should not be construed as limiting. The contents of all references, published patents and patents cited throughout the present application are hereby incorporated by reference in their entireties.

EXAMPLE 1

PCR Amplification of Ovomucoid Promoter

Sense primer OVINs2, 5'-TAGGCAGAGCAATAGGACTCTCAACCTCGT-3' (SEQ ID NO: 1) and the anti-sense primer, OVMUa2, 5'-AAGCTTCTGCAGCACTCTGGGAGTTACTCA-3' (SEQ ID NO: 2) were designed according to the sequences of chick ovoinhibitor exon 16 (Genbank Accession No: M16141) and a fragment of the chick ovomucoid promoter region (Genbank Accession No: J00897) respectively. The template DNA for PCR amplification of the ovomucoid promoter region was prepared from white leghorn chick blood.

Figure 2:
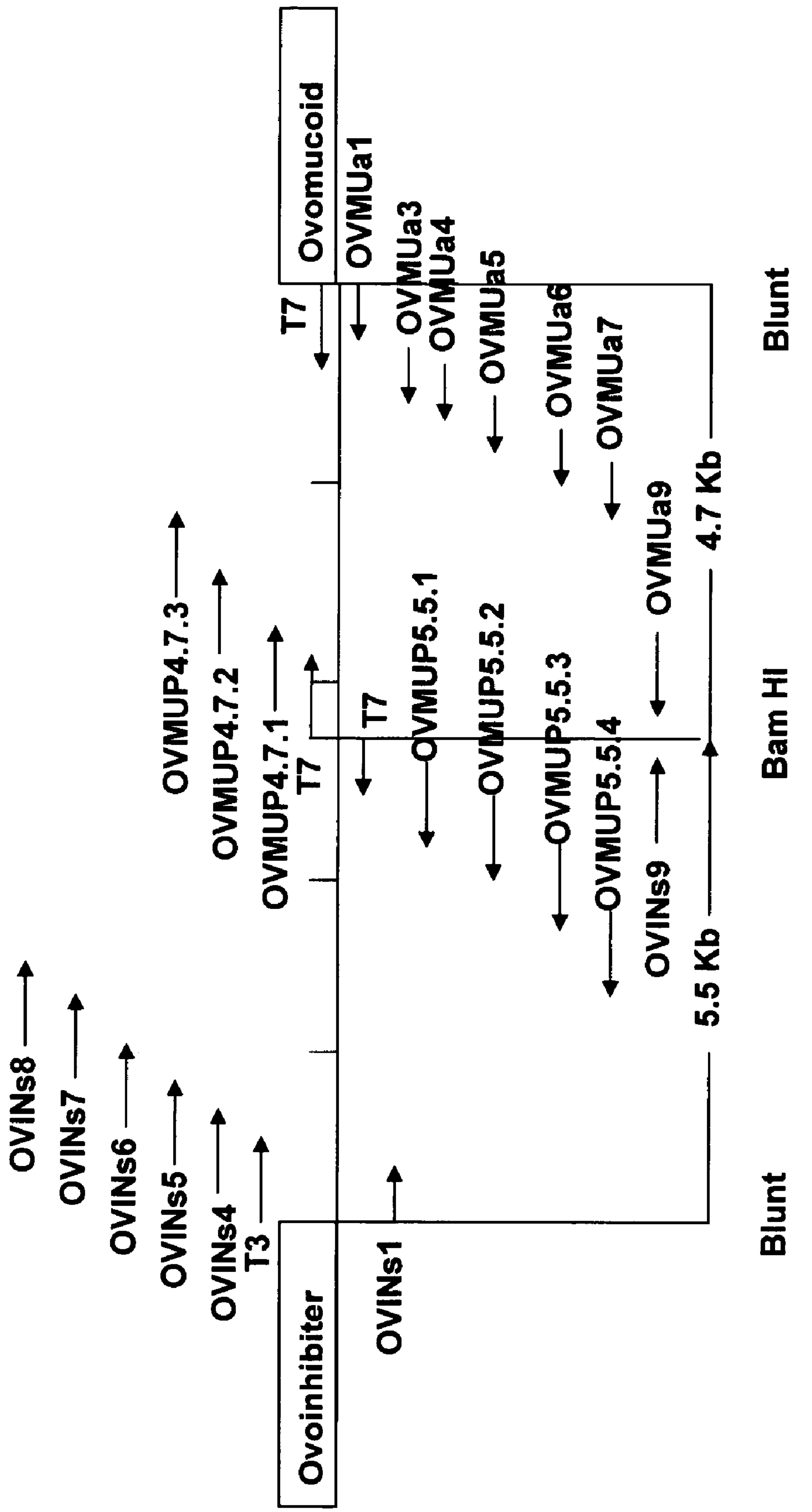
FIG. 2 illustrates the approximately 10 kb nucleic acid region that is 5' upstream of the chicken ovomucoid transcription start site, and the positions and orientations of primers used to sequence this region.
Figure 5:
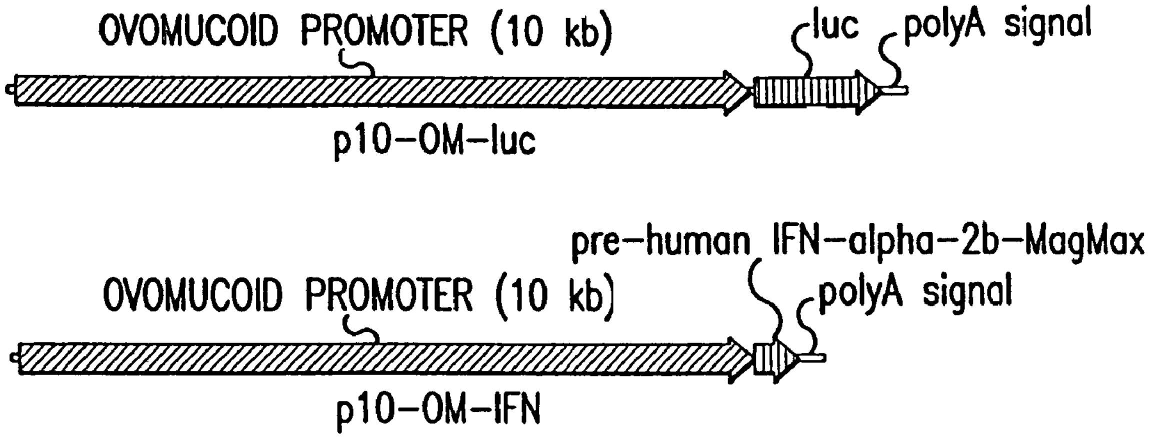
FIG. 5 illustrates the 10 kb ovomucoid promoter linked to the luciferase or human IFNα-2b coding sequences.

A series of different PCR conditions were carried out to optimize synthesis of the approximately 10.0 kb product, the results of which are shown in FIG. 2. In these tests, the template DNA concentrations were 500 ng, 100 ng, 50 ng, or 10 ng. Two sets of primers, OVINs1 (SEQ ID NO: 3) and OVMUa1 (SEQ ID NO: 4), or OVINs2 (SEQ ID NO: 1) and OVMUa2 (SEQ ID NO: 2) shown in FIG. 3, three $Mg^{++}$ concentrations (1.0 mM, 1.5 mM and 2.0 mM) and annealing temperatures from 50° C. to 70° C. were used.

The results of the tests were as shown in FIG. 2. As shown in lanes 1 through 8, test reactions having 500 ng DNA template, the OVINs1 (SEQ ID NO: 3) and OVMUa1 (SEQ ID NO: 4) primers, 60 mM Tris-$SO_4$, pH 9.1, 18 mM $(NH_4)_2SO_4$, 1.0 mM $Mg^{2+}$, and annealing temperatures between 50° C. to 58° C. gave no specific DNA product. Also, as shown in lanes 17 through 24 of FIG. 2, in test reactions having 100 ng DNA template, the OVINs1 and OVMUa1 primers, 60 mM Tris-$SO_4$, pH 9.1, 18 mM $(NH_4)_2SO_4$, 1.0 mM $Mg^{2+}$, and annealing temperatures between 50° C. to 58° C., no specific bands were seen. However, as shown in lanes 9 through 16 of FIG. 2, test reactions having 500 ng DNA template, the OVINs2 (SEQ ID NO: 1) and OVMUa2 (SEQ ID NO: 2) primers, 60 mM Tris-$SO_4$, pH 9.1, 18 mM $(NH_4)_2SO_4$, 2 mM $Mg^{2+}$ and annealing temperatures between 60° C. to 68° C. have the band of the desired length of approximately 10 kb. As shown in lanes 25 through 32, reaction conditions containing 100 ng DNA template, the OVINs2 (SEQ ID NO: 1) and OVMUa2 (SEQ ID NO: 2) primers, 60 mM Tris-$SO_4$, pH 9.1, 18 mM $(NH_4)_2SO_4$, 2 mM $Mg^{2+}$ and annealing temperatures between about 60° C. to about 68° C. gave an increased yield of the desired product.

An approximately 10 kb product was, therefore, detected when the following conditions were used: the optimum DNA template concentration was between about 50 ng to 500 ng; the primers were OVINs2 (SEQ ID NO: 1) and OVMUa2 (SEQ ID NO: 2); the $Mg^{2+}$ concentration was 2 mM; the annealing temperature was at or between about 60° C. to about 68° C. Each 50 μl PCR reaction consisted of 50 ng or 100 ng of template DNA, 0.1 μg each primer, 5 μl buffer B (from Elongase Enzyme Mix kit, Invitrogen Corp., Carlsbad, Calif.), 1 ml of 10 μM dNTP solution, and distilled deionized water. The PCR protocol was one cycle at 94° C. for 30 secs; thirty cycles at 94° C. for 30 secs, 60° C. for 30 secs and 68° C. for 10 mins. One cycle was performed at 68° C. for 10 mins, 35° C. for 30 mins with a final hold at 4° C. The PCR products were examined by 0.65% agarose gel analysis.

EXAMPLE 2

Cloning of PCR Products

The PCR products were purified by standard methods. Briefly, PCI (phenol: chloroform: isoamyl alcohol, 24:25:1) and chloroform extraction were performed once. The DNA was precipitated by adding 3M sodium acetate pH 5.2 to a final concentration of 0.3M together with 2.5 volumes of 100% ethanol. The DNA pellet was dried and dissolved in distilled deionized water and then sequenced on a ABI3700 automatic sequencer (Applied Biosystems, Foster City, Calif.) using the primers OVINs2 (SEQ ID NO: 1) and OVMUa2 (SEQ ID NO: 2) to confirm the identity of each PCR product. After confirmation of the identities, the approximately 10 kb PCR product was treated with T4 polynucleotide kinase to add a phosphate to the 5' end. Mung bean nuclease removed any overhanging adenines from the ends of the PCR products, thereby producing a blunt end. The PCR product was purified by PCI and chloroform extraction and precipitated by standard methods. This 10 kb product was then cleaved with Bam HI to give two fragments, of about 4.7 and about 5.5 kb respectively.

The vector plasmid pBluescript II KS (±) was cut by Bam HI and Eco RV and treated with calf intestinal alkaline phosphatase. DNA fragments to be ligated into the vector were analyzed by agarose gel electrophoresis and purified from agarose gel slices using a NucleoTrap Nucleic Acid Purification Kit (BD Biosciences Clontech, Palo Alto, Calif.). Fragments of 4.7 kb and 5.5 kb were inserted into the Bam HI/Eco RV-treated pBluescript to give the constructs pBS-OVMUP4.7 and pBS-OVMUP5.5 respectively.

Positive clones were screened by Xba I/Xho I digestion. Clone pBS-OVMUP4.7, gave fragments of about 4.7 kb and 2.96 kb. Clone pBS-OVMUP5.5 gave fragments of about 5.5 kb and 2.96 kb. Apparent positive clones having the 4.7 kb insert were further confirmed by Xba I/Hind III digestion that gave three fragments of 0.5 kb, 4.2 kb and 2.9 kb. The apparent positive clones with an insert of about 5.5 kb insert were further confirmed by Xba I/Kpn I digestion that gave three fragments of 2 kb, 3.5 kb and 2.96 kb.

A construct, pBS-OVMUP-10, containing the entire 10 kb PCR product cloned into the pBluescript KS II (±) vector was made by taking a 4.7 kb Bam HI/Xho I fragment from the pBS-OVMUP4.7 plasmid and inserting it into the Bam HI/Xba I cleaved sites of pBS-OVMUP5.5. The Xho I and Xba I cut ends were blunt-ended by treating the digested fragments with Klenow enzyme and dNTPs at 25° C. for 15 mins before the digestion with Bam HI.

EXAMPLE 3

Sequencing

The plasmids pBS-OVMUP4.7 and pBS-OVMUP5.5 were sequenced from both ends of each insert as shown in FIG. 1. The initial primers were T7 and T3 having the nucleic acid sequences 5'-TAATACGACTCACTATAGGG-3' (SEQ ID NO: 5) and 5'-ATTAACCCTCACTAAAGGGA-3' (SEQ ID NO: 6) respectively. Subsequent primers (SEQ ID NOS: 7-25), as shown in FIG. 3, were designed according to the sequence results as they became available. The approximately 10 kb sequence was edited and assembled by the ContigExpress software of the Vector NTI Suite, version 6.0 (InforMax, Inc.). The region of the approximately 10 kb PCR product described in Example 1 above that encompassed the Bam HI junction was sequenced using the primers OVMUa9 (SEQ ID NO 27) and OVINs9 (SEQ ID NO 28) (shown in FIG. 3).

Each sequence chromatogram was visually checked for sequence accuracy and to locate base ambiguities. Regions containing ambiguous bases were re-sequenced with the same primer or, if still ambiguous, with a new primer designed to sequence the complementary strand. Sequencing of the original 10 kb PCR fragment using the primers OVMUa9 (SEQ ID NO 27) and OVINs9 (SEQ ID NO 28) showed that the subcloned inserts of the plasmids pBS-OVMUP4.7 and pBS-OVMUP5.5 included all of the nucleic acid sequence of the parent fragment and no intervening Bam HI-Bam HI fragments were included in the final sequence SEQ ID NO: 26. The sequence (SEQ ID NO: 26) of the region lying between the 3' end of the ovoinhibitor gene and the transcription start site of the ovomucoid-encoding region is shown in FIG. 4.

EXAMPLE 4

Expression in Transfected Cultured Avian Myeloid and Oviduct Cells of Luciferase Regulated by the 10 kb Ovomucoid Promoter Construction of p10-OM-luc To facilitate insertion of coding sequences behind the ovomucoid promoter and in frame with the second ATG of the ovomucoid coding sequence, the Nco I site which overlaps the second ATG was changed to a Pci I site as depicted below. On the top is the wild type ovomucoid sequence at the start site of translation. On the bottom, the second Nco I site was changed to a Pci I site.

Nco I Nco I

MetAlaMet
CTCACCATGGCCATGGC (SEQ ID NO: 32)

GAGTGGTACCGGTACCG (SEQ ID NO: 33)

Nco I Pci I

MetAspMet
CTCACCATGGACATGGA (SEQ ID NO: 34)

GAGTGGTACCGGTACCG (SEQ ID NO: 35)

The Pci I site in the Bluescript backbone of pBS-OVMUP-10 was destroyed by cutting with Pci I, filling in the ends with Klenow polymerase and religating, creating pOM-10-alpha. The proximal promoter region was PCR amplified with primers OM-5 (SEQ ID NO.:29) and OM-6 (SEQ ID NO.:30) and template pBS-OVMUP-10. The resulting PCR product (SEQ ID NO.:31) was cut with Not I and Tth111 I and cloned into the 12059 bp Not I-Tth111 I fragment of pOM-10-alpha, thereby creating pOM-10-Pci. The 1964 Nco I-SI-treated Kpn I frament of gWiz-luciferase (Gene Therapy Systems, Inc., San Diego, Calif.) was cloned into the 12824 Pci I-Sma I fragment of pOM-10-Pci, creating p10-OM-luc.

Primer Sequences

CGGGCAGTACCTCACCATGGACATGT (NOTE: sequence of OM5 may not be 100% complementary to the target ovomucoid sequence)

-continued

```
OM-5
5'-GCGCGGCCGCCCGGGACATGTCCATGGTGAGAGTACTGCCC-3'
(SEQ ID NO: 29)

OM-6
5'-GGCCCGGGATTCGCTTAACTGTGACTAGG-3'
(SEQ ID NO: 30)

PCR product                        (SEQ ID NO: 31)

GCGCGGCCGCCCGGGACATGTCCATGGT-
GAGAGTACTGCCCGGCTCTG

CAGGCGGCTGCCGGTGCTCTGCTCCT-
GAGATGGTCCCCCCGAGGCTGC

CTGCAAATATATACAAACGTGGCGTC-
CGAACTGTTGGACTGGAACACG

GAGCAGCCAGCTGAATCTGTCAGCGGCA-
CAATGAGGCTGGTAATATTT

ATTGAGGTCCTGACCTCCAGGTAATG-
GTCTGCGTCTCCCAGGCAATTG

ATTTTGGCTGGACACTTGGTTAATAGCT-
TGAGACAAGTGTCACATGCT

CTCAGTGGTCAAAACCAAACAAACA-
GACTTTTGGACCAAAAAAAAAA

AAAACCTCTTAAGGACTCTGGTAGAAC-
CCTAAATAGCACAGAATGCTG

AGGGGAGTAAGGGACAGGTCCTTCAT-
TCGTCTCTGCATCCACATCTCC

CAGCAGGAAGCAGCTAAGGCTCAGCAC-
CATCGTGCCTGCAGCTCTGCT

TTCCATGCAGTTCTGCATTCTTGGATAT-
TCACCTCTAGGTAAAAGCACA

GGCCAGGGAGGCTTTGTCACCAGCA-
GAACTGACCAACCACTGCCAGG

TGAAGCTGGCAGCACCGTATCTAAC-
CTATGAAGTTAATGGTATTTAGC

ACTAGCTTGATAAAAGGAAGGGTTTCT-
TGGCGGTTTCACTGCTTAAGT

ATAGAAGAGCTTGGTAGAAGACT-
TGAAAGCAAGGTAAATGCTGTCAA

ATACCACTAAAAATGTCACTTGAACCT-
TATCAGCAGGGAGCACTTATT

TACAGACCTAGTCACAGTTAAGCGAAT-
TCCCGGGCC
```

The 1st and 2nd ATGs of the ovomucoid sequence are shown underlined. Note that the ovomucoid coding sequence is in reverse. The underlined, bold A is not in the wildtype sequence but was incorporated into pOM-10-Pci due to a error in the oligo OM-5.

Expression of Luciferase

For expression in avian cells of non-magnum origin, HD11 cells, a chicken myeloid cell line was used. Cells were cultured as described in Beug, H., et al. (Chicken hematopoietic cells transformed by seven strains of defective avian leukemia viruses display three distinct phenotypes of differentiation. (1979) Cell, 18: 375-90, in which these cells were referred to as HBCI cells), herein incorporated by reference in its entirety. Plasmid DNA was transfected into HD11 cells with Lipofectamine 2000 (Invitrogen Corporation, Carlsbad, Calif.) according to the manufacturer's instructions.

48 hours post-transfection, the cells were harvested and pelleted. The supernatant was removed and 20 ml of 10 mM Tris, pH 7.8, 1 mM EDTA (TE) was added. The cells were frozen at −80° C. and thawed. 5 ml of the cell suspension was mixed with 25 ml of Bright-Glo™ reagent (Bright-Glo™ Luciferase Assay System, Promega, Madison, Wis.) and relative light units per second measured on a Berthold Detection Systems (Oak Ridge, Tenn.) FB12 luminometer.

Figure 6A:
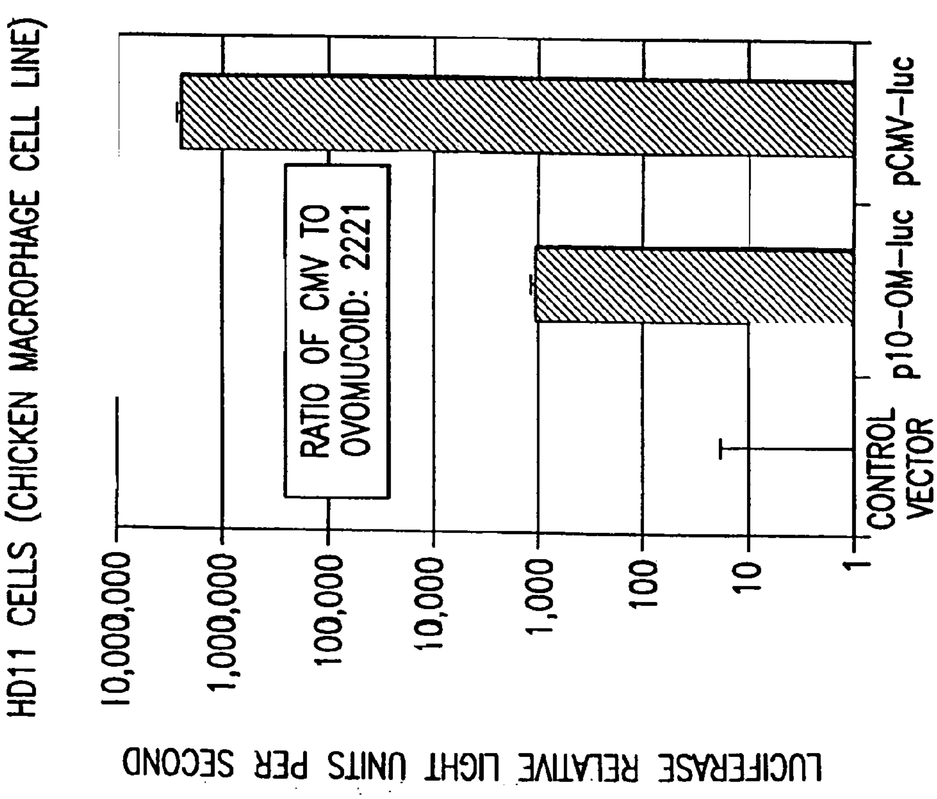
FIG. 6A shows the results of transfections of plasmids containing the ovomucoid promoter or CMV promoter linked to a luciferase gene into HD11 cells, a chicken myeloid cell line.

Results are depicted in FIG. 6A. HD11 cells are permissive for the CMV promoter and should be able to only weakly activate the ovomucoid promoter. Some expression of the luciferase gene linked to the 10 kb ovomucoid is evident.

For expression in avian oviduct cells, primary tubular gland cells were isolated as follows. The oviduct of a Japanese quail (*Coturnix coturnix* japonica) was removed and the magnum portion minced and enzymatically dissociated with 0.8 mg/ml collagenase (Sigma Chemical Co., St. Louis, Mo.) and 1.0 mg/ml dispase (Roche Molecular Biochemicals, Indianapolis, Ind.) by shaking and titurating for 30 minutes at 37° C. The cell suspension was then filtered through sterile surgical gauze, washed three times with F-12 medium (Life Technologies, Grand Island, N.Y.) by centrifugation at 200×g, and resuspended in OPTIMEM™ (Life Technologies) such that the $OD_{600}$ was approximately 2. 800 μl of the cell suspension was plated in each well of a 6-well dish. For each transfection, 4.0 μl of DMRIE-C liposomes (Life Technologies) and 2.0 μg of plasmid DNA was preincubated for 15 minutes at room temperature in 200 μl of OPTIMEM™, and then added to the oviduct cells. Cells with DNA/liposomes were incubated for about 5 hours at 37° C. in 5% $CO_2$. Next, 2.0 ml of DMEM (Life Technologies), supplemented with 15% fetal bovine serum (FBS) (Atlanta Biologicals, Atlanta, Ga.), 2× penicillin/streptomycin (Life Technologies), 50 ng/ml insulin (Sigma), $10^{-7}$ M α-estradiol (Sigma), and $10^{-6}$ M corticosterone (Sigma) were added to each well, and incubation continued for about 40 hours. Medium was then harvested and centrifuged at 110×g for 5 minutes.

For quantitation, the cells were scraped into the media with a rubber policeman. One milliliter was transferred to an eppendorf tube and the cells pelleted. The supernatant was removed and 20 ml of 10 mM Tris, ph 7.8, 1 mM EDTA (TE) was added. The cells were frozen at −80° C. and thawed. 5 ml of the cell suspension was mixed with 25 ml of Bright-Glo™ reagent (Bright-Glo™ Luciferase Assay System, Promega, Madison, Wis.) and relative light units per second measured on a Berthold Detection Systems (Oak Ridge, Tenn.) FB12 luminometer.

Figure 6B:
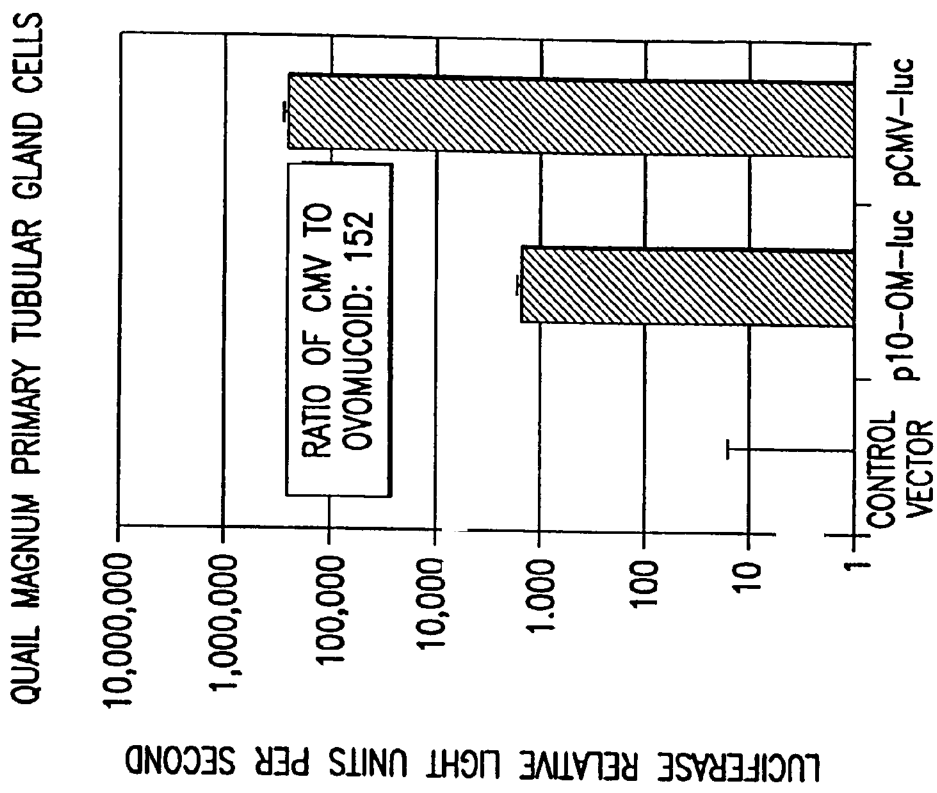
FIG. 6B shows the results of transfections of plasmids containing the ovomucoid promoter or CMV promoter linked to a luciferase gene into primary quail tubular gland cells isolated from the magnum portion of the oviduct of a laying quail hen.
Figure 6C:
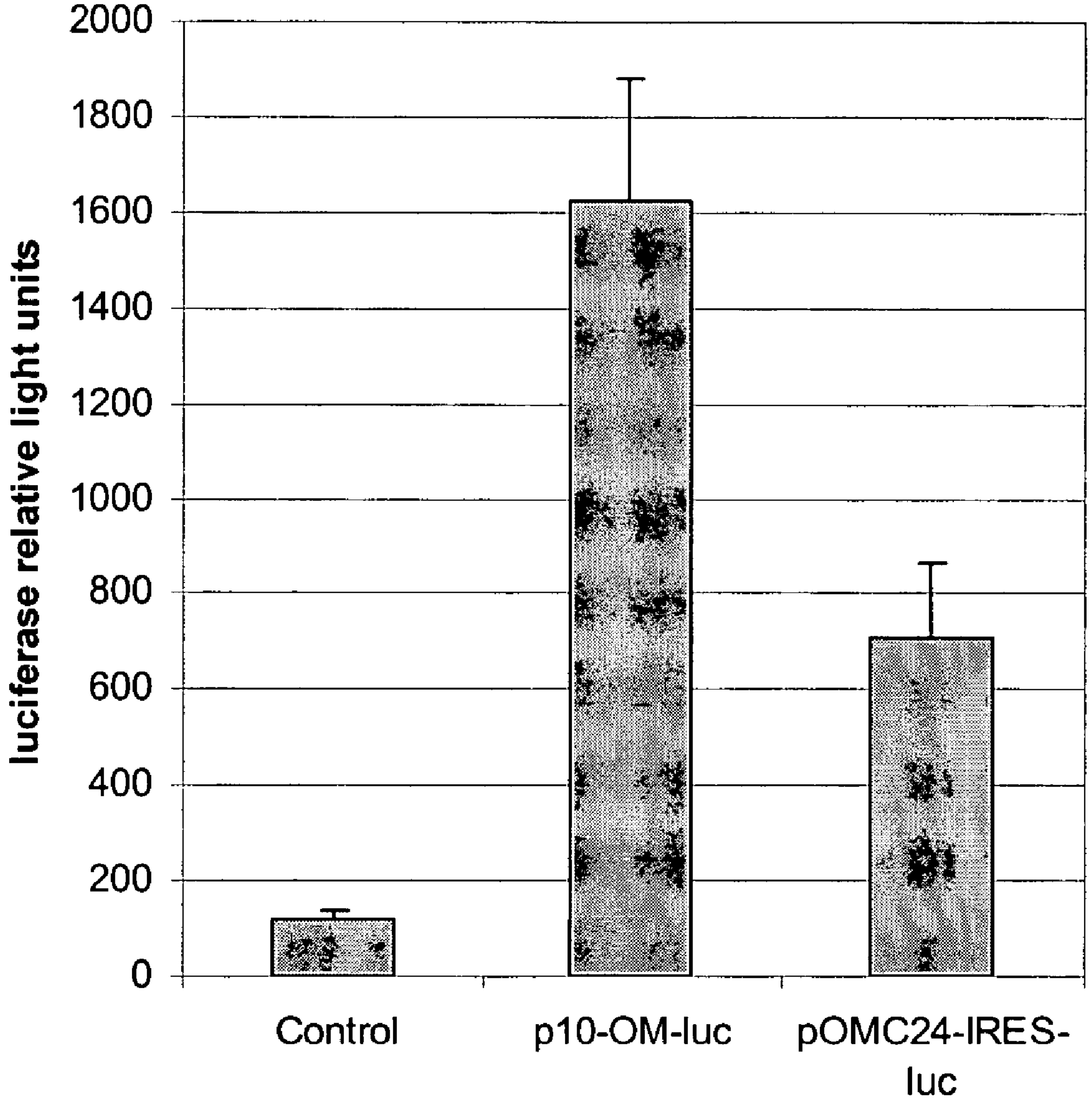
FIG. 6C. shows the results of transfection into primary quail tubular gland cells isolated from the magnum of a laying quail hen for the 10 kb ovomucoid promoters and the ovomucoid BAC-IRES construct each comprising an operably linked luciferase coding sequence.

The results are depicted in FIG. 6B. Expression of luciferase is evident from the CMV and 10 kb ovomucoid promoters. The ovomucoid promoter has more activity relative to the CMV promoter in the tubular gland cells (ratio of CMV to ovomucoid is 152) than in the HD11 cells (ratio of CMV to ovomucoid is 2221). FIG. 6C shows the expression of luciferase from a OMC24-IRES-luc vector. This vector is the OMC24-IRES clone described in Example 6 with a luciferase coding sequence inserted 3' to the IRES.

EXAMPLE 5

Expression in Transfected Cultured Avian Oviduct Cells of Human Interferon α2b Regulated by the 10 kb Ovomucoid Promoter Construction of p10-OM-IFN The CMV promoter region of pAVIJCR-A137.91.1.2 flanked by Nco I sites (pCMV-human IFN-alpha-2b-MagMax) was replaced with the 1051 bp Nco I-Nco I fragment from pBS-OVMUP-4.4, thereby inserting the 1 kb ovomucoid promoter in front of the IFN coding sequence and SV40 polyadenylation signal and creating p1kb-OM-IFNMM. A 1816 bp Cla I-Sac I fragment of p1kb-OM-IFNMM was inserted into the 6245 bp Cla I-Sac I fragment of pBS-OVMUP-4.4, thereby fusing the 4.4 kb ovomucoid fragment with the IFN coding sequence and creating p4.4OM-IF-NMM. The 8511 bp BamH I-Sal I fragment of pBS-OVMUP-10 was ligated to the 5148 bp BamH I-Sal I fragment of p4.4OM-IFN, thereby placing the 10 kb ovomucoid promoter in front of the IFN coding sequence, creating p10-OM-IFN.

Expression of Interferon

Figure 7:
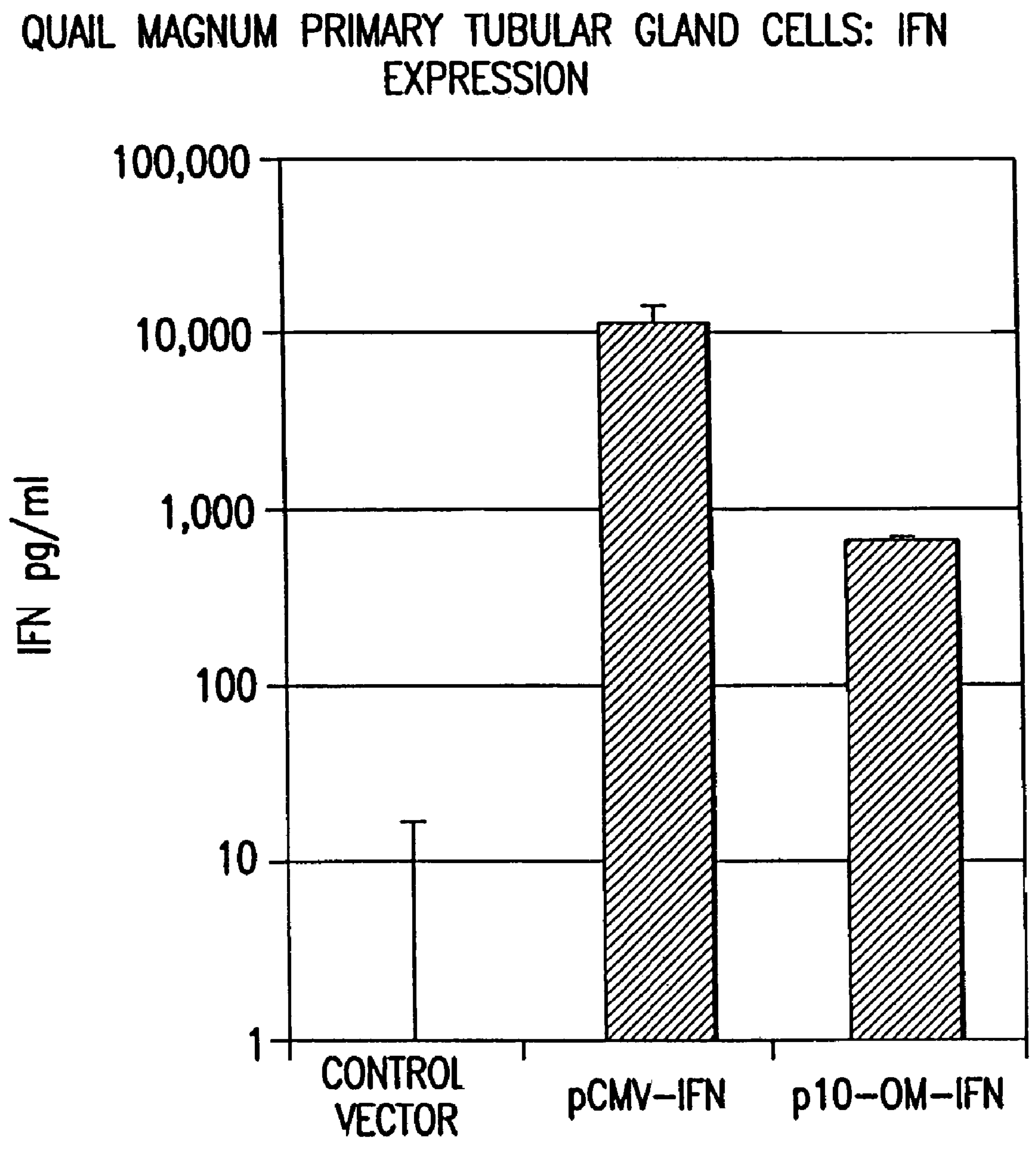
FIG. 7 shows the results of transfections of plasmids containing the ovomucoid promoter or CMV promoter linked to an interferon gene into primary quail tubular gland cells isolated from the magnum portion of the oviduct of a laying quail hen.

Quail primary tubular gland cells were isolated and treated as described in Example 4. 100 ml of supernatants were analyzed by ELISA (PBL Biomedical Laboratories, Flanders, N.J.) for human interferon α2b content. The results are depicted in FIG. 7. Expression of interferon is evident from the CMV and 10 kb ovomucoid promoters.

EXAMPLE 6

Construction of an Ovomucoid Promoter-Bacterial Artificial Chromosome Expression Vector with an Antibody Heavy Chain or Antibody Light Chain Coding Sequence A chicken BAC library constructed with HindIII inserts ligated into pECBAC1 (see, Crooijmans et al., Mammalian Genome 11: 360-363, 2000, the disclosure of which is incorporated herein in its entirety by reference) was screened by PCR with two sets of primers using methods well known in the art. One primer set, OM7 and OM8, was designed to anneal in the 5' untranslated region of the ovomucoid gene. The other primer set, Ovoinhibitor 1 and Ovoinhibitor 2, was designed to anneal in exon 3 and exon 4 of the ovoinhibitor gene.

A BAC clone was identified which yielded the expected size PCR fragment for each primer set. The BAC clone which included an insert encompassing the ovoinhibitor and ovomucoid gene was sequenced by standard techniques and designated OMC24 The sequence for OMC24 is shown in SEQ ID NO: 36.

| Primer Sequences | |
|---|---|
| OM7:<br>CGGGCAGTACCTCACCATGGACATGT | (SEQ ID NO: 37) |
| OM8:<br>ATTCGCTTAACTGTGACTAGG | (SEQ ID NO: 38) |
| OVOINHIBITOR-1:<br>CGAGGAACTTGAAGCCTGTC | (SEQ ID NO: 39) |
| OVOINHIBITOR-2:<br>GGCCTGCACTCTCCATCATA | (SEQ ID NO: 40) |

Figure 8:
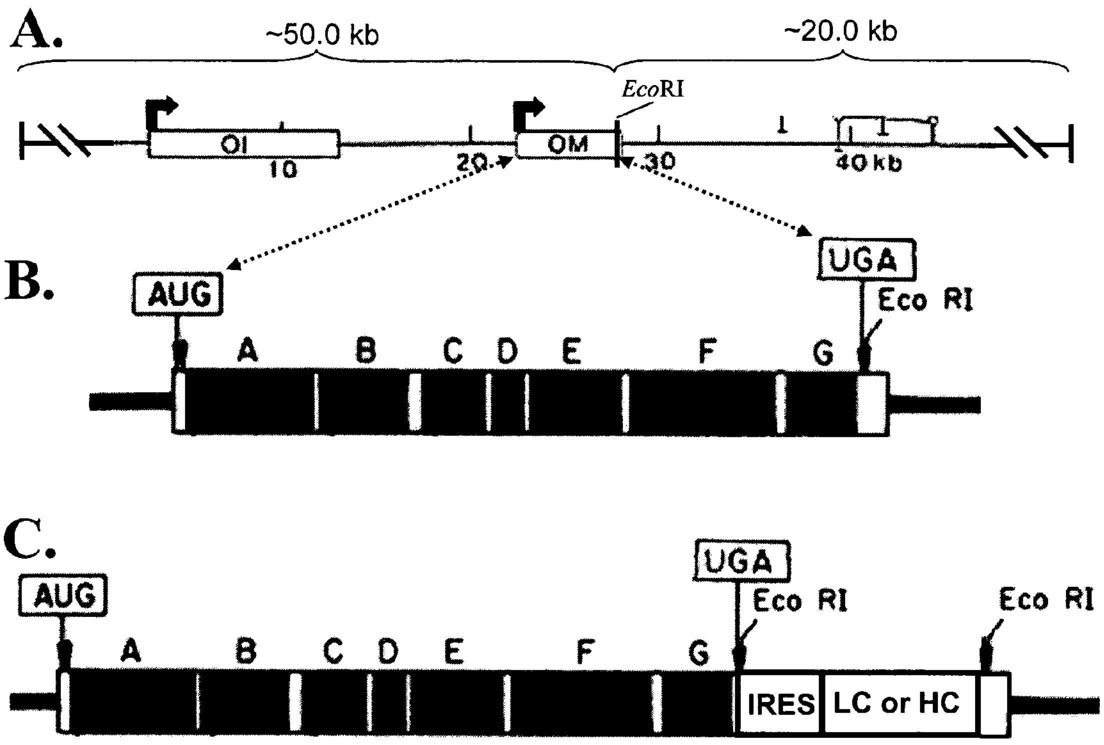
FIG. 8 shows an ovomucoid gene and bacterial artificial chromosome.

Polynucleotide sequences encoding the heavy chain and light chain of an IgG1 (IgG1K) monoclonal antibody were inserted into the 3' UTR of the ovomucoid transcript coding region in two separate OMC24 clones. The heavy chain and light chain coding sequences each included a signal sequence located at their 5' ends. For each clone, the coding sequence of each antibody chain and signal sequence was inserted into the OMC24 vector as an IRES-LC or IRES-HC cassette with the light chain and heavy chain inserts each positioned in the sense orientation SEQ ID NO: 41 shows the IRES-LC cassette inserted in the OMC24 clone. SEQ ID NO: 42 shows the IRES-HC cassette inserted in the OMC24 clone. The IRES sequence is shown in bold. The conserved regions of the IgG1 antibody light chain and heavy chain coding sequence are underlined. The nucleotides for the coding sequences of the variable regions for the IgG1 light chain and heavy chains are represented by N's. The nucleotides encoding the signal sequences in each clone are represented by italicized N's with the start codon indicated as ATG. OMC24 nucleotide sequence flanking the IRES and the antibody coding sequence is also shown for each of the two sequences. These constructs are shown in FIG. 8.

The IRES-antibody light chain and heavy chain cassettes were each inserted into an OMC24 clone at a natural EcoRI site that resides in the 3' UTR of ovomucoid at position 49,145 of SEQ ID NO: 36. Because there are many EcoRI sites in OMC24, RecA-assisted restriction endonuclease cleavage (RARE) was used to cut only at the desired site. RecA assisted restriction endonuclease cleavage is described in Molecular Biotechnology (2001) Vol 18, pp 233 to 241, the disclosure of which is incorporated herein in its entirety by reference. A portion of the vector from which the cassettes were obtained of about 26 nucleotides in length can be seen 3' of the coding sequence of the light chain and heavy chain in SEQ ID NO: 41 and SEQ ID NO: 42.

OMC24-IRES-LC (SEQ ID NO: 41)

gatttcactc atctcctaat aatcaggtag ctgaggagat gctgagtctg ccagttcttg ggctctgggc aggatcccat ctcctgcctt ctctaggaca gagctcagca ggcagggctc tgtggctctg tgtctaaccc acttcttcct ctcctcgctt tcagggaaag caacgggact ctcactttaa gccattttgg aaaatgctga atatcagagc tgagag aatt ccgcccctct ccctcccccc cccctaacgt tactggccga agccgcttgg aataaggccg gtgtgcgttt gtctatatgt tattttccac catattgccg tcttttggca atgtgagggc ccggaaacct ggccctgtct tcttgacgag cattcctagg ggtctttccc ctctcgccaa aggaatgcaa

-continued ggtctgttga atgtcgtgaa ggaagcagtt cctctggaag cttcttgaag acaaacaacg tctgtagcga ccctttgcag gcagcggaac cccccacctg gcgacaggtg cctctgcggc caaaagccac gtgtataaga tacacctgca aaggcggcac aaccccagtg ccacgttgtg agttggatag ttgtggaaag agtcaaatgg ctctcctcaa gcgtattcaa caaggggctg aaggatgccc agaaggtacc ccattgtatg ggatctgatc tggggcctcg gtgcacatgc tttacgtgtg tttagtcgag gttaaaaaac gtctaggccc cccgaaccac ggggacgtgg ttttcctttg aaaaacacga tgataagctt gccacaacca tgnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnacggtgg cggcgccatc tgtcttcatc ttcccgccat ctgatgagca gttgaaatct ggaactgcct ctgttgtgtg cctgctgaat aacttctatc ccagagaggc caaagtacag tggaaggtgg ataacgccct ccaatcgggt aactcccagg agagtgtcac agagcaggac agcaaggaca gcacctacag cctcagcagc accctgacgc tgagcaaagc agactacgag aaacacaaag tctacgcctg cgaagtcacc catcagggcc tgagctcgcc cgtcacaaag agcttcaaca ggggagagtg ttagggatcc actagtccag tgtggtggaa ttcaccacag gatccccact ggcgaatccc agcgagaggt ctcacctcgg ttcatctcgc actctgggga gctcagctca ctcccgattt tctttctcaa taaactaaat cagcaacact cctttgtctt

OMC24-IRES-HC (SEQ ID NO: 42)

gatttcactc atctcctaat aatcaggtag ctgaggagat gctgagtctg ccagttcttg ggctctgggc aggatcccat ctcctgcctt ctctaggaca gagctcagca ggcagggctc tgtggctctg tgtctaaccc acttcttcct ctcctcgctt tcagggaaag caacgggact ctcactttaa gccattttgg aaaatgctga atatcagagc tgagagaatt ccgcccctct ccctcccccc cccctaacgt tactggccga agccgcttgg aataaggccg gtgtgcgttt gtctatatgt tattttccac catattgccg tcttttggca atgtgagggc ccggaaacct ggccctgtct tcttgacgag cattcctagg ggtctttccc ctctcgccaa aggaatgcaa ggtctgttga atgtcgtgaa ggaagcagtt cctctggaag cttcttgaag acaaacaacg tctgtagcga ccctttgcag gcagcggaac cccccacctg gcgacaggtg cctctgcggc caaaagccac gtgtataaga tacacctgca aaggcggcac aaccccagtg ccacgttgtg agttggatag ttgtggaaag agtcaaatgg ctctcctcaa gcgtattcaa caaggggctg aaggatgccc agaaggtacc ccattgtatg ggatctgatc tggggcctcg gtgcacatgC tttacgtgtg tttagtcgag gttaaaaaac gtctaggccc cccgaaccac ggggacgtgg ttttcctttg aaaaacacga tgataagctt gccacaacca tgnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn nnnnnnnnnn -continued

```
nnnnnnnnnn nnnnnnnnnn nnnnnnnnnn nnnnnnnnnn nnnnnnnnnn nnnnnnnnnn

nnnnnnnnnn nnnnnnnnnn nnnnnnnnnn nnnnnnnnnn nnnnnnnnnn nnnnnnnnnn

nnnnnnnnnn nnnnnnnnnn nnnntcagct agcaccaagg gcccatcggt cttcccctg

gcaccctcct ccaagagcac ctctgggggc acagcggccc tgggctgcct ggtcaaggac

tacttccccg aaccggtgac ggtgtcgtgg aactcaggcg ccctgaccag cggcgtgcac

accttcccgg ccgtcctaca gtcctcagga ctctactccc tcagcagcgt ggtgaccgtg

ccctccagca gcttgggcac ccagacctac atctgcaacg tgaatcacaa gcccagcaac

accaaggtgg acaagagagt tgagcccaaa tcttgtgaca aaactcacac atgcccaccg

tgcccagcac ctgaactcct ggggggaccg tcagtcttcc tcttcccccc aaaacccaag

gacaccctca tgatctcccg gaccocagag gtcacatgcg tggtggtgga cgtgagccac

gaagaccctg aggtcaagtt caactggtac gtggacggcg tggaggtgca taatgccaag

acaaagccgc gggaggagca gtacaacagc acgtaccgtg tggtcagcgt cctcaccgtc

ctgcaccagg actggctgaa tggcaaggag tacaagtgca aggtctccaa caaagccctc

ccagccccca tcgagaaaac catctccaaa gccaaagggc agccccgaga accacaggtg

tacaccctgc ccccatcccg ggatgagctg accaagaacc aggtcagcct gacctgcctg

gtcaaaggct tctatcccag cgacatcgcc gtggagtggg agagcaatgg gcagccggag

aacaactaca agaccacgcc tcccgtgctg gactccgacg gctccttctt cctctacagc

aagctcaccg tggacaagag caggtggcag caggggaacg tcttctcatg ctccgtgatg

catgaggctc tgcacaacca ctacacgcag aagagcctct ccctgtctcc gggtaaatag

ggatccacta gtccagtgtg gtggaattca ccacaggatc cccactggcg aatcccagcg

agaggtctca cctcggttca tctcgcactc tggggagctc agctcactcc cgattttctt
```

The resulting mRNA transcript from the ovomucoid promoter for each clone contains two coding sequences; one for the ovomucoid protein and another for the downstream light chain or heavy chain coding sequence. The internal ribosome entry site (IRES) engineered into the vectors is useful to facilitate translation of the downstream heavy chain or light chain coding sequence.

EXAMPLE 7

Production of Transgenic Hens with an Ovomucoid Promoter-Bacterial Artificial Chromosome Expression Vector Transgene 100 µg each of BAC clone OMC24-IRES-LC and OCM24-IRES-HC were linearized by enzymatic restriction digest. The digested DNA was phenol/$CHCl_3$ extracted, ethanol precipitated, suspended in 0.25 M KCl and diluted to a working concentration of approximately 60 µg/ml. The DNA was mixed with SV40 T antigen nuclear localization signal peptide (NLS peptide, amino acid sequence CGGPKKKRKVG (SEQ ID NO: 43) with a peptide DNA molar ratio of 100:1 (Collas and Alestrom, 1996, Mol. Reprod. Develop. 45: 431-438, the disclosure of which is incorporated by reference in its entirety). The DNA samples were allowed to associate with the SV40 T antigen NLS peptide by incubation at room temperature for 15 minutes.

Introduction of the DNA-NLS complex into an avian egg was accomplished essentially as described in U.S. patent application Ser. No. 10/251,364, filed Sep. 18, 2002, the disclosure of which is incorporated in its entirety herein by reference. Briefly, the germinal disc of an avian egg was illuminated by an incident light beam and visualized by an oblique macromonitering system. A micropipette injection needle was positioned by micromanipulation such that the tip of the needle was pressed into the vitelline membrane of the avian egg to a depth of about 20 µM. The injection needle was inserted through the membrane into the germinal disc to a point where only the end of the beveled opening of the needle was visible above the membrane, while the remaining of the opening was present inside the germinal disk. The DNA-NLS was then injected into the germinal disc. Approximately 100 nanoliters of DNA were injected into a germinal disc of stage I White Leghorn embryos obtained two hours after oviposition of the previous egg.

Injected embryos were surgically transferred to recipient hens via ovum transfer according to the method of Christmann et al. (PCT Publication WO 02/20752, the disclosure of which is incorporated herein in its entirety by reference) and hard shell eggs were incubated and hatched. See, Olsen and Neher, 1948, J. Exp. Zoo. 109: 355-366, the disclosure of which is incorporated in its entirety herein by reference.

Genomic DNA samples from one-week old chicks were analyzed for the presence of OMC24-IRES-LC or HC by PCR using methods well known in the field of avian transgenics. Briefly, three hundred nanograms of genomic DNA and 1.25 units of Taq DNA polymerase (Promega) were added to a 50 µl reaction mixture of 1× Promega PCR Buffer with 1.5 mM $MgCl_2$, 200 µM of each dNTP, 5 µM primers. The reaction mixtures were heated for 4 minutes at 94° C., and then amplified for 34 cycles each consisting of: 94° C. for 1 min, 60° C. for 1 min and 72° C. for 1 min. A final cycle of 4 minutes at 72° C. was performed. PCR products were detected by visualization on a 0.8% agarose gel stained with ethidium bromide.

EXAMPLE 8

Production of Antibody by Transgenic Hens

Transgenic chicks produced as described in Example 7 were grown to maturity. Eggs were collected from the hens and egg white material was assayed for the IgG1 using sandwich ELISA.

The eggs were cracked and opened and the whole yolk portion was discarded. Both the thick and thin egg white portions were kept. 1 ml of egg white was measured and added to a plastic Stomacher 80 bag. A volume of egg white buffer (5% 1M Tris-HCl pH 9 and 2.4% NaCl) equal to two times the volume of egg white was added to the egg white. The egg white-buffer mixture was paddle homogenized in the Stomacher 80 at normal speed for one minute. The sample was allowed to stand overnight and homogenation was repeated. A 1 ml sample of the mixture was used for testing.

A Costar flat 96-well plate was coated with 100 ul of C. Goat-anti-Human kappa at a concentration of 5 μg/ml in PBS. The plate was incubated at 37° C. for two hours and then washed. 200 μl of 5% PBA was added to the wells followed by an incubation at 37° C. for about 60-90 minutes followed by a wash. 100 ul of egg white samples (diluted in 1% PBA:LBP) was added to each well and the plate was incubated at 37° C. for about 60-90 min followed by a wash. 100 ul of a 1:2000 dilution of F'2 Goat anti-Human IgG Fc-AP in 1% PBA was added to the wells and the plate was incubated at 37° C. for 60-90 min followed by a wash.

The transgenic antibody was detected by placing 75 ul of 1 mg/ml PNPP (p-nitrophenyl phosphate) in 5× developing buffer in each well and incubating for about 10-30 mins at room temperature. The detection reaction was stopped using 75 ul of 1N NaOH. The OD405-650 nm was then determined for each sample well. Each OD405-650 nm value was compared to a standard curve to determine the amount of recombinant antibody present in each sample Approximately 0.3% of hens analyzed expressed antibody in their eggs. Two hens which expressed antibody are Hen 1251 which was found to produce an average of 19 ng of IgG per ml of egg white and Hen 4992 which was found to produce an average of 150 ng of IgG per ml of egg white.

Figure 9:
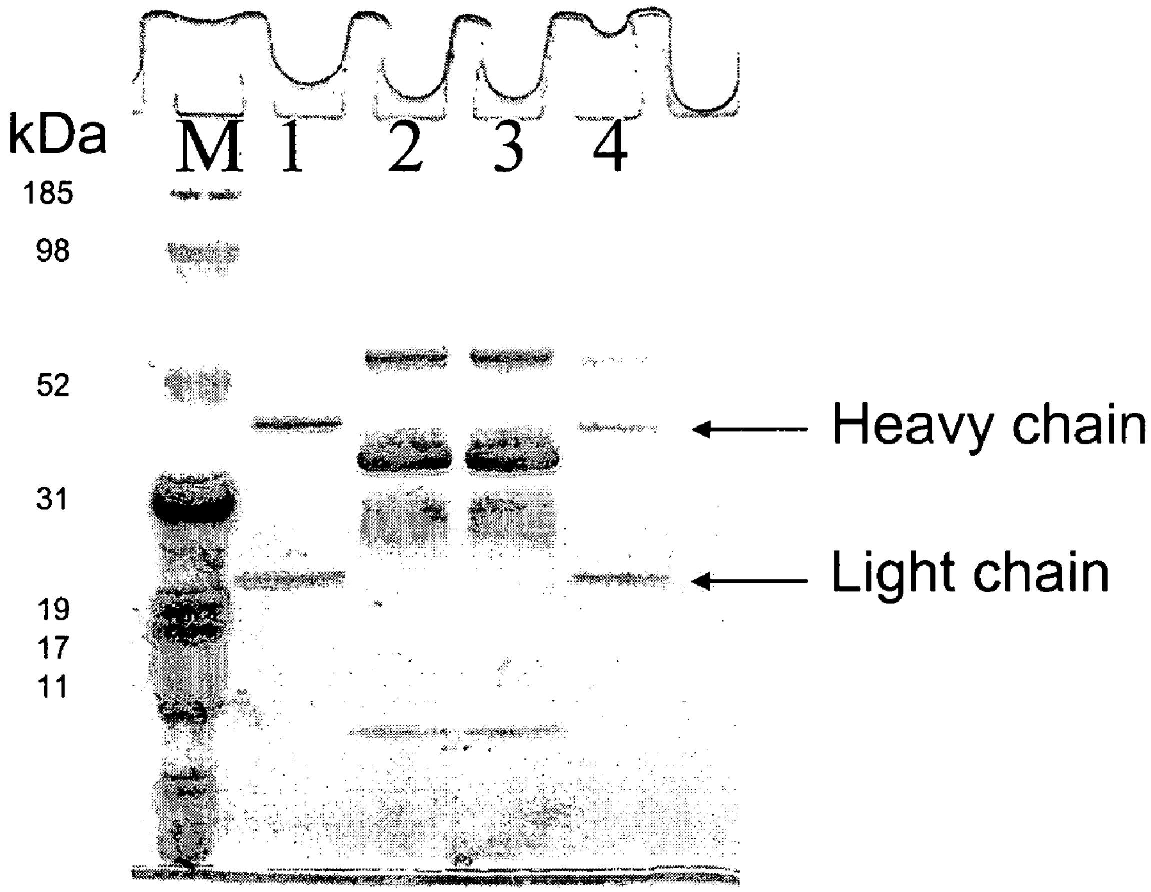
FIG. 9 shows an SDS-PAGE analysis of partially purified hMab derived from a single transgenic hen. (M) Multi-mark standard, lane 1) 1 mg purified hMab (produced by mammalian cells), lane 2) 5 mg pre-column (transgenic avian egg white), lane 3) 5 mg column flow thru from transgenic avian egg white, lane 4) partially purified hMab from transgenic avian egg white.

FIG. 9 shows the results of an SDS-PAGE analysis of the transgenic avian derived hMab compared to the same antibody produced in mammalian cells. The antibody was first purified from egg white proteins by protein A affinity chromatography. The transgenic protein (lane 4) heavy chain and light chain had virtually an identical mobility compared to heavy and light chains of the same antibody produced by standard mammalian cell culture (lane 1). Also shown are pre-chromatography transgenic egg white (lane 2) and affinity chromatography transgenic egg white flow through (lane 3).

EXAMPLE 9

Human Antibody Produced by Transgenic Hens Demonstrates Target Antigen Binding

The human monoclonal antibody produced and identified as described in Examples 7 and 8 was assayed for target antigen binding.

Antibody was captured from the egg white in microplate wells coated with the antibodies target antigen. Antigen-antibody complexes were quantitated using isotype-specific secondary antibody conjugated with alkaline phosphatase. The ability of the transgenic avian produced hMab to bind its target antigen was compared with the binding ability of the same hMab produced in mammalian cells.

Figure 10:
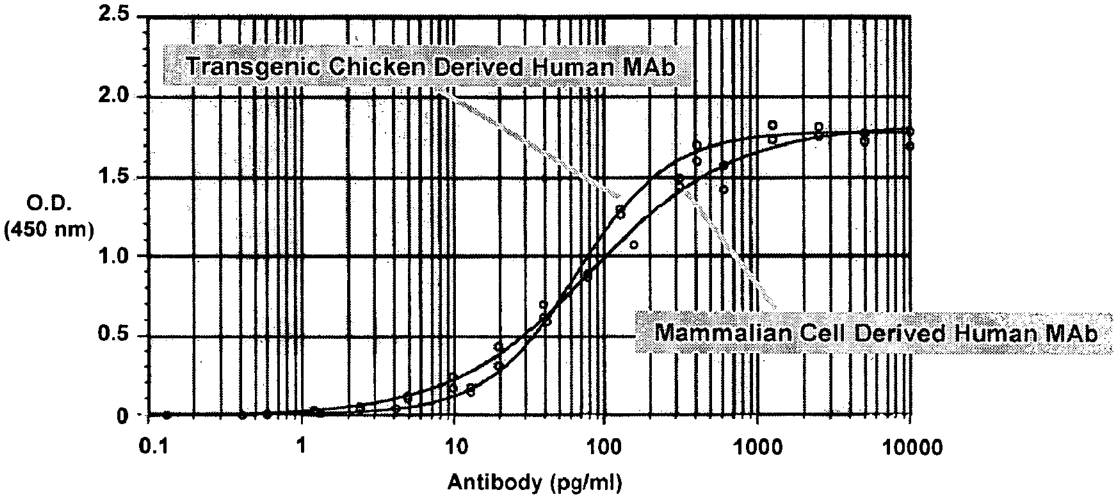
FIG. 10 shows plots of the binding ability of an IgG1 monoclonal antibody produced by a transgenic chicken and the binding ability of the same IgG1 monoclonal antibody produced by mammalian cells.

Plots showing the binding ability of each antibody are shown in FIG. 10. The plots show the level of antigen binding per picogram of antibody tested for both the antibody from transgenic chicken egg white and the antibody from a mammalian cell line. The similarity of the binding curves produced by these two antibodies indicate that the transgenic human antibody has an affinity that is substantially similar to the affinity of the antibody produced by standard methods (i.e., produced in mammalian cells).

A CHO cell line stably transfected with a plasmid that expressed the corresponding cell-surface antigen for the antibody produced by the transgenic avian was used in FACS analysis of the antibody.

Figure 11:
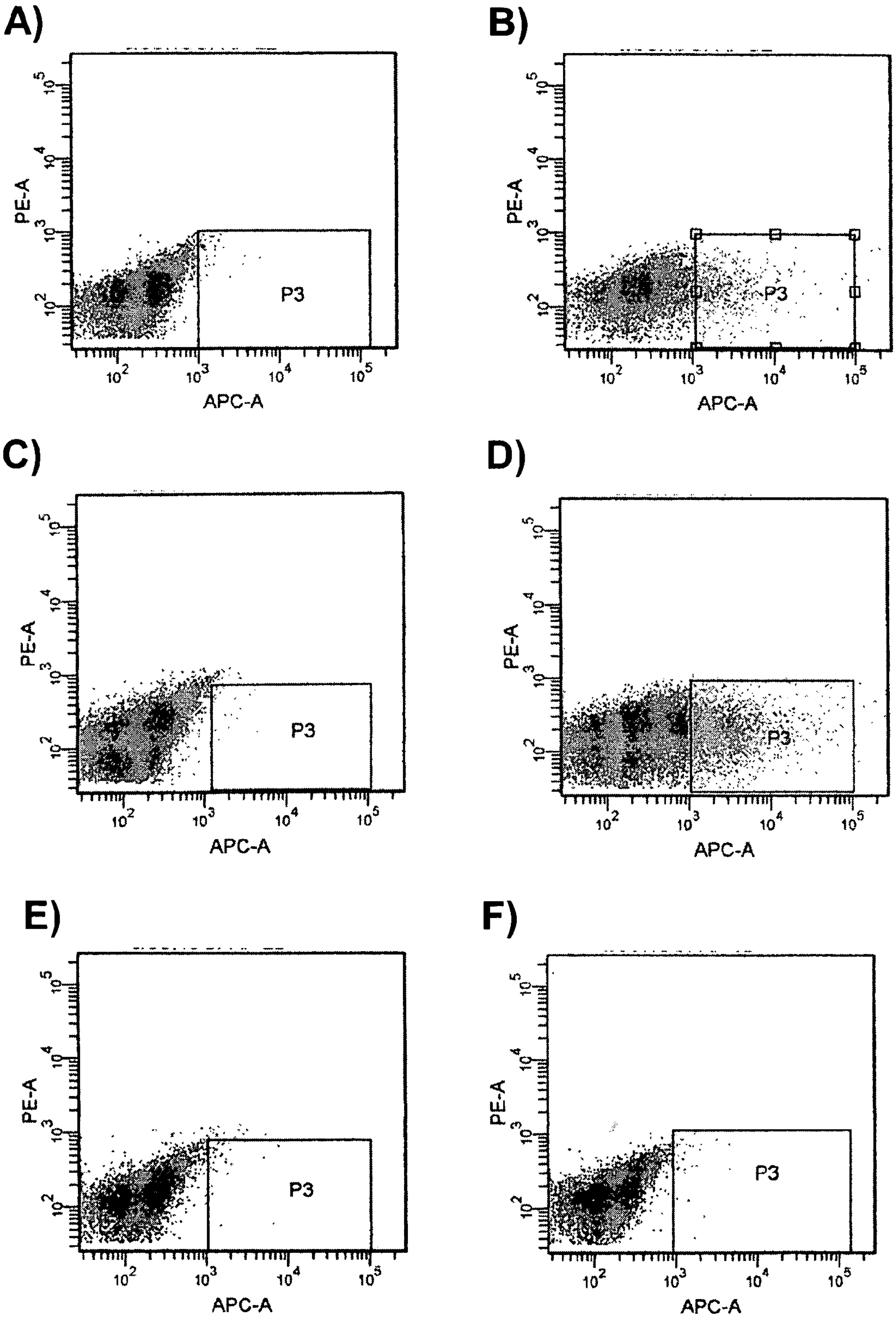
FIG. 11A-11F shows the ability of avian derived hMab to bind target antigen expressed on a cell surface relative to the ability of the mammalian cell derived hMab.

FIG. 11 shows the ability of the transgenic avian derived hMab to bind target antigen expressed on the cell surface of CHO cells relative to the ability of the antibody produced in mammalian cells. CHO cells were transfected with either a luciferase expression plasmid (6 A, 6 C, and 6 E) or an expression plasmid carrying cDNA of the hMab's target antigen (6 B, 6 D, and 6 F). Cells were collected and treated with one of three primary antibodies: 1) the antigen specific hMab produced by mammalian cells (6 A and 6 B), the antigen specific hMab produced by a transgenic hen (6 C. and 6 D), or 3) human antibody of the same isotype as the antibody produced by the transgenic hen but with different antigen specificity (6 E and 6 F). An isotype specific antibody conjugated with APC. (Allophycocyanin) was used to detect primary antibodies bound to the cells. Cells were sorted by FACS, counted and signal generated by the APC of the secondary antibody was quantitated. Cells that exhibited APC-associated fluorescence are delineated with a box within each graph.

Together the ELISA and FACS data show that a human antibody molecule produced by transgenic hens can bind efficiently to its target antigen.

EXAMPLE 10

Human Antibody Produced by Transgenic Hens Demonstrates Stability

Figure 12:
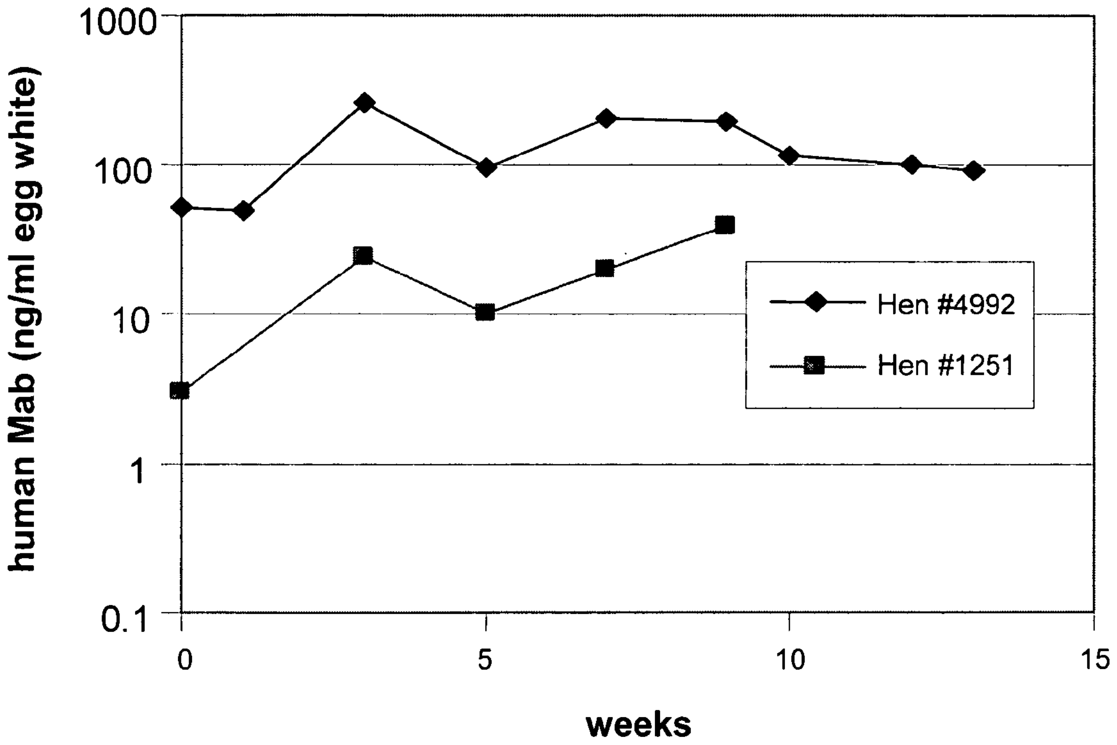
FIG. 12 shows the stability of hMab expression in transgenic hen. Eggs from transgenic hens #4992 and #1251 were collected over several weeks. The amount of hMab in egg white material was quantitated over time via sandwich ELISA for the specific human IgG1 (H+L).

FIG. 12 shows the stability of hMab expression in transgenic hen. Eggs from transgenic hens #4992 and #1251 of Example 8 were collected over several weeks. The amount of hMab in egg white material was quantitated via sandwich ELISA for the specific human IgG1. The results indicate that the antibody produced by an avian and collected in the egg white are stable over a significant period of time.

EXAMPLE 11

Human Antibody Produced by Transgenic Hens Demonstrates Target Cell Killing

The primary mechanism of action of many antibody therapeutics is the cytolysis of target antigen expressing cells via serum complement. This activity may require secondary modifications of the antibody in the form of proper glycosylation of the Fc portion of the antibody. Proper glycosylation has been shown to be essential for the antibody interaction with the C1q molecule of complement and with the Fcγ-family of receptors on effector cells.

The activity of the transgenic IgG1 antibody produced in Example 8 was assessed in antibody-dependent cellular cytotoxicity (ADCC) and complement-dependent cellular cytotoxicity (CDCC) assays using the antigen-expressing CHO cell line described in Example 9 as target cells.

ADCC assay: Surface antigen expressing CHO cells were incubated with purified transgenic MAb at 0.5 µg/ml or no MAb in serum free media. Human PBMCs (peripheral blood mononuclear cells) were added at an effector:target cell ratio of 20:1. The mixture was incubated at 37° C. for 4 hours. Cell lysis was assayed by LDH release and maximal release accomplished by addition of 1% Triton.

CDCC assay: Surface antigen expressing CHO cells were incubated overnight 37° C. with 0.5 µg/ml purified transgenic MAb or no MAb in the presence of 20% normal human serum. Plates were then washed and cell viability was assayed by LDH assay release and maximal release accomplished by addition of 1% Triton.

Activity was calculated for both the ADCC assay and the CDCC assay by methods well known in the art.

Figure 13:
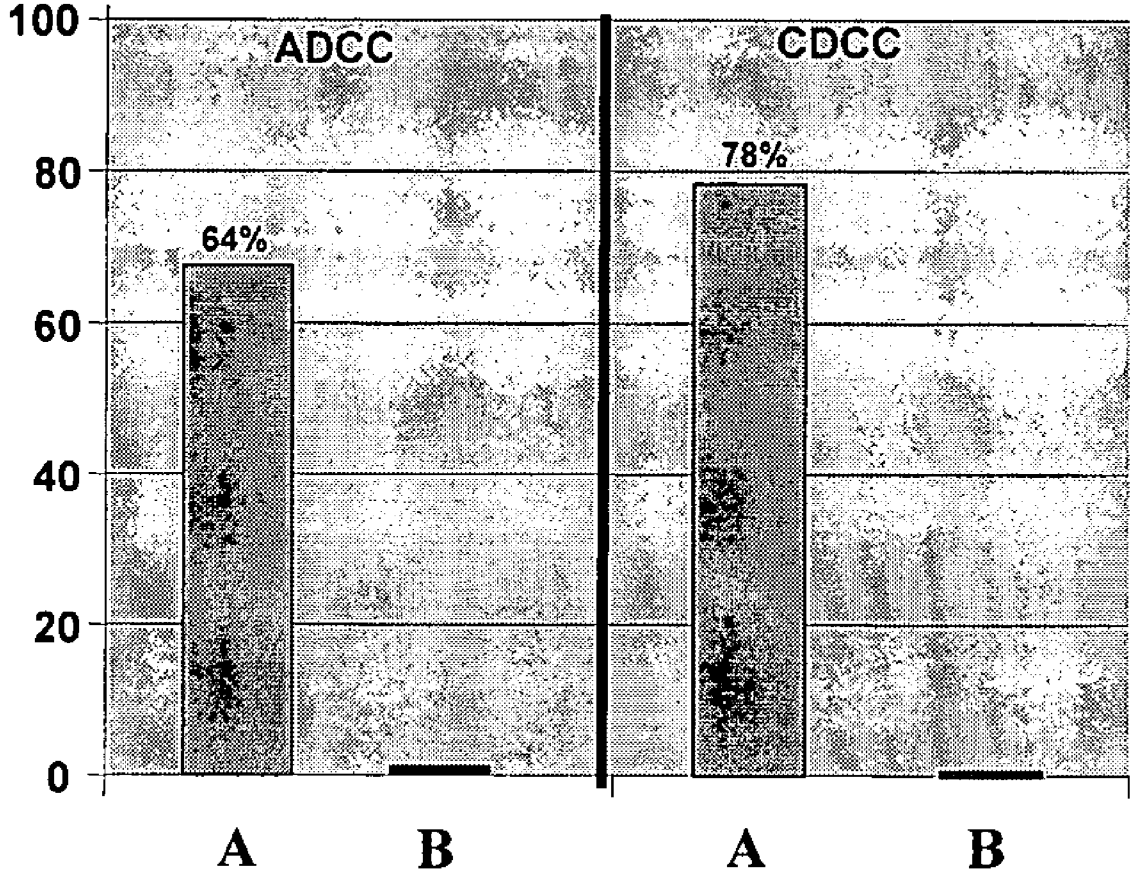
FIG. 13 shows ADCC. (antibody dependent cellular cytotoxicity) and CDCC. (complement-dependent cellular cytotoxicity) for an IgG1 produced in transgenic avians.

FIG. 13 shows the percent cytotoxicity for incubations with the transgenic antibody (columns A) and incubations with no antibody in serum free medium (columns B). As can be seen in FIG. 13, the transgenic human antibody efficiently mediated both ADCC and CDCC activities indicating that the antibody is appropriately glycosylated during production in avians and is effective in cytolysis of target cells.

EXAMPLE 12

Construction of an Ovomucoid Promoter-Bacterial Artificial Chromosome Expression Vector with a CTLA4-Fc Fusion Coding Sequence and an attB Site An ovomucoid gene expression controlling region-bacterial artificial chromosome expression vector with a CTLA4-Fc fusion coding sequence and attB site was constructed using nucleotide coding sequences for the extracellular domains of the CTLA4 (cytotoxic T lymphocyte antigen 4) receptor protein linked to nucleotide coding sequences for an immunoglobulin constant region (IgG1 Fc). The nucleotide sequence for the vector is shown in SEQ ID NO: 44

To produce this construct, an attB fragment was inserted into an EcoR1 site of the OMC24-IRES-LC clone described in Example 6. RecA-assisted restriction endonuclease cleavage (RARE) was used to cut only at the desired EcoRI site in the OMC24-IRES-LC clone. The attB fragment is shown inserted approximately at nucleotide number 26,722 to 27,029 of SEQ ID NO: 44. The attB site is shown in bold below in SEQ ID NO: 45 as it appears in the OMC24-attB-IRES-LC construct.

```
SEQ ID NO: 45
CCCAGAGCTG TGCAGTTGGG ATCCTAACAC CATGCAGATG CTCCAGGACC TGCACCGAGC

CCCAGCACTG GCACTCATCT CTTCTTTCCA CCCCTCTGAG AGCAACAAGT GGCTCTGCAA

TGGCAATGTA AGTGAAACCG GGCGGGTATC TTAGAGCACC TGGAAGCTTG CATGCCTGCA

GGTCGACTCT AGAGGATCCC CGGGTACCGA GCTCGAATTC CAGGTACCGT CGACGATGTA

GGTCACGGTC TCGAAGCCGC GGTGCGGGTG CCAGGGCGTG CCCTTGGGCT CCCCGGGCGC

GTACTCCACC TCACCCATCT GGTCCATCAT GATGAACGGG TCGAGGTGGC GGTAGTTGAT

CCCGGCGAAC GCGCGGCGCA CCGGGAAGCC CTCGCCCTCG AAACCGCTGG GCGCGGTGGT

CACGGTGAGC ACGGGACGTG CGACGGCGTC GGCGGGTGCG GATACGCGGG GCAGCGTCAG

CGGGTTCTCG ACGGTCACGG CGGGCATGTC GACAGCCAAG CCGAATTCGC CCTATAGTGA

GTCGTATTAC AATTCACTGG CCGTCGTTTT ACAACGTCGT GACTGGGAAA ACCCTGGCGT

TACCCAACTT AATCGCCTTG CAGCACATCC CCCTTTCGCC AGCTGGCGTA ATAGCGAAGA

GGCCCGCACC GATCGCCCTT CCCAACAGTT GCGCAGCCTG AATGGCGAAT GGCGCCTGAT

GCGGTATTTT CTCCTTACGC ATCTGTGCGG TATTTCACAC CGCATATGGT GCACTCTCAG
```

To produce the OMC24-attB-IRES-CTLA4 clone shown in SEQ ID NO: 44, the IRES-LC portion of the OMC24-attB-IRES-LC clone was deleted using RARE and was replaced with an IRES-CTLA4-Fc coding sequence (spanning approximately from nucleotides 76,124 to 77,872 of SEQ ID NO: 44). The portion of the OMC24-attB-IRES-CTLA4-Fc clone comprising the IRES and CTLA4-Fc portions is shown below in SEQ ID NO: 46. The IRES is shown in bold and the CTLA4-Fc coding region is underlined.

SEQ ID NO: 46

ATAATCAGGT AGCTGAGGAG ATGCTGAGTC TGCCAGTTCT TGGGCTCTGG GCAGGATCCC

ATCTCCTGCC TTCTCTAGGA CAGAGCTCAG CAGGCAGGGC TCTGTGGCTC TGTGTCTAAC

CCACTTCTTC CTCTCCTCGC TTTCAGGGAA AGCAACGGGA CTCTCACTTT AAGCCATTTT

GGAAAATGCT GAATATCAGA GCTGAGAGAA TTCCGCCCCT CTCCCTCCCC CCCCCCTAAC

GTTACTGGCC GAAGCCGCTT GGAATAAGGC CGGTGTGCGT TTGTCTATAT GTTATTTTCC

ACCATATTGC CGTCTTTTGG CAATGTGAGG GCCCGGAAAC CTGGCCCTGT CTTCTTGACG

AGCATTCCTA GGGGTCTTTC CCCTCTCGCC AAAGGAATGC AAGGTCTGTT GAATGTCGTG

AAGGAAGCAG TTCCTCTGGA AGCTTCTTGA AGACAAACAA CGTCTGTAGC GACCCTTTGC

AGGCAGCGGA ACCCCCCACC TGGCGACAGG TGCCTCTGCG GCCAAAAGCC ACGTGTATAA

GATACACCTG CAAAGGCGGC ACAACCCCAG TGCCACGTTG TGAGTTGGAT AGTTGTGGAA

AGAGTCAAAT GGCTCTCCTC AAGCGTATTC AACAAGGGGC TGAAGGATGC CCAGAAGGTA

CCCCATTGTA TGGGATCTGA TCTGGGGCCT CGGTGCACAT GCTTTACATG TGTTTAGTCG

AGGTTAAAAA AACGTCTAGG CCCCCCGAAC CACGGGGACG TGGTTTTCCT TTGAAAAACA

CGATGATAAG CTTGCCACAA CCATGGGTGT ACTGCTCACA CAGAGGACGC TGCTCAGTCT

GGTCCTTGCA CTCCTGTTTC CAAGCATGGC GAGCATGGCA ATGCACGTGG CCCAGCCTGC

TGTGGTACTG GCCAGCAGCC GAGGCATCGC CAGCTTTGTG TGTGAGTATG CATCTCCAGG

CAAAGCCACT GAGGTCCGGG TGACAGTGCT TCGGCAGGCT GACAGCCAGG TGACTGAAGT

CTGTGCGGCA ACCTACATGA TGGGGAATGA GTTGACCTTC CTAGATGATT CCATCTGCAC

GGGCACCTCC AGTGGAAATC AAGTGAACCT CACTATCCAA GGACTGAGGG CCATGGACAC

GGGACTCTAC ATCTGCAAGG TGGAGCTCAT GTACCCACCG CCATACTACC TGGGCATAGG

CAACGGAACC CAGATTTATG TAATTGATCC AGATACCGTG CCCAGATTCT GATCAGGAGC

CCAAATCTTC TGACAAAACT CACACATCCC CACCGTCCCC AGCACCTGAA CTCCTGGGTG

GATCGTCAGT CTTCCTCTTC CCCCCAAAAC CCAAGGACAC CCTCATGATC TCCCGGACCC

CTGAGGTCAC ATGCGTGGTG GTGGACGTGA GCCACGAAGA CCCTGAGGTC AAGTTCAACT

GGTACGTGGA CGGCGTGGAG GTGCATAATG CCAAGACAAA GCCGCGGGAG GAGCAGTACA

ACAGCACGTA CCGGGTGGTC AGCGTCCTCA CCGTCCTGCA CCAGGACTGG CTGAATGGCA

AGGAGTACAA GTGCAAGGTC TCCAACAAAG CCCTCCCAGC CCCCATCGAG AAAACCATCT

CCAAAGCCAA AGGGCAGCCC CGAGAACCAC AGGTGTACAC CCTGCCCCCA TCCCGGGATG

AGCTGACCAA GAACCAGGTC AGCCTGACCT GCCTGGTCAA AGGCTTCTAT CCCAGCGACA

TCGCCGTGGA GTGGGAGAGC AATGGGCAGC CGGAGAACAA CTACAAGACC ACGCCTCCCG

TGCTGGACTC CGACGGCTCC TTCTTCCTCT ACAGCAAGCT CACCGTGGAC AAGAGCAGGT

GGCAGCAGGG GAACGTCTTC TCATGCTCCG TGATGCATGA GGCTCTGCAC AACCACTACA

CGCAGAAGAG CCTCTCCCTG TCTCCGGGTA AATGAGGAAT TCACCACAGG ATCCCCACTG

GCGAATCCCA GCGAGAGGTC TCACCTCGGT TCATCTCGCA CTCTGGGGAG CTCAGCTCAC

EXAMPLE 13

Production of Transgeunic Hens with an OMCZ4-IRES-attB-CTLA4-Fc Fusion Coding Sequence Twenty-five μg of OMC24-attB-IRES-CTLA4-Fc and 2.5 μg of SV40 integrase mRNA was placed in 200 μl of 28 mM Hepes (pH 7.4). The DNA/Hepes was mixed with an equal volume of PEI was diluted 10-fold with water and the mixture was incubated at room temperature for 15 mins. About 5 μl of the mixture was injected into chicken eggs essentially as described in Example 7.

Birds that produce egg white which includes CTLA4-Fc were identified using a procedure essentially as described in Example 8 but tailored specifically for CTLA4-Fc as is understood by a practitioner of ordinary skill in the art. Approximately 20% of the birds analyzed produced eggs positive for CTLA4-Fc.

EXAMPLE 14

Construction of an Ovomucoid Promoter-Bacterial Artificial Chromosome Expression Vector Encoding an Antibody which Binds to CD3

A single vector is constructed to include a cassette comprising an IRES attached to the coding sequence of the light chain of an IgG antibody which binds to CD3 and a cassette comprising an IRES attached to the coding sequence of the heavy chain of an IgG antibody which binds to CD3. The coding sequences for each of the antibody chains are produced by assembling synthetic oligonucleotides to form double stranded DNA segments which encode either the amino acid sequence for the antibody light chain (LC) or heavy chain (HC). Sequences for this particular antibody have been described in, for example, U.S. Pat. No. 6,706, 265, the disclosure of which is incorporated in its entirety herein by reference. The IRES-LC cassette and IRES-HC cassette are each inserted into the ovomucoid UTR of a single OMC24 clone described in Example 6.

Transgenic hens which produce egg white which includes IgG antibody that binds to CD3 are produced essentially as described in Example 7.

EXAMPLE 15

Construction of an Ovomucoid Promoter-Human Artificial Chromosome Expression Vector Encoding an Antibody which Binds to CD3

A chicken HAC library constructed with genomic chicken DNA restriction digest inserts ligated into HAC vector is screened by PCR with two sets of primers using methods well known in the art. One primer set is designed to anneal in the 5' untranslated region of the ovomucoid gene. The other primer set is designed to anneal in exon 3 and exon 4 of the ovoinhibitor gene. A single HAC-chicken DNA clone is identified that includes both the UTR and the ovoinhibitor sequences and is designated HAC-O.

Two vectors are constructed to include a cassette comprising an IRES attached to the coding sequence of either the light chain or the heavy chain of an IgG antibody which binds to CD3. The coding sequences are produced by assembling synthetic oligonucleotides to form two double stranded DNA segments which encode either the amino acid sequence of the antibody light chain (LC) or heavy chain (HC). The IRES-LC cassette and IRES-HC cassette are each inserted into the ovomucoid UTR of a HAC-O clone to produce HAC-O-IRES-LC. and HAC-O-IRES-HC.

Transgenic hens which produce egg white which includes IgG antibody that binds to CD3 are produced essentially as described in Example 7.

EXAMPLE 16

Construction of an Ovomucoid Promoter P1 Derived Artificial Chromosome Expression Vector Encoding EPO A chicken PAC library constructed with chicken genomic DNA restriction digest inserts ligated into PAC vector is screened by PCR with two sets of primers using methods well known in the art. One primer set is designed to anneal in the 5' untranslated region of the ovomucoid gene. The other primer set is designed to anneal in exon 3 and exon 4 of the ovoinhibitor gene. A single PAC-chicken DNA clone is identified that includes both the UTR and the ovoinhibitor sequences and is designated PAC-O.

A vector is constructed which includes a cassette comprising an IRES attached to the coding sequence of human erythropoietin. Sequences for erythropoietin have been described in, for example, U.S. Pat. No. 4,703,008, the disclosure of which is incorporated in its entirety herein by reference. The IRES-EPO cassette is inserted into the ovomucoid UTR of the PAC-O clone.

Transgenic hens which produce egg white which includes EPO are produced essentially as described in Example 7.

EXAMPLE 17

Construction of an Ovomucoid Promoter-Bacterial Artificial Chromosome Expression Vector Encoding Human Gamma-Interferon A vector is constructed which includes a cassette coding sequence of an IRES and human gamma-interferon. Sequences for gamma-interferon have been previously described in, for example, U.S. Pat. No. 4,970,161, the disclosure of which is incorporated in its entirety herein by reference. The interferon coding sequence is inserted into the ovomucoid UTR in an OMC24 clone of Example 6.

Transgenic hens which produce egg white which includes gamma-interferon are produced essentially as described in Example 7.

EXAMPLE 18

Construction of an Ovomucoid Promoter-Yeast Artificial Chromosome Expression Vector Encoding the Fc Portion of an Antibody which Binds to CD3

A chicken YAC library constructed with restriction digest inserts ligated into YAC vector is screened by PCR with two sets of primers using methods well known in the art. One primer set is designed to anneal in the 5' untranslated region of the ovomucoid gene. The other primer set is designed to anneal in exon 3 and exon 4 of the ovoinhibitor gene. A single YAC-chicken DNA clone is identified that includes both the UTR and the ovoinhibitor sequences and is designated YAC-O.

One vector is constructed to include a cassette comprising an IRES attached to the coding sequence of the Lc portion of an IgG antibody which binds to CD3. The coding sequences are produced by assembling synthetic oligonucleotides to form two double stranded DNA segments which encode the Lc portion of an IgG antibody which binds to CD3. The IRES-Lc cassette is inserted into the ovomucoid UTR of a YAC-O clone to produce YAC-O-IRES-Lc.

Transgenic hens which produce egg white which includes the Lc portion of an IgG antibody that binds to CD3 are produced essentially as described in Example 7.

EXAMPLE 19

Construction of an Ovomucoid Promoter-Bacterial Artificial Chromosome Expression Vector Encoding a Monoclonal Antibody that Specifically Recognizes Phosphatidylinositol-3,4-Bisphosphate Two vectors are constructed to include a cassette comprising an IRES attached to the coding sequence of either the light chain or the heavy chain of a monoclonal antibody that specifically recognizes phosphatidylinositol-3,4-bisphosphate. The coding sequences are produced by assembling synthetic oligonucleotides to form two double stranded DNA segments which encode the amino acid sequence of either the antibody light chain (LC) or heavy chain (HC). Sequences for this particular antibody are disclosed in, for example, U.S. Pat. No. 6,709,833, the disclosure of which is incorporated in its entirety herein by reference. The IRES-LC cassette and IRES-HC cassette are each inserted into an OMC24 clone essentially as described in Example 6.

Transgenic hens which produce egg white that includes a monoclonal antibody that specifically recognizes phosphatidylinositol-3,4-bisphosphate are produced essentially as described in Example 7.

All references cited herein are incorporated by reference herein in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

While this invention has been described with respect to various specific examples and embodiments, it is to be understood that the invention is not limited thereto and that it can be variously practiced with the scope of the following claims.

What is claimed is:

1. A nucleic acid molecule comprising an ovomucoid gene expression controlling region isolated from a chicken which comprises a nucleotide sequence 95% homologous to nucleotides 1 to 68,295 of SEQ ID NO: 36.

2. The nucleic acid molecule of claim 1 wherein the nucleic acid is DNA.

3. The nucleic acid molecule of claim 1 comprising an attB site.

4. The nucleic acid molecule of claim 1 comprising a signal sequence coding region.

5. The nucleic acid of claim 1 comprising an artificial chromosome.

6. The nucleic acid of claim 1 comprising an IRES.

7. The nucleic acid molecule of claim 1 comprising an artificial chromosome selected from the group consisting of a BAC (bacterial artificial chromosome), YAC (yeast artificial chromosome), HAC (human artificial chromosome), MAC (mammalian artificial chromosome), BBPAC (bacteriophage derived artificial chromosome) and PAC (P1 derived artificial chromosome).

8. The nucleic acid of claim 1 wherein the ovomucoid gene expression controlling region comprises a sequence at least 99% homologous to nucleotides 1 to 68,295 of SEQ ID NO: 36.

9. The nucleic acid of claim 1 wherein the ovomucoid gene expression controlling region comprises a the sequence of nucleotides 1 to 68,295 of SEQ ID NO: 36.

10. The nucleic acid molecule of claim 1 comprising a nucleotide sequence encoding a polypeptide other than ovomucoid protein operably linked to the ovomucoid gene expression controlling region.

11. The nucleic acid molecule of claim 1 wherein a nucleotide sequence encoding a protein of pharmaceutical interest is operably linked to the ovomucoid gene expression controlling region.

12. The nucleic acid molecule of claim 1 wherein a nucleotide sequence encoding a light chain or a heavy chain of an antibody is operably linked to the ovomucoid gene expression controlling region.

13. The nucleic acid molecule of claim 12 wherein the antibody is selected from the group consisting of IgG, IgA, IgD, IgM and IgE.

14. The nucleic acid molecule of claim 12 wherein the antibody is IgG.

15. The nucleic acid molecule of claim 12 wherein the antibody is IgG1.

16. The nucleic acid molecule of claim 1 wherein a nucleotide sequence encoding a portion of light chain or portion of a heavy chain of an antibody is operably linked to the ovomucoid gene expression controlling region.

17. The nucleic acid molecule of claim 16 wherein the antibody is selected from the group consisting of IgG, IgA, IgD, IgM and IgE.

18. The nucleic acid molecule of claim 16 wherein the antibody is IgG.

19. The nucleic acid molecule of claim 16 wherein the antibody is IgG1.

20. The nucleic acid molecule of claim 1 wherein a nucleotide sequence encoding a hormone is operably linked to the ovomucoid gene expression controlling region.

21. A nucleic acid molecule comprising an ovomucoid gene expression controlling region isolated from a chicken which comprises a nucleotide sequence 95% homologous to nucleotides 1 to 68,295 of SEQ ID NO: 36 and a coding sequence encoding a polypeptide other than ovomucoid wherein the polypeptide other than ovomucoid protein is operably linked to the ovomucoid gene expression controlling region.

22. The nucleic acid molecule claim 21 wherein the nucleic acid is DNA.

23. The nucleic acid molecule of claim 21 comprising an attB site.

24. The nucleic acid molecule of claim 21 comprising a signal sequence coding region.

25. The nucleic acid molecule of claim 21 comprising an IRES.

26. The nucleic acid of claim 21 comprising an artificial chromosome.

27. The nucleic acid molecule of claim 21 comprising an artificial chromosome selected from the group consisting of a BAG (bacterial artificial chromosome), YAC (yeast artificial chromosome), HAC (human artificial chromosome), MAC (mammalian artificial chromosome), BBPAC (bacteriophage derived artificial chromosome) and PAC (P1 derived artificial chromosome).

28. The nucleic acid molecule of claim 21 wherein the ovomucoid gene expression controlling region comprises a sequence at least 99% homologous to nucleotides 1 to 68,295 of SEQ ID NO: 36.

29. The nucleic acid of claim 21 wherein the ovomucoid gene expression controlling region comprises a the sequence of nucleotides 1 to 68,295 of SEQ ID NO: 36.

30. A cell in culture containing the nucleic acid molecule of claim 21.

31. The nucleic acid molecule of claim 21 wherein the polypeptide is a fusion protein.

32. The nucleic acid molecule of claim 21 wherein the polypeptide is a CTLA4-Fc fusion protein.

33. The nucleic acid molecule of claim 21 wherein a nucleotide sequence encoding a protein of pharmaceutical interest is operably linked to the ovomucoid gene expression controlling region.

34. The nucleic acid molecule of claim 21 wherein a nucleotide sequence encoding a light chain or a heavy chain of an antibody is operably linked to the ovomucoid gene expression controlling region.

35. The nucleic acid molecule of claim 34 wherein the antibody is selected from the group consisting of IgG, IgA, IgD, IgM and IgE.

36. The nucleic acid molecule of claim 34 wherein the antibody is IgG.

37. The nucleic acid molecule of claim 34 wherein the antibody is IgG1.

38. The nucleic acid molecule of claim 21 wherein a nucleotide sequence encoding a portion of light chain or portion of a heavy chain of an antibody is operably linked to the ovomucoid gene expression controlling region.

39. The nucleic acid molecule of claim 38 wherein the antibody is selected from the group consisting of IgG, IgA, IgD, IgM and IgB.

40. The nucleic acid molecule of claim 38 wherein the antibody is IgG.

41. The nucleic acid molecule of claim 38 wherein the antibody is IgG1.

42. The nucleic acid molecule of claim 21 wherein a nucleotide sequence encoding a hormone is operably linked to the ovomucoid gene expression controlling region.

* * * * *

SEQUENCE LISTING

```
<160> NUMBER OF SEQ ID NOS: 46

<210> SEQ ID NO 1
<211> LENGTH: 30
<212> TYPE: DNA
<213> ORGANISM: Artificial Sequence
<220> FEATURE:
<223> OTHER INFORMATION: Primer OVINs2

<400> SEQUENCE: 1

taggcagagc aataggactc tcaacctcgt                                  30


<210> SEQ ID NO 2
<211> LENGTH: 30
<212> TYPE: DNA
<213> ORGANISM: Artificial Sequence
<220> FEATURE:
<223> OTHER INFORMATION: Primer OVMa2

<400> SEQUENCE: 2

aagcttctgc agcactctgg gagttactca                                  30


<210> SEQ ID NO 3
<211> LENGTH: 20
<212> TYPE: DNA
<213> ORGANISM: Artificial Sequence
<220> FEATURE:
<223> OTHER INFORMATION: Primer OVINs1

<400> SEQUENCE: 3

gggaaacaat ctgccttgca                                              20


<210> SEQ ID NO 4
<211> LENGTH: 21
<212> TYPE: DNA
<213> ORGANISM: Artificial Sequence
<220> FEATURE:
<223> OTHER INFORMATION: Primer OVMUa1
```

-continued

<400> SEQUENCE: 4
aagccacaaa gcacgaaaga g 21

<210> SEQ ID NO 5
<211> LENGTH: 20
<212> TYPE: DNA
<213> ORGANISM: Artificial Sequence
<220> FEATURE:
<223> OTHER INFORMATION: Primer T3

<400> SEQUENCE: 5
taatacgact cactataggg 20

<210> SEQ ID NO 6
<211> LENGTH: 20
<212> TYPE: DNA
<213> ORGANISM: Artificial Sequence
<220> FEATURE:
<223> OTHER INFORMATION: Primer T7

<400> SEQUENCE: 6
attaaccctc actaaaggga 20

<210> SEQ ID NO 7
<211> LENGTH: 20
<212> TYPE: DNA
<213> ORGANISM: Artificial Sequence
<220> FEATURE:
<223> OTHER INFORMATION: Primer OVINs4

<400> SEQUENCE: 7
agatgaggtg gatggtttac 20

<210> SEQ ID NO 8
<211> LENGTH: 20
<212> TYPE: DNA
<213> ORGANISM: Artificial Sequence
<220> FEATURE:
<223> OTHER INFORMATION: Primer OVINs5

<400> SEQUENCE: 8
cagcttctgc tagcgtaggt 20

<210> SEQ ID NO 9
<211> LENGTH: 20
<212> TYPE: DNA
<213> ORGANISM: Artificial Sequence
<220> FEATURE:
<223> OTHER INFORMATION: Primer OVINs6

<400> SEQUENCE: 9
acgtgaactc aaagaggcac 20

<210> SEQ ID NO 10
<211> LENGTH: 20
<212> TYPE: DNA
<213> ORGANISM: Artificial Sequence
<220> FEATURE:
<223> OTHER INFORMATION: Primer OVINs7

<400> SEQUENCE: 10
atctcctgag ctcggtgctt 20

<210> SEQ ID NO 11
<211> LENGTH: 20

-continued

<212> TYPE: DNA
<213> ORGANISM: Artificial Sequence
<220> FEATURE:
<223> OTHER INFORMATION: Primer OVINs8

<400> SEQUENCE: 11
acgaggttcc atgtctttca 20

<210> SEQ ID NO 12
<211> LENGTH: 31
<212> TYPE: DNA
<213> ORGANISM: Artificial Sequence
<220> FEATURE:
<223> OTHER INFORMATION: Primer OVMUa3

<400> SEQUENCE: 12
taaatagcac agaacgctga ggggagtaag g 31

<210> SEQ ID NO 13
<211> LENGTH: 20
<212> TYPE: DNA
<213> ORGANISM: Artificial Sequence
<220> FEATURE:
<223> OTHER INFORMATION: Primer OVMUa4

<400> SEQUENCE: 13
gaagagcttg gtagaagact 20

<210> SEQ ID NO 14
<211> LENGTH: 21
<212> TYPE: DNA
<213> ORGANISM: Artificial Sequence
<220> FEATURE:
<223> OTHER INFORMATION: Primer OVMUa5

<400> SEQUENCE: 14
atggaaatat gggtttcctt c 21

<210> SEQ ID NO 15
<211> LENGTH: 20
<212> TYPE: DNA
<213> ORGANISM: Artificial Sequence
<220> FEATURE:
<223> OTHER INFORMATION: Primer OVMUa6

<400> SEQUENCE: 15
gcagcttatg gctaatcgct 20

<210> SEQ ID NO 16
<211> LENGTH: 20
<212> TYPE: DNA
<213> ORGANISM: Artificial Sequence
<220> FEATURE:
<223> OTHER INFORMATION: Primer OVMUa7

<400> SEQUENCE: 16
agtgaccact atctgacctg 20

<210> SEQ ID NO 17
<211> LENGTH: 20
<212> TYPE: DNA
<213> ORGANISM: Artificial Sequence
<220> FEATURE:
<223> OTHER INFORMATION: Primer OVMUa8

<400> SEQUENCE: 17

-continued taatcaggaa ggcacacagc 20

<210> SEQ ID NO 18
<211> LENGTH: 20
<212> TYPE: DNA
<213> ORGANISM: Artificial Sequence
<220> FEATURE:
<223> OTHER INFORMATION: Primer OVMUP4. 7. 1

<400> SEQUENCE: 18
agatctggag cagcacttgt 20

<210> SEQ ID NO 19
<211> LENGTH: 20
<212> TYPE: DNA
<213> ORGANISM: Artificial Sequence
<220> FEATURE:
<223> OTHER INFORMATION: Primer OVMUP4. 7. 2

<400> SEQUENCE: 19
agcatgaagt tcctcaccca 20

<210> SEQ ID NO 20
<211> LENGTH: 20
<212> TYPE: DNA
<213> ORGANISM: Artificial Sequence
<220> FEATURE:
<223> OTHER INFORMATION: Primer OVMUP4. 7. 3

<400> SEQUENCE: 20
atggagagga atattccctt 20

<210> SEQ ID NO 21
<211> LENGTH: 18
<212> TYPE: DNA
<213> ORGANISM: Artificial Sequence
<220> FEATURE:
<223> OTHER INFORMATION: Primer OVMUP4. 7. 4

<400> SEQUENCE: 21
atttctccag gcgtgtgg 18

<210> SEQ ID NO 22
<211> LENGTH: 18
<212> TYPE: DNA
<213> ORGANISM: Artificial Sequence
<220> FEATURE:
<223> OTHER INFORMATION: Primer OVMUP5. 5. 1

<400> SEQUENCE: 22
atttctccag gcgtgtgg 18

<210> SEQ ID NO 23
<211> LENGTH: 20
<212> TYPE: DNA
<213> ORGANISM: Artificial Sequence
<220> FEATURE:
<223> OTHER INFORMATION: Primer VMUP5. 5. 2

<400> SEQUENCE: 23
atgcgagtga aggagagttc 20

<210> SEQ ID NO 24
<211> LENGTH: 20
<212> TYPE: DNA
<213> ORGANISM: Artificial Sequence -continued
<220> FEATURE:
<223> OTHER INFORMATION: Primer OVMUP5. 5. 3

<400> SEQUENCE: 24
gcagcacgtg taagcttgta 20

<210> SEQ ID NO 25
<211> LENGTH: 20
<212> TYPE: DNA
<213> ORGANISM: Artificial Sequence
<220> FEATURE:
<223> OTHER INFORMATION: Primer OVMUP5. 5. 4

<400> SEQUENCE: 25
caaggcaaat tatcagcaga 20

<210> SEQ ID NO 26
<211> LENGTH: 9980
<212> TYPE: DNA
<213> ORGANISM: Gallus gallus
<220> FEATURE:
<221> NAME/KEY: 3'UTR
<222> LOCATION: (1)..(255)
<223> OTHER INFORMATION: 3' untranslated region of ovoinhibitor
<220> FEATURE:
<221> NAME/KEY: misc_feature
<222> LOCATION: (2761)..(3024)
<223> OTHER INFORMATION: CR1-like element
<220> FEATURE:
<221> NAME/KEY: 5'UTR
<222> LOCATION: (9403)..(9920)
<223> OTHER INFORMATION: 5' untranslated region of ovomucoid

<400> SEQUENCE: 26
taggcagagc aataggactc tcaacctcgt gagtatggca gcatgttaac tctgcactgg 60
agtccagcgt gggaaacaat ctgccttgca catgagtctt cgtgggccaa tattccccaa 120
cggttttcct tcagcttgtc ttgtctccta agctctcaaa acaccttttt ggtgaataaa 180
ctcacttggc aacgtttatc tgtcttacct tagtgtcacg tttcatccct attccccttt 240
ctcctcctcc gtgtggtaca cagtggtgca cactggttct tctgttgatg ttctgctctg 300
acagccaatg tgggtaaagt tcttcctgcc acgtgtctgt gttgttttca cttcaaaaag 360
ggccctgggc tccccttgga gctctcaggc atttccttaa tcatcacagt cacgctggca 420
ggattagtcc ctcctaaacc ttagaatgac ctgaacgtgt gctccctctt tgtagtcagt 480
gcagggagac gtttgcctca agatcagggt ccatctcacc cacagggcca ttcccaagat 540
gaggtggatg gtttactctc acaaaaagtt ttcttatgtt tggctagaaa ggagaactca 600
ctgcctacct gtgaattccc ctagtcctgg ttctgctgcc actgctgcct gtgcagcctg 660
tcccatggag ggggcagcaa ctgctgtcac aaaggtgatc ccaccctgtc tccactgaaa 720
tgacctcagt gccacgtgtt gtataggcta taaagtacgg gagggggatg cccggctccc 780
ttcagggttg cagagcagaa gtgtctgtgt atagagtgtg tcttaatcta ttaatgtaac 840
agaacaactt cagtcctagt gttttgtggg ctggaattgc ccatgtggta gggacaggcc 900
tgctaaatca ctgcaatcgc ctatgttctg aaggtatttg ggaaagaaag ggatttgggg 960
gattgcctgt gattggcttt aattgaatgg caaatcacag gaaagcagtt ctgctcaaca 1020
gttggttgtt tcagccaatt cttgcagcca aagagccggg tgcccagcga tataatagtt 1080
gtcacttgtg tctgtatgga tgacagggag gtagggtgac ctgaggacca ccctccagct 1140
tctgctagcg taggtacagt caccacctcc agctccacac gagtcccatc gtggtttacc 1200

-continued

```
aaagaaacac aattatttgg accagtttgg aaagtcaccc gctgaattgt gaggctagat   1260
taatagagct gaagagcaaa tgttcccaac ttggagatac tagttggtat tagtatcaga   1320
ggaacagggc catagcacct ccatgctatt agattccggc tggcatgtac ttttcaagat   1380
gatttgtaac taacaatggc ttattgtgct tgtcttaagt ctgtgtccta atgtaaatgt   1440
tcctttggtt tatataacct tcttgccatt tgctcttcag gtgttcttgc agaacactgg   1500
ctgctttaat ctagtttaac tgttgcttga ttattcttag ggataagatc tgaataaact   1560
ttttgtggct ttggcagact ttagcttggg cttagctccc acattagctt ttgctgcctt   1620
ttctgtgaag ctatcaagat cctactcaat gacattagct gggtgcaggt gtaccaaatc   1680
ctgctctgtg gaacacattg tctgatgata ccgaaggcaa acgtgaactc aaagaggcac   1740
agagttaaga agaagtctgt gcaattcaga ggaaaagcca aagtggccat tagacacact   1800
ttccatgcag catttgccag taggtttcat ataaaactac aaaatggaat aaaccactac   1860
aaatgggaaa agcctgatac tagaatttaa atattcaccc aggctcaagg ggtgtttcat   1920
ggagtaatat cactctataa aagtagggca gccaattatt cacagacaaa gctttttttt   1980
ttctgtgctg cagtgctgtt tttcggctga tccagggtta cttattgtgg gtctgagagc   2040
tgaatgattt ctccttgtgt catgttggtg aaggagatat ggccaggggg agatgagcat   2100
gttcaagagg aaacgttgca ttttggtggc ttgggagaaa ggtagaacga tatcaggtcc   2160
atagtgtcac taagagatct gaaggatggt tttacagaac agttgacttg gctgggtgca   2220
ggcttggctg taaatggatg gaaggatgga cagatgggtg gacagagatt tctgtgcagg   2280
agatcatctc ctgagctcgg tgcttgacag actgcagatc catcccataa ccttctccag   2340
catgagagcg cggggagctt tggtactgtt cagtctgctg cttgttgctt cctgggtgca   2400
cagtggtgat tttcttactc acacagggca aaaacctgag cagcttcaaa gtgaacaggt   2460
tgctctcata ggccattcag ttgtcaagat gaggtttttg gtttcttgtt ttgtaaggtg   2520
ggaagaagca ctgaaggatc agttgcgagg gcaggggttt agcactgttc agagaagtct   2580
tattttaact cctctcatga acaaaaagag atgcaggtgc agattctggc aagcatgcag   2640
tgaaggagaa agccctgaat ttctgatata tgtgcaatgt tgggcaccta acattccccg   2700
ctgaagcaca gcagctccag ctccatgcag tactcacagc tggtgcagcc ctcggctcca   2760
gggtctgagc agtgctggga ctcacgaggt tccatgtctt tcacactgat aatggtccaa   2820
tttctggaat gggtgcccat ccttggaggt ccccaaggcc aggctggctg cgtctccgag   2880
cagcccgatc tggtggtgag tagccagccc atggcaggag ttagagcctg atggtcttta   2940
aggtcccttc caacctaagc catcctacga ttctaggaat catgacttgt gagtgtgtat   3000
tgcagaggca atattttaaa gttataaatg ttttctcccc ttccttgttt gtcaaagtta   3060
tcttgatcgc cttatcaatg cttttggagt ctccagtcat ttttcttaca mcaaaaagag   3120
gaggaagaat gaagagaatc atttaatttc ttgattgaat agtaggattc agaaagctgt   3180
acgtaatgcc gtctctttgt atcgagctgt aaggtttctc atcatttatc agcgtggtac   3240
atatcagcac ttttccatct gatgtggaaa aaaaaatcct tatcatctac agtctctgta   3300
cctaaacatc gctcagactc tttaccaaaa aagctatagg ttttaaaact acatctgctg   3360
ataatttgcc ttgttttagc tcttcttcca tatgctgcgt ttgtgagagg tgcgtggatg   3420
ggcctaaact ctcagctgct gagcttgatg ggtgcttaag aatgaagcac tcactgctga   3480
aactgttttc atttcacagg aatgttttag tggcattgtt tttataacta catattcctc   3540
agataaatga aatccagaaa taattatgca aactcactgc atccgttgca caggtcttta   3600
```

-continued

```
tctgctagca aaggaaataa tttggggatg gcaaaaacat tccttcagac atctatattt   3660
aaaggaatat aatcctggta cccacccact tcatccctca ttatgttcac actcagagat   3720
actcattctc ttgttgttat catttgatag cgttttcttt ggttctttgc cacgctctgg   3780
gctatggctg cacgctctgc actgatcagc aagtagatgc gagggaagca gcagtgagag   3840
gggctgccct cagctggcac ccagccgctc agcctaggag gggaccttgc ctttccacca   3900
gctgaggtgc agccctacaa gcttacacgt gctgcgagca ggtgagcaaa gggagtcttc   3960
atggtgtgtt tcttgctgcc cggaagcaaa actttacttt cattcattcc ccttgaagaa   4020
tgaggaatgt ttggaaacgg actgctttac gttcaatttc tctcttccct ttaaggctca   4080
gccaggggcc attgctgagg acggcatcgg ggcccccctgg accaaatctg tggcacagat   4140
ggtttcactt acatcagtgg atgtgggatc tgcgcctgta atgtgtcctt ctgaaggaag   4200
gaacgtgcct tccaagtgcc agccccacag cccccagccc ctccctgtgc tgctccaatt   4260
catctcctct tcctccttct ccctttgctg tttgtgctcg ggtagaaatc atgaagattt   4320
agaagagaaa acaaaataac tggagtggaa acccaggtga tgcagttcat tcagctgtca   4380
taggtttgtc gttgctatag gtctgtatca gagatgctar caccactttg ctgtcggtgc   4440
ttaactcggg tgaactctcc ttcactcgca tcatttgcgg gccttattta catccccagc   4500
atccatcacc ctctgggaaa atgggcgcac tggatctcta atggaagact ttccctcttt   4560
cagagcctgt gggatgtgca gtgacaagaa acgtggaggg gctgagcagc agcactgccc   4620
ccagggagca ggagcggatg ccatcggtgg cagcatccca aatgatgtca gcggatgctg   4680
agcaggcagc ggacgaacgg acagaagcga tgcgtacacc ttctgttgac atggtatttg   4740
gcagcgattt aacactcgct tcctagtcct gctattctcc acaggctgca ttcaaatgaa   4800
cgaagggaag ggaggcaaaa agatgcaaaa tccgagacaa gcagcagaaa tatttcttcg   4860
ctacggaagc gtgcgcaaac aaccttctcc aacagcacca gaagagcaca gcgtaacctt   4920
tttcaagacc agaaaaggaa attcacaaag cctctgtgga taccagcgcg ttcagctctc   4980
ctgatagcag atttcttgtc aggttgcgaa tggggtatgg tgccaggagg tgcagggacc   5040
atatgatcat atacagcaca gcagtcattg tgcatgtatt aatatatatt gagtagcagt   5100
gttactttgc caaagcaata gttcagagat gagtcctgct gcatacctct atcttaaaac   5160
taacttataa atagtaaaac cttctcagtt cagccacgtg ctcctctctg tcagcaccaa   5220
tggtgcttcg cctgcaccca gctgcaagga atcagcccgt gatctcatta acactcagct   5280
ctgcaggata aattagattg ttccactctc ttttgttgtt aattacgacg gaacaattgt   5340
tcagtgctga tggtcctaat tgtcagctac agaaaacgtc tccatgcagt tccttctgcg   5400
ccagcaaact gtccaggcta tagcaccgtg atgcatgcta cctctcactc catccttctt   5460
ctctttccca ccagggagag ctgtgtgttt tcactctcag ccactctgaa caataccaaa   5520
ctgctacgca ctgcctccct cggaaagaga atccccttgt tgcttttttta tttacaggat   5580
ccttcttaaa aagcagacca tcattcactg caaacccaga gcttcatgcc tctccttcca   5640
caaccgaaaa cagccggctt catttgtctt ttttaaatgc tgttttccag gtgaattttg   5700
gccagcgtgt tggctgagat ccaggagcac gtgtcagctt tctgctctca ttgctcctgt   5760
tctgcattgc ctctttctgg ggtttccaag agggggggag actttgcgcg gggatgagat   5820
aatgcccctt ttcttagggt ggctgctggg cagcagagtg gctctgggtc actgtggcac   5880
caatgggagg caccagtggg ggtgtgtttt gtgcaggggg gaagcattca cagaatgggg   5940
```

-continued ctgatcctga agcttgcagt ccaaggcttt gtctgtgtac ccagtgaaat ccttcctctg 6000
ttacataaag cccagatagg actcagaaat gtagtcattc cagcccccct cttcctcaga 6060
tctggagcag cacttgtttg cagccagtcc tccccaaaat gcacagacct cgccgagtgg 6120
agggagatgt aaacagcgaa ggttaattac ctccttgtca aaaacacttt gtggtccata 6180
gatgtttctg tcaatcttac aaaacagaac cgagaggcag cgagcactga agagcgtgtt 6240
cccatgctga gttaatgaga cttggcagct cgctgtgcag agatgatccc tgtgcttcat 6300
gggaggctgt aacctgtctc cccatcgcct tcacaccgca gtgctgtcct ggacacctca 6360
ccctccataa gctgtaggat gcagctgccc agggatcaag agacttttcc taaggctctt 6420
aggactcatc tttgccgctc agtagcgtgc agcaattact catcccaact atactgaatg 6480
ggtttctgcc agctctgctt gtttgtcaat aagcatttct tcattttgcc tctaagtttc 6540
tctcagcagc accgctctgg gtgacctgag tggccacctg gaacccgagg ggcacagcca 6600
ccacctccct gttgctgctg ctccagggac tcatgtgctg ctggatgggg ggaagcatga 6660
agttcctcac ccagacacct gggttgcaat ggctgcagcg tgctcttctt ggtatgcaga 6720
ttgtttccag ccattacttg tagaaatgtg ctgtggaagc cctttgtatc tctttctgtg 6780
gcccttcagc aaaagctgtg ggaaagctct gaggctgctt tcttgggtcg tggaggaatt 6840
gtatgttcct tctttaacaa aaattatcct taggagagag cactgtgcaa gcattgtgca 6900
cataaaacaa ttcaggttga aagggctctc tggaggtttc cagcctgact actgctcgaa 6960
gcaaggccag gttcaaagat ggctcaggat gctgtgtgcc ttcctgatta tctgtgccac 7020
caatggagga gattcacagc cactctgctt cccgtgccac tcatggagag gaatattccc 7080
ttatattcag atagaatgtt atcctttagc tcagccttcc ctataacccc atgagggagc 7140
tgcagatccc catactctcc ccttctctgg ggtgaaggcc gtgtccccca gccccccttc 7200
ccaccctgtg ccctaagcag cccgctggcc tctgctggat gtgtgcctat atgtcaatgc 7260
ctgtccttgc agtccagcct gggacattta attcatcacc agggtaatgt ggaactgtgt 7320
catcttcccc tgcagggtac aaagttctgc acggggtcct ttcggttcag gaaaaccttc 7380
actggtgcta cctgaatcaa gctctattta ataagttcat aagcacatgg atgtgttttc 7440
ctagagatac gttttaatgg tatcagtgat ttttatttgc tttgttgctt acttcaaaca 7500
gtgcctttgg gcaggaggtg agggacgggt ctgccgttgg ctctgcagtg atttctccag 7560
gcgtgtggct caggtcagat agtggtcact ctgtggccag aagaaggaca aagatggaaa 7620
ttgcagattg agtcacgtta agcaggcatc ttggagtgat ttgaggcagt ttcatgaaag 7680
agctacgacc acttattgtt gttttcccct tttacaacag aagttttcat caaaataacg 7740
tggcaaagcc caggaatgtt tgggaaaagt gtagttaaat gttttgtaat tcatttgtcg 7800
gagtgctacc agctaagaaa aaagtcctac ctttggtatg gtagtcctgc agagaataca 7860
acatcaatat tagtttggaa aaaaacacca ccaccaccag aaactgtaat ggaaaatgta 7920
aaccaagaaa ttccttgggt aagagagaaa ggatgtcgta tactggccaa gtcctgccca 7980
gctgtcagcc tgctgaccct ctgcagttca ggaccatgaa acgtggcact gtaagacgtg 8040
tcccctgcct ttgcttgccc acagatctct gcccttgtgc tgactcctgc acacaagagc 8100
atttccctgt agccaaacag cgattagcca taagctgcac ctgactttga ggattaagag 8160
tttgcaatta agtggattgc agcaggagat cagtggcagg gttgcagatg aaatcctttt 8220
ctaggggtag ctaagggctg agcaacctgt cctacagcac aagccaaacc agccaagggt 8280
tttcctgtgc tgttcacaga ggcagggcca gctggagctg gaggaggttg tgctgggacc 8340

-continued cttctccctg tgctgagaat ggagtgattt ctgggtgctg ttcctgtggc ttgcactgag 8400
cagctcaagg gagatcggtg ctcctcatgc agtgccaaaa ctcgtgtttg atgcagaaag 8460
atggatgtgc acctccctcc tgctaatgca gccgtgagct tatgaaggca atgagccctc 8520
agtgcagcag gagctgtagt gcactcctgt aggtgctagg gaaaatctct ggttcccagg 8580
gatgcattca taagggcaat atatcttgag gctgcgccaa atctttctga aatattcatg 8640
cgtgttccct taatttatag aaacaaacac agcagaataa ttattccaat gcctcccctc 8700
gaaggaaacc catatttcca tgtagaaatg taacctatat acacacagcc atgctgcatc 8760
cttcagaacg tgccagtgct catctcccat ggcaaaatac tacaggtatt ctcactatgt 8820
tggacctgtg aaaggaacca tggtaagaaa cttcggttaa aggtatggct gcaaaactac 8880
tcataccaaa acagcagagc tccagacctc ctcttaggaa agagccactt ggagagggat 8940
ggtgtgaagg ctggaggtga gagacagagc ctgtcccagt tttcctgtct ctattttctg 9000
aaacgtttgc aggaggaaag gacaactgta ctttcaggca tagctggtgc cctcacgtaa 9060
ataagttccc cgaacttctg tgtcatttgt tcttaagatg ctttggcaga acactttgag 9120
tcaattcgct taactgtgac taggtctgta aataagtgct ccctgctgat aaggttcaag 9180
tgacattttt agtggtattt gacagcattt accttgcttt caagtcttct accaagctct 9240
tctatactta agcagtgaaa ccgccaagaa acccttcctt ttatcaagct agtgctaaat 9300
accattaact tcataggtta gatacggtgc tgccagcttc acctggcagt ggttggtcag 9360
ttctgctggt gacaaagcct ccctggcctg tgcttttacc tagaggtgaa tatccaagaa 9420
tgcagaactg catggaaagc agagctgcag gcacgatggt gctgagcctt agctgcttcc 9480
tgctgggaga tgtggatgca gagacgaatg aaggacctgt cccttactcc cctcagcatt 9540
ctgtgctatt tagggttcta ccagagtcct taagaggttt tttttttttt tggtccaaaa 9600
gtctgtttgt ttggttttga ccactgagag catgtgacac ttgtctcaag ctattaacca 9660
agtgtccagc caaaatcaat tgcctgggag acgcagacca ttacctggag gtcaggacct 9720
caataaatat taccagcctc attgtgccgc tgacagattc agctggctgc tccgtgttcc 9780
agtccaacag ttcggacgcc acgtttgtat atatttgcag gcagcctcgg ggggaccatc 9840
tcaggagcag agcaccggca gccgcctgca gagccgggca gtactctcac catggccatg 9900
gcaggtgtct tcgtgctgtt ctctttcgtg ctttgtggct tcctcccagg tgagtaactc 9960
ccagagtgct gcagaagctt 9980

<210> SEQ ID NO 27
<211> LENGTH: 20
<212> TYPE: DNA
<213> ORGANISM: Artificial Sequence
<220> FEATURE:
<223> OTHER INFORMATION: Primer OVMUa9

<400> SEQUENCE: 27
aaatgaagcc ggctgttttc 20

<210> SEQ ID NO 28
<211> LENGTH: 20
<212> TYPE: DNA
<213> ORGANISM: Artificial Sequence
<220> FEATURE:
<223> OTHER INFORMATION: Primer OVINs9

<400> SEQUENCE: 28

-continued

```
ctctcagcca ctctgaacaa                                              20


<210> SEQ ID NO 29
<211> LENGTH: 40
<212> TYPE: DNA
<213> ORGANISM: Artificial Sequence
<220> FEATURE:
<223> OTHER INFORMATION: Primer

<400> SEQUENCE: 29

gcgcggccgc ccgggacatg tccatggtga gagtactgcc                        40


<210> SEQ ID NO 30
<211> LENGTH: 29
<212> TYPE: DNA
<213> ORGANISM: Artificial Sequence
<220> FEATURE:
<223> OTHER INFORMATION: Primer

<400> SEQUENCE: 30

ggcccgggat tcgcttaact gtgactagg                                    29


<210> SEQ ID NO 31
<211> LENGTH: 802
<212> TYPE: DNA
<213> ORGANISM: Artificial Sequence
<220> FEATURE:
<223> OTHER INFORMATION: primer

<400> SEQUENCE: 31

gcgcggccgc ccgggacatg tccatggtga gagtactgcc cggctctgca ggcggctgcc     60

ggtgctctgc tcctgagatg gtccccccga ggctgcctgc aaatatatac aaacgtggcg    120

tccgaactgt tggactggaa cacggagcag ccagctgaat ctgtcagcgg cacaatgagg    180

ctggtaatat ttattgaggt cctgacctcc aggtaatggt ctgcgtctcc caggcaattg    240

attttggctg gacacttggt taatagcttg agacaagtgt cacatgctct cagtggtcaa    300

aaccaaacaa acagactttt ggaccaaaaa aaaaaaaaac ctcttaagga ctctggtaga    360

accctaaata gcacagaatg ctgaggggag taagggacag gtccttcatt cgtctctgca    420

tccacatctc ccagcaggaa gcagctaagg ctcagcacca tcgtgcctgc agctctgctt    480

tccatgcagt tctgcattct tggatattca cctctaggta aaagcacagg ccagggaggc    540

tttgtcacca gcagaactga ccaaccactg ccaggtgaag ctggcagcac cgtatctaac    600

ctatgaagtt aatggtattt agcactagct tgataaaagg aagggtttct tggcggtttc    660

actgcttaag tatagaagag cttggtagaa gacttgaaag caaggtaaat gctgtcaaat    720

accactaaaa atgtcacttg aaccttatca gcagggagca cttatttaca gacctagtca    780

cagttaagcg aattcccggg cc                                             802


<210> SEQ ID NO 32
<211> LENGTH: 17
<212> TYPE: DNA
<213> ORGANISM: Artificial Sequence
<220> FEATURE:
<223> OTHER INFORMATION: Primer

<400> SEQUENCE: 32

ctccacatgg ccatggc                                                 17


<210> SEQ ID NO 33
<211> LENGTH: 17
```

-continued

<212> TYPE: DNA
<213> ORGANISM: Artificial Sequence
<220> FEATURE:
<223> OTHER INFORMATION: Primer

<400> SEQUENCE: 33
gagtggtacc ggtaccg 17

<210> SEQ ID NO 34
<211> LENGTH: 17
<212> TYPE: DNA
<213> ORGANISM: Artificial Sequence
<220> FEATURE:
<223> OTHER INFORMATION: Primer

<400> SEQUENCE: 34
ctcaccatgg acatgga 17

<210> SEQ ID NO 35
<211> LENGTH: 17
<212> TYPE: DNA
<213> ORGANISM: Artificial Sequence
<220> FEATURE:
<223> OTHER INFORMATION: Primer

<400> SEQUENCE: 35
gagtggtacc ggtaccg 17

<210> SEQ ID NO 36
<211> LENGTH: 75815
<212> TYPE: DNA
<213> ORGANISM: chicken

<400> SEQUENCE: 36
aagctttgtg ctttctgcct gaataaaaga aacctgaact ctgttcaccc agtccctgtc 60
aggcaattac tgacagagca cctatggtct gtgtttggcc agaacatagg ctaaggaaga 120
tacctcctgt ttataaagca cgcctttggc atctggcaag taattagtga tggcgcatga 180
gagctctgac tagggcaggg tgtgggacag gctggctcta attgtgccct gtttatcttg 240
ttgatgcaca cggctggttt ctttcaccca cagctgtctc tctagacaac atacctttat 300
ggagaggaac gtgtcttttc caatcttggg ttttcattca gaattggagt gaactggtct 360
ccatcagata gcattggctg cggtgattta ttcttttaca cttcctagtt aagcaggata 420
actctctggc tctgctgtgt ctaggcaatt taaatgattt ataaagcata gctgttttaa 480
ggaaatcttt ttttaaacat ttgacttgcc aatgtgtggt cctaaaggca gaaggactgt 540
tccagagtgt caggcagaga cctaccctgg atttcgttgt tcagctaccc attcagtgtg 600
gcttttggca aggaattctc tggacctgac ttccctacct gcagagctgg gataagctat 660
caaaccatct cctccacaca ctgtgagggt gggaaaaaaa cccaaaccct taaaagtgct 720
gtataaaggc gccttaaggc tcagtatagc atgtgtgctg ctgatgcccc agacctgttt 780
gcgggtcctg aaggtcatag gagaactgct cagaagagac agaaatgctt aagaaggttt 840
tactacaaaa gtcttgtgat gttaacacat aatatcacat tgtgcagaag gtacaaatgc 900
cccctcctat ccctgcacac ctggaagctc aaggtatgga agggtttgtt gtctgcagcc 960
tcttcgctgc cctctgcttt ttaagatcct gggtagtgtg ctcagtgtgt gccctcagca 1020
gtttgggaaa cggacatctt catgcaaaat taagcaagga agtgttgctt ttatactcag 1080
agtagaatct aagttcttca ggcaggctct tgtgtgccgc ctctattaga aataaaactc 1140

-continued

```
ccccggatca gaagatgaat gtgctcagct aagaacacag atttatttgc tttacaatgc   1200
gtgctatggt ttaagaaaaa cacatcaggc aaacaattta tggtttgcca ctgagttgtg   1260
cctgaaggaa acacaactgt tagagatgta attgattggg cggtgacgct gtgtggattc   1320
atgggagatg catcttggtc agcatgtctg tgtgaaacca catttctggt gctgctgcag   1380
gacgagtgcc gggagttccg ggatctgttc aagaatggga agctttcctg cacgagggag   1440
aatgatcccg tccgggattc ctcggggaag cagcacagca ataagtgcat catgtgtgcg   1500
gagaagttgt gagtagagga agccaatgtt tgttatcgag agtggcaatg gggccggggt   1560
gggctcctac agcaatgttc tcctcacttt ctcatccttc tctttcagca aaagggagaa   1620
tgagcagaag gcgacctcaa ccagagggaa acaaaaggtg aggttaaagt attgggttca   1680
tatacaagtc tataggattc ttacccaata ttaccacact tgatttcttt gtcactctgg   1740
ggatccatgt ggcttttcct gcttgtatct cgttgatgct ctttcatgcc ctgagagaat   1800
agtttgtctg aacgctgcag tctatcccac tgaccgcagt gacatgggag caaaccccat   1860
cgcaataaga agctgagcag aactgccctg acatctggca caagggcaag aaggcactgc   1920
tgctgagagc gctaatgagg ttgaaaagaa aatctgggtg agaagcttta aatgtgagct   1980
ctgagatgct caaaagttca ttatgtcgtg ggaggagagt tcagccctgt gctgtccctg   2040
gggtggctcg gtttcagctt tccctgattg gaaacctcac tctcatgatg cagctgctgt   2100
gcccttgtgc accgatactt ctctggtgag agcaattcag caaggggaag gaaaaagaag   2160
cactaagtaa atcttgccat ttctgtcttg cgaggaactg gtacggtccc cttaagcctc   2220
attcttgggg ataatcctgt ttcagtgctt ttcctaatga cagtggcaca aaaaaaatgg   2280
aagcgttaat gaaacttgct gatggcaaag ctgggaggga ggatcagcag atcactcagg   2340
actaattgga tagcactgag gcctggagta atagaaacaa gataaaatgt aataacagag   2400
agtgcaagat cacacaggca gtgattaacg agaattcctg ctcatcaatt agaaatgaca   2460
aaggataaga aagctctgca tttattagtg ggtcacggat gcggcaggcc tgagaaggag   2520
gcaaatgcac atctcagcaa ggtctgtgca gcagaggtcg ggctggcagc aaatctccag   2580
aaatactgct ttgaagagag agggtttgag agacgctgtt agggagaagc agctctgcca   2640
cagcaggtct ggggttcacc tggggtttgg ctcattgcct ccctgtgtcc ctcctccacg   2700
ctgccagtgc tgcactggga aggtgtgggt aagaagcaat ggctaaggga tctggttata   2760
cacctcctgt atctgctatt tgggattggc tactgcaggg cctcaggtcc ctgacttaaa   2820
agtggggact tcgaagcatg tttgcattgt gctgtcgtgc cttagatgtt gctgctgggt   2880
cctcaaagtc ctgttggttg tggggtgggg gggacttctt gcttcctatg tgaagttttc   2940
tgagctgcaa cttcagcaac agctgtaaga gtgcattaag ggcagtggga gaagtgggag   3000
ggaccccatt acctcatcgg gtatcgctgg catgctttgg atagccccac gtggagcgtg   3060
acaattagag cacggcagag agctcccaac acgtgccatg caggcagagg cacccgccgc   3120
tcttctgact cactctgttt gtagccatga ggctgtgcca cgtgccctct tctctctctc   3180
acacctgggc tctcctgggg cgcgtttggg aagcctctgg aggatcggag ggatgtggca   3240
gggtgccctg actgctgctc cttccgcagg atgactgcag tgagtaccgc tcccagtttg   3300
aggctggcgg acgcctgtcc tgcacgcggg agaacgaccc cgtcagggat tcctctggca   3360
agcagcacac caacaagtgc ctcatgtgtg ccgagaagct gtgagtacag ttcctggcaa   3420
cagcaaagag ggaaacctca cattgcgaaa ctgcagcttc tgcctgtgtg gctgcgcctg   3480
ggggagtccc gagtcccagc ggccccccag gagctgctcc tgctgtaggg ctgtggctac   3540
```

-continued

```
tgcccctctt cccacctccc ccctaacccc tcagggagca gaggagaagc agggttgata   3600
gagagcagcc ctttccttgg ggcagctccc aaggaaagtt tcccacgcgt gtactttgcc   3660
ttccagatgc tctctctact cccatagagc atatgcagaa gcagccctga tatgaaagca   3720
gccacctgga gccgggatgt agcatacagt gggaatggtg aggagaaggg agaaggctta   3780
ggggtgggaa ttaggtgcag ggccaccagg gatggggagg ctggtgccta atgacatgat   3840
gctggcttgc agggcagccc caggtcctgg cagcgttcgc actgccatag tgctcctttc   3900
tttctcctct cccttttttc cagcaaaaaa gaagctcaaa gaggaggtca gtctggtgga   3960
actgcccagc gcaacaagca gtccactgca gagtgtgcaa accaggtgag actgagctca   4020
gagcctcacc aggcttggga aaaggggttg gtggatctgg ggaccccgat ggtcaagggc   4080
tgcctgtggt cctggtgttt ggggtgcagg agcctgctgg tgatggcaga gaggcaggtt   4140
gcattgcaag ccctgctagt tcatgggatg ggtttgtgta tgagcgtgca tagtgggcag   4200
ttctggactc ctctatgggg cacgcatcag agctatttct tcagaaagag ccccatggtt   4260
cctagggtcc agggggatga gagggaagga caggagctgc tttaatctca ctgctttact   4320
gcttggttgt caaacacgat cctgcccctt ttccagaaga gctgcagtgg ctcagggtta   4380
cagcggggtg taaatgagag acggccgttc tccacaaaca gagggtgagt acagcagcac   4440
tgggatccca gcctggcccc acaagtcctg gggtcttgac actgagaaga aacacataaa   4500
atagggcata tacaaccctt tctcctttcc aaagacattc ttgcttcccc tgcacacgaa   4560
gcactggtga ctgctacact caaaatccct ccccagcctt gccccctgaa tcctgcctcc   4620
tggcaggcac acacttgtcc tgctgcctgg tccagcgcat cctcatctgc tgacctgagg   4680
cagtgctgtg tgtgcaccat gtgctgtctg ggcactgagc gactcctctg ggtttttagg   4740
gctgccaggc tctggcaggg tgcagatgct gtgttatcta agccttgagg aactctctta   4800
gtcttcctgt ttttgttggt gaggcccatt catctgcccc cagtcagcac tgccagcaga   4860
caaacagtgc acagctctcc atggcagcaa tggctgtagc atatgtaggg gccaggtttc   4920
tgggatcatc tctgtgacgg acatctcttg ctgaccgccc ataaggactc aaaagtcccg   4980
ttgcagggag tgcctccatc ccatggcaag ccaagtgccc tgttgaaaaa acaaggtgca   5040
gaataatggc aatggacctt agtgcagttt aattccaccc tggggtgatg atgtggctga   5100
gtgggtctgc atacccttgg ctgtgccatg agctctgtgc tttctctccc tgccagccca   5160
caaggagact tggctcagga ctgcagcccg gcacctggcc gccagggaca gagcggaggc   5220
accaacacct accagccggt atgcccagct catgtgggtc aggcacagcc tttcccagca   5280
gctgccccag tttccattgt caacctaaag cctcacaatg ggacctgtat ccttggaggg   5340
gtttaaatgg gtggtagagt ccgtaccctg atgctgtccc ctggcctcaa agaggagtga   5400
ggctgcacac gtccaaacgg gagtcactga agccagtgct gctgctggtg ttggctcact   5460
gtagaagtat gtcaggtatg agagagcatc ctccaggagg tgatggtggt gtcccttcct   5520
gcatgctgag atgttgggtt gaagactgtg gccagagcag ggtgctgggg ctgagcgggg   5580
gataaggaca aggctgataa gaggagggga gagggagtag tgggggagga cacggtgagc   5640
aatagataac gactgtttgt ggaatcatgt gggagggaga agagggtgta tgctctctcc   5700
atctccacaa aaagaaaatt tgttattttc aaccaagcta aagcagaaat tatgaaacta   5760
ataggagaaa ataagttact ataaaaagga tgactaacct gtggatcttg ctgtcacggg   5820
gtgttgccaa gagctacagt gattaaaaaa aatgacttgc cacttatagt ccatacagca   5880
```

-continued

```
atttaggtaa cattttggaa gggataggaa atgcctttct gtggggctgg agggacctga   5940
gtgcagactg ccttaactct ctctgaagtc tctgtcactg actgccctta gaaaaatgat   6000
attagaatag aaaaaccagg gaggcggttc aggtatggca gttttaatgc attccagagg   6060
aagcattagg cataataatg ccagtctgct tcagggctta gtggtatttc ctggtagctc   6120
cggtgaagga gtggatgctg atcagcctga ctgacgaggg gtgattcaga gagcagatct   6180
gtgtctctcc tcgctgcagg gccacccgtg ggctctgtcc cagggagatg ctgtcctgaa   6240
ggagaggtgg cagtcactgt gaggactgtg gggactgtt ggtgtggcgg cggttgcaca   6300
cgcgtgggtc acaccgtggg cagtggtgtc tggtgtgtgg gaaggcatct ggcagggaac   6360
tgcaaaggtc agcgctgtct gtctttgtgt catcgttaat tacccaggtg agggaggaag   6420
cagcacatta atgaaattag caagtgatgt ttaaacagag ggtgttactg cagcaacctg   6480
tgccactgaa ccccctgcat tgcccagctg ggaaaccttt cttctccatg gtgctttcaa   6540
ccccatagtg ctgctgaccc cagcaaagca atgagccatt gcttagtgct gaatggggtt   6600
ttttttctcc aagtgggaca ggaggtgaga tgtccttcct gcagctcttc tccaattgca   6660
ccatttgcag tcattgcaac attttttata ggacctggag aaggggatgg gaacagagaa   6720
ttcactcctt ttgtctctgc atcttttttt ttttggcctt tggtgcagag gtgggcagtg   6780
aggctgagga agagaggggg ctgtaggatc tctgacctct gctgtctgaa acttgccatg   6840
attctgcagg cacctgtgcc agaatgctca tgggctgata atctaatcat gaggagtctt   6900
gttcctcctg ctccgagctc tttctagctg tgccacgtct gctttgtagg aaattcgatg   6960
cctagatgct cctgctgtta tgctggagaa taaaacgaga gggcacgctt aattagtcag   7020
agcttttcat acatgtttgc atctcttcat tccgtgggtg tcaagttgtg ctgtgtgtcg   7080
ggctgccctt gggcagctgg actcaattgt caaggttttc cctttgtttc tgccaagtgg   7140
cttgcagaag caacaggtgt gaaagctctg ataaaggaca aaggacaggt agcagaagtt   7200
tattgtattc tcgtggattt gcagggagaa gtaaaagtgc cctggactga gatgtcaggg   7260
tggatcagat gagtgtatcc atgcctggca atggggtcag ggcagctttg tccccacatc   7320
gtggctggtt ggcccaatag gaggcgttac ctctttgctg aaggtgtgat ggagctcagg   7380
gcaacgcctg gtttgtgagt gctttgagcg gtgcgcagga gggtcttgca agagaaccag   7440
caccaaatgt gatttctttc tctcttcagc tggactgtga tcgaattctg cacggggtaa   7500
agggtggaag gattttctgc agcgaatcct cacaacccgt ctgtggcact gatgggaaaa   7560
catacagaaa tgaatgtgac ttgtgttcag ctgccatgtg agtaggcgga gagatttcag   7620
taatacaggg ccatccacca ttcccgagtg tcttttgcag cacagtgttt gttttgatat   7680
accatgactc actatcaagt gtgtccttgg tgcctcgctg ttaagcaaac atagatcaaa   7740
tgtctgagat taatatgatg acagctaatt aagatacaca actttccaga gtcccttatt   7800
ccctttctgc tcaatcatag gattgtttgg ggagtaataa atgccatcaa attggaagta   7860
gcatcaaagg tttaaggagc ccacagagga ccaccgtgac gatgtcaggg agctgtggca   7920
ctggaagtga ataagcaatg tcttgttctc cctttgcagg agagcatcag tttacatcac   7980
ggtaaactac cgaggtgaat gccgaaagac tgtccctgaa atggtaagtg cctccctgct   8040
gtggcatccc atttcttgtt ctgggtgtgt gctggagacc cagcctggat cccgtatctg   8100
tggtgggatc atcagagccc tgttagcagg gtgcttgtgg ttcacatgcg taaatacact   8160
tcaggcttgg atttaaggca ttttgaggca taatctccac gttttttcca ggctgtgtgg   8220
taggggagtg acatgtctgg gaaaacatgt ggctttcctc ctgggatttt ggtgaggcca   8280
```

-continued

```
agaaaagatt gcaatcgcac aaaccataag ggcctaattt cccaaatgat atccaggcag   8340
ttggttggga aggaaatata ttccctaagt ggtatccttt tgggaaaggt cttgaatctt   8400
gtgtgattgc cttgtagtag atgagtcaaa gatttgttag tggtgctttg tcttcccgct   8460
cgtggcagct cagcggcatt cagagctttg gtttggagcc agggtgtccc agtttgtgtg   8520
tcttgagtgt atgggactga ccttagtgtt ggcatggact gttggaaagc tgagtattca   8580
tttccccagg gaaacaccga catctatccc cattccaaac ttggaatgaa tcaaaatatc   8640
aaatcagcca aatggagaag ttgtgcaagt ttttttgca atgagagaga tggcttctga   8700
atatgaattt gctgacagtt tgtaggtaaa acagtattgc ccgttgaaaa gctttagagc   8760
aaaattacca tcatagggct tttactctcc tctgcttatt gacaggatgc ccacccatcc   8820
ccacaacatt agaaatgagg catccccatt cctcttcctc tcttctgtga agtaccagag   8880
tgctctcaac gctgtttaaa gctgaagaaa aaatgcagag aaagagtttt gcttgtgatc   8940
gtgctggagg tctttgtgtc tcgccctttg gtgcgatgga gccattgctg gtttgtgtat   9000
gctgggagtg gaggcactat gcatacctgc tggtggctgt gctaatgatg ctggagacag   9060
acaaggttgg gtgtaccacg gcaactgaaa accagagagg actccctcag agttgtgcct   9120
ggctgggatt cctcaccatt ttgtgtttta ccaagacgtt ttaccagctc tccagtcttt   9180
gcagttagag gaatatgcca tacactaaaa gtcagacaat ttgtagctat tccaaggaga   9240
gctggaagca attaaaggga aagtgataag gtttttccac tggggaaaat cccccacaaa   9300
aaacacccct ccaaacaaag acttattatt tcgttcttta tgtatattgt gtcacctgaa   9360
gaatcagatt ggaaatttat ggaagcccat ttccttagca aaccccttgt gtccatcaaa   9420
gacttccctt tttttctca gttggaagct tatgaacaat gtactgacca gtgttatttt   9480
atgcctctga aattcatgct aacattcagc ttaatgcatc cttctgaagg cccaggcact   9540
cgctgtgtga aggagatcac agtgcctttg gcgtcagaaa tgatttcagg ctgttgcaat   9600
acgcagcacg aagatgcaaa ggcccaaaga cttgagcctt ggaaaaagat aggagattgc   9660
tgcccgaaaa tgtagtttgt ccttgagttg tgttttgaaa ttagccacgg taatgctgtg   9720
ttgcctgcca aaatgtgtgt ccaagctcag agcctgcagc cattcctgct agcaaagccc   9780
ctcctggatt tccagcagtt tgtggcagtc cttccctagc agtggctgga ttgccatcag   9840
ggagggatgg ctgtaggaag ggacaggaga aatgtggttg gagagagatc tgacattaaa   9900
gggtgcatcc ggacagcctg cactgatgtg gtggaaaacc ttcctgcaga gagagccctg   9960
gggctggctg gcagctgggc ccctgctgcc tgtgtgagct ctgtgccaca accagcctcc  10020
tctgatcctg ttctgcttta ctgcagatga atgtagctga gtctagggtt tagatttcta  10080
tgtttatttt taacaaggca gctggcctct gcgtcctcca tgctgtgaca tacagctgta  10140
ttaatggtgg gtctttccag aatgtttcac tttcaatgct gtattttttt ttattttgca  10200
gtttctcttt ttgttcagat gctttttcac acatctccca tgtgacagat accagtctgt  10260
ccatgttagt tgacaggtca ggcaaaaaaa aaaaagggat atccagtttc tcctttttaa  10320
tctgttttct aaagaacaaa gaactcccag ctttctaatg ggcaaggcca ttttcttaca  10380
gtgctctttt tgtcatacct ttcttaagaa tgtagtagaa gggaaaagaa acaaacaaaa  10440
aacccaggac cttttccagc ttgatattgg ttttggaaag cacacagatc caggctgaaa  10500
tctgtttgtt ttctgagtct ggcagtgacc catccactgc cccatcccac ctggttcctg  10560
tggccactga gctgcccaaa ggggctgtca tgtagcccct aatgctctgc cagcgtaaca  10620
```

-continued

```
gcagtggatg tacttgtgga tccacttata ttttgctctt tctttccaga aataatggag  10680
ttcagactgc cagcaaatac cagggatcag ctgtgaccaa aggtacagtg gtgcggtgat  10740
ttgctccctc ttggacaact tgtccgcatt tcacaagggt ttgggtgtca gaccttgcct  10800
gggcaggctg ctgggtatgt ctggggcaaa gggctctgca acacaccctt ccctattgcc  10860
acagcacaag aatgaggcgt gtgtcttttg cagaagtagc aaggtgatgg gaagcccctg  10920
ccaagggggc tgagcccttt ggggtgtgca aacttcatga ggacctcctc atctctcagg  10980
ggtgggcctt gcccgttcct tttccctcag atatccctgc agagggggaa ggatgctggc  11040
agagcagagt actgcagtcc ctcctcacaa ggaggtggag gtggcccaaa gcaacctggc  11100
tttgagcttt ccttgtggtt cttctgtgtc ccttgccttt tggagccata gtaataaacc  11160
cgtctgcccc ctgtttctct aggacaagta aaggaagatc tgatgtcagg caccagggaa  11220
gctgctgagt tccccagtgc tgttggatcc accttcatct ccttctgcag ccaacgggcc  11280
tgtccttgct caggtggagg gtgaagggct gtggggaccc agtggtggct tcccacgttg  11340
gccccacgca tgttgttgta gtcgctgctc ggctcgggct ctgccgcctc gctgtgtctt  11400
agcatgtttc tacaataaag ataactccac agcgtcctgt cgcttttctt cactgagcct  11460
cacgggaggg acgtgtgagt ccccgctccg gctgctcgcc acgcgtccct tgagctctaa  11520
agcaccaaac ccaagcggag atgtcagacg cagagaagaa gaacgtggtc tgggttctgt  11580
tagcagggac cagcagttgg gttctctgac tcgctgtgta gggctttggg tgtatctctt  11640
tgtctccctt cagccctttt ctcttgcctg taaaaacgga cattaaagga tgcttaccta  11700
cctcagaggg ttgtttggag attttaattg gtttacgtta gagagcccac gggtggaatt  11760
ctgttcctat gtgccaatgc tggtgtgcag gaggtttaac tgttgcagtc atggcctctt  11820
ccagccaaca cccgatgggc cgtatgtatt tcctgttctt tcgtttatgg ctgttactta  11880
aagcaaatat gttcttattt gtataaactt tattgcagga catttccaga agaccttgag  11940
tgaacgtaca gtgtttgagt ccactttagc tgtgacctga tctgcaaata cactctgctg  12000
tagataaggc tggagtaact ttcagatttt ggcagggttt cgctcaatgc caattaattt  12060
ggctccctcc acagatattg attttttttt ttcttttcaa ttaagttatc gagatctttt  12120
tttcttaatg cagctaatga aaatcgattt ttactctcat aaagtacttc cgcatgtgtc  12180
acattgatct gtctatggct tgattatcgg caggctttga catgaggtta atattttgtg  12240
tgctggtttt ttttcaccgt gtgcaaacac tgtggtttag aaatatgtta ccgctgctta  12300
tttctacgtg gaaaatccca cggcgtggtt atgcatggca gaagtcacca gtttgatcca  12360
atttagctgt ttctagggat gcaagattcc tctgcctttg agcgggtgaa tcctcgggtg  12420
ttatttatac attctgagaa ggatgaacag aagacggtaa aaacgtttgc taatgatgtc  12480
tgctggctga ttccggctaa aatcgtgtgc agggacctcg acgtgatttt tataaaggca  12540
gctcacaatt tgaggcttaa agtaagttct tgcaaatgaa aatgggcgca cttgagcgcg  12600
ctattataac ttgtagtgat ttcaagcact tagattttga aataatcgcc cataaaaacc  12660
tgcattaatt gtgctccaaa accaatgagc tgatgaggag ggtgccctgg tagcctcttt  12720
tgctggattt gagcaccttc tgaatttctc ctgccaccag cagaaattag ccacagaaat  12780
catagctgct ataagggttt attaatcaga ttacgaaact gctaagaagg cacacaacag  12840
tgacttgctg aagctgcctg tgctgctgtt agcgagcctc ccgtaggtag caatgctaac  12900
tccttccttt tagcagttta cccactgctt ccttccatca ctccttcctt ttgtagggcc  12960
tacttttgca gtttgatcca gtggcttgca ggcaatatct gtccccagcg gtgctctatg  13020
```

-continued

```
cagctgacct ccaggtaggg ctccatgtga gcgatgcaat gtgttatttc catggggttc  13080
ctaagaagga ggaagcaaaa agctcaggag gtgctccaaa tatattatcc tgtcctctgt  13140
tttgctcttt gtggtgccct ttaacactgt aaagagacca taggagtcct ctatgaacct  13200
ggaaaggtac cagcactatg ggaggtcttc agtttgctgt aaattatgct ttattagagg  13260
tatttcttct gccaagaccc actgacccca tgcggctcac agtgttttct aaggctttgc  13320
aggactggtg ttacgaattg gcaccctcca ggcctctcac aaatctcctg cttctcacag  13380
cgtttcttca agttctccca agcacagctg agttttgagc tcaactgctc cctgcagggg  13440
ccttgagcct cctgcctttt tgcataaaag gtgtcaggta cttatgcaat ccttagaggc  13500
atgcaaatgc tgctctggtt atatactgag gactgttgat tctggcagaa ccctttgcag  13560
accttgtact cccttgctat ttcccaatcc ctgcagccta gcagctctgc ctaacaactg  13620
ccatagccaa cacagcagca ggctgtgcat ggtgcaaggt gatgtggaaa gggatgattg  13680
tatgaaagcg tgatgctgtg gtactgcctc tgcaggagac tcgcactatt tgtgtaagag  13740
gaccttattt gtctgctgca gagctgtttc aaggctgtcc atacacccct gtgatgctga  13800
gcccctccaa gcaatgcact gggaaaagga ggctgggggg agaccttatt gctctcctcc  13860
aatatttgaa aggtgcttac agcgagagca gggttggtct cttctcactg gtgacaggat  13920
gaggggaaat ggcctcaagt tgcaccaggg tatgtttaga ttggatatca ggaaacactt  13980
atttactaaa aggttgttaa gcactggaat cagctcccca gggaggtggt tgagtcacca  14040
tccctggatg tgtttaaaaa ctgtttggat atggtgctca gggacatgat ttagcggagg  14100
gttgttagtt agggtagtgt ggttaggttg tggttcactc gatggtcttt aaggtctttt  14160
ccaacctgag caattctatg atatggatcc ctggggcttt cagtcttatc tccctggatt  14220
atcacaggtt cagctctatg gcccatttga tttataccgg ggtctgatga acaggttttt  14280
ctcttggctc ttcagggatc ctatttagca ctttttggta cattcccctg ccctacaagt  14340
ctccctgata cacagagctc ttatccaaga cttgggacct tccctactcc agccctctgc  14400
aggaggtttc ttgctaacca gtcctccaac caggactgca gtacacgaca aagagctgga  14460
agaggtctgc aatacttccc cagcatgaag gtatgagcac tccttttgag taggttactg  14520
aaagtagtaa gatgtcaata caaccaactg caagatacaa aaccgcatga aaattcagtt  14580
tactttgatg ctgaagggct gaaaagaaat gctgtggtgt tagcacagat gcactgctgg  14640
caaagtgaaa atgagcaaag aggatgagat ggatggacag ctgatggaaa aactcttcct  14700
aattgctcca cagagcagct tgctcgcctg cagggctgca gcatggagct gcttgtgcat  14760
aatgcagaca ccccaagacc agtgctgttt gtcttagcca agacacagtt gcagctgcag  14820
caatttttc tagatgtcag ttccttccct atgttgctga caggtgtttg ctgttctgtc  14880
cctttaatct gtatcctaca gcaaacattc cttgaattta ataacttagc tggaagacaa  14940
ttgctgtgat cttgatagaa catgctgagc caatctattt taactgcaga tttagtttgc  15000
aaatactgtc tccttgccga taagattcag gtgtcatctt tgtggacatt ggcaggaatt  15060
ttcttgaccg tgacaggttt tacagagtct ggcaattaag ctgtcaagac acattttcct  15120
ctgccaggaa gcattaattg atgatagtct tggctgcaat aggcacagag agatggatat  15180
tgtaatcaga atgaatagag gtccttgtag ttgagagcta cgttggtcca aagttttgta  15240
gtcgttgacg tttggtgata ctgagataag gaacaaggca cgagatatta gagctaaata  15300
tcaggcacag catgagaata aagacctctc tagctggaac tgttggtatc tggggagatt  15360
```

-continued ttaactttct ggatgcatac tgcaaagtac taatattagt agagctactg gatgcgagag 15420
caaatagttt tccattaagt aatcccaaaa atcatgttgt tgttggtttg cttttcaagt 15480
gcgaggggtg ttggagatgt atttccctca gaaaataaac ctgatatgat tcaacctgag 15540
ctctctctgt ttaaatcaca ctgaaaatag atctgcaaat ggggattttg attaccgagt 15600
acagaatatg aaagattaaa acttgggaaa gttagggttc tgattgagaa aacttttgtt 15660
tttgtggccg acccttgcag cttacaaaaa tctgcctaaa taaaggagaa aaccacattt 15720
agaacccatc caagctatgc tacttcagta ctgggcaaaa cttcaggaga cgtttgaaga 15780
aaactgaaga cgtgaagtat aaaggaatga ttgatgtgca cagtaaactt tcttggaagg 15840
taatcacgca tgggctaata tcaatcttta caaagttggc tgacttccta gataaaggaa 15900
gtacagtaga tctagtctac ccaggcagca aaaatgtttg acctgttgcc ctgtggggtg 15960
gtgtcacctg ggcttgggga ggggggtcag gatgaggtta caggggatgt ggaagcatac 16020
tgtggaggag caggtggggc acccacagga gttagcagtg agcagacaga aaggtggatc 16080
tgaggaccga acttcgtatt tttgttcctt gcattaatac acaaaaagca gacacacaca 16140
cagagcagat tgctgctggt ttttgttttc ttttttaaac agcagaagag caggattttt 16200
cccacagaga atggggtgac cttctaggct gtgattgcct gggctcaagc tgagatgaaa 16260
cgcagtgatg aggagcacaa aaccgtgctc tgaggttaaa taatgagggc ttcggctatc 16320
agttcagagc tcagtaaaaa ctgcagagga ggaggaagac ctaattgcat gtagccagcc 16380
acagggcaaa tgagagctgc agcgtgctgg ggcagatccg ggagcagagg ggccgtggca 16440
cgctccctgt tcactggctc ccctggagcc acacaaaagg ccccttcctg gcaattgtgc 16500
ccacatcaat cattagctag aaacccagag ctgggtaaat acgttttggc ttcccgtctt 16560
gatgacagat tgggtgttac atcacaaggt gggaccactt gatatgacaa cacgctatat 16620
attcccgctg ctacctctgc ccttcctccc ccactctgag agcaagcggg ctgtgtgtgc 16680
accgaggtgc tctgccatga ggactgccag gcagtttgta caggtggctc tggccctctg 16740
ctgctttgca ggtgagtgtt tcctgctata ccccgtaggt gactatagct agaccagaga 16800
ctaggctatc tgtgagagta tctgggtatt gtaatgtgtt agagagcctt gttccatgaa 16860
ggaatgctct ttctgacagt gtagcaaaac accagactgc aagatccagg tttcagcaaa 16920
cctcatacag acgactgttt tcgtcgtggt ttataggagc aaattgctga gggagcagtg 16980
ctagtgcagg gcaggagctt gcacgtgcaa gcactgagta taacggcaaa gcaaagctat 17040
gtgaaatggc tcctgtgtcc atgtaagcaa tacaaacact gcatcttgta tcatctataa 17100
attttctgtg ctgttcctgg cagctgagaa gtttgttgtg ggaagaacag tgctagtggt 17160
caacagccac ctgaaacgtg catgtctgag ctcctgcaag tcaaatacag agtcttgcag 17220
aagagtttaa actcagtgca ggcttgaaaa tacctacatt tcttccctgg ggcatcttag 17280
gaactggcta acacatgtgg cctcctactg aaagtgcagt gaaacttcat ttaataacct 17340
ctgattcatt ttatggacgt acatcactgg cataatgtaa aattgcattt tcctaaaccc 17400
aataagccaa tcaacaacgg tatctaaatg taactgtttc atcgaaagat ttgcatatgt 17460
catctctgca tattaataat atgtatttat tttctgtctc tacttttctt ttagatattg 17520
cctttggaat tgaggtgagt tacagatttt ttttcccatt tattcttttc tattccaggc 17580
ttctggtcaa ataagagcag tatataatta cctgatgagc aagtggatta atctaatgaa 17640
agcctggttg ctcaaataat acttgccagt gcatgattga atgatattgc caagtcacga 17700
aaaagtaaaa cacaccccgt ttatactatt ttccattcat gcaataaaat gaagaaagga 17760

-continued

```
agaattgtac gatcctatta tgttaacttt tggatataac tgcgttagtc caagtcaagg  17820
ggtggtagtt acctcctcga gaggaaagct gtcttaagat gataagctcc aaagcatcaa  17880
agacagtgat tctggtatct ttttctatac agtaagacac acactacagt gttcctgcct  17940
atacccatat caaagcgagg aaagcagcag ggtctgtgca gtgcatttgt ctgcaggttc  18000
ttcccacgca gttatgagat tcctgcaaat caccagagac tgcagcgtga ttggaaacga  18060
tcagattttg agttgagcgg ctgtggagca tggccaggct cccaattacc agctgccttc  18120
gttaggcgct gtctcaccca cagctctcct tcctccatgt catgcttccc ccagtccccc  18180
gcaggaaagc gtgatcagaa gaagattccc acctcctgac tgcctgagca gattccaaat  18240
gatacctcag gtgtttgtcc cggctggagc tgtgggtggc aggaggtttc catactgtct  18300
tttgttgtgg aaactgaccc cagggctgat gttgtgctgc ttccataggt taattgcagc  18360
ctgtatgcca gcggcatcgg caaggatggg acgagttggg tagcctgccc gaggaacttg  18420
aagcctgtct gtggcacaga tggctccaca tacagcaatg agtgcgggat ctgcctctac  18480
aacaggtgag cttatgtgga agcccagggg agctgcaggg caggagactc gaggtgaggg  18540
cggcagctct gtccccaaaa tatggtctgt gtggaggagt atgtgagtta gtaccaggat  18600
gctgacctcc agcctggggg tggtggctgc tctctgccat ctctgacaca gatctgcgtt  18660
cttccaggga gcacggggca aacgtggaga aggaatatga tggagagtgc aggccaaagc  18720
acgttacggt aagtccaaca gtaagatgaa gtcttgctct gttggtgccc ataaagactt  18780
atttttattt catagaatca ttgaacagct taggttggaa gggaccttaa agatcattgg  18840
gctctaaccc ccctggcctg gccgggctgc cttcaaccaa atcagtttgc ccagtcaaat  18900
gggccttggg cacctccagg gatggggcac ctgctctgct cagcctgtta cttatttact  18960
tgtttttttc ccattcctgc tatccttaca gattgattgc tctccgtacc tccaagttgt  19020
aagagatggt aacaccatgg tagcctgccc aaggattctg aaaccagtct gtggctcaga  19080
tagcttcact tatgacaacg aatgtgggat ttgcgcctac aacgcgtaag tcttttctgt  19140
ggagcatcct tctgggtaat tagagatggc taagtccctt ggaaacgctt acataaaaca  19200
ctttctaagc ctttcttagg gtagatgttt ctgtgggact ctttgaagct ggctacttgt  19260
gattctccag ccagctgcag atttcttccc catcctctgt ctgtgctcat gaagggaatc  19320
acaaaaaaga cagaggacaa cccacagcag aggcatgaat agatcaaagt gttgctcagt  19380
gctgtgtgat atggaaatac catgcatttt ctgctcacaa gtggttgcta ccacctgtgg  19440
gctgcatcca gaccactcag cagttcctta cgtgaagggt gggaccttgc tttcttgccc  19500
cagtatctaa ggcttttcac gaggctctct aactaaaaca gctctttctt tcagagaaca  19560
tcacaccaac atttccaaac tgcacgatgg agaatgcaag ctggagatcg gctcggtaag  19620
tgtaacagaa ataaaaatcc atctcctagg gctgttaacg gagagaatcc cattgatttt  19680
cctaagaaaa tgtatgaccg ggctgatcgg gggtcccggt ccacgctctg cttcctgcct  19740
ggtgagggtg gcttctgaaa caaagcggta aaggaagagg ccccagattt tccttgcatt  19800
gtgctgtgca gattggcagg tttctctctg gaggcgacaa gcatttccac cctttgtaac  19860
aagcattcaa aattctagtg ctggtagctt ggttagatat agtgagattc ataagagcac  19920
caagcataca tatttatagg gtatagctta ttgtatattt atactggggt aagagtccag  19980
tgcctcagga agaaaagctt atatatttca gcacaaaaat tctgggatgc agggagtccg  20040
ttctccaaca gacggattcc tcctttatca cttcaactcc cgtgcttaac tgcagggaat  20100
```

-continued

```
ctgaattatt aagcaatcac agcactgggg aaggaaggag aaaaaccaac acaaaccaaa  20160
acaatgttaa tcagatttcc agctgttgga aaatatttcc cacttaattc aaggctgttg  20220
tgtcgatgag aagagggctg aaaaggctgt tttcagttcc tctgcctgaa ggtttcattc  20280
tctaagagag gtccctttc ttgtctccta gagaatgagg gtagtgttct gaaagcctat  20340
ttctgataga cagtttagtt aagtgtagca gggctttgtc ctgtcacaaa aactaggaag  20400
ccgggaatac aggatgaaaa ggtgttacat tgacttctcc cgtgtagcac aggctccggg  20460
agggcttatt ctccttattt tggcaggttg actgcagtaa gtacccatcc acagtctcta  20520
aggatggcag gactttggta gcctgcccaa ggatcctgag cccggtttgc ggcaccgatg  20580
gtttcaccta tgacaacgaa tgcgggatct gcgcccacaa tgcgtaagtg ctgctcatct  20640
cccactcctc caaagtagcc agcaatgctt tgccgtgctg ggagccttcc ttctacgttg  20700
ctgcttatgc ctgtttcttc aagcctctta gaaactgcat ttttttgtt gttgttctta  20760
ctgagttttc ttctgatgcc ttctttgtga tcacgagggg aaatctgcaa gactcagaac  20820
acagctcctt ggattagtct gtgggctggg cagtgactga gcagagaaag gaatagttca  20880
gaatcttgct ttaaataaca cgagaagacg tgatgagctt gttaacgagc agagtaatgt  20940
agctatatca atacaatcgt gcagagaggc tgaagcccta ctttgttagg tacctgcttt  21000
aggctacgtc tggttcattc tgcatgcaag tgtttaaacc aagagttaaa gcatctcctt  21060
actcactttg tctccctctt tcagagagca gaggacccat gtcagcaaga agcatgatgg  21120
aaaatgcagg caggagattc ctgaagtgag tatacaacgt aaggtgtatt tctccccttg  21180
cctctgccca ctgagctatt tgctgaggcc acgtctactc tgaaagtgag ctggcttgaa  21240
gcctggctct ctgcacgtgt cctttgggat gtgccaacgt gtatccaaca cacaaacagt  21300
gtggaagttg ggcaggggga acttaggtct tttaaggatg atcactaaat gcattgccag  21360
caaagtcctt ttgtgccagt gaagtcctat tatgtttgcc ttcttttgtt tcattctata  21420
gtgcagagag aaaaggagat gatatatctt tgttggtttt ttttttgttt gtttgttttg  21480
cttttctgcc atatctagca aactgtttca gtaggttgtg accccttttgg atcacaagtg  21540
aagctcagtg gcatttggga ttgactgagc tgtctgccct ggtgatttgg catctcacag  21600
attacacagc gccatgtagc tcctcctggg catgagagag tttctgcaga gctgactcag  21660
gctggctttg agagaactga agtgtagcac cagcgttgtt tcagcatccc agcgtaaaag  21720
acatggattg cagcaggagg caatgctagg gtttgtcttt gagagcaagg gctttttcag  21780
ggctgacgct cctacttttt gcagattgac tgtgatcaat acccaacaag aaaaaccact  21840
ggtggcaaac tcctggtgcg ctgcccaagg attctgctcc cagtctgtgg cacagacgga  21900
tttacttatg acaacgagtg tggcatttgt gcccataatg cgtaagtact gcaaacagga  21960
cttccttttg tagcgactag ccacgttagt actgcagatg gcttcccctc caccettcat  22020
cttcttcttt ctttcttttt ttttgatagc agtatgtcta tatgtctcct gttcttcctt  22080
caacctcctg aagctctgtc gcctcggttt cctttcctga tgtgctcctc agggagctgt  22140
gggagagcca gctaacagct gagtgtccta tgagggctgt ggcatttgtg cagaggaaaa  22200
agagaatggg tctgctacaa gtagacctga gaagcctgta acttcttagg atcatgatcc  22260
ctaatggcag cctttccctt tcagacaaca tgggactgag gttaagaaga gccacgatgg  22320
aagatgcaag gagcggagca ccccggtaag tggggatgga tgtcagatga gcgccagctc  22380
ctgtacgtgc cttgtggctg cagaggttgc taaccagggt ctgtccattc aggcagcaga  22440
gaaggggaat gggccaggat ttaggtaaca aaatgtccca atactgcagg tctctggagg  22500
```

-continued

```
gaaacatcag aggcagccca gaacagcaca gcctgtttta gcacagtagg agaggaagag  22560
cagaagctgt gttagatgcc tgtgtagtca ttcagtgcta ggatttccat tgcagcagac  22620
aggttaaaaa atctctgtac cgtggtcagc caagaaaagg ctgcttgcag gaatgcacgc  22680
agaaatagct ctataaacat gcacggtaac aatatgtgct gataatatct cagcacattt  22740
attctgctta tgcagagcag ctctaaaaca ctgaaaataa ctttgtgcat ctcaagggat  22800
tgctgtatct tttctgtagt aaagacacac tgttatggtg ctgtctttgc tataatttgc  22860
tcttggactg tgtggggaaa tatgggtaat aagagctact acacagggga aggtatgcaa  22920
aacgattgtg aagtgtcaga agcttagcca gtgtagactg acttccagtg ccatcagtag  22980
atacttgctt atttatcctc aaatattgga actgttttta agtactgtga ggatttctgc  23040
agcagcagct gatgagctga tggaacagtt tcttcttgcc gttttgaaaa cgtggaaaca  23100
aaatctaagg cttagctaag tcaggcatga cctaatgtca aactggacat aacatcaaac  23160
tccttatatc aaattccttt gaataatgct tgttttgaaa cttggacata cgctgcataa  23220
ggaagatgat ctttctggtc tgctattcct ttgcgttccc tttgttagtg agcaatatca  23280
aacccaacca caattagttc atttataatg ggagactaaa ctgaaatcaa ccctgatttt  23340
tcctatggct cgaggcagtc tgtcccccag ctcccagcac ctgactcagc atccttactg  23400
ttttctcccc agcttgactg cacccaatac ctgagcaata cccaaaacgg tgaagccatt  23460
accgcctgcc ccttcatcct gcaggaggtc tgtggcactg acggcgtcac ctacagcaac  23520
gactgttctc tgtgtgccca caacatgtaa gccctgcagg tcacccactc gtgtgtcacc  23580
gcagctgctt gttgagcttt gtcaactctg ttttctctct cttccagtga attgggaacc  23640
agcgttgcca aaaagcacga tgggaggtgc agagaggagg ttcctgaggt aagcgataaa  23700
gaaaacaaga gcttgaggtg gtgcttattg cctaacaagt acaacgctgg ctggttttgg  23760
tgatgctggg tcatgccctc ctgctgccat ccttcctgca ggtaaacatc aaccctggca  23820
gcagggatgc tgtgcatttt ctgcatgtag tcagggaaag aaagagaaga ggacgggtga  23880
ggaatgagtt atgatgcagg tagcataaat gatttaaggc gttacgaaga aatctctttc  23940
ccacagcagt ctatcatacc tgccgtggga gtgtagctgt ctgttctggc aatatgggaa  24000
agggacacag agcacccgca ggtacctggt gccttctgga tacctgtgct gtgcaaaagg  24060
atgttgtgca aagatcagaa aactacctgc attttgaatg cttttaccta atgtaccaga  24120
ggattcaaac acctctctct tcctattgta aatgcgatat aatgtaatgt ataccaacaa  24180
tgaatcttgt aaaaatacca gataaactat atttggccag ctctaaacta tttacgctca  24240
ctggggaata gaaaaacaaa gccatctcat tatcttgtgt ttgaaagagt caacgtcgtg  24300
agtcagatat ttcatttcta tgcaaacaga ctatgaaatg tcattgcttt gtttcctgcg  24360
tatgctctgt gctcagacca agtcagatgc ataaatcagt gaggaagagc tcacactgga  24420
gaaactggga tagctgaaac tcaaggccag ttcttcaaat ggcataaatc attttgaact  24480
gctgttggtc cttctgtccg attgcaacac acagaaccag cccctcgcaa caaaaggcat  24540
gtcagcacat ctcctcagtt cttgtgggcc gtgacacact ccttggccac actgagcttc  24600
tcttgcagga attgcataaa tcacgccagt ttgatttgca gattatttat gagctgcgtt  24660
ttgcagcgtc ccagcaagtg gttcagcaag ctctaagggc atcgtgataa atgcagggct  24720
gaatgagtga tacgcgcctt caagctttga ttcagtcttc tccagtataa ggctgtgaca  24780
gaaaattgat agttttcaat gaagaatgag tcaatgcata accataatcc atcctgtggc  24840
```

-continued

```
agatcttgaa aggcagaggc gtaaggaagg gggttgtgtc tgagcaccct tacacagagc  24900
atttgctgcc tttgtttcct agcttgactg cagcaagtac aaaacctcca cgctgaagga  24960
tggcagacag gtggtggcct gcaccatgat ctacgatccc gtctgtgcta ccaatggtgt  25020
cacctatgcc agcgaatgca cgctgtgcgc tcacaacctg taagtactca ttcatctcca  25080
gggggaccca ccgtggctgt gactggacac atctttgagt gctgaataac atgcaagggc  25140
tctgtctaaa atctcgtgct gcatgggtcc tgtctgccta tccccgtttc cctggttgcc  25200
atggttggtg tttgagatgg gcatttagca aggcccactg cccccagtga cccagaaaaa  25260
gggttcactg cctgggaaag cattattcca aaagacacat ccctagtcct taagggcatg  25320
ttcttgctaa tgcttctcag gcaatgctta gctaatttat ctgaaattgt cctgtgtacc  25380
acatgggaac gaggttgtgc tcttgtacta cggttgtaaa tgggaagggt ttctgctaat  25440
atccatctct ccttcctcca gggagcagcg gaccaatctt ggcaagagaa agaatggaag  25500
atgtgaagag gatataacaa aggtgagtgt gaaaggatgg gcacaaagag ttacagtcgt  25560
aggggaccgt cctctgctcc acatcaaaaa ctgggggagc ggtgtgcagc cctggcgagg  25620
tcgcttggga atgtcatact ggttatagaa tagctgccat ccatcccatg ggaatggaca  25680
tggcagtgaa caggaacagt gtgaggtcac atccctcacc aggaggaact gagctgatta  25740
ctgccgtaat tttccagttt cactctttgt gctgggggaa tactgtttgc tcccaggcag  25800
agactcacat cttccttgtg tgtgcaggaa cattgccgtg agttccagaa agtctctccc  25860
atctgcacca tggaatacgt accccactgt ggctctgatg gcgtaacata cagcaacaga  25920
tgtttcttct gcaacgcata tgtgtaagta taggagtgaa acccttcctg taactgctac  25980
aaacgcagag ttgattttat aaggagttct ttactaacac tttatgggtg tgtgctagac  26040
atttcggatg caccgtgacg tgcaaggagg tgctttttttg ctttttaaga aaaaatgcaa  26100
agcacccaca tctgcccatg tgtatgtggc ttcctgtttt atttagtttc aaagacattt  26160
tgctaatttt caccagcata gtttgtccca caagctcatc agggtatggg gaaagtactt  26220
caccaaacta cctggagcgt ttcaagtgtg tgaaacctgt catctttcct ttaattttca  26280
taatgaaagg aagtggttgg ccttctgaga ctgttcttta tcttctgcca acattatcaa  26340
catttgggct ggtaaggaga ggaacaaggc tgcagcacaa attctattgt gtttaatcct  26400
ttcttctctt ttcattaggc agagcaatag gactctcaac ctcgtgagta tggcagcgtg  26460
ttaactctgc actggagtcc atcgtgggaa acaatctgcc ttgcacatga gtcttcgtgg  26520
gccaatattc cccaacggtt ttccttcagc ttgtcttgtc tcccaagctc tcaaaacacc  26580
tttttggtga ataaactcac ttggcaacgt ttatctgtct taccttagtg tcacgtttca  26640
tccctattcc cctttctcct cctccgtgtg gtacacagtg gtgcacactg gttcttctgt  26700
tgatgttctg ctctgacagc caatgtgggt aaagttcttc ctgccatgtg tctgtgttgt  26760
tttcacttca aaaagggccc tgggctcccc ttggagctct caggcatttc cttaatcatc  26820
acagtcacgc tggcaggatt agtctctcct aaaccttaga atgacctgaa cgtgtgctcc  26880
ctctttgtag tcagtgcagg gagacgtttg cctcaagatc agggtccatc tcacccacag  26940
ggcaattccc aagatgaggt ggatggttta ctctcacaaa aagttttctt acgttttgct  27000
agaaaggaga gctcactgcc tacctgtgaa ttcccctagt cctggttctg ctgccaccgc  27060
tgcctgtgca gcctgtccca tggagggggc agcaactgct gtcacaaagg tgatcccacc  27120
ctgtctccac tgaaatgacc tcagtgccac gtgttgtata ggatataaag tacgggaggg  27180
gaatgcccgg ctcccttcag ggttgcaggg cagaagtgtc tgtgtataga gtgtgtgtct  27240
```

-continued taatctatta atgcaacaga acaacttcag tcctggtgtt ttgtgggctg gaattgccca 27300
tgtggtaggg acaggcctgc taaatcactg caatcgccta tgttctgaag gtatttggga 27360
aagaaaggga tttgggggat tgcctgtgat tggctttaat tgaatggcaa atcacaggaa 27420
agcagttctg ctcaacagtt ggttgtttca gccaattctt gcagccaaag agccgggtgc 27480
ccagcgatat aatagttgtc acttgtgtct gtatggatga cagggaggta gggtgacctg 27540
aggaccaccc tccagcttct gccagcgtag gtacagtcac cacctccagc tccacacgag 27600
tcccatcgtg gtttaccaaa gaaacacaat tatttggacc agtttggaaa gtcacccggt 27660
gtattgtgag gctagattaa taggctgaag gcaaatgttc ccaacttgga gatactgttg 27720
gtattgtatc agggaacagg gccatagcac ctccatgcta ttagattccg gctggcatgt 27780
acttttcaag atgatttgta actaacaatg gcttattgtg cttgtcttaa gtctgtgtcc 27840
taatgtaaat gttcctttgg tttatataac cttcttgccg tttgctcttc aggtgttctt 27900
gcagaacact ggctgcttta atctagttta actgttgctt gattattctt agggataaga 27960
tctgaataaa ctttttgtgg ctttggcaga ctttagcttg ggcttagctc ccacattagc 28020
ttttgcagcc ttttctgtga agctatcaag atcctactca gtgacattag ctgggtgcag 28080
gtgtaccaaa tcctgctctg tggaacacat tgtctgatga taccgaaggc aaacgtgaac 28140
tcaaagaggc acagagttaa gaagaagtct gtgcaattca gaggaaaagc caaagtggcc 28200
attagacaca ctttccatgc agtatttgcc agtaggtttc atataaaact acaaaatgga 28260
ataaaccact acaaatggga aaaacctgat actggaattt aaatattcac ccaggctcaa 28320
ggggtgtttc atggagtaac atcactctat aaaagtaggg cagccaatta ttcacagaca 28380
aagctttttt ttttttctgt gctgcagtgc tgtttttcgg ctgatccagg gttacttatt 28440
gtgggtctga gagctgaatg atttctcctt gtgtcatgtt ggtgaaggag atatggccag 28500
ggggagatga gcatgttcga gaggaaacgt tgcattttgg tggcttggga gaaaggtaga 28560
acgatatcag gtctacagtg tcactaaggg atctgaagga tggttttaca gaacagttga 28620
cttggctggg tgcaggcttg gctgtaaatg gatggaagga tggacagatg ggtggacaga 28680
gatttctgtg caggagatca tctcctgagc tcggtgcttg acagactgca gatccatccc 28740
ataaccttct ccagcatgag agcgcgggga gctttggtac tgttcagtct gctgcttgtt 28800
gcttcctggg tgcacagtgg tgattttctt actcacacag ggcaaaaacc tgagcagctt 28860
caaagtgaac aggttgctct cataggccat tcagttgtca agatgaggtt tttggtttct 28920
tgttttgtaa ggtgggaaga agcactgaag gatcggttgc gagggcaggg gtttagcact 28980
gttcagagaa gtcttatttt aactcctctc atgaacaaaa agagatgcag gtgcagattc 29040
tggcaaggat gcagtgaagg agaaagccct gaatttctga tatatgtgca atgttgggca 29100
cctaacattc cctgctgaag cacagcagct ccagctccat gcagtactca cagctggtgc 29160
agccctcggc tccagggtct gagcagtgct gggactcatg aggttccatg tctttcacac 29220
tgataatggt ccaatttctg gaatgggtgc ccatccttgg aggtccccaa ggccaggctg 29280
gctgcgtctc cgagcagccc gatctggtgg tgagtagcca gcccatggca ggagttagag 29340
cctgatggtc tttaaggtcc cttccaacct aagccatcct acgattctag gaatcatgac 29400
ttgtgagtgt gtattgcaga ggcaatattt taaagttata aatgttttct ccccttcctt 29460
gtttgtcaaa gttatcttga tcgccttatc aatgcttttg gagtctccag tcatttttct 29520
tacaacaaaa agaggaggaa gaatgaagag aatcatttaa tttcttgatt gaatagtagg 29580

-continued attcagaaag ctgtacgtaa tgccgtctct ttgtatcgag ctgtaaggtt tctcatcatt 29640
tatcagcgtg gtacatatca gcacttttcc atctgatgtg gaaaaaaaaa tccttatcat 29700
ctacagtctc tgtacctaaa catcgctcag actctttacc aaaaaagcta taggttttaa 29760
aactacatct gctgataatt tgccttgttt tagctcttct tccatatgct gcgtttgtga 29820
gaggtgcgtg gatgggccta aactctcagt tgctgagctt gatgggtgct taagaatgaa 29880
gcactcactg ctgaaactgt tttcatttca caggaatgtt ttagtggcat tgtttttata 29940
actacatatt cctcagataa atgaaatcca gaaataatta tgcaaactca ctgcatccgt 30000
tgcacaggtc tttatctgct agcaaaggaa ataatttggg gatggcaaaa acattccttc 30060
agacatctat atttaaagga atataatcct ggtacccacc cacttcatcc ctcattatgt 30120
tcacactcag agatactcat tctcttgttg ttatcatttg atagcgtttt ctttggttct 30180
ttgccacgct ctgggctatg gctgcacgct ctgcactgat cagcaagtag atgcgaggga 30240
agcagcagtg agaggggctg ccctcagctg gcacccagcc gctcagccta ggaggggacc 30300
ttgcctttcc accagctgag gtgcagccct acaagcttac acgtgctgcg agcaggtgag 30360
caaagggagt cctcatggtg tgtttcttgc tgcccggaag caaaacttta ctttcattca 30420
ttccccttga agaatgagga atgtttggaa acggactgct ttacgttcaa tttctctctt 30480
ccctttaagg ctcagccagg ggccattgct gaggacggca tcggggcccc ctggaccaaa 30540
tctgtggcac agatggtttc acttacatca gtggatgtgg gatctgcgcc tgtaatgtgt 30600
ccttctgaag gaaggaacgt gccttccaag tgccagcccc acagccccca gcccctccct 30660
gtgctgctcc aattcatctc ctcttcctcc ttctcccttt gctgtttgtg ctcgggtaga 30720
aatcatgaag atttagaaga gaaaacaaaa taactggagt ggaaacccag gtgatgcagt 30780
tcattcagct gtcataggtt tgtcattgct ataggtctgt atcagagatg ctaacaccac 30840
tttgctgtcg gtgcttaact cgggtgaact ctccttcact cgcatcattt gcgggcctta 30900
tttacatccc cagcatccat caccctctgg gaaaatgggc acactggatc tctaatggaa 30960
gactttccct ctttcagagc ctgtgggatg tgcagtgaca agaaacgtgg aggggctgag 31020
cagcagcact gcccccaggg agcaggagcg gatgccatcg gtggcagcat cccaaatgat 31080
gtcagcggat gctgagcagg cagcggacga acagacagaa gcgatgcgta caccttctgt 31140
tgacatggca tttggcagcg atttaacact cgcttcctag tcctgctatt ctccacaggc 31200
tgcattcaaa tgaacgaagg gaagggaggc aaaaagatgc aaaatccgag acaagcagca 31260
gaaatatttc ttcgctacgg aagcgtgcgc aaacaacctt ctccaacagc accagaagag 31320
cacagcgtaa cctttttcaa gaccagaaaa ggaaattcac aaagcctctg tggataccag 31380
cgcgttcagc tctcctgata gcagatttct tgtcaggttg caaatggggt atggtgccag 31440
gaggtgcagg gaccatatga tcatatacag cacagcagtc attgtgcatg tattaatata 31500
tattgagtag cagtgttact ttgccaaagc aatagttcag agatgagtcc tgctgcatac 31560
ctctatctta aaactaactt ataaatagta aaaccttctc agttcagcca cgtgctcctc 31620
tctgtcagca ccaatggtgc ttcgcctgca cccagctgca aggaatcagc ccgtgatctc 31680
attaacactc agctctgcag gataaattag attgttccac tctcttttgt tgttaattac 31740
gacggaacaa ttgttcagtg ctgatggtcc taattgtcag ctacagaaaa cgtctccatg 31800
cagttccttc tgctccagca aactgtccag gctatagcac cgtgatgcat gctacctctc 31860
actccatcct tcttctcttt cccaccaggg agagctgtgt gttttcactc tcagccgctc 31920
tgaacaatac caaactgcta cgcactgcct ccctcggaaa gagaatcccc ttgttgcttt 31980

-continued

```
tttatttaca ggatccttct taaaaagcag accatcattc actgcaaacc cagagcttcc  32040
tgcctctcct tccacaaccg aaaacagccg gcttcatttg tcttttttaa atgctgtttt  32100
ccaggtgaat tttggccagc gtgttggctg agatccagga gcacgtgtca gctttctgct  32160
ctcattgctc ctgttctgca ttgcctcttt ctggggcttc caagaggggg ggagactttg  32220
cacggggatg agataatgcc ccttttctta gggtggctgc tgggcagcag agtggctctg  32280
ggtcactgtg gcaccaatgg gaggcaccag tgggggtgtg ttttgtgcag ggaggaagca  32340
ttcacagaat ggggctgatc ctgaagcttg cagtccaagg ctttgtctgt gtacccagtg  32400
aaatccttcc tctgttacat aaagcccaga taggactcag aaatgtagtc attccagccc  32460
ccctcttcct cagatctgga gcagcacttg tttgcagcca gtcctcccca aaatgcacag  32520
acctcgccga gtggagggag atgtaaacag cgaaggttaa ttacctcctt gtcaaaaaca  32580
ctttgtggtc catagatgtt tctgtcaatc ttacaaaaca gaaccgaggg cagcgagcac  32640
tgaaggcgtg ttcccatgct gagttaatga gacttggcag ctcgctgtgc agagatgatc  32700
cctgtgcttc atgggaggct gtaacctgtc tccccatcgc cttcacaccg cagtgctgtc  32760
ctggacacct caccctccat aagctgtagg atgcagctgc ccagggatca agagactttt  32820
cctaaggctc ttaggactca tctttgccgc tcagtagcgt gcagcaatta ctcatcccaa  32880
ctatactgaa tgggtttctg ccagctctgc ttgtttgtca ataagcattt tttcattttg  32940
cctctaagtt tctctcagca gcaccgcttt gggtgacttc agtggccgcc tggaacccga  33000
ggggcacagc caccacctcc ctgttgctgc tgctccgggg actcacgtgc tgctggatgg  33060
ggggaagcat gaagttcctc acccagacac ctgggttgca atggttgcag tgtgctcttc  33120
ttggtatgca gattgtttct agccattact tgtagaaatg tgctgtggaa gccctttgta  33180
tctctttctg tggcccttca gcaaaagctg tgggaaagct ctgaggctgc tttcttgggt  33240
cgtggaggaa ttgtatgttc cttctttaac aaaaattatc cttaggagag agcactgtgc  33300
aagcattgtg cacataaaac aattcaggtt gaaagggctc tctggaggtt tccagcctga  33360
ctactgctcg aagcaaggcc aggttcaaag atggctcagg atgctgtgtg ccttcctgat  33420
tatctgtgcc accaatggag gagattcaca gccactctgc ttcccgtgcc actcatggag  33480
aggaatattc ccttatattc agatagaatg tcatccttta gctcagcctt ccctataacc  33540
ccatgaggga gctgcagatc cccatactct cctcttctct ggggtgaagg ccgtgtcctc  33600
cagccccoct tcccaccctg tgccctgagc agcccgctgg cctctgctgg atgtgtgccc  33660
atatgtcaat gcctgtcctt gcagtccagc ctggaacatt taattcatca ccagggtaat  33720
gtggaactgt gtcatcttcc cctgcagggt acaaagttct gcacggggtc ctttcggttc  33780
aggaaaacct tcgctggtgc tacctgaatc aagctctatt taataagttc ataagcacat  33840
ggatgtgttt tcctagagat acgttttaat ggtatcagtg atttttattt gctttgttgc  33900
ttacttcaaa cagtgccttt gggcaggagg tgagggacgg gtctgccgtt ggctctgcag  33960
tgatttctcc aggcgtgtgg ctcaggtcag atagtggtca ctctgtggcc agaagaagga  34020
caaagatgga aattgcagat tgagtcatgt taagcaggca tcttggagtg atttgaggca  34080
gtttcatgaa agagctacga ccacttattg ttgttttccc cttttacaac agaagttttc  34140
atcaaaataa cgtggcaaag cccaggaatg tttgggaaaa gtgtagttaa atgttttgta  34200
attcatttgt cggagtgtta ccagctaaga aaaaagtcct acctttggta tggtagtcct  34260
gcagagaata cgacatcaat attagtttgg aaaaaaacac caccaccacc agaaactgta  34320
```

-continued

```
atggaaaatg taaaccaaga aattccttgg gtaagagaga aaggatgtcg tatactggcc  34380
aagtcctgcc cagctgtcag cctgctgacc ctctgcagct caggaccatg aaacgtggca  34440
ctgtaagacg tgtccctgcc tttgcttgct cacagatctc tgccctcgtg ctgactcctg  34500
cacacaagag catttccctg tagccaaaca gcgattagcc ataagctgca cctgactttg  34560
aggattaaga gtttgcaatt aagtggattg cagcaggaga tcagtggcag ggttgcagat  34620
gaaatccttt ctaggggtag ctaagggctg agcaacctgt cctacagcac aagccaaacc  34680
agccaagggt tttcctgtgc tgttcacaga ggcagggcca gctggagctg gaggaggttg  34740
tgctgggact cttctccctg tgctgagaat ggagtgattt ctgggtgctg ttcctgtggc  34800
ttgcactgag cagctcaagg gagatcggtg ctcctcatgc agtgccaaaa ctcgtgtttg  34860
atgcagaaag atggatgtgc acctccctcc tgctaatgca gccgtgagct tatgaaggca  34920
atgagccctc agtgcagcag gagctgtagt gcactcctgt aggtgctagg gaaaatctct  34980
ggttcccagg gatgcattca taaggacaat atatcttgag gctgtgccaa atctttctga  35040
aatattcatg catgttccct taatttatag aaacaaacac agcagaataa ttattccaat  35100
gcctcccctc gaaggaaacc catatttcca tgtagaaatg taacctatat acacacagcc  35160
atgctgcatc cttcagaaca tgccagtgct catctcccat ggcaaaatac tacaggtatt  35220
ctcactatgt tggacctgtg aaaggaacca tggtaagaaa ctcaggttaa aggtatggct  35280
gcaaaactac tcataccaaa acagcagagc tccagacctc ctcttaggaa agagccactt  35340
ggagagggat ggtgtgaagg ctggaggtga gagacagagc ctgtcccagt tttcctgtct  35400
ctattttctg aaatgtctgc aggaggaaag gacaactgta ctttcaggca tagctggtgc  35460
cctcacgtaa ataagttccc cgaacttctg tgtcatttgt tcttaagatg ctttggcaga  35520
acactttgag tcaattcgct taactgtgac taggtctgta aataagtgct ccctgctgat  35580
aaggttcaag tgacattttt agtggtattt gacagcattt accttgcttt caagtcttct  35640
accaagctct tctatactta agcagtgaaa ccgccaagaa acccttcctt ttatcaagct  35700
agtgctaaat accattaact tcataggtta gatacggtgc tgccagcttc acctggcagt  35760
ggttggtcag ttctgctggt gacaaagcct ccctggcctg tgcttttacc tagaggtgaa  35820
tatccaagaa tgcagaactg catggaaagc agagctgcag gcacgatggt gctgagcctt  35880
agctgcttcc tgctgggaga tgtggatgca gagacgaatg aaggacctgt cccttactcc  35940
cctcagcgtt ctgtgctatt tagggttcta ccagagtcct taagaggttt tttttttttt  36000
ttggtccaaa agtctgtttg tttggttttg accactgaga gcatgtgaca cttgtctcaa  36060
gctattaacc aagtgtccag ccaaaatcaa ttgcctggga gacgcagacc attacctgga  36120
ggtcaggacc tcaataaata ttaccagcct cattgtgccg ctgacagatt cagctggctg  36180
ctctgtgttc cagtccaaca gttcggacgc cacgtttgta tatatttgca ggcagcctcg  36240
gggggaccat ctcaggagca gagcaccggc agccgcctgc agagccgggc agtacctcac  36300
catggccatg gcaggcgtct tcgtgctgtt ctctttcgtg ctttgtggct tcctcccagg  36360
tgagtaactc ccagagtgct gcagaagctt tgtgcctgcc agtcctggct ctccttagca  36420
gaacatggtg gtgaccatca gagagagact cccctacaaa gtgcctgcaa aggctgcctc  36480
agtacatcag tattaaacgg attactgttg tgctgggtgt ctgttgggtt ctgtgctccc  36540
aacacatttc ttacgctctc agctctgtta cactgcttgc atttgctgca cagttgcata  36600
gaatggataa atgcttgaaa caaggccata acgaggtggt cagacctcca ggaactagtt  36660
agggaaatat tgtcatggcc caagcaagct ctgtgcagga acctggcagc tttcctgcaa  36720
```

-continued

```
tgcttttgct gctaatggag aaacaagaga tgcaaacaag ccaggatctg atgttctcct  36780
tctgtattta catctcatga aattacaaag tcaaagacaa gcgtggttta tttcttacac  36840
tcagcttctt taaaatgtat atccctgaca acagatgctg tgtatgtttg cttatcctgt  36900
atgtgactat ttgcatttgc atttatctct attgactcag gtttcttttc agatatgtga  36960
tagatgtttt ctagggacaa aacggatgtg tgaatagata aggaaggaaa agatattcat  37020
ttttcaatta ataaatctac ctatctctta actttttttt ttttttaaga acagagctat  37080
tcaagaactc gtttcatcag ccagcaataa gaagctaaat tatgtttatc agcattaaac  37140
aaaaatcata tatagtttgc ttagttcaag aatcgaatcg gtggaaatca ctcagtttgg  37200
ttctctgtgc tggagttttg cacacacatt tcagctagct gtggtctcac tgatcagact  37260
gcctttgttt cccatttttg tccccttttt ttccccagat gctgcctttg gggctgaggt  37320
gagtaagaga gttcttcttg tccacttttc tcttttctct tttctctctc tctctttttt  37380
tccccccgtc ttaattagta tcactataat cagatcccag agtgtaaaat gttaaattat  37440
gcagttctga gctctacatc tatgctgcat gtaagtaatg tagcagtgat ataaaactgt  37500
tagatgaatt aatttctgac caactctgaa ctggtctaag ctttaagttg atcatatgtt  37560
ctactaaata atacagtggt ttgggttgga agggtccttt aagatcatct acttccaacc  37620
cctctgctat aggcagggac aactcccact agacaagatt gctcaaagct ccatccatat  37680
gatcagctgt agactgatgg ctgtagacta tagcattaaa aactacccca aagcagccta  37740
ctgaaagaag aaagtactgt gaggtgctac agcttccaaa tcccatgttg ttagacctgt  37800
tcttttgaat aaacgtgttt gtacgttgag aatgaatgag taacaatggc agaacactgg  37860
aggggccaac tctcaggctt tgcaaaatgg tgcctggggg gcatgataga tccctgctgg  37920
tttatcacat ggggagctgc atggctataa ccccattgcc cagttctctc ccactgcatg  37980
gagagaaggc tggatctggt cgctgccctg ctgaaaatgg cagatgtaac tacaaaatgt  38040
cactttgtcc tgttactgtg tgtttctttg tcaggtggac tgcagtaggt ttcccaacgc  38100
tacagacaag gaaggcaaag atgtattggt ttgcaacaag gacctccgcc ccatctgtgg  38160
taccgatgga gtcacttaca ccaacgattg cttgctgtgt gcctacagca tgtgtgtact  38220
gcagagagag ctcatactgc aagcaagcag ctgtgcttag ggctcctgac agcacccctt  38280
tccaacaaac agtgatctgt cacatgtcac ttatgtcaac tctttcaggg aaagcttgag  38340
tatcactgcg tgacactcgg ttgcctagac atcactttgg ttactgtgtc ttttttgttg  38400
atgtaattta ttcaggtttt tctcctccat ctcggggatg aggcagatga cagcccctag  38460
ggcatatttc atcccagcaa aaaaggagca aaaggatgga gaggtgctcc agtctgaatg  38520
gtccaaaaca gtcctaaaga tttcagagtc tttagatccc tgccagccac tcagtatggc  38580
actaccctct ccaatacaaa tatatatata tacaaagatg acttagccag actcagcctc  38640
attgcattag gtacatattc ccaataacga gaagctgagc ttcctaatac ctgttttccc  38700
tcttcagaga atttggaacc aatatcagca aagagcacga tggagaatgc aaggaaactg  38760
ttcctgtaag tgaaaccaag ttcatccttt gtgcagccaa aactgcttat tgacttgccc  38820
aataaataat gtaaatgctg actaagaggc catgtgagat gtcagaatct tgtattgatc  38880
atcttcaggt gaagtttcat cacaataaca caaaaaaaga ctttatttcc tgctgaggtg  38940
gcattttagg agacccaacg cacgcgctcc gctggtctac gtggtccctg taagccctca  39000
ccagcgcttt gctgtgtgct ccttccacag atgaactgca gtagttatgc caacacgaca  39060
```

-continued agcgaggacg gaaaagtgat ggtcctctgc aacagggcct tcaaccccgt ctgtggtact 39120
gatggagtca cctacgacaa tgagtgtctg ctgtgtgccc acaaagtgta agtaccgagc 39180
tgtgctccct tggcaggaat gggtcctgcg ctcctggcag ccactctttg agcactggga 39240
tttccaatga ggctttttct gtatggctct tggactccgt ccctcctctc cctgataacc 39300
tcatgctgtt ttcctttgtg attagaaaga gaactgtggc tttgatcttg agagagaagc 39360
agagagctgg gtggggactt aagagaagca ctctgttctg tgttaactaa gttaaaaggg 39420
tctgtgtggc acacactgcc ttgcagagga cagcagtgaa cctctgctgc acctatattg 39480
taaaacaacc tagctcctag gccatgacag cctgtcacct ctcctccttt gcatcatgca 39540
atactgcaac actgtggcac atagtaccac ctcccataag gactgatatg ttgaaccagt 39600
gtgtcagaga ccagtagcat ctctgtcttc aggatcatca ggtagcattc tatatacagg 39660
gtgttgccca ggactccgag tcccatgaag tatggcaggg gttttggaac tggatgacct 39720
tcgaggtcac ttccaaccca agccattcta ttattctgtg aaagccaggg aggtgggggt 39780
gcttgcaggg ctggtatctt gagcagtgtg ggcacaaact aggctgggca tctgcagccc 39840
atcagcactg cggggatgtg gagttcagca cagcaggatg caggcacagc tccctaacat 39900
ggattttttt cctttcagag agcagggggc cagcgttgac aagaggcatg atggtggatg 39960
taggaaggaa cttgctgctg tgagtgtgag tagcacaatg aaggagcagg ttctggtccc 40020
actgatgtca agggaaacat ggccagcatc tttagtagcc tcaggagcat cagttgtgct 40080
tcagcacaga gaagatttta ctttctacac acgtaataca cattatccac agtaatgtca 40140
ggaagggaag aggatgactg cacaggcagg gatcagtaaa agaccataag cagaaataac 40200
ccatgagggc agaactgaga ataagaactg agactagatc caggggggtca gaccaatggg 40260 ccatcaaacc catgatggtt tgatgcagag tccactcttt cagcattcat aagaattgag 40320 tagggggggag taagggtggg gtgagtacgt acggatcttc ccaaacaccc ttccaaccta 40380
cagctatgca cctcagccag gtgtgatttc tgtgtagttc acaagcctca gtggatttct 40440
ctcccatggg attctccagc ctctttctgg acctgtatac acggtagttg ggttggtttt 40500 tttttctgt ctctcttttt ttccccccac tacaatgtcc ctcagcaaac atagtcctca 40560
tctctcaaac aaacaaatct cattctctaa gtacccagat aagagctgat ttttgcttta 40620
agcctgtggg ggagatgctg gactattata aaggtatcag tgctgcctct tctccagaca 40680
ccaatgtttt ttccatttaa tttcctgaac aggtcaggaa cacggtgcaa catgattgta 40740
agcacagcac gttcatggag cgagctgctg ctgcagctca gaaatgcagc agtcagattg 40800
tgatatgcat ctcttacaca ggaaattatg ctctattttt atattattaa atctagcata 40860
cgagaaagga catccagttt atatcagatc gtgcaaggaa gttaattatt tttagtttga 40920
tcattatcat cggcactgca gctgtagcta gggaggggtt gaagctcttc agctatcgac 40980
tccttcatat cctccacgtt acaattgtgt ttttgcaggt tgactgcagc gagtacccta 41040
agcctgactg cacggcagaa gacagacctc tctgtggctc cgacaacaaa acatatggca 41100
acaagtgcaa cttctgcaat gcagtcgtgt acgtacagcc ctgattgcat tcacgttgtc 41160
ggctgcctcc tacaggcacc agcttgcaca gttcctgctt tcgttgctga ttgctgacca 41220
ggatctgggg gcagaaaaga acaccgggca tcacgccagc cattcatttg atttttcacc 41280
agagcttgtc tggtttgtta ggatggatgt tttgaacgcc attaacctta agggaagttt 41340
tccttgctgc gaagaaaatc agatttggtg tttcattata gttttcagaa ggggttaaac 41400
gatttcactc atctcctaat aatcaggtag ctgaggagat gctgagtctg ccagttcttg 41460

-continued

```
ggctctgggc aggatcccat ctcctgcctt ctctaggaca gagctcagca ggcagggctc  41520
tgtggctctg tgtctaaccc acttcttcct ctcctcgctt tcagggaaag caacgggact  41580
ctcactttaa gccattttgg aaaatgctga atatcagagc tgagagaatt caccacagga  41640
tccccactgg cgaatcccag cgagaggtct cacctcggtt catctcgcac tctggggagc  41700
tcagctcact cccgattttc tttctcaata aactaaatca gcaacactcc tttgtcttgt  41760
ttaatgctct gcctcatgca atgttttctt ctgatttgtt ggacggtgat accagactca  41820
atatgttcca tgctcgtggc tctggggtat aacaagaaca acatcttgct cccatccctg  41880
tcataaaagg cagaaaatta aatacagatg cataaacctc ggctgtgtga ctttgcgcat  41940
aaatgacagt cagcctccat tagtgttcag accctttag acagctgaaa tactgctacg  42000
aactgctgat gctggctgag ctccccatgg tacgtgtggt gcactttccc tgcgcagcat  42060
tagcagtgaa agcagctcag ggtgcggtgg tggccaaacc cagggccgat cccacggcct  42120
cctgtacctg gtcataccca cgggcacagc tgctagtgag gtgcgtgctt ttcagacacg  42180
tcatataagt gtgccctgcc tacatgtctg ggtcctccaa atgacgttgc aaggtttatc  42240
tcatcttgga attgtccctt actgaccacc aagtgttttg agatgaatgc cctcctaggt  42300
ctggttctgc tcttgcctgc tggtcttttc tcatagtagt ccttgccagc ccaagtatct  42360
gagcagtgtt ttgcaatcca aggacaaagt acccctctgc ctttgagagt gtgacctctg  42420
tcattggcac attgtccgtg aaatatattt tgcttttgtc ctttgttggt gtattgaact  42480
gatgttttct tgatccacat gagagaaact ttaataaaaa ttataaaaaa taatgcctcc  42540
cttaagcatt tcttttccct gatggaatga ggccattcaa aagaaggatg ctttggcggt  42600
aaaacagagg atttatgttg agatgggcag atgaatcaag cagtgatttc cagtttggat  42660
tgaacttttc tgggatccag gctgtgggcc tcatgtcatt ctgtcatcat caggctatca  42720
gtctgctgct gcaaatcctc cccacaacgc taatggcttt tagggaaaat cgcaattgtt  42780
agttctttgc taatgcccat aaaacttctt ccatcacttg tccagctcca ggactccctt  42840
cagccccagg tttccctctt gctctctctc ccagttcagt ttttctggat ttgctatgat  42900
ttgatgatgc attattgaca ggacaagggg aaatggtttc aaaccagagg agaggagatt  42960
tagactggac ataagcaaga cattttttac aatggtggtg aggcactgac agaggttgcc  43020
cagagaggtg gtggtgcccc atccatggag acagccaagg tcaggagggg ctctgagcac  43080
tgatggagct gtgggtgccc ctgttcattg caggggggttg gaccagatgg cctttaaaga  43140
tcccttccaa ctcaaatgct tcaatgattc tgtgattcta ttgggttgaa gcatgccaac  43200
taagactttc cactctggaa aacattcaat tcagttcaac aacattttcc agcaacagtg  43260
agaaagcact gcatataggt aagcactgat aacatgcaca tggaggaaat cctgcagcat  43320
tctctcttca ggtttgtaca gttgcccttt tgcccacagg aattttccat ggtccttcag  43380
caggcacctg tcacacactt cactggaaat aatgaagccg agggcgtact tcacatattt  43440
aaacctgcaa ttgctgttga taaagaagca ttctttgtgg ctcacttgtg taagtgccat  43500
caagatttac aaccctgaca ccagagctgg aacgctggtt atttcaaagt agggggtggc  43560
taaaccaaac gtgaatgcac acagccacgc acacacagat caggtggcca tccaagggca  43620
gaagggccgc attccatgag cacgatgcac ttctgccctt tgctgctgcc caggtgagtg  43680
gctgtgctcc tgctccgtgc ttcgtcgagt gctggctgta aaaacacaac aaacatcctc  43740
agactggaaa gagctgtgtt ctacaaggac ttatttactc ctagagggat ggtgttgaaa  43800
```

-continued

```
agacttgaca tcaaagacta tcacttatgg ggtaatattt tagcaacaga actgagtggg  43860
taagaacaac tgtgggaaca gctccgcgct cggtgctagt ttatgcataa tgaaagcagt  43920
gacacgtacg tggtaccacg acatccacca ttgaacctcc gaaacgctgc agaatcacaa  43980
attcttttac tgaatggaag cgagcgtttc ccgcagtcat cctgaactga gatgcaattg  44040
gaggggctga gcggctgcag cagcgttagg ggagtttcac ctcgctgagc cctcccgtta  44100
tttcagtgct gttgtggagc tgcacgcagg agctgccgcc agtccgtgcc agctctgcgg  44160
ccctgcttcc ccggcacctt gcttatctct gagcacctgt ccttgctcat cctgtgaatc  44220
acggagaatt gctttctctt cctccctttc atttcgcgcg tccttctcca cccgggctgt  44280
aaccctcctg agaaaaaacg tagtacggaa tcgatgttgt aaacactcag cgtggcacaa  44340
cgttttgcct gaaatccctt ttgtctgaga gtcacacact gaattgcaag ttgtttattc  44400
aggacatgca ctcacggatt ttaacactaa cgaaggagat gaattgcatt tgtgtcacac  44460
ttcctattcc cttctttact ccagacccca ctgcactgaa ggtaagggac agatctttca  44520
ggtttttttt tttttttctc catcatttct ttcctcaaag cagtttccgt ataaatcatt  44580
actaatcgca ttgtgatcga gcgtttgaaa gccctgagtc atcccacagc ctgagcaata  44640
tttgctacag atattaccga gtgaaatggc cattttcatc tgatggtttc aaaaaaaaaa  44700
aaaagataat aataataata ataataataa ataaatagcg cagcattcag ttggtgtcca  44760
agttattgtc acggttactg cagcagcact gaggatgttt acatgggatt tacatcactg  44820
gaggctgaaa gggcactgca ggcgtgtacc gcgctattcg ctgccccatc cttaagctct  44880
tctttgacat ctgctgatgg tcggtgctgg gggaagcccg gggctgtggg ggtctcctgg  44940
catctgccct gctgatagct gtgctgctga gggtatttct gtgagcacaa ggctgcatcg  45000
atccacaggg cgactgcagt gcctgcgccg taccccgcaa tttctgctct cgggagcgca  45060
tcccacactg cgggtctgat ggcgtaacat atgccagcga gtgtttattc cgcaatgcat  45120
ttctgggtgt atgaaaataa atctcttcgc tcactgagtg gtgaacttca actgtcttat  45180
caacctcagg gactgcctgg agatggaagg tggttgtgtt tggcgctctc ctcttctctt  45240
gctagcaagg gcagcacttt tttttttaaa ctgggaggat ttaccaggga ctcctttctt  45300
tcaggtaaaa agaagtcaca tttagcagag atcttcatct ccacgttggg taatttgctg  45360
aagagctcgc ttccagcaaa tacagtctat ttcctacagc ctatttgttc ttcttttaaa  45420
ttaagtcttt atcgtgcctt tgaatgttag taataagagg aagtagctgg aatagctttc  45480
cgaatgttct gttttggtta agttcctctg tgatgtatcc ttaagcagag ggagggatgc  45540
acagcagaag cgcagaggtt caatctctga ggccctgagc tctttctctc cagaactcat  45600
tgagttctca ccttgctgtg ccctgcgcag cgctcacatc acagcccacc gggctccagc  45660
tcagacagga ggaccctctc tggctgtgtt ccttacaggg gatgctgccc aaagcctcgt  45720
cctgaacttt gagtgctcct gataaagcct gaagctatgc tcaataaaaa aaaaaaacct  45780
tcagcatttt ggtcttgctt tcatactacg tatcatgctg ttgttttttt ttcttaagat  45840
gctgtgtgat tgcatcactg caacagtcct ggggtgtggg tcttaatggg aaaattacag  45900
ggagaaagaa cgggttgtct gatttatgaa gaaatcaacc cctccaaaag gccatgagct  45960
tctgctttct tccagatttc caaaagaaag ccactgctgg ggatgagatc cagtgcagtg  46020
ttcagggcat cctgtgcaga cattgactcc ttaggagctg aaaataaagt agtggtgggt  46080
acccgtaggt gtgggaagcc tttctgcagc cacctggtct gcctcccaaa gcagaggatg  46140
ggatgttttc ccctccgggc agcaccaaca gaggggtggc agcagggtga ggaagatgat  46200
```

-continued

```
tggcccctct gctctgctct tgtggggacc acatgcagta ttgcatccag gcctggggcc  46260
ccagcatgag aaagacgtgg aactgttgga gtgggtccat aggaggccat gaagacaatc  46320
acagggctgg agcacctctc ttatgaagaa aggctgaggg agctgggctt gttcagcatc  46380
aagaagggaa agctgagagg acacctcatt ggagtcttcc agtacttgaa gggagcttgc  46440
aagcaggaag gggaacaaac ttctacatgg tctgacagag atagaacaag gggggagtggc  46500
tttaagctaa aagagggaag atttgggtga gatgttggga agaaatactt tactcagagg  46560
ttggtgtgac actggcactg ctgcccagag ctgtgggtgc cccatccctg tacatgagct  46620
gaaggccaga ttggatgggg ctctgtgcag cctgatctgg tggggggcag ccagcccatg  46680
gcaggggttg gggtagatgg gttgtatggc ccttttcaac ccaaaccatt caatgattct  46740
atgattctca gataagcctg cctgcccaca tctgagctca cggtgctcgc tgggggtggg  46800
gtatggtaca ctaaatgatg ctcagaggac tgcacgcagg acctgccgca gacgtttatc  46860
acctcaccca ccacttagct gctgcttgta gttaattacg tcagctgtca cttgtagaga  46920
atcctttgag atccttgggc ctccggaaat cttggctgat gaaaggaagg gctcagagtc  46980
atagcgttaa tttattattc attaacacca aagtgtcggc tgtacgggca gtgggctcac  47040
agtcaaatag ttaatgatct taagtgacaa tgtgtcactt tgcagacagc agagagaaca  47100
gctctcctaa gggagacagc atctttccaa ttctgcagcc attcagtgcc aagctcctct  47160
ttgggacgaa agtgaagatg aggaaggcaa tgaggatgag gaggggcctc aaggaacctg  47220
gctggcttgg agacaagtga tgatcccagc tgctctcagg gtcccagcgg tcttcaaagg  47280
gcatcttgca ggggctgtgt cctctgaaca gcaaaaccca ggtcatagag gggaaagtgt  47340
gagcagagat gggacaaatc tcccatcctg ccacggagct gcactgctaa gggggtgatg  47400
gggagcagca tgggaccccca gcgttccccc catccctgca ccaggcccag ctctgcggga  47460
tggcgaggag gacaaggctc tgtcacaagc atcgctggca attattattt tgttgttgct  47520
gctcaataaa atcctgacac agtacaacac aatatcctct catcattact aatctaactc  47580
tccctccagg aaatttcagg caggaaacgt tgtctgcctg ccgaggtgct ttatggcact  47640
gttctttagt ggtacctcag cacttcgtgt cattatctgg tgtcagtgaa tttaggaaat  47700
gccattcaat taccccgcaa actgattaac gcattgcgtg cagttatttt gttctgctct  47760
attttatatc agttcctctg ttttatgtat ttctctactt gttgctggcc agaacacacc  47820
tcgggccagt ctagaccttg ctgttgatgc agcttttccc cagggcttca tcagcacaaa  47880
tggtttgtca acgtggggaa aaataaaatt atgctttaaa ataaaaccac ctggagatgc  47940
tgttctgggg tctggctgtg tcacagctat tgcagcgatg gagctgaggg attgggatgt  48000
gctgggccgg atcctcagcg ctttgctata agccaaataa ttccagacac ccttcttccc  48060
tcagatatca tctgtgctta agcagcagga gatatgcagg cagcgatcag atagctgagc  48120
tgcaaggaga aatatcacaa gagcgcggct tagagcaggg gctttgctcg ctctaaattg  48180
aattcccatc ctcataggag atccagtcct gcccccgtgt gcatcgctcc ggtaacagca  48240
atgtgttttg ctccatcttg cagagggtcc agaagctggg gaaaggaaat gtgtcgtgcg  48300
ttcgtccctg cagcagctcg gcccataaaa ttaatgaaaa tctttttttag gtcatggtag  48360
attacagatt tctttgagat agagaatctc aagagcagag gagaagattc tcagaaaata  48420
gcagtgatat gagatggcat aacgctgagt tggaaactgg ggaggatttc cagggttact  48480
ggaaatttac ttaagcacga gagaatgcat cgtgtgactg ccagtgcttc cccactcaca  48540
```

-continued

```
tggctataac cttcttgcat acaattacca tcttggaact tgaaatagct gaaagagttt  48600
tatttgatct tttcaatgga tcttacatct gcagaaaaaa aaaaaaaagg ctagaaataa  48660
tcctgcactc aaactcactt tactgaacca ccatcatgaa actccagcaa cacacaggga  48720
tttgggcagg cgtgttcatc ttcctcttcc catttgcaac atgtgtatgg catttcctga  48780
agctcactcc tccaaatgca ttgagacagt tgtttttcat tcttcctaat gcctgcatcc  48840
acccatctgc tgatcggcaa ttatttctat cccattccct tctgtttctt attaatcaag  48900
ctctttatgc aatcccacgt aacactttgc ccagctgccc tgccctaacc actaccaatt  48960
atctcatcct gttttataga ccctgtagca agactctggc cttgctcctc ttcctctccc  49020
tgatagagct tttggtgcag ggctggctgg ctcctcaggt gttcagagga tcagaggtct  49080
cccagaagga tcttgttaat caaggacagg tgctggctat atgggaggat ggcaccgtat  49140
cctaaagctc tacaagaagg agacggagct cagcctggga ggacagagag aagcagcagc  49200
acaggtttca ggatccaggg atggcagacc tgggtgtggg ctcataggat tgaagaaggg  49260
ataggctgtg ctcctgtagc ctcactgcag aagcagcact gctatctccc cagcgaagct  49320
gtgtgtgccc catccctgga ggtgctcagg accaggtggg atggggccct gggcagtctg  49380
agccggaggg agcagccggc ccacagcagg ggttggaatg gggtgggttt taagttcccc  49440
tccaaccaaa gccatttctt gatctctgtt ggtggctggt gcaagttctg aggaaacctc  49500
attttcagct caggcgttct tgtccctggg gaaaaatcaa tattaatgct tcagtgatta  49560
ctgctcgcct tccaaatgtg cttctgatca gttcaagaaa tctgacagtc acgtcgctca  49620
ggatgctaag aatacaacag aaacagcttt gaaaggaacc cttcaactct tgatatttgt  49680
gaatgagctc caaagaacat tactcattta tttttcagga aaatgatttc attgacatga  49740
acaggccaaa gcctacaagc tctgttttgt gactgcagct ccttacactt tcagctgcat  49800
tttcatgatt tatgtgccca tgatgagact tgaacacctc ccaggataat gggaaaagca  49860
gttctgattt cccatttaaa acgtaggctg cctttaagcc atgtgtgtgg ctcaggctcc  49920
ttctgaagca caaaggtgtt ccacccctcg ctccttttc attacaactt tcaatcaaaa  49980
atgtgtttta tgagatattt gttttgccat gtatctgtga cggagttgaa cccctttagtg  50040
aaacctctgt tcttcactta gctgagaggt atttcttagg gaatgtgatg ccctaaattt  50100
attgtggtgt aatagaaggg gggatgtgtg gactcacctt ctgtttgttg tggctgcagt  50160
ggttttatgc actacctgag tattaagcaa gcccttttca tctgcacgga acacctcctg  50220
cttgccagtg ggatgaaaca acaacaacaa agatttaagg tttgctattc tcaatgtttc  50280
ttaatcgggt tcacattgat tgccaacaga tgaataattc ctccttctcc atggatgtac  50340
ctcttaaact tgtgaagtct taggtaacgc ttttctgctg tgatgactgt ttcagtcccc  50400
tcagtgagaa atcaggcgca ccagtaagac acaaaggaga ccgtggagat gttcattgtg  50460
ccctcagcat ctccaaaagg cactgctgcc tgccgagccc cagacttcgc tcctgtaaaa  50520
gcaaagcatg tccaattctg ctgtgccata agagtcctgt ggagcccaga cacggcgtag  50580
cgtgtgtaac atagcgtgca cgagctcaaa cgctttcaac aaatcagctt ttttgctttg  50640
ccaacttcca tatgtaattt cacaacatct agtattgaga cagtgctgtt gtttgggcag  50700
cataaatcac tcattgtaca gcagggcgcc tctcttaaca agttgggtgt agttcatgtt  50760
tttgtctaat tcctctgcgc atctctctaa caaacaacta ttctttaggg ctcgactcaa  50820
taatcaatac attttttca gtttacagag caaataatta cttgacctga tgacttcaca  50880
aggttaggga gatgggtgta taaagtctgc agtgtgaagg cagagcaaca tctctgcaga  50940
```

-continued ccttgagagc aacaggtctg caagtaacag gctgcacagc cacctctgcc atggaggcaa 51000
tgagagctgc tgccctcctt ggattggtgc ttctcagctc ctttcctggt aagttgtttt 51060
tgttacattc tctgcttata tctctactcc tactgaacta aatgtggttc aggatgcctt 51120
tagaatccta aaagagagct cagcctgccg gagaagtgat ggtttggtaa aacatgagct 51180
ctcttctaat gatctttatc cttgtgcaaa tatttacgta actctagcag gatgcctctg 51240
tctgacataa actcattatc ctcagtaagt ctcatagcac tcgagagaga aaatgtatac 51300
cctatttctt ccttagtgag tcaaagttta tattttcacc caaaatggct attttttttta 51360 atcataggat atagcttgct tataggaact ggataaaata tttaggaaac aagtaattct 51420
cagtgataaa aaagaagtat gtgatgactc tgtagggaaa ttgataattc cagaggaatt 51480
gtaaccaagg acgccgtaac attctgtatt ttataacctc tgttttttcc agatattgtt 51540
tctggtcatc aacgggtgag tagcagatct gcatcattta gttgtggttt ctatgaatag 51600
atgaataatt catactcaca ccatatccta cgggagccta gagggagaaa aaaaaaaaag 51660
aaaagaaaat aacaagggaa ggagaaaaag ggcccccagg aattatgtga catttttccc 51720
ccagcaaata agaaaacatc tttgtcagag aaagataacg taccacgttg gtgataagag 51780
ttggcaatta ataatgcaga gtgggagccg gcgtggcaca gcgtgccagc agaaaatctg 51840
cacagctttt ccctaactgc ctccatatct cccctgcctg attccctgag gacccatcag 51900
tcagtcgtgt gtctgccatg ccaaaagcct cagtagtgac actgtgctca ggcatactgt 51960
aaggaacgct gtaatttgct cccacttctt caccgtggag gagtgacaga gaataaaatg 52020
accgcctgca gcacggctat gcgtggaaaa cacaagcaga cccttccgtg ccctgcagag 52080
ctgtcccact tgtgctcttc ccaggcctcc tgcggtgagt accggctgtt aggcagcagg 52140
aacctcgcct gttccaggat cttccagccc gtctgtggca ccaataacat cacctacccc 52200
aatgagtgct cgctctgcag agaaatcctg tgagtagcga tcgcccgatt acccatcgtg 52260
atggctcagg tggcagacag aagccttttg aattgtgact aatcacgggt ggattcgatt 52320
ttttttcccc ctgtttctgt cttcccagag tgcaggctgt gtttcttcct tgtcaaaact 52380
cctgagtcta attaattagt ggggctgggc gtggagaggc ttgatgagtg aggtgactgc 52440
atggcaccac caggttaacc cttcccctcc ttctctccta gccggagtgg gacggttgac 52500
aagaagcacg atgggaggtg tgtgaaggta tggttccagc tcagccactg tgtggagcga 52560
tggcagaatc ccttcccagc actgattgta catttagaat ggacagctcc aaacccattg 52620
gaaatgtaac agaaaggaag aatttcaggt cttttatata tatatatata tatatatata 52680
tgtatgtatt aatttcattt tgaacagtgc aaatctgttt caacggtgag ttttgagatg 52740
ttatcttgtg tagcacagct gacttaaaaa cagaatcctc tcatttcaat aatcctttgg 52800
tgttgttgaa atagttccct ttagacttag acagaagtct gttgaaatta agaagttccc 52860
caaggaagtc tggattttga ctaaatcata attttgtaac agggaaaaag aaaaaaaaaa 52920
aggattccat cagaacatct accctgaggt ttgtttatca atacacggag ctgccacgaa 52980
gtggagaagt gtctctattt ttagattaga gagataatgt aaagaaacac tccggctgtg 53040
caattgaaca taatgctaca attttcactt cagtacactc agagtaatgg caggaacacc 53100
gaggtgagca tcagctccat tttcaagtgg agcagacatt tcacagcagc agttgctgcc 53160
atgtagggca tgttaggcac agatcctatg tggtggcatt tggggtggaa agccctaaga 53220
tgacaccaac aaaacccatt ctgtgaaccc atttcctcca ggattctgct gggctcatgt 53280

-continued

```
cctcaaaggc aggacttcac ctgcctgtgc tcccttgccc gcactgtgct gggttggaag  53340
ctcacatctc catacagccc cactcaccgt gagtctgggg gtgggagaca cctctcacac  53400
catgcaccat tacacagggc tgacggaagt gttgttctgt ggctgtttca ggttgattgc  53460
actggctaca tgagaacaac tgatgggctt ggaacagcct gcatccagca gtacagcccg  53520
ctctatgcca ccaacgggct cgtctacagc aacaagtgca ccttctgctc ggcagtggcg  53580
tgagtggtgg gtcacaccct gggtgctggg gtctgggtgg tggtgtttgc agcatattga  53640
ggcttctgga gtggctgtgc tgtgctcatt cattctcaac ttgctttctt ccccaaggaa  53700
tggagaggac atagatctgc tcgctgttgg aaaagagccc gaggtaaagc tcgaaagtct  53760
gcgctatgaa ctgttgttat aatatattat acagcacaaa ttcagtgagt cagaactacg  53820
caatagcaat gtcttcactg tgctggtgta tttgtcctgg aaaaagggtt tgaggaaaat  53880
gactcaagta tgccagggtc agaggacgat gaacaaaact cctggctcct gtgtcagtat  53940
cacctgcaca gcccctgaca ggggttgatg ctcagagcat tgttcagatg gtggctgtgc  54000
cagaggtgct caccgctcct ggtgagcgtg gggctcatgc agcaccagct gtcattactt  54060
gggtgggtgg acttcatagt gtgctgttgg agacacactg cttcctggca gcccctctct  54120
gctggctgct gaaccagagc agagcaggta gcgggccgcc agccggggag cactgctttg  54180
gctgtgtcgc tgcttctgag ggtatttagt agatttttcc ctctgacttc tccttttgtg  54240
ctctgctggg caagagcatt agaatttgca gagttgctag aacaacagga gcctgcatct  54300
gaaaaaatgt tttttttgct ttgccatgac ataaatgtaa agcgcccatg taggaaaata  54360
caccaaacaa aggcttctca atacgttctt gctccattac ctacagattg actgcagtga  54420
attcaagagc actgatgcct actgcactga agagtacatg ccccttttgcg gctctgacgg  54480
cgtaacgtat gggaacaaat gccacttctg cattgcagtt ttgtaagtac agtgctcccc  54540
atgcagccat gaaaccactg ctgtgccgga gtatgaaggc agaagctgcc aggaagcctt  54600
tgtgctcccg ttatcccctt ggtaaatccg tccccatccc caacctgatc ccagctctac  54660
ctctgctgtg ccttccccaa gcactgcaga tcttgaacac aggtgagtct tctccctccc  54720
tcaccattaa attcagattc tcatttgcgg gctcatagcg ctcctgatcc atccctgcga  54780
gagtaatttg agtggtaact gtagaaggag tatccaaaat tacagggttt gtcccagatc  54840
tctctaacat gacaaaacgt gtaacctggg gaatcaggag acgggtgaag gtgcaactgg  54900
gacagcatgg agcattggct tgcccatgca aagtcagcag tggcaccatc agggctataa  54960
aaccaccttc catgtcagtg attttggcct cctcctttct ctgcaggaag agtcatggat  55020
ctctgtctct gcagcaccgt ggagaatgct gaatgctgga tcgtaacctt taccctcatc  55080
catctttcac ttccaaagcc tgcaattcca acacgctctt ccccgctccc tgctgtacat  55140
tgctttctgc cttgacccgc cagtaaatca cagacagcaa ctctcttcgc catgggctgg  55200
tgtgttattt atttatttat ttatttattg ttgttattat tttttccagg gcagaggtaa  55260
aagtcttcag gctttcaggc acttatctgt caggcaggag aagttttgaa ataaaccaca  55320
ataaaggcca aagtgcaaca cccatcacac aaaagccata agccctcacg aaagtgcgtc  55380
accccattcc aaaccatcag aagaggaaat gttgctataa aacacatgct gctctcccca  55440
gttctgtgtc ttacagcaca taaatggatt tgctttaaga gtcaggatgt ggctttgtag  55500
aagcacggag ccctggagga agcagtcctt ttgggagcct tggtatggag gaaagatggc  55560
tttgatacac ctgagcaagg ggcaagtctg gcggcacgtt acaaggaggc ttatggcaaa  55620
gggaggagac tatctcacag ggaagaaaat taggaactgt tgcttccttg aagggtgtgt  55680
```

-continued cccttgagag tgtggtgatc agcagaaaat tgcagccagc tgggcaaggc tgtaatgagc 55740
ctaatgagga ccagaggaga aaccagattg ggctcaggct tcttggaaaa gagatctgaa 55800
aagctgcact gggagcgttt gaggcagagg aaagagaaag gactcttcag gaaaaggttt 55860
gggagtcttc atgcctagaa aagaaaggac agaaggagtg cttggtagct ccaaggtcgt 55920
ttctgtctgc agtgaaaggt gatgtgtgga tgatgcgtgt gagcgttcac agtgatgtgc 55980
catctctttg ggcgagtcaa ggaatgagta tgcaaacaac aggtgaaaag tcccaagtgc 56040
ctccactcat gccaccttcc ccttcctttc tccacctccc atcctctcat tacgtaggaa 56100
gacattcagc tgttcaggct gatattgagg acaaaatctg tgacttccaa gcttttctct 56160
ggctttattt cctgaaatag gctgtatctt gacctagaaa tcttatgggt gcttcctgcc 56220
agaagatggg aagctgtcct ttaatagcgt gtcagggcag tgctccgtcc taggaagaca 56280
gatggaactt tgaaatgttt attctattag cacaggcagt ataaagcaca gtgtgcctct 56340
gtgcctgctg gtgagaaaag gcaagctgca gagccgtgag ggtgctccct gctaatctgc 56400
ctagaaggga aaagagtaga caagaaatag catatgctac tactgaatgt gagcagaaga 56460
cctttagtga aggacacagc tcagctgtaa tgtcctgttg gccaggaggt ttgttgagtt 56520
atcgcagagc ggtagagttc tggtcagagc aggaaggtgc cttcaacagc aagatcccat 56580
ggtaggcctc ttctgcagtg tgctggcaca agcctggtac ctgctcagga gcaaaaaaag 56640
gctttggaaa agctcaaaga agggctgatg tcttacaggg aaagggaggg caaaaggcaa 56700
gtgcagagca tatggctgta cagacaaaaa cccttcagaa aatggaaaag gtttttatca 56760
agtaagccca gaagttggcc cagtgcaggt aaacacttgg ctaggtaaca gtgaggctct 56820
gcccagccat acccattcct ctgtaaggca aatcccaggt gcctttgtct tgtctggtcc 56880
tgttctgttc ctatttttct gagaaatcag acagaacttc cccacctaca gcatcaagca 56940
gctactttat aggtgaagaa gtgcaaagag aagcaataag gataatcacc acttggctaa 57000
tttagtctct tcctctcagc ccacaaagga ctggtccctg tggtacattt tctaaggctt 57060
ttcccagtca gctgtgctgt agcaaatgaa atgtttggct agataaagag ctgaggtatt 57120
agtgctgggg cggcgagcag tgtctggagc aagaaaaggc aaacgaggga ttctgcgagt 57180
ggcagaacta agcctgattt tgaatggcgt tgtggctggc ggacttgtaa attatatgag 57240
aggctgtgct gtgagctcac cctaatagac atctgagaac tcacctgtca atcgcggttc 57300
ctctgctgtg tgggttttat ggtgtctagt gagctgcaag ctctaatgct ttcccaggtg 57360
cagggcagtt gtggcattgc tctcctacag aaactctcac ttgctggctg aggatgttta 57420
ggaagtcctt ggttgctaga aaaaatatat tgaagtgctt tttttgtttg tttgttttcc 57480
attcttgtgt gaaattttgt tggaatcaca gaatcataga ggttgaaaga gaaactctgg 57540
aaattatcaa gttcaacccc ttgctaaagc aggcttcata cagtaggttg cagttacaac 57600
atttgctggg gaaatgaata tgaagatctg tctataaaga gtgttcccat agcacttgtt 57660
tctttaggaa agcatgctga aattctaaag gctgtgccta tctgaagaga tactttgcaa 57720
gtggtgcaac taaatgctgc tcttggtgga gagatggctg gagatggatc gatggttggg 57780
tgatcttcgt ggtcttttcc aactttaatg attctatgat tctatactct ttacacagaa 57840
tcagctggga atagagtgag agtctcctga ttccccacca aattcctttg attgatgctt 57900
ggtgtggaag cagagctctg ggacacgttg gtgagtgtga aaactggaaa acattgacag 57960
ctatagttta aatagttcag ggaggagagg cagccatcct atgtgggact ctgcacacgg 58020

-continued

```
ctatgagagc atcagtgcgc ttctccaccc caacccaaca aatttagagc catcctccaa  58080
aatagccagg gaacaacgca taattggttt cacagacaac acattctcat gctgtgattt  58140
atttcgtaat gtctggtgag tgtcatcacg ccgtgctcaa agcctggagc tggcattcag  58200
cgaggaccca gagaatgaaa attaccagct tccccgatga atcaccactt tgaaaattca  58260
cccttgtgag aatcctgtga ctattcagaa aaaaaaaaaa aaaagaagaa gaagaagaag  58320
aagatattac aggcccaagt ctatcagtca tgtaattagc cctttctagg tttgatgtgg  58380
acagggcggc attcctaaag caccataaac acggccggga ccaataatgg ctctagaatc  58440
gaagcggaga agttctcaca attaaggtga ggaatgaggc cagcagcgga taggtacata  58500
aatacacgga ggcagggccg tgagcacgct gtgggcttgt ggctgagaca acacctccca  58560
aaccggtcgc ttgccgggga ctaaaagagc agcatgaagg caacaggcac ctcggtgctc  58620
ctcagcctgc tgctgctgct gtcgttcttc tcgggtaagt tatatttctg tagcctagaa  58680
agaaacttta tgacgagagc aacttcagag agccttgatc aacggatgac aggcttgaag  58740
agaaagctga gcaagtagaa aatatctgcg ggactcgctt gcttgtgtca catctttcca  58800
ttcctcgtgt gcctccgcag tgaataacac tgtggaggtg tcactgggag acagaatgag  58860
caaattgtaa gcagctcgtt cagcagaggc accaaagcag agcgtaatta tgagttttgg  58920
tggaaatgtt tgctggagag ctttgctgaa ccagttagag aagaaactca tacctcaggg  58980
tcatcagctc ctgttctgat gctaagcact tgggggttgg tgttctcctc agagatgtgg  59040
cagcgtaatt agatgaaagt ttcagcttcc aaatacgttg cagaggaggg ctcgaaaatt  59100
aaattcagat gtcctcgagg aacccgaaca aagagggcaa attgaaaggg tccagcgttt  59160
atttatcttg aggtttacac gtctctctgt tggtctgggg aggctggctg atggtttggg  59220
ggtgtgtagg gcacaccggg gtgctcaaat gctcgcgtgc ggccgatgcg aatgtggaag  59280
cgttgcggtg gccattactg aagactgcag accaaggatt atttatactt gtttttctgt  59340
gaataatttg aataaagaat tcgcttgaga aaatcgcagg ctgtgcatgg agagaagagg  59400
tgaattactt tgtacacatc attaattatg aaatattcat ctgtctttaa ttgagtctta  59460
attggggctg ggttccgtca gagtgctaaa gcttctttcc aaggccaggc agaatagcag  59520
caaactctgt gatctcaaat aagataaaca gatgccaaga gacgttctca caaagtcttg  59580
tgtagctgca tgtaatattt ataaaaatta tctaatgagc tgttttgtaa ataatatgca  59640
gatagcccta acggcggctt ccctgtccag cctagctgag gatgtgacag atacagcagt  59700
ggcaaggatc aaacactgaa aggcatcgca gcaggcagaa gctgggtggg gtgatggatg  59760
gtcccgctga gcgtgatgct gcaatgctcc cagcctgcac cctaaccaaa gggatgcccc  59820
attgcaatgc gccccagccc ctgcagcgct gtgtgcagcc cactccctgt ccccgacacc  59880
acaggatcca tcccgtggct gtgacctggc cccatgcaaa gtttgcaggc aggaaatagc  59940
aaagaggatg gactgattgt ctccaggccc agagcctgtg cctgcagcag gtatttttgc  60000
tctgctgctg tctggcactg cctgttctgc cccagatcac gccaggctat ccctttgtat  60060
ctcatccgga tgaggctgtt ctgggagcct cggctgtgct gtactgcaga cggctctgat  60120
gctgactgcg gggtctcctc catctcccct gtgtgctttt gttaccgtac tggccagttt  60180
tgtaattcag aggtgcaaga gcctaaaagc cataagactc aatgaagctt taaaatctct  60240
gctgagagag gctcagctct tacatagctc cccgcttccc cggcggtggc tgcctgccag  60300
ggagatgggt ttatgtgtct gtggtgcagt tagcagctga atgactgatt acatggtatt  60360
ttagtaacat ttttcaaata gcaaaatact gaaaagcaat tccgataatg tatttcctac  60420
```

-continued

```
ccctcctcca ccacacagaa cggcagagga gggaaaacct ggtgtgtgct gtgctgcagt  60480
ttgcaaaggg atttgtgact tcggttcagt cctctcagaa aataatgcta atgtggataa  60540
aatctttttt tttgttgcaa ttctaggtgt agcagctcaa gacattgaag aggttagtgc  60600
agctctttct gctttctgaa tctgcatttt ctcctggctc tggaagaatg cttttctaac  60660
agatcttggt gcattggtgc atgctgaact gctttgggtt ttgctgggat caggtgggtc  60720
ctgccaaggt gccccaatgc ttcggagtgc tcacacagta caggggtgtt agctatggcc  60780
acagtagcaa acaagttggg gatgatttag ctggtttagc acatgctccc catggtctga  60840
tccagcacag ggctgtctgc agtatcgctt ctgtctgctt tgctcctcca cgaaacaaat  60900
gtgatatcag gagtgatata ctcctttaaa ccatatccat aactggggct tgtccaaaag  60960
cctgttcact tcatagaatc attaaggttg gaaagaccac tatggtcatc gagtgcaacc  61020
actccatgcc cagatccctg tgtatggcag ccccaggcca cgtggtggtg tgagctgcat  61080
ggtaccgggc actgatatgg ggctgcatca gtgctgatgc tctcctgttg aacccactca  61140
tgttcttgga acaccagagc tgctccctgg tggtgacagc ttccctcctc tgccacaggg  61200
cagaaattcc cccatttcag ccagttctga caggcctttg tttttcaagt aagcaggccg  61260
tgcctcgttg ctgcttttgg cctctgggtg ggaagaagat cacattagag atcttctttc  61320
ctgtttggaa agcgaaaccc gacggtttat tgctgttatt atttttgatt tcttttgcag  61380
atctgcaaag agttcttaaa caggagcgtg ttctgcacca gggagtccaa ccctcactgc  61440
ggcacggatg gcgtgacgta cggcaacaag tgtgccttct gcaaggccgt gctgtaagtg  61500
ggggcggtgg gatacggacc cacacaggga tggtccactt ccaaccccgc gctgctgctc  61560
ccctcacaca gagcaatccc tggccataga atcatagaac tagagaatgg ttaaggttgg  61620
aaaagaccaa taagtgcatc tagttcaaat ggcagctcct caccgccacg cttgggaata  61680
tttcagctta atgttgattc atttctaggc ttagtgtgat gctcatagcc gtacagagat  61740
ggcacagagc ctgggaggcc attgtacctg cctgtacctt ctgcgtgggc taaattgatg  61800
cacattttcc tctgtgtgcc acaggctgaa gctctccctg tccacacctc tggatgctga  61860
agtgtgtgga ggaacgcagg cttatgcatg ccaaattatt agaggaaagt catagactcg  61920
tagaatcata gattcgtttg agtcgaatgg gacctttgaa ggtcatctgg tccagcatcc  61980
ctgcaacgag cagggaaagt gctgaaatga aagtctgaat ggacttagtg gaaaagtaca  62040
caaaatctca gaggaagggc tgcagtttct cctctcctgt ctcctctaaa ggagctgtaa  62100
taggagccaa cacctctgga ctgaaggcct gcaaaaattg atttatcctt atcaatcctg  62160
cactctggag gctgccttat cctaagggaa attagagaag agggaaagat ggcttgatgc  62220
tccctgtgag gcaccagagt gaggcaaatg atcgtgctcg gagggacaag ctccctgtcc  62280
cagccgctgt gtctgtgctg gatgccatac actgctttgt ttccataccg ctccttttac  62340
aggaggagtg gagggaagat acgattgaag cacatgggga agtgctgagc ctgagcacca  62400
agcactgatc ttcgtcggtc acaggtgcag gagcctgggc acggcagcag ctgtcctcat  62460
ctctgccata tctgctcaat aaagtaaagc tcagcacacc tccttgactg gattcctttt  62520
tccataacac ccggataagc cttccatgca gccgtgctag cagctaaaat gtttgccgca  62580
ctgtgctgtt acatcttaga atcacagaat caggcaccat gctgcctgag caggagcaat  62640
gattcccaca gctcttccat gccatgccat gccatgccat gccatgccat gccatgccat  62700
gccatgccat gccatgccat gccatgccat gccatgccat cccatcccat cccatcccat  62760
```

-continued

```
cccatcccac tgacaaatgg acacatggcc acccagcttg actgtcccat gggtgggtga  62820
cagcatgcaa cgttgcctct cagcagcctc cccatatgtg tccctctcgc tgaggtgtga  62880
gcatgaaggt ggcagagagc tatgagtggt gtggctgtgg atgcctcatc tgcttgggaa  62940
gccagaagca aacaggctga ggctgaggag tgttgctgca tgtaagcctg caccgggaag  63000
gtggcagggg aagctggctt taggcagaaa cacaaaggct ttgctttcct tgtgtgtcct  63060
aagagaggac tttgcctcaa agactgtcaa ctcgccagca tcaggttgca gttgcacaca  63120
aacttgattt ctttctttag ttttcacact gctgctctct ctctccttga tgctggctgg  63180
aaaatccttc tttgcgccag cgagggaaaa taaagcctat agtctctccc cattcgctgt  63240
acaaaatata cacagggaaa tgcttgtggc atcccctcgt taaaacgttg gcagcacatc  63300
aatgggactc tactcactta atgttgaaca cttaagtttc aaagggagct ttagatttta  63360
tcgtgaggtc agccaactca ttttgcaaac acctctatgc tgagcatctc agctcctgga  63420
tggtgtttgg acagagctga gtgtttgcct gtggtgccac gctgcaggct ttgaagtgaa  63480
ttgggacatt atattttgta gccaaggaga gttgcagttt gctttgttcc aattcagatg  63540
tttctttagt aaacacaaca gctagacctc cagaacatgg ataagcttga ggggaggaaa  63600
aagcacctcc tgcacgagga cagctgatca caaaggaccc cagtgggcag tgggagaacc  63660
ttcatcatcc tctctaccgc ctggatcagg atgagccctg catacccttt ccaactggag  63720
ttaccctgtg agccaacttg tggctctgga gtagtgctgt atctcaatac agtttctcag  63780
atgggaagag gcatttcaat gagagggggg atatgggaca tttctatgcc tgagatggct  63840
ctcggagact ccaaaagcct cacggcgtat ccccatgcct aatccttttt aatctggagg  63900
ctgaaataac aaggacagat cacaagagaa cagaagcggc gagacttctc tgctttataa  63960
tcagcctgca ttttgctctt tcagtgcaaa cagcaaatag aaccgcctct gtacccctcc  64020
agacccaacc accatcccca gcaacactgt ggcaggctgg agaagggtgg ctctgcccct  64080
ccttgcctca actggttgtg tcagcacgac cataaccaga gctctccttg gccccagctg  64140
ggcttatcca tgtaaacctc tcagtgcccc aggagctggc tggtggtcct gtccatttca  64200
ctttcctcca gcaggtgttc cctttaacaa gcatccaagt gcctggagca ggagcaggca  64260
ctgcagaaga tgagctcagg caaggacatg gcatgtgggg atccatgctg ttgtgcaatg  64320
cagatgacgt tagatacgtg caaagcagat ctcagcaatc acccaacgac tcataactgc  64380
aatcatggaa cgcaattgca tctggaagta taaaagcaca gtgataccag gaagctcttg  64440
ttaatggcac agccattttg gagcaatttg cccaggtggg gagagccctc acagcgcctt  64500
cagtcacagg gagtggtgtg agtgccccca tggctgctcc cagcccccag ccctgggtga  64560
tgggggtcac ttggctgtaa ccctctgaac acagggacag tgagacagcc ctctggcctg  64620
gctgagctct tggctacgtc cagctgcagt cctgggcaca tactgaacca gaaagcaagc  64680
attcagctgg tatttttcct ttaatttcct tcctccacat tttaagttgt gggatttttt  64740
tttttttttt ttgacagctt tgagagatga gtgagtcacg aagcactcga gatctctatt  64800
agataacaga gcatctctgc agctcttcct ggggagggag ttccttggac caagggccaa  64860
ggctgggtga gaattgtccc agcatcacag tggctgctcc atcacctgac acagcccctc  64920
tgcagtgaaa caagggaagc attacatctt tgcacggctg ctttcactga acaaaaagcg  64980
ctgcttcaca gctgagcacc atgatgaagg ggaaggagca tctccatgat gaaggggaag  65040
gagcatctcc acatctccat cacgagctct gctctgctgg tgatgcggct gacaccatgg  65100
tgtgccctga ctcctggccc atttaactgc tgtgcaccag tgcctcctcc ccagcatagc  65160
```

-continued

```
cctgtgtccc tgccacaact cattgcaatc ctttgtccta cttcttccct tgacattcac  65220
agctcttgat aaggcttttt gagccactcc tggctgatgt gggctggtgg ttcctgctgc  65280
agggttccca ccacccagct gggcagcatt cggttgttgt tccagttccc aggggattgg  65340
gacagattgg aagggtcttt gggactgtgg aagagtatct cctgaagtca gggcagactg  65400
ctcagcgctt tgtcccatcc agacttgaaa acatccaagg gtggagaaca cacagactcc  65460
ctgggctgcc agtcccagag tttgactgtc atcacgttga agactttttg ccttgtctcc  65520
atttgcaacc tctttccttt cagctgcccc atctctcagc catgcaccac tggggagccc  65580
agctctgtct ggtcaggaac agagccctta cagagccaca gcatcctcct gaagtgtcca  65640
tctcaccact cagcctcagc aagtgctcca gccctcaact cccattttcc attatctttc  65700
tatcactgga tatgggaggg aaggcagagc tgtggggcca agagaaacga ttgctcagga  65760
ggcagttggg agaactttat tgcaaagcac tgaagagata taaagtgaca tttgcaggaa  65820
aaagtagaag ggtatctgtg tgtgttggtt cctttaagga ttagagagca gctgagcttt  65880
gggatgagag ggctcccaga tgctgtgaat cagctaacag atccctccac cccgtcattg  65940
gtggtgaagt taaatagggg cccaggggaa acatcagggt tgtttttctt tttacggact  66000
ccagagcaag gagaaggtga gggggttgtg ctttggaatg ggagtgaaag agtttgttgg  66060
tgttttcctc tccccagaat aagtagtgtg gtgtaggagc gtctcatagg agtagctgcg  66120
ttaattgtgg ctggtgttag catcctataa tgttgctcca gaaatgctgg agcaggctta  66180
taatgatgtg tatgtattac cataatacat gaagggagaa tgggggggggg gggggtagat  66240
ttaagatgta tgcccttaga aaggcgggtg tcacttaaag aagtacttgc tttatagctc  66300
cagtgataga attcattgag atactctgaa cctatggggc atgaagtgac cagatcttca  66360
gtttggtcag ctctgggggt ttctgggggg agcggggata gagcctcaat ccaggtctga  66420
aagacaaggc tgagatgtgc tgggcctggg gtgctgccct gagcaacgtg gggctggccc  66480
tagagagcag cattagtgcc tgcagcaggg ctggcccttg tgcccagtgt gtggggtaag  66540
gtggggaacg taggtgctgc ataatgtggt gcttctgatc taaaactgct ctgttaattg  66600
ggagtgacca gagatggccc tatggctttc ttcccaaaga gctctgtgtc cttctctgca  66660
gggtaatctg tgataaaaac atcgcctatg ctctgccctg cagatgcagg ggtttttgtc  66720
atcctccttc tcgagacata ctctaatcct tacgcaagca gggagctcca agcttttggt  66780
gataacctct caaggaggag ctggaagggc agctctgccg agcagtgact gcgctgcacg  66840
gggcgcatcc tgcaggaggc ggtggtgtaa gcgggactcc gctcgttccc ggctatgggg  66900
ctccccctgc tgaccgccgg gcggtggcca ggagacctcg gggccgctgc tgcccctcgg  66960
tggtgctttt cgggacagct ttcaggatgg ggcagcccag ctgctctcgc ggggaattaa  67020
gcggctcggt gcagggcggc acggcgctga gctgccccag caaagcgccg ctcgtcccgc  67080
ggcaccttcg gtagatgctc tctgcttggc agctccttgg tcgttctctt ggccggtggc  67140
caccccagca tcgctcgggg ctcggtgcca tcccccccag ggcctgcgga ggtgccggtg  67200
cccgtcccgg gggtggcgga cggcggtgc agtaccgatg ctgggcgctg ggtgctgccg  67260
cagaccgagc ggcgctgcgc ggctccgggg cgctcctgga gtgcgagctg agcaacctgg  67320
tagaaaaata agtgttgtcc cgtgataaac gtcatcgtgc tgagctctca gactctgcca  67380
gaggcctgaa tgaagctgcg tcaggggaga atcaggttgg ggctaaggaa aggtcctgcc  67440
ccagagggcg gtgggtatag aaggggtgcc cagggcagtg ggtgcagtgc tgggctccca  67500
```

-continued

```
gagctggagg agcgtctgga cagtgctcag gtttggatgt tgggtggttt tctgaaggga  67560
cggattctgg gctcgtttat cctgagggtc ccttccaact tgggttgttc tattcaatga  67620
atattgttta tgttcattct attctatgat cttgttcagg ctctcactgc tgcctccaag  67680
ggttcagctc ccccagagct ggcagggctt cagccacttg cttacagtgc tcatttcatg  67740
cctggcccat ggcttctgcc tgagccttgt gggagatcag ctgctgccag aaacccagcc  67800
ctcagcactc cacttgccca gcttgctgcc ttagtagtct aacttggcag tggtctgaca  67860
tgacttgagg ttgtttttta tttccaaggt gccactgact tttttccttc catagtttct  67920
ggaagcattt ccttcctact tgactgagtc gtgctctgtg gatctgtaat tatccacctt  67980
ggctatgtgt cctttacggg attttatatg ttaacctccc aagatcattt tgctgctctc  68040
atcttagtgg ctgctgtgag ctccaccagc accacactgg atgagctgca ggctgaggcc  68100
gggcacctct cctgactctg ctcttctctg accccagagc tgtgcagttg ggatcctaac  68160
accatgcaga tgctccagga cctgcaccga gccccagcac tggcactcat ctcttctttc  68220
cacccctctg agagcaacaa gtggctctgc aatggcaatg taagtgaaac cgggcgggta  68280
tcttagagca cctggaagct tgcatgcctg caggtcgact ctagaggatc cccgggtacc  68340
gagctcgaat tcgccctata gtgagtcgta ttacaattca ctggccgtcg ttttacaacg  68400
tcgtgactgg gaaaaccctg gcgttaccca acttaatcgc cttgcagcac atcccccttt  68460
cgccagctgg cgtaatagcg aagaggcccg caccgatcgc ccttcccaac agttgcgcag  68520
cctgaatggc gaatggcgcc tgatgcggta ttttctcctt acgcatctgt gcggtatttc  68580
acaccgcata tggtgcactc tcagtacaat ctgctctgat gccgcatagt taagccagcc  68640
ccgacacccg ccaacacccg ctgacgcgaa ccccttgcgg ccgcatcgaa tataacttcg  68700
tataatgtat gctatacgaa gttattagcg atgagctcgg acttccattg ttcattccac  68760
ggacaaaaac agagaaagga aacgacagag gccaaaaagc tcgctttcag cacctgtcgt  68820
ttcctttctt ttcagagggt attttaaata aaaacattaa gttatgacga agaagaacgg  68880
aaacgcctta aaccggaaaa ttttcataaa tagcgaaaac ccgcgaggtc gccgccccgt  68940
aacctgtcgg atcaccggaa aggacccgta aagtgataat gattatcatc tacatatcac  69000
aacgtgcgtg gaggccatca aaccacgtca aataatcaat tatgacgcag gtatcgtatt  69060
aattgatctg catcaactta acgtaaaaac aacttcagac aatacaaatc agcgacactg  69120
aatacggggc aacctcatgt ccgagctcgc gagctcgtcg acagcgacac acttgcatcg  69180
gatgcagccc ggttaacgtg ccggcacggc ctgggtaacc aggtattttg tccacataac  69240
cgtgcgcaaa atgttgtgga taagcaggac acagcagcaa tccacagcag gcatacaacc  69300
gcacaccgag gttactccgt tctacaggtt acgacgacat gtcaatactt gcccttgaca  69360
ggcattgatg gaatcgtagt ctcacgctga tagtctgatc gacaatacaa gtgggaccgt  69420
ggtcccagac cgataatcag accgacaaca cgagtgggat cgtggtccca gactaataat  69480
cagaccgacg atacgagtgg gaccgtggtc ccagactaat aatcagaccg acgatacgag  69540
tgggaccgtg gttccagact aataatcaga ccgacgatac gagtgggacc gtggtcccag  69600
actaataatc agaccgacga tacgagtggg accatggtcc cagactaata atcagaccga  69660
cgatacgagt gggaccgtgg tcccagtctg attatcagac cgacgatacg agtgggaccg  69720
tggtcccaga ctaataatca gaccgacgat acgagtggga ccgtggtccc agactaataa  69780
tcagaccgac gatacgagtg ggaccgtggt cccagtctga ttatcagacc gacgatacaa  69840
gtggaacagt gggcccagag agaatattca ggccagttat gctttctggc ctgtaacaaa  69900
```

-continued

```
ggacattaag taaagacaga taaacgtaga ctaaaacgtg gtcgcatcag ggtgctggct  69960
tttcaagttc cttaagaatg gcctcaattt tctctataca ctcagttgga acacgagacc  70020
tgtccaggtt aagcaccatt ttatcgccct tatacaatac tgtcgctcca ggagcaaact  70080
gatgtcgtga gcttaaacta gttcttgatg cagatgacgt tttaagcaca gaagttaaaa  70140
gagtgataac ttcttcagct tcaaatatca ccccagcttt tttctgctca tgaaggttag  70200
atgcctgctg cttaagtaat tcctctttat ctgtaaaggc tttttgaagt gcatcacctg  70260
accgggcaga tagttcaccg gggtgagaaa aaagagcaac aactgattta ggcaatttgg  70320
cggtgttgat acagcgggta ataatcttac gtgaaatatt ttccgcatca gccagcgcag  70380
aaatatttcc agcaaattca ttctgcaatc ggcttgcata acgctgacca cgttcataag  70440
cacttgttgg gcgataatcg ttacccaatc tggataatgc agccatctgc tcatcatcca  70500
gctcgccaac cagaacacga taatcacttt cggtaagtgc agcagcttta cgacggcgac  70560
tcccatcggc aatttctatg acaccagata ctcttcgacc gaacgccggt gtctgttgac  70620
cagtcagtag aaaagaaggg atgagatcat ccagtgcgtc ctcagtaagc agctcctggt  70680
cacgttcatt acctgaccat acccgagagg tcttctcaac actatcaccc cggagcactt  70740
caagagtaaa cttcacatcc cgaccacata caggcaaagt aatggcatta ccgcgagcca  70800
ttactcctac gcgcgcaatt aacgaatcca ccatcggggc agctggtgtc gataacgaag  70860
tatcttcaac cggttgagta ttgagcgtat gttttggaat aacaggcgca cgcttcatta  70920
tctaatctcc cagcgtggtt taatcagacg atcgaaaatt tcattgcaga caggttccca  70980
aatagaaaga gcatttctcc aggcaccagt tgaagagcgt tgatcaatgg cctgttcaaa  71040
aacagttctc atccggatct gacctttacc aacttcatcc gtttcacgta caacattttt  71100
tagaaccatg cttccccagg catcccgaat ttgctcctcc atccacgggg actgagagcc  71160
attactattg ctgtatttgg taagcaaaat acgtacatca ggctcgaacc ctttaagatc  71220
aacgttcttg agcagatcac gaagcatatc gaaaaactgc agtgcggagg tgtagtcaaa  71280
caactcagca ggcgtgggaa caatcagcac atcagcagca catacgacat taatcgtgcc  71340
gatacccagg ttaggcgcgc tgtcaataac tatgacatca tagtcatgag caacagtttc  71400
aatggccagt cggagcatca ggtgtggatc ggtgggcagt ttaccttcat caaatttgcc  71460
cattaactca gtttcaatac ggtgcagagc cagacaggaa ggaataatgt caagccccgg  71520
ccagcaagtg ggctttattg cataagtgac atcgtccttt tccccaagat agaaaggcag  71580
gagagtgtct tctgcatgaa tatgaagatc tggtacccat ccgtgataca ttgaggctgt  71640
tccctggggg tcgttacctt ccacgagcaa aacacgtagc cccttcagag ccagatcctg  71700
agcaagatga acagaaactg aggttttgta aacgccacct ttatgggcag caaccccgat  71760
caccggtgga aatacgtctt cagcacgtcg caatcgcgta ccaaacacat cacgcatatg  71820
attaatttgt tcaattgtat aaccaacacg ttgctcaacc cgtcctcgaa tttccatatc  71880
cgggtgcggt agtcgccctg ctttctcggc atctctgata gcctgagaag aaaccccaac  71940
taaatccgct gcttcaccta ttctccagcg ccgggttatt ttcctcgctt ccgggctgtc  72000
atcattaaac tgtgcaatgg cgatagcctt cgtcatttca tgaccagcgt ttatgcactg  72060
gttaagtgtt tccatgagtt tcattctgaa catcctttaa tcattgcttt gcgttttttt  72120
attaaatctt gcaatttact gcaaagcaac aacaaaatcg caaagtcatc aaaaaaccgc  72180
aaagttgttt aaaataagag caacactaca aaaggagata agaagagcac atacctcagt  72240
```

-continued

```
cacttattat cactagcgct cgccgcagcc gtgtaaccga gcatagcgag cgaactggcg  72300
aggaagcaaa gaagaactgt tctgtcagat agctcttacg ctcagcgcaa gaagaaatat  72360
ccaccgtggg aaaaactcca ggtagaggta cacacgcgga tagccaattc agagtaataa  72420
actgtgataa tcaaccctca tcaatgatga cgaactaacc cccgatatca ggtcacatga  72480
cgaagggaaa gagaaggaaa tcaactgtga caaactgccc tcaaatttgg cttccttaaa  72540
aattacagtt caaaaagtat gagaaaatcc atgcaggctg aaggaaacag caaaactgtg  72600
acaaattacc ctcagtaggt cagaacaaat gtgacgaacc accctcaaat ctgtgacaga  72660
taaccctcag actatcctgt cgtcatggaa gtgatatcgc ggaaggaaaa tacgatatga  72720
gtcgtctggc ggcctttctt tttctcaatg tatgagaggc gcattggagt tctgctgttg  72780
atctcattaa cacagacctg caggaagcgg cggcggaagt caggcatacg ctggtaactt  72840
tgaggcagct ggtaacgctc tatgatccag tcgattttca gagagacgat gcctgagcca  72900
tccggcttac gatactgaca cagggattcg tataaacgca tggcatacgg attggtgatt  72960
tcttttgttt cactaagccg aaactgcgta aaccggttct gtaacccgat aaagaaggga  73020
atgagatatg ggttgatatg tacactgtaa agccctctgg atggactgtg cgcacgtttg  73080
ataaaccaag gaaaagattc atagcctttt tcatcgccgg catcctcttc agggcgataa  73140
aaaaccactt ccttccccgc gaaactcttc aatgcctgcc gtatatcctt actggcttcc  73200
gcagaggtca atccgaatat ttcagcatat ttagcaacat ggatctcgca gataccgtca  73260
tgttcctgta gggtgccatc agattttctg atctggtcaa cgaacagata cagcatacgt  73320
ttttgatccc gggagagact atatgccgcc tcagtgaggt cgtttgactg gacgattcgc  73380
gggctatttt tacgtttctt gtgattgata accgctgttt ccgccatgac agatccatgt  73440
gaagtgtgac aagtttttag attgtcacac taaataaaaa agagtcaata agcagggata  73500
actttgtgaa aaaacagctt cttctgaggg caatttgtca cagggttaag ggcaatttgt  73560
cacagacagg actgtcattt gagggtgatt tgtcacactg aaagggcaat ttgtcacaac  73620
accttctcta gaaccagcat ggataaaggc ctacaaggcg ctctaaaaaa gaagatctaa  73680
aaactataaa aaaaataatt ataaaaatat ccccgtggat aagtggataa ccccaaggga  73740
agtttttttca ggcatcgtgt gtaagcagaa tatataagtg ctgttccctg gtgcttcctc  73800
gctcactcga gggcttcgcc ctgtcgctcg actgcggcga gcactactgg ctgtaaaagg  73860
acagaccaca tcatggttct gtgttcatta ggttgttctg tccattgctg acataatccg  73920
ctccacttca acgtaacacc gcacgaagat ttctattgtt cctgaaggca tattcaaatc  73980
gttttcgtta ccgcttgcag gcatcatgac agaacactac ttcctataaa cgctacacag  74040
gctcctgaga ttaataatgc ggatctctac gataatggga gattttcccg actgtttcgt  74100
tcgcttctca gtggataaca gccagcttct ctgtttaaca gacaaaaaca gcatatccac  74160
tcagttccac atttccatat aaaggccaag gcatttattc tcaggataat tgtttcagca  74220
tcgcaaccgc atcagactcc ggcatcgcaa actgcacccg gtgccgggca gccacatcca  74280
gcgcaaaaac cttcgtgtag acttccgttg aactgatgga cttatgtccc atcaggcttt  74340
gcagaacttt cagcggtata ccggcataca gcatgtgcat cgcataggaa tggcggaacg  74400
tatgtggtgt gaccggaaca gagaacgtca caccgtcagc agcagcggcg gcaaccgcct  74460
ccccaatcca ggtcctgacc gttctgtccg tcacttccca gatccgcgct ttctctgtcc  74520
ttcctgtgcg acggttacgc cgctccatga gcttatcgcg aataaatacc tgtgacggaa  74580
gatcacttcg cagaataaat aaatcctggt gtccctgttg ataccgggaa gccctgggcc  74640
```

-continued

```
aacttttggc gaaaatgaga cgttgatcgg cacgtaagag gttccaactt tcaccataat  74700
gaaataagat cactaccggg cgtatttttt gagttatcga gattttcagg agctaaggaa  74760
gctaaaatgg agaaaaaaat cactggatat accaccgttg atatatccca atggcatcgt  74820
aaagaacatt ttgaggcatt tcagtcagtt gctcaatgta cctataacca gaccgttcag  74880
ctggatatta cggccttttt aaagaccgta aagaaaaata agcacaagtt ttatccggcc  74940
tttattcaca ttcttgcccg cctgatgaat gctcatccgg aatttacatc tggaattacg  75000
tatggcaatg aaagacggtg agctggtgat atgggatagt gttcaccctt gttacaccgt  75060
tttccatgag caaactgaaa cgttttcatc gctctggagt gaataccacg acgatttccg  75120
gcagtttcta cacatatatt cgcaagatgt ggcgtgttac ggtgaaaacc tggcctattt  75180
ccctaaaggg tttattgaga atatgttttt cgtctcagcc aatccctggg tgagtttcac  75240
cagttttgat ttaaacgtgg ccaatatgga caacttcttc gcccccgttt tcaccatggg  75300
caaatattat acgcaaggcg acaaggtgct gatgccgctg gcgattcagg ttcatcatgc  75360
cgtttgtgat ggcttccatg tcggcagaat gcttaatgaa ttacaacagt actgcgatga  75420
gtggcagggc ggggcgtaat ttttttaagg cagttattgg tgcccttaaa cgcctggttg  75480
ctacgcctga ataagtgata ataagcggat gaatggcaga aattcgatga taagctgtca  75540
aacatgagaa ttggtcgacg gcccgggcgg ccgcaagggg ttcgcgttgg ccgattcatt  75600
aatgcagctg gcacgacagg tttcccgact ggaaagcggg cagtgagcgc aacgcaatta  75660
atgtgagtta gctcactcat taggcacccc aggctttaca ctttatgctt ccggctcgta  75720
tgttgtgtgg aattgtgagc ggataacaat ttcacacagg aaacagctat gaccatgatt  75780
acgccaagct atttaggtga cactatagaa tactc                             75815
```

<210> SEQ ID NO 37
<211> LENGTH: 26
<212> TYPE: DNA
<213> ORGANISM: chicken

<400> SEQUENCE: 37

```
cgggcagtac ctcaccatgg acatgt                                          26
```

<210> SEQ ID NO 38
<211> LENGTH: 21
<212> TYPE: DNA
<213> ORGANISM: chicken

<400> SEQUENCE: 38

```
attcgcttaa ctgtgactag g                                               21
```

<210> SEQ ID NO 39
<211> LENGTH: 20
<212> TYPE: DNA
<213> ORGANISM: chicken

<400> SEQUENCE: 39

```
cgaggaactt gaagcctgtc                                                 20
```

<210> SEQ ID NO 40
<211> LENGTH: 20
<212> TYPE: DNA
<213> ORGANISM: chicken

<400> SEQUENCE: 40

-continued

```
ggcctgcact ctccatcata                                              20


<210> SEQ ID NO 41
<211> LENGTH: 1680
<212> TYPE: DNA
<213> ORGANISM: chicken
<220> FEATURE:
<221> NAME/KEY: misc_feature
<222> LOCATION: (823)..(1203)
<223> OTHER INFORMATION: n is a, c, g, or t

<400> SEQUENCE: 41

gatttcactc atctcctaat aatcaggtag ctgaggagat gctgagtctg ccagttcttg     60

ggctctgggc aggatcccat ctcctgcctt ctctaggaca gagctcagca ggcagggctc    120

tgtggctctg tgtctaaccc acttcttcct ctcctcgctt tcagggaaag caacgggact    180

ctcactttaa gccattttgg aaaatgctga atatcagagc tgagagaatt ccgcccctct    240

ccctcccccc cccctaacgt tactggccga agccgcttgg aataaggccg gtgtgcgttt    300

gtctatatgt tattttccac catattgccg tcttttggca atgtgagggc ccggaaacct    360

ggccctgtct tcttgacgag cattcctagg ggtctttccc ctctcgccaa aggaatgcaa    420

ggtctgttga atgtcgtgaa ggaagcagtt cctctggaag cttcttgaag acaaacaacg    480

tctgtagcga ccctttgcag gcagcggaac cccccacctg gcgacaggtg cctctgcggc    540

caaaagccac gtgtataaga tacacctgca aaggcggcac aaccccagtg ccacgttgtg    600

agttggatag ttgtggaaag agtcaaatgg ctctcctcaa gcgtattcaa caaggggctg    660

aaggatgccc agaaggtacc ccattgtatg ggatctgatc tggggcctcg gtgcacatgc    720

tttacgtgtg tttagtcgag gttaaaaaac gtctaggccc cccgaaccac ggggacgtgg    780

ttttcctttg aaaaacacga tgataagctt gccacaacca tgnnnnnnnn nnnnnnnnnn    840

nnnnnnnnnn nnnnnnnnnn nnnnnnnnnn nnnnnnnnnn nnnnnnnnnn nnnnnnnnnn    900

nnnnnnnnnn nnnnnnnnnn nnnnnnnnnn nnnnnnnnnn nnnnnnnnnn nnnnnnnnnn    960

nnnnnnnnnn nnnnnnnnnn nnnnnnnnnn nnnnnnnnnn nnnnnnnnnn nnnnnnnnnn   1020

nnnnnnnnnn nnnnnnnnnn nnnnnnnnnn nnnnnnnnnn nnnnnnnnnn nnnnnnnnnn   1080

nnnnnnnnnn nnnnnnnnnn nnnnnnnnnn nnnnnnnnnn nnnnnnnnnn nnnnnnnnnn   1140

nnnnnnnnnn nnnnnnnnnn nnnnnnnnnn nnnnnnnnnn nnnnnnnnnn nnnnnnnnnn   1200

nnnacggtgg cggcgccatc tgtcttcatc ttcccgccat ctgatgagca gttgaaatct   1260

ggaactgcct ctgttgtgtg cctgctgaat aacttctatc ccagagaggc caaagtacag   1320

tggaaggtgg ataacgccct ccaatcgggt aactcccagg agagtgtcac agagcaggac   1380

agcaaggaca gcacctacag cctcagcagc accctgacgc tgagcaaagc agactacgag   1440

aaacacaaag tctacgcctg cgaagtcacc catcagggcc tgagctcgcc cgtcacaaag   1500

agcttcaaca ggggagagtg ttagggatcc actagtccag tgtggtggaa ttcaccacag   1560

gatccccact ggcgaatccc agcgagaggt ctcacctcgg ttcatctcgc actctgggga   1620

gctcagctca ctcccgattt tctttctcaa taaactaaat cagcaacact cctttgtctt   1680


<210> SEQ ID NO 42
<211> LENGTH: 2340
<212> TYPE: DNA
<213> ORGANISM: chicken
<220> FEATURE:
<221> NAME/KEY: misc_feature
<222> LOCATION: (823)..(1224)
<223> OTHER INFORMATION: n is a, c, g, or t
```

-continued

<400> SEQUENCE: 42

```
gatttcactc atctcctaat aatcaggtag ctgaggagat gctgagtctg ccagttcttg      60
ggctctgggc aggatcccat ctcctgcctt ctctaggaca gagctcagca ggcagggctc     120
tgtggctctg tgtctaaccc acttcttcct ctcctcgctt tcagggaaag caacgggact     180
ctcactttaa gccattttgg aaaatgctga atatcagagc tgagagaatt ccgcccctct     240
ccctcccccc ccccctaacgt tactggccga agccgcttgg aataaggccg gtgtgcgttt   300
gtctatatgt tattttccac catattgccg tcttttggca atgtgagggc ccggaaacct     360
ggccctgtct tcttgacgag cattcctagg ggtctttccc ctctcgccaa aggaatgcaa     420
ggtctgttga atgtcgtgaa ggaagcagtt cctctggaag cttcttgaag acaaacaacg     480
tctgtagcga ccctttgcag gcagcggaac cccccacctg gcgacaggtg cctctgcggc     540
caaaagccac gtgtataaga tacacctgca aaggcggcac aaccccagtg ccacgttgtg     600
agttggatag ttgtggaaag agtcaaatgg ctctcctcaa gcgtattcaa caaggggctg     660
aaggatgccc agaaggtacc ccattgtatg ggatctgatc tggggcctcg gtgcacatgc     720
tttacgtgtg tttagtcgag gttaaaaaac gtctaggccc cccgaaccac ggggacgtgg     780
ttttcctttg aaaaacacga tgataagctt gccacaacca tgnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnntcagct agcaccaagg gcccatcggt cttcccccctg   1260
gcaccctcct ccaagagcac ctctgggggc acagcggccc tgggctgcct ggtcaaggac    1320
tacttccccg aaccggtgac ggtgtcgtgg aactcaggcg ccctgaccag cggcgtgcac    1380
accttcccgg ccgtcctaca gtcctcagga ctctactccc tcagcagcgt ggtgaccgtg    1440
ccctccagca gcttgggcac ccagacctac atctgcaacg tgaatcacaa gcccagcaac    1500
accaaggtgg acaagagagt tgagcccaaa tcttgtgaca aaactcacac atgcccaccg    1560
tgcccagcac ctgaactcct ggggggaccg tcagtcttcc tcttcccccc aaaacccaag    1620
gacaccctca tgatctcccg gacccctgag gtcacatgcg tggtggtgga cgtgagccac    1680
gaagaccctg aggtcaagtt caactggtac gtggacggcg tggaggtgca taatgccaag    1740
acaaagccgc gggaggagca gtacaacagc acgtaccgtg tggtcagcgt cctcaccgtc    1800
ctgcaccagg actggctgaa tggcaaggag tacaagtgca aggtctccaa caaagccctc    1860
ccagccccca tcgagaaaac catctccaaa gccaaagggc agccccgaga accacaggtg    1920
tacaccctgc ccccatcccg ggatgagctg accaagaacc aggtcagcct gacctgcctg    1980
gtcaaaggct tctatcccag cgacatcgcc gtggagtggg agagcaatgg gcagccggag    2040
aacaactaca agaccacgcc tcccgtgctg gactccgacg gctccttctt cctctacagc    2100
aagctcaccg tggacaagag caggtggcag caggggaacg tcttctcatg ctccgtgatg    2160
catgaggctc tgcacaacca ctacacgcag aagagcctct ccctgtctcc gggtaaatag    2220
ggatccacta gtccagtgtg gtggaattca ccacaggatc cccactggcg aatcccagcg    2280
```

-continued agaggtctca cctcggttca tctcgcactc tggggagctc agctcactcc cgattttctt 2340

<210> SEQ ID NO 43
<211> LENGTH: 11
<212> TYPE: PRT
<213> ORGANISM: SV40

<400> SEQUENCE: 43

Cys Gly Gly Pro Lys Lys Lys Arg Lys Val Gly
1 5 10

<210> SEQ ID NO 44
<211> LENGTH: 77872
<212> TYPE: DNA
<213> ORGANISM: chicken

<400> SEQUENCE: 44
attcaccaca ggatccccac tggcgaatcc cagcgagagg tctcacctcg gttcatctcg 60
cactctgggg agctcagctc actcccgatt ttctttctca ataaactaaa tcagcaacac 120
tcctttgtct tgtttaatgc tctgcctcat gcaatgtttt cttctgattt gttggacggt 180
gataccagac tcaatatgtt ccatgctcgt ggctctgggg tataacaaga acaacatctt 240
gctcccatcc ctgtcataaa aggcagaaaa ttaaatacag atgcataaac ctcggctgtg 300
tgactttgcg cataaatgac agtcagcctc cattagtgtt cagacccttt tagacagctg 360
aaatactgct acgaactgct gatgctggct gagctcccca tggtacgtgt ggtgcacttt 420
ccctgcgcag cattagcagt gaaagcagct cagggtgcgg tggtggccaa acccagggcc 480
gatcccacgg cctcctgtac ctggtcatac ccacgggcac agctgctagt gaggtgcgtg 540
cttttcagac acgtcatata agtgtgccct gcctacatgt ctgggtcctc caaatgacgt 600
tgcaaggttt atctcatctt ggaattgtcc cttactgacc accaagtgtt ttgagatgaa 660
tgccctccta ggtctggttc tgctcttgcc tgctggtctt ttctcatagt agtccttgcc 720
agcccaagta tctgagcagt gttttgcaat ccaaggacaa agtacccctc tgcctttgag 780
agtgtgacct ctgtcattgg cacattgtcc gtgaaatata ttttgctttt gtcctttgtt 840
ggtgtattga actgatgttt tcttgatcca catgagagaa actttaataa aaattataaa 900
aaataatgcc tcccttaagc atttcttttc cctgatggaa tgaggccatt caaaagaagg 960
atgctttggc ggtaaaacag aggatttatg ttgagatggg cagatgaatc aagcagtgat 1020
ttccagtttg gattgaactt ttctgggatc caggctgtgg gcctcatgtc attctgtcat 1080
catcaggcta tcagtctgct gctgcaaatc ctccccacaa cgctaatggc ttttagggaa 1140
aatcgcaatt gttagttctt tgctaatgcc cataaaactt cttccatcac ttgtccagct 1200
ccaggactcc cttcagcccc aggtttccct cttgctctct ctcccagttc agtttttctg 1260
gatttgctat gatttgatga tgcattattg acaggacaag gggaaatggt ttcaaaccag 1320
aggagaggag atttagactg gacataagca agacattttt tacaatggtg gtgaggcact 1380
gacagaggtt gcccagagag gtggtggtgc cccatccatg gagacagcca aggtcaggag 1440
gggctctgag cactgatgga gctgtgggtg cccctgttca ttgcaggggg ttggaccaga 1500
tggcctttaa agatcccttc caactcaaat gcttcaatga ttctgtgatt ctattgggtt 1560
gaagcatgcc aactaagact ttccactctg gaaaacattc aattcagttc aacaacattt 1620
tccagcaaca gtgagaaagc actgcatata ggtaagcact gataacatgc acatggagga 1680
aatcctgcag cattctctct tcaggtttgt acagttgccc ttttgcccac aggaattttc 1740

-continued

```
catggtcctt cagcaggcac ctgtcacaca cttcactgga aataatgaag ccgagggcgt   1800
acttcacata tttaaacctg caattgctgt tgataaagaa gcattctttg tggctcactt   1860
gtgtaagtgc catcaagatt tacaaccctg acaccagagc tggaacgctg gttatttcaa   1920
agtagggggt ggctaaacca aacgtgaatg cacacagcca cgcacacaca gatcaggtgg   1980
ccatccaagg gcagaagggc cgcattccat gagcacgatg cacttctgcc ctttgctgct   2040
gcccaggtga gtggctgtgc tcctgctccg tgcttcgtcg agtgctggct gtaaaaacac   2100
aacaaacatc ctcagactgg aaagagctgt gttctacaag gacttattta ctcctagagg   2160
gatggtgttg aaaagacttg acatcaaaga ctatcactta tggggtaata ttttagcaac   2220
agaactgagt gggtaagaac aactgtggga acagctccgc gctcggtgct agtttatgca   2280
taatgaaagc agtgacacgt acgtggtacc acgacatcca ccattgaacc tccgaaacgc   2340
tgcagaatca caaattcttt tactgaatgg aagcgagcgt ttcccgcagt catcctgaac   2400
tgagatgcaa ttggaggggc tgagcggctg cagcagcgtt aggggagttt cacctcgctg   2460
agccctcccg ttatttcagt gctgttgtgg agctgcacgc aggagctgcc gccagtccgt   2520
gccagctctg cggccctgct tccccggcac cttgcttatc tctgagcacc tgtccttgct   2580
catcctgtga atcacggaga attgctttct cttcctccct ttcatttcgc gcgtccttct   2640
ccacccgggc tgtaaccctc ctgagaaaaa acgtagtacg gaatcgatgt tgtaaacact   2700
cagcgtggca caacgttttg cctgaaatcc cttttgtctg agagtcacac actgaattgc   2760
aagttgttta ttcaggacat gcactcacgg attttaacac taacgaagga gatgaattgc   2820
atttgtgtca cacttcctat tcccttcttt actccagacc ccactgcact gaaggtaagg   2880
gacagatctt tcaggttttt tttttttttt ctccatcatt tctttcctca aagcagtttc   2940
cgtataaatc attactaatc gcattgtgat cgagcgtttg aaagccctga gtcatcccac   3000
agcctgagca atatttgcta cagatattac cgagtgaaat ggccattttc atctgatggt   3060
ttcaaaaaaa aaaaaaagat aataataata ataataataa taaataaata gcgcagcatt   3120
cagttggtgt ccaagttatt gtcacggtta ctgcagcagc actgaggatg tttacatggg   3180
atttacatca ctggaggctg aaagggcact gcaggcgtgt accgcgctat tcgctgcccc   3240
atccttaagc tcttctttga catctgctga tggtcggtgc tgggggaagc ccggggctgt   3300
gggggtctcc tggcatctgc cctgctgata gctgtgctgc tgagggtatt tctgtgagca   3360
caaggctgca tcgatccaca gggcgactgc agtgcctgcg ccgtaccccg caatttctgc   3420
tctcgggagc gcatcccaca ctgcgggtct gatggcgtaa catatgccag cgagtgttta   3480
ttccgcaatg catttctggg tgtatgaaaa taaatctctt cgctcactga gtggtgaact   3540
tcaactgtct tatcaacctc agggactgcc tggagatgga aggtggttgt gtttggcgct   3600
ctcctcttct cttgctagca agggcagcac tttttttttt aaactgggag gatttaccag   3660
ggactccttt ctttcaggta aaaagaagtc acatttagca gagatcttca tctccacgtt   3720
gggtaatttg ctgaagagct cgcttccagc aaatacagtc tatttcctac agcctatttg   3780
ttcttctttt aaattaagtc tttatcgtgc ctttgaatgt tagtaataag aggaagtagc   3840
tggaatagct ttccgaatgt tctgttttgg ttaagttcct ctgtgatgta tccttaagca   3900
gagggaggga tgcacagcag aagcgcagag gttcaatctc tgaggccctg agctctttct   3960
ctccagaact cattgagttc tcaccttgct gtgccctgcg cagcgctcac atcacagccc   4020
accgggctcc agctcagaca ggaggaccct ctctggctgt gttccttaca ggggatgctg   4080
cccaaagcct cgtcctgaac tttgagtgct cctgataaag cctgaagcta tgctcaataa   4140
```

-continued

```
aaaaaaaaaa ccttcagcat tttggtcttg ctttcatact acgtatcatg ctgttgtttt   4200
tttttcttaa gatgctgtgt gattgcatca ctgcaacagt cctggggtgt gggtcttaat   4260
gggaaaatta cagggagaaa gaacgggttg tctgatttat gaagaaatca acccctccaa   4320
aaggccatga gcttctgctt tcttccagat ttccaaaaga aagccactgc tggggatgag   4380
atccagtgca gtgttcaggg catcctgtgc agacattgac tccttaggag ctgaaaataa   4440
agtagtggtg ggtacccgta ggtgtgggaa gcctttctgc agccacctgg tctgcctccc   4500
aaagcagagg atgggatgtt ttcccctccg ggcagcacca acagaggggt ggcagcaggg   4560
tgaggaagat gattggcccc tctgctctgc tcttgtgggg accacatgca gtattgcatc   4620
caggcctggg gccccagcat gagaaagacg tggaactgtt ggagtgggtc cataggaggc   4680
catgaagaca atcacagggc tggagcacct ctcttatgaa gaaaggctga gggagctggg   4740
cttgttcagc atcaagaagg gaaagctgag aggacacctc attggagtct tccagtactt   4800
gaagggagct tgcaagcagg aaggggaaca aacttctaca tggtctgaca gagatagaac   4860
aagggggagt ggctttaagc taaaagaggg aagatttggg tgagatgttg ggaagaaata   4920
ctttactcag aggttggtgt gacactggca ctgctgccca gagctgtggg tgccccatcc   4980
ctgtacatga gctgaaggcc agattggatg gggctctgtg cagcctgatc tggtgggggg   5040
cagccagccc atggcagggg ttggggtaga tgggttgtat ggcccttttc aacccaaacc   5100
attcaatgat tctatgattc tcagataagc ctgcctgccc acatctgagc tcacggtgct   5160
cgctggggt ggggtatggt acactaaatg atgctcagag gactgcacgc aggacctgcc    5220
gcagacgttt atcacctcac ccaccactta gctgctgctt gtagttaatt acgtcagctg   5280
tcacttgtag agaatccttt gagatccttg ggcctccgga aatcttggct gatgaaagga   5340
agggctcaga gtcatagcgt taatttatta ttcattaaca ccaaagtgtc ggctgtacgg   5400
gcagtgggct cacagtcaaa tagttaatga tcttaagtga caatgtgtca ctttgcagac   5460
agcagagaga acagctctcc taagggagac agcatctttc caattctgca gccattcagt   5520
gccaagctcc tctttgggac gaaagtgaag atgaggaagg caatgaggat gaggaggggc   5580
ctcaaggaac ctggctggct tggagacaag tgatgatccc agctgctctc agggtcccag   5640
cggtcttcaa agggcatctt gcaggggctg tgtcctctga acagcaaaac ccaggtcata   5700
gaggggaaag tgtgagcaga gatgggacaa atctcccatc ctgccacgga gctgcactgc   5760
taagggggtg atggggagca gcatgggacc ccagcgttcc ccccatccct gcaccaggcc   5820
cagctctgcg ggatggcgag gaggacaagg ctctgtcaca agcatcgctg gcaattatta   5880
ttttgttgtt gctgctcaat aaaatcctga cacagtacaa cacaatatcc tctcatcatt   5940
actaatctaa ctctccctcc aggaaatttc aggcaggaaa cgttgtctgc ctgccgaggt   6000
gctttatggc actgttcttt agtggtacct cagcacttcg tgtcattatc tggtgtcagt   6060
gaatttagga aatgccattc aattaccccg caaactgatt aacgcattgc gtgcagttat   6120
tttgttctgc tctattttat atcagttcct ctgttttatg tatttctcta cttgttgctg   6180
gccagaacac acctcgggcc agtctagacc ttgctgttga tgcagctttt ccccagggct   6240
tcatcagcac aaatggtttg tcaacgtggg gaaaaataaa attatgcttt aaaataaaac   6300
cacctggaga tgctgttctg gggtctggct gtgtcacagc tattgcagcg atggagctga   6360
gggattggga tgtgctgggc cggatcctca gcgctttgct ataagccaaa taattccaga   6420
cacccttctt ccctcagata tcatctgtgc ttaagcagca ggagatatgc aggcagcgat   6480
```

-continued

```
cagatagctg agctgcaagg agaaatatca caagagcgcg gcttagagca ggggctttgc   6540
tcgctctaaa ttgaattccc atcctcatag gagatccagt cctgcccccg tgtgcatcgc   6600
tccggtaaca gcaatgtgtt ttgctccatc ttgcagaggg tccagaagct ggggaaagga   6660
aatgtgtcgt gcgttcgtcc ctgcagcagc tcggcccata aaattaatga aaatcttttt   6720
taggtcatgg tagattacag atttctttga gatagagaat ctcaagagca gaggagaaga   6780
ttctcagaaa atagcagtga tatgagatgg cataacgctg agttggaaac tggggaggat   6840
ttccagggtt actggaaatt tacttaagca cgagagaatg catcgtgtga ctgccagtgc   6900
ttccccactc acatggctat aaccttcttg catacaatta ccatcttgga acttgaaata   6960
gctgaaagag ttttatttga tcttttcaat ggatcttaca tctgcagaaa aaaaaaaaaa   7020
aggctagaaa taatcctgca ctcaaactca ctttactgaa ccaccatcat gaaactccag   7080
caacacacag ggatttgggc aggcgtgttc atcttcctct tcccatttgc aacatgtgta   7140
tggcatttcc tgaagctcac tcctccaaat gcattgagac agttgttttt cattcttcct   7200
aatgcctgca tccacccatc tgctgatcgg caattatttc tatcccattc ccttctgttt   7260
cttattaatc aagctcttta tgcaatccca cgtaacactt tgcccagctg ccctgcccta   7320
accactacca attatctcat cctgttttat agaccctgta gcaagactct ggccttgctc   7380
ctcttcctct ccctgataga gcttttggtg cagggctggc tggctcctca ggtgttcaga   7440
ggatcagagg tctcccagaa ggatcttgtt aatcaaggac aggtgctggc tatatgggag   7500
gatggcaccg tatcctaaag ctctacaaga aggagacgga gctcagcctg ggaggacaga   7560
gagaagcagc agcacaggtt tcaggatcca gggatggcag acctgggtgt gggctcatag   7620
gattgaagaa gggataggct gtgctcctgt agcctcactg cagaagcagc actgctatct   7680
ccccagcgaa gctgtgtgtg ccccatccct ggaggtgctc aggaccaggt gggatggggc   7740
cctgggcagt ctgagccgga gggagcagcc ggcccacagc aggggttgga atggggtggg   7800
ttttaagttc ccctccaacc aaagccattt cttgatctct gttggtggct ggtgcaagtt   7860
ctgaggaaac ctcattttca gctcaggcgt tcttgtccct ggggaaaaat caatattaat   7920
gcttcagtga ttactgctcg ccttccaaat gtgcttctga tcagttcaag aaatctgaca   7980
gtcacgtcgc tcaggatgct aagaatacaa cagaaacagc tttgaaagga acccttcaac   8040
tcttgatatt tgtgaatgag ctccaaagaa cattactcat ttatttttca ggaaaatgat   8100
ttcattgaca tgaacaggcc aaagcctaca agctctgttt tgtgactgca gctccttaca   8160
ctttcagctg cattttcatg atttatgtgc ccatgatgag acttgaacac ctcccaggat   8220
aatgggaaaa gcagttctga tttcccattt aaaacgtagg ctgcctttaa gccatgtgtg   8280
tggctcaggc tccttctgaa gcacaaaggt gttccacccc tcgctccttt ttcattacaa   8340
ctttcaatca aaaatgtgtt ttatgagata tttgttttgc catgtatctg tgacggagtt   8400
gaacccctta gtgaaacctc tgttcttcac ttagctgaga ggtatttctt agggaatgtg   8460
atgccctaaa tttattgtgg tgtaatagaa ggggggatgt gtggactcac cttctgtttg   8520
ttgtggctgc agtggtttta tgcactacct gagtattaag caagcccttt tcatctgcac   8580
ggaacacctc ctgcttgcca gtgggatgaa acaacaacaa caaagattta aggtttgcta   8640
ttctcaatgt ttcttaatcg ggttcacatt gattgccaac agatgaataa ttcctccttc   8700
tccatggatg tacctcttaa acttgtgaag tcttaggtaa cgcttttctg ctgtgatgac   8760
tgtttcagtc ccctcagtga gaaatcaggc gcaccagtaa gacacaaagg agaccgtgga   8820
gatgttcatt gtgccctcag catctccaaa aggcactgct gcctgccgag ccccagactt   8880
```

-continued

```
cgctcctgta aaagcaaagc atgtccaatt ctgctgtgcc ataagagtcc tgtggagccc   8940
agacacggcg tagcgtgtgt aacatagcgt gcacgagctc aaacgctttc aacaaatcag   9000
ctttttttgct ttgccaactt ccatatgtaa tttcacaaca tctagtattg agacagtgct   9060
gttgtttggg cagcataaat cactcattgt acagcagggc gcctctctta acaagttggg   9120
tgtagttcat gtttttgtct aattcctctg cgcatctctc taacaaacaa ctattcttta   9180
gggctcgact caataatcaa tacatttttt tcagtttaca gagcaaataa ttacttgacc   9240
tgatgacttc acaaggttag ggagatgggt gtataaagtc tgcagtgtga aggcagagca   9300
acatctctgc agaccttgag agcaacaggt ctgcaagtaa caggctgcac agccacctct   9360
gccatggagg caatgagagc tgctgccctc cttggattgg tgcttctcag ctcctttcct   9420
ggtaagttgt ttttgttaca ttctctgctt atatctctac tcctactgaa ctaaatgtgg   9480
ttcaggatgc ctttagaatc ctaaaagaga gctcagcctg ccggagaagt gatggtttgg   9540
taaaacatga gctctcttct aatgatcttt atccttgtgc aaatatttac gtaactctag   9600
caggatgcct ctgtctgaca taaactcatt atcctcagta agtctcatag cactcgagag   9660
agaaaatgta taccctattt cttccttagt gagtcaaagt ttatattttc acccaaaatg   9720
gctatttttt ttaatcatag gatatagctt gcttatagga actggataaa atatttagga   9780
aacaagtaat tctcagtgat aaaaaagaag tatgtgatga ctctgtaggg aaattgataa   9840
ttccagagga attgtaacca aggacgccgt aacattctgt attttataac ctctgttttt   9900
tccagatatt gtttctggtc atcaacgggt gagtagcaga tctgcatcat ttagttgtgg   9960
tttctatgaa tagatgaata attcatactc acaccatatc ctacgggagc ctagagggag  10020
aaaaaaaaaa aagaaaagaa aataacaagg gaaggagaaa aagggccccc aggaattatg  10080
tgacattttt cccccagcaa ataagaaaac atctttgtca gagaaagata acgtaccacg  10140
ttggtgataa gagttggcaa ttaataatgc agagtgggag ccggcgtggc acagcgtgcc  10200
agcagaaaat ctgcacagct tttccctaac tgcctccata tctcccctgc ctgattccct  10260
gaggacccat cagtcagtcg tgtgtctgcc atgccaaaag cctcagtagt gacactgtgc  10320
tcaggcatac tgtaaggaac gctgtaattt gctcccactt cttcaccgtg gaggagtgac  10380
agagaataaa atgaccgcct gcagcacggc tatgcgtgga aaacacaagc agacccttcc  10440
gtgccctgca gagctgtccc acttgtgctc ttcccaggcc tcctgcggtg agtaccggct  10500
gttaggcagc aggaacctcg cctgttccag gatcttccag cccgtctgtg gcaccaataa  10560
catcacctac cccaatgagt gctcgctctg cagagaaatc ctgtgagtag cgatcgcccg  10620
attacccatc gtgatggctc aggtggcaga cagaagcctt ttgaattgtg actaatcacg  10680
ggtggattcg attttttttc cccctgtttc tgtcttccca gagtgcaggc tgtgtttctt  10740
ccttgtcaaa actcctgagt ctaattaatt agtggggctg ggcgtggaga ggcttgatga  10800
gtgaggtgac tgcatggcac caccaggtta acccttcccc tccttctctc ctagccggag  10860
tgggacggtt gacaagaagc acgatgggag gtgtgtgaag gtatggttcc agctcagcca  10920
ctgtgtggag cgatggcaga atcccttccc agcactgatt gtacatttag aatggacagc  10980
tccaaaccca ttggaaatgt aacagaaagg aagaatttca ggtcttttat atatatatat  11040
atatatatat atatgtatgt attaatttca ttttgaacag tgcaaatctg tttcaacggt  11100
gagttttgag atgttatctt gtgtagcaca gctgacttaa aaacagaatc ctctcatttc  11160
aataatcctt tggtgttgtt gaaatagttc cctttagact tagacagaag tctgttgaaa  11220
```

-continued

```
ttaagaagtt ccccaaggaa gtctggattt tgactaaatc ataattttgt aacagggaaa    11280

aagaaaaaaa aaaaggattc catcagaaca tctaccctga ggtttgttta tcaatacacg    11340

gagctgccac gaagtggaga agtgtctcta tttttagatt agagagataa tgtaaagaaa    11400

cactccggct gtgcaattga acataatgct acaattttca cttcagtaca ctcagagtaa    11460

tggcaggaac accgaggtga gcatcagctc cattttcaag tggagcagac atttcacagc    11520

agcagttgct gccatgtagg gcatgttagg cacagatcct atgtggtggc atttggggtg    11580

gaaagcccta agatgacacc aacaaaaccc attctgtgaa cccatttcct ccaggattct    11640

gctgggctca tgtcctcaaa ggcaggactt cacctgcctg tgctcccttg cccgcactgt    11700

gctgggttgg aagctcacat ctccatacag ccccactcac cgtgagtctg ggggtgggag    11760

acacctctca caccatgcac cattacacag ggctgacgga agtgttgttc tgtggctgtt    11820

tcaggttgat tgcactggct acatgagaac aactgatggg cttggaacag cctgcatcca    11880

gcagtacagc ccgctctatg ccaccaacgg gctcgtctac agcaacaagt gcaccttctg    11940

ctcggcagtg gcgtgagtgg tgggtcacac cctgggtgct ggggtctggg tggtggtgtt    12000

tgcagcatat tgaggcttct ggagtggctg tgctgtgctc attcattctc aacttgcttt    12060

cttccccaag gaatggagag gacatagatc tgctcgctgt tggaaaagag cccgaggtaa    12120

agctcgaaag tctgcgctat gaactgttgt tataatatat tatacagcac aaattcagtg    12180

agtcagaact acgcaatagc aatgtcttca ctgtgctggt gtatttgtcc tggaaaaagg    12240

gtttgaggaa aatgactcaa gtatgccagg gtcagaggac gatgaacaaa actcctggct    12300

cctgtgtcag tatcacctgc acagcccctg acaggggttg atgctcagag cattgttcag    12360

atggtggctg tgccagaggt gctcaccgct cctggtgagc gtggggctca tgcagcacca    12420

gctgtcatta cttgggtggg tggacttcat agtgtgctgt tggagacaca ctgcttcctg    12480

gcagcccctc tctgctggct gctgaaccag agcagagcag gtagcgggcc gccagccggg    12540

gagcactgct ttggctgtgt cgctgcttct gagggtattt agtagatttt tccctctgac    12600

ttctcctttt gtgctctgct gggcaagagc attagaattt gcagagttgc tagaacaaca    12660

ggagcctgca tctgaaaaaa tgttttttttt gctttgccat gacataaatg taaagcgccc    12720

atgtaggaaa atacaccaaa caaaggcttc tcaatacgtt cttgctccat tacctacaga    12780

ttgactgcag tgaattcaag agcactgatg cctactgcac tgaagagtac atgcccckttt    12840

gcggctctga cggcgtaacg tatgggaaca aatgccactt ctgcattgca gttttgtaag    12900

tacagtgctc cccatgcagc catgaaacca ctgctgtgcc ggagtatgaa ggcagaagct    12960

gccaggaagc ctttgtgctc ccgttatccc cttggtaaat ccgtccccat ccccaacctg    13020

atcccagctc tacctctgct gtgccttccc caagcactgc agatcttgaa cacaggtgag    13080

tcttctccct ccctcaccat taaattcaga ttctcatttg cgggctcata gcgctcctga    13140

tccatccctg cgagagtaat ttgagtggta actgtagaag gagtatccaa aattacaggg    13200

tttgtcccag atctctctaa catgacaaaa cgtgtaacct ggggaatcag gagacgggtg    13260

aaggtgcaac tgggacagca tggagcattg gcttgcccat gcaaagtcag cagtggcacc    13320

atcagggcta taaaaccacc ttccatgtca gtgattttgg cctcctcctt tctctgcagg    13380

aagagtcatg gatctctgtc tctgcagcac cgtggagaat gctgaatgct ggatcgtaac    13440

ctttaccctc atccatcttt cacttccaaa gcctgcaatt ccaacacgct cttcccgct    13500

ccctgctgta cattgctttc tgccttgacc cgccagtaaa tcacagacag caactctctt    13560

cgccatgggc tggtgtgtta tttatttatt tatttattta ttgttgttat tattttttcc    13620
```

-continued

```
agggcagagg taaaagtctt caggctttca ggcacttatc tgtcaggcag gagaagtttt  13680
gaaataaacc acaataaagg ccaaagtgca acacccatca cacaaaagcc ataagccctc  13740
acgaaagtgc gtcaccccat tccaaaccat cagaagagga aatgttgcta taaaacacat  13800
gctgctctcc ccagttctgt gtcttacagc acataaatgg atttgcttta agagtcagga  13860
tgtggctttg tagaagcacg gagccctgga ggaagcagtc cttttgggag ccttggtatg  13920
gaggaaagat ggctttgata cacctgagca aggggcaagt ctggcggcac gttacaagga  13980
ggcttatggc aaagggagga gactatctca cagggaagaa aattaggaac tgttgcttcc  14040
ttgaagggtg tgtcccttga gagtgtggtg atcagcagaa aattgcagcc agctgggcaa  14100
ggctgtaatg agcctaatga ggaccagagg agaaaccaga ttgggctcag gcttcttgga  14160
aaagagatct gaaaagctgc actgggagcg tttgaggcag aggaaagaga aaggactctt  14220
caggaaaagg tttgggagtc ttcatgccta gaaaagaaag gacagaagga gtgcttggta  14280
gctccaaggt cgtttctgtc tgcagtgaaa ggtgatgtgt ggatgatgcg tgtgagcgtt  14340
cacagtgatg tgccatctct ttgggcgagt caaggaatga gtatgcaaac aacaggtgaa  14400
aagtcccaag tgcctccact catgccacct tccccttcct ttctccacct cccatcctct  14460
cattacgtag gaagacattc agctgttcag gctgatattg aggacaaaat ctgtgacttc  14520
caagctttc tctggcttta tttcctgaaa taggctgtat cttgacctag aaatcttatg  14580
ggtgcttcct gccagaagat gggaagctgt cctttaatag cgtgtcaggg cagtgctccg  14640
tcctaggaag acagatggaa ctttgaaatg tttattctat tagcacaggc agtataaagc  14700
acagtgtgcc tctgtgcctg ctggtgagaa aaggcaagct gcagagccgt gagggtgctc  14760
cctgctaatc tgcctagaag ggaaaagagt agacaagaaa tagcatatgc tactactgaa  14820
tgtgagcaga agacctttag tgaaggacac agctcagctg taatgtcctg ttggccagga  14880
ggtttgttga gttatcgcag agcggtagag ttctggtcag agcaggaagg tgccttcaac  14940
agcaagatcc catggtaggc ctcttctgca gtgtgctggc acaagcctgg tacctgctca  15000
ggagcaaaaa aaggctttgg aaaagctcaa agaagggctg atgtcttaca gggaaaggga  15060
gggcaaaagg caagtgcaga gcatatggct gtacagacaa aaacccttca gaaaatggaa  15120
aaggttttta tcaagtaagc ccagaagttg gcccagtgca ggtaaacact tggctaggta  15180
acagtgaggc tctgcccagc catacccatt cctctgtaag gcaaatccca ggtgcctttg  15240
tcttgtctgg tcctgttctg ttcctatttt tctgagaaat cagacagaac ttccccacct  15300
acagcatcaa gcagctactt tataggtgaa gaagtgcaaa gagaagcaat aaggataatc  15360
accacttggc taatttagtc tcttcctctc agcccacaaa ggactggtcc ctgtggtaca  15420
ttttctaagg cttttcccag tcagctgtgc tgtagcaaat gaaatgtttg gctagataaa  15480
gagctgaggt attagtgctg gggcggcgag cagtgtctgg agcaagaaaa ggcaaacgag  15540
ggattctgcg agtggcagaa ctaagcctga ttttgaatgg cgttgtggct ggcggacttg  15600
taaattatat gagaggctgt gctgtgagct caccctaata gacatctgag aactcacctg  15660
tcaatcgcgg ttcctctgct gtgtgggttt tatggtgtct agtgagctgc aagctctaat  15720
gctttcccag gtgcagggca gttgtggcat tgctctccta cagaaactct cacttgctgg  15780
ctgaggatgt ttaggaagtc cttggttgct agaaaaaata tattgaagtg cttttttgt  15840
ttgtttgttt tccattcttg tgtgaaattt tgttggaatc acagaatcat agaggttgaa  15900
agagaaactc tggaaattat caagttcaac cccttgctaa agcaggcttc atacagtagg  15960
```

-continued

```
ttgcagttac aacatttgct ggggaaatga atatgaagat ctgtctataa agagtgttcc  16020
catagcactt gtttctttag gaaagcatgc tgaaattcta aaggctgtgc ctatctgaag  16080
agatactttg caagtggtgc aactaaatgc tgctcttggt ggagagatgg ctggagatgg  16140
atcgatggtt gggtgatctt cgtggtcttt tccaacttta atgattctat gattctatac  16200
tctttacaca gaatcagctg ggaatagagt gagagtctcc tgattcccca ccaaattcct  16260
ttgattgatg cttggtgtgg aagcagagct ctgggacacg ttggtgagtg tgaaaactgg  16320
aaaacattga cagctatagt ttaaatagtt cagggaggag aggcagccat cctatgtggg  16380
actctgcaca cggctatgag agcatcagtg cgcttctcca ccccaaccca acaaatttag  16440
agccatcctc caaaatagcc agggaacaac gcataattgg tttcacagac aacacattct  16500
catgctgtga tttatttcgt aatgtctggt gagtgtcatc acgccgtgct caaagcctgg  16560
agctggcatt cagcgaggac ccagagaatg aaaattacca gcttccccga tgaatcacca  16620
ctttgaaaat tcacccttgt gagaatcctg tgactattca gaaaaaaaaa aaaaaaagaa  16680
gaagaagaag aagaagatat tacaggccca agtctatcag tcatgtaatt agccctttct  16740
aggtttgatg tggacagggc ggcattccta aagcaccata aacacggccg ggaccaataa  16800
tggctctaga atcgaagcgg agaagttctc acaattaagg tgaggaatga ggccagcagc  16860
ggataggtac ataaatacac ggaggcaggg ccgtgagcac gctgtgggct tgtggctgag  16920
acaacacctc ccaaaccggt cgcttgccgg ggactaaaag agcagcatga aggcaacagg  16980
cacctcggtg ctcctcagcc tgctgctgct gctgtcgttc ttctcgggta agttatattt  17040
ctgtagccta gaaagaaact ttatgacgag agcaacttca gagagccttg atcaacggat  17100
gacaggcttg aagagaaagc tgagcaagta gaaaatatct gcgggactcg cttgcttgtg  17160
tcacatcttt ccattcctcg tgtgcctccg cagtgaataa cactgtggag gtgtcactgg  17220
gagacagaat gagcaaattg taagcagctc gttcagcaga ggcaccaaag cagagcgtaa  17280
ttatgagttt tggtggaaat gtttgctgga gagctttgct gaaccagtta gagaagaaac  17340
tcatacctca gggtcatcag ctcctgttct gatgctaagc acttggggt tggtgttctc  17400
ctcagagatg tggcagcgta attagatgaa agtttcagct tccaaatacg ttgcagagga  17460
gggctcgaaa attaaattca gatgtcctcg aggaacccga acaaagaggg caaattgaaa  17520
gggtccagcg tttatttatc ttgaggttta cacgtctctc tgttggtctg gggaggctgg  17580
ctgatggttt gggggtgtgt agggcacacc ggggtgctca aatgctcgcg tgcggccgat  17640
gcgaatgtgg aagcgttgcg gtggccatta ctgaagactg cagaccaagg attatttata  17700
cttgtttttc tgtgaataat ttgaataaag aattcgcttg agaaaatcgc aggctgtgca  17760
tggagagaag aggtgaatta ctttgtacac atcattaatt atgaaatatt catctgtctt  17820
taattgagtc ttaattgggg ctgggttccg tcagagtgct aaagcttctt tccaaggcca  17880
ggcagaatag cagcaaactc tgtgatctca aataagataa acagatgcca agagacgttc  17940
tcacaaagtc ttgtgtagct gcatgtaata tttataaaaa ttatctaatg agctgttttg  18000
taaataatat gcagatagcc ctaacggcgg cttccctgtc cagcctagct gaggatgtga  18060
cagatacagc agtggcaagg atcaaacact gaaaggcatc gcagcaggca gaagctgggt  18120
ggggtgatgg atggtcccgc tgagcgtgat gctgcaatgc tcccagcctg caccctaacc  18180
aaagggatgc cccattgcaa tgcgccccag cccctgcagc gctgtgtgca gcccactccc  18240
tgtccccgac accacaggat ccatcccgtg gctgtgacct ggccccatgc aaagtttgca  18300
ggcaggaaat agcaaagagg atggactgat tgtctccagg cccagagcct gtgcctgcag  18360
```

-continued

```
caggtatttt tgctctgctg ctgtctggca ctgcctgttc tgccccagat cacgccaggc  18420
tatccctttg tatctcatcc ggatgaggct gttctgggag cctcggctgt gctgtactgc  18480
agacggctct gatgctgact gcggggtctc ctccatctcc cctgtgtgct tttgttaccg  18540
tactggccag ttttgtaatt cagaggtgca agagcctaaa agccataaga ctcaatgaag  18600
ctttaaaatc tctgctgaga gaggctcagc tcttacatag ctccccgctt ccccggcggt  18660
ggctgcctgc cagggagatg ggtttatgtg tctgtggtgc agttagcagc tgaatgactg  18720
attacatggt attttagtaa catttttcaa atagcaaaat actgaaaagc aattccgata  18780
atgtatttcc taccccctcct ccaccacaca gaacggcaga ggagggaaaa cctggtgtgt  18840
gctgtgctgc agtttgcaaa gggatttgtg acttcggttc agtcctctca gaaaataatg  18900
ctaatgtgga taaaatcttt ttttttgttg caattctagg tgtagcagct caagacattg  18960
aagaggttag tgcagctctt tctgctttct gaatctgcat tttctcctgg ctctggaaga  19020
atgcttttct aacagatctt ggtgcattgg tgcatgctga actgctttgg gttttgctgg  19080
gatcaggtgg gtcctgccaa ggtgccccaa tgcttcggag tgctcacaca gtacaggggt  19140
gttagctatg gccacagtag caaacaagtt ggggatgatt tagctggttt agcacatgct  19200
ccccatggtc tgatccagca cagggctgtc tgcagtatcg cttctgtctg ctttgctcct  19260
ccacgaaaca aatgtgatat caggagtgat atactccttt aaaccatatc cataactggg  19320
gcttgtccaa aagcctgttc acttcataga atcattaagg ttggaaagac cactatggtc  19380
atcgagtgca accactccat gcccagatcc ctgtgtatgg cagccccagg ccacgtggtg  19440
gtgtgagctg catggtaccg ggcactgata tggggctgca tcagtgctga tgctctcctg  19500
ttgaacccac tcatgttctt ggaacaccag agctgctccc tggtggtgac agcttccctc  19560
ctctgccaca gggcagaaat tcccccattt cagccagttc tgacaggcct ttgtttttca  19620
agtaagcagg ccgtgcctcg ttgctgcttt tggcctctgg gtgggaagaa gatcacatta  19680
gagatcttct ttcctgtttg gaaagcgaaa cccgacggtt tattgctgtt attatttttg  19740
atttcttttg cagatctgca aagagttctt aaacaggagc gtgttctgca ccagggagtc  19800
caaccctcac tgcggcacgg atggcgtgac gtacggcaac aagtgtgcct tctgcaaggc  19860
cgtgctgtaa gtgggggcgg tgggatacgg acccacacag ggatggtcca cttccaaccc  19920
cgcgctgctg ctcccctcac acagagcaat ccctggccat agaatcatag aactagagaa  19980
tggttaaggt tggaaaagac caataagtgc atctagttca aatggcagct cctcaccgcc  20040
acgcttggga atatttcagc ttaatgttga ttcatttcta ggcttagtgt gatgctcata  20100
gccgtacaga gatggcacag agcctgggag gccattgtac ctgcctgtac cttctgcgtg  20160
ggctaaattg atgcacattt tcctctgtgt gccacaggct gaagctctcc ctgtccacac  20220
ctctggatgc tgaagtgtgt ggaggaacgc aggcttatgc atgccaaatt attagaggaa  20280
agtcatagac tcgtagaatc atagattcgt ttgagtcgaa tgggaccttt gaaggtcatc  20340
tggtccagca tccctgcaac gagcagggaa agtgctgaaa tgaaagtctg aatggactta  20400
gtggaaaagt acacaaaatc tcagaggaag ggctgcagtt tctcctctcc tgtctcctct  20460
aaaggagctg taataggagc caacacctct ggactgaagg cctgcaaaaa ttgatttatc  20520
cttatcaatc ctgcactctg gaggctgcct tatcctaagg gaaattagag aagagggaaa  20580
gatggcttga tgctccctgt gaggcaccag agtgaggcaa atgatcgtgc tcggagggac  20640
aagctccctg tcccagccgc tgtgtctgtg ctggatgcca tacactgctt tgtttccata  20700
```

-continued

```
ccgctccttt tacaggagga gtggagggaa gatacgattg aagcacatgg ggaagtgctg  20760
agcctgagca ccaagcactg atcttcgtcg gtcacaggtg caggagcctg ggcacggcag  20820
cagctgtcct catctctgcc atatctgctc aataaagtaa agctcagcac acctccttga  20880
ctggattcct ttttccataa cacccggata agccttccat gcagccgtgc tagcagctaa  20940
aatgtttgcc gcactgtgct gttacatctt agaatcacag aatcaggcac catgctgcct  21000
gagcaggagc aatgattccc acagctcttc catgccatgc catgccatgc catgccatgc  21060
catgccatgc catgccatgc catgccatgc catgccatgc catgccatgc catcccatcc  21120
catcccatcc catcccatcc cactgacaaa tggacacatg gccacccagc ttgactgtcc  21180
catgggtggg tgacagcatg caacgttgcc tctcagcagc ctccccatat gtgtccctct  21240
cgctgaggtg tgagcatgaa ggtggcagag agctatgagt ggtgtggctg tggatgcctc  21300
atctgcttgg gaagccagaa gcaaacaggc tgaggctgag gagtgttgct gcatgtaagc  21360
ctgcaccggg aaggtggcag gggaagctgg ctttaggcag aaacacaaag gctttgcttt  21420
ccttgtgtgt cctaagagag gactttgcct caaagactgt caactcgcca gcatcaggtt  21480
gcagttgcac acaaacttga tttctttctt tagttttcac actgctgctc tctctctcct  21540
tgatgctggc tggaaaatcc ttctttgcgc cagcgaggga aaataaagcc tatagtctct  21600
ccccattcgc tgtacaaaat atacacaggg aaatgcttgt ggcatcccct cgttaaaacg  21660
ttggcagcac atcaatggga ctctactcac ttaatgttga acacttaagt ttcaaaggga  21720
gctttagatt ttatcgtgag gtcagccaac tcattttgca aacacctcta tgctgagcat  21780
ctcagctcct ggatggtgtt tggacagagc tgagtgtttg cctgtggtgc cacgctgcag  21840
gctttgaagt gaattgggac attatatttt gtagccaagg agagttgcag tttgctttgt  21900
tccaattcag atgtttcttt agtaaacaca acagctagac ctccagaaca tggataagct  21960
tgaggggagg aaaaagcacc tcctgcacga ggacagctga tcacaaagga ccccagtggg  22020
cagtgggaga accttcatca tcctctctac cgcctggatc aggatgagcc ctgcataccc  22080
tttccaactg gagttaccct gtgagccaac ttgtggctct ggagtagtgc tgtatctcaa  22140
tacagtttct cagatgggaa gaggcatttc aatgagaggg gggatatggg acatttctat  22200
gcctgagatg gctctcggag actccaaaag cctcacggcg tatccccatg cctaatcctt  22260
tttaatctgg aggctgaaat aacaaggaca gatcacaaga gaacagaagc ggcgagactt  22320
ctctgcttta taatcagcct gcattttgct ctttcagtgc aaacagcaaa tagaaccgcc  22380
tctgtacccc tccagaccca accaccatcc ccagcaacac tgtggcaggc tggagaaggg  22440
tggctctgcc cctccttgcc tcaactggtt gtgtcagcac gaccataacc agagctctcc  22500
ttggccccag ctgggcttat ccatgtaaac ctctcagtgc cccaggagct ggctggtggt  22560
cctgtccatt tcactttcct ccagcaggtg ttccctttaa caagcatcca agtgcctgga  22620
gcaggagcag gcactgcaga agatgagctc aggcaaggac atggcatgtg gggatccatg  22680
ctgttgtgca atgcagatga cgttagatac gtgcaaagca gatctcagca atcacccaac  22740
gactcataac tgcaatcatg gaacgcaatt gcatctggaa gtataaaagc acagtgatac  22800
caggaagctc ttgttaatgg cacagccatt ttggagcaat ttgcccaggt ggggagagcc  22860
ctcacagcgc cttcagtcac agggagtggt gtgagtgccc ccatggctgc tcccagcccc  22920
cagccctggg tgatgggggt cacttggctg taaccctctg aacacaggga cagtgagaca  22980
gccctctggc ctggctgagc tcttggctac gtccagctgc agtcctgggc acatactgaa  23040
ccagaaagca agcattcagc tggtattttt cctttaattt ccttcctcca cattttaagt  23100
```

-continued

```
tgtgggattt tttttttttt tttttgacag ctttgagaga tgagtgagtc acgaagcact  23160
cgagatctct attagataac agagcatctc tgcagctctt cctggggagg gagttccttg  23220
gaccaagggc caaggctggg tgagaattgt cccagcatca cagtggctgc tccatcacct  23280
gacacagccc ctctgcagtg aaacaaggga agcattacat ctttgcacgg ctgctttcac  23340
tgaacaaaaa gcgctgcttc acagctgagc accatgatga aggggaagga gcatctccat  23400
gatgaagggg aaggagcatc tccacatctc catcacgagc tctgctctgc tggtgatgcg  23460
gctgacacca tggtgtgccc tgactcctgg cccatttaac tgctgtgcac cagtgcctcc  23520
tccccagcat agccctgtgt ccctgccaca actcattgca atcctttgtc ctacttcttc  23580
ccttgacatt cacagctctt gataaggctt tttgagccac tcctggctga tgtgggctgg  23640
tggttcctgc tgcagggttc ccaccaccca gctgggcagc attcggttgt tgttccagtt  23700
cccaggggat tgggacagat tggaagggtc tttgggactg tggaagagta tctcctgaag  23760
tcagggcaga ctgctcagcg ctttgtccca tccagacttg aaaacatcca agggtggaga  23820
acacacagac tccctgggct gccagtccca gagtttgact gtcatcacgt tgaagacttt  23880
ttgccttgtc tccatttgca acctctttcc tttcagctgc cccatctctc agccatgcac  23940
cactggggag cccagctctg tctggtcagg aacagagccc ttacagagcc acagcatcct  24000
cctgaagtgt ccatctcacc actcagcctc agcaagtgct ccagccctca actcccattt  24060
tccattatct ttctatcact ggatatggga gggaaggcag agctgtgggg ccaagagaaa  24120
cgattgctca ggaggcagtt gggagaactt tattgcaaag cactgaagag atataaagtg  24180
acatttgcag gaaaaagtag aagggtatct gtgtgtgttg gttcctttaa ggattagaga  24240
gcagctgagc tttgggatga gagggctccc agatgctgtg aatcagctaa cagatccctc  24300
caccccgtca ttggtggtga agttaaatag gggcccaggg gaaacatcag ggttgttttt  24360
ctttttacgg actccagagc aaggagaagg tgaggggggtt gtgctttgga atgggagtga  24420
aagagtttgt tggtgttttc ctctccccag aataagtagt gtggtgtagg agcgtctcat  24480
aggagtagct gcgttaattg tggctggtgt tagcatccta taatgttgct ccagaaatgc  24540
tggagcaggc ttataatgat gtgtatgtat taccataata catgaaggga gaatgggggg  24600
gggggggta gatttaagat gtatgccctt agaaaggcgg gtgtcactta aagaagtact  24660
tgctttatag ctccagtgat agaattcatt gagatactct gaacctatgg ggcatgaagt  24720
gaccagatct tcagtttggt cagctctggg ggtttctggg gggagcgggg atagagcctc  24780
aatccaggtc tgaaagacaa ggctgagatg tgctgggcct ggggtgctgc cctgagcaac  24840
gtggggctgg ccctagagag cagcattagt gcctgcagca gggctggccc ttgtgcccag  24900
tgtgtggggt aaggtgggga acgtaggtgc tgcataatgt ggtgcttctg atctaaaact  24960
gctctgttaa ttgggagtga ccagagatgg ccctatggct ttcttcccaa agagctctgt  25020
gtccttctct gcagggtaat ctgtgataaa aacatcgcct atgctctgcc ctgcagatgc  25080
aggggttttt gtcatcctcc ttctcgagac atactctaat ccttacgcaa gcagggagct  25140
ccaagctttt ggtgataacc tctcaaggag gagctggaag ggcagctctg ccgagcagtg  25200
actgcgctgc acggggcgca tcctgcagga ggcggtggtg taagcgggac tccgctcgtt  25260
cccggctatg gggctccccc tgctgaccgc cgggcggtgg ccaggagacc tcggggccgc  25320
tgctgcccct cggtggtgct tttcgggaca gctttcagga tggggcagcc cagctgctct  25380
cgcggggaat taagcggctc ggtgcagggc ggcacggcgc tgagctgccc cagcaaagcg  25440
```

-continued

```
ccgctcgtcc cgcggcacct tcggtagatg ctctctgctt ggcagctcct tggtcgttct  25500
cttggccggt ggccacccca gcatcgctcg gggctcggtg ccatcccccc cagggcctgc  25560
ggaggtgccg gtgcccgtcc cgggggtggc ggacgggcgg tgcagtaccg atgctgggcg  25620
ctgggtgctg ccgcagaccg agcggcgctg cgcggctccg gggcgctcct ggagtgcgag  25680
ctgagcaacc tggtagaaaa ataagtgttg tcccgtgata aacgtcatcg tgctgagctc  25740
tcagactctg ccagaggcct gaatgaagct gcgtcagggg agaatcaggt tggggctaag  25800
gaaaggtcct gccccagagg gcggtgggta tagaaggggt gcccagggca gtgggtgcag  25860
tgctgggctc ccagagctgg aggagcgtct ggacagtgct caggtttgga tgttgggtgg  25920
ttttctgaag ggacggattc tgggctcgtt tatcctgagg gtcccttcca acttgggttg  25980
ttctattcaa tgaatattgt ttatgttcat tctattctat gatcttgttc aggctctcac  26040
tgctgcctcc aagggttcag ctcccccaga gctggcaggg cttcagccac ttgcttacag  26100
tgctcatttc atgcctggcc catggcttct gcctgagcct tgtgggagat cagctgctgc  26160
cagaaaccca gccctcagca ctccacttgc ccagcttgct gccttagtag tctaacttgg  26220
cagtggtctg acatgacttg aggttgtttt ttatttccaa ggtgccactg actttttttcc  26280
ttccatagtt tctggaagca tttccttcct acttgactga gtcgtgctct gtggatctgt  26340
aattatccac cttggctatg tgtcctttac gggattttat atgttaacct cccaagatca  26400
ttttgctgct ctcatcttag tggctgctgt gagctccacc agcaccacac tggatgagct  26460
gcaggctgag gccgggcacc tctcctgact ctgctcttct ctgaccccag agctgtgcag  26520
ttgggatcct aacaccatgc agatgctcca ggacctgcac cgagccccag cactggcact  26580
catctcttct ttccacccct ctgagagcaa caagtggctc tgcaatggca atgtaagtga  26640
aaccgggcgg gtatcttaga gcacctggaa gcttgcatgc ctgcaggtcg actctagagg  26700
atccccgggt accgagctcg aattccaggt accgtcgacg atgtaggtca cggtctcgaa  26760
gccgcggtgc gggtgccagg gcgtgccctt gggctccccg ggcgcgtact ccacctcacc  26820
catctggtcc atcatgatga acgggtcgag gtggcggtag ttgatcccgg cgaacgcgcg  26880
gcgcaccggg aagccctcgc cctcgaaacc gctgggcgcg gtggtcacgg tgagcacggg  26940
acgtgcgacg gcgtcggcgg gtgcggatac gcggggcagc gtcagcgggt tctcgacggt  27000
cacggcgggc atgtcgacag ccaagccgaa ttcgccctat agtgagtcgt attacaattc  27060
actggccgtc gttttacaac gtcgtgactg ggaaaaccct ggcgttaccc aacttaatcg  27120
ccttgcagca catcccccctt tcgccagctg gcgtaatagc gaagaggccc gcaccgatcg  27180
cccttcccaa cagttgcgca gcctgaatgg cgaatggcgc ctgatgcggt attttctcct  27240
tacgcatctg tgcggtattt cacaccgcat atggtgcact ctcagtacaa tctgctctga  27300
tgccgcatag ttaagccagc cccgacaccc gccaacaccc gctgacgcga accccttgcg  27360
gccgcatcga atataacttc gtataatgta tgctatacga agttattagc gatgagctcg  27420
gacttccatt gttcattcca cggacaaaaa cagagaaagg aaacgacaga ggccaaaaag  27480
ctcgctttca gcacctgtcg tttcctttct tttcagaggg tattttaaat aaaaacatta  27540
agttatgacg aagaagaacg gaaacgcctt aaaccggaaa attttcataa atagcgaaaa  27600
cccgcgaggt cgccgccccg taacctgtcg gatcaccgga aaggacccgt aaagtgataa  27660
tgattatcat ctacatatca caacgtgcgt ggaggccatc aaaccacgtc aaataatcaa  27720
ttatgacgca ggtatcgtat taattgatct gcatcaactt aacgtaaaaa caacttcaga  27780
caatacaaat cagcgacact gaatacgggg caacctcatg tccgagctcg cgagctcgtc  27840
```

-continued

```
gacagcgaca cacttgcatc ggatgcagcc cggttaacgt gccggcacgg cctgggtaac  27900
caggtatttt gtccacataa ccgtgcgcaa aatgttgtgg ataagcagga cacagcagca  27960
atccacagca ggcatacaac cgcacaccga ggttactccg ttctacaggt tacgacgaca  28020
tgtcaatact tgcccttgac aggcattgat ggaatcgtag tctcacgctg atagtctgat  28080
cgacaataca agtgggaccg tggtcccaga ccgataatca gaccgacaac acgagtggga  28140
tcgtggtccc agactaataa tcagaccgac gatacgagtg ggaccgtggt cccagactaa  28200
taatcagacc gacgatacga gtgggaccgt ggttccagac taataatcag accgacgata  28260
cgagtgggac cgtggtccca gactaataat cagaccgacg atacgagtgg gaccatggtc  28320
ccagactaat aatcagaccg acgatacgag tgggaccgtg gtcccagtct gattatcaga  28380
ccgacgatac gagtgggacc gtggtcccag actaataatc agaccgacga tacgagtggg  28440
accgtggtcc cagactaata atcagaccga cgatacgagt gggaccgtgg tcccagtctg  28500
attatcagac cgacgataca agtggaacag tgggcccaga gagaatattc aggccagtta  28560
tgctttctgg cctgtaacaa aggacattaa gtaaagacag ataaacgtag actaaaacgt  28620
ggtcgcatca gggtgctggc ttttcaagtt ccttaagaat ggcctcaatt ttctctatac  28680
actcagttgg aacacgagac ctgtccaggt taagcaccat tttatcgccc ttatacaata  28740
ctgtcgctcc aggagcaaac tgatgtcgtg agcttaaact agttcttgat gcagatgacg  28800
ttttaagcac agaagttaaa agagtgataa cttcttcagc ttcaaatatc accccagctt  28860
ttttctgctc atgaaggtta gatgcctgct gcttaagtaa ttcctcttta tctgtaaagg  28920
ctttttgaag tgcatcacct gaccgggcag atagttcacc ggggtgagaa aaaagagcaa  28980
caactgattt aggcaatttg gcggtgttga tacagcgggt aataatctta cgtgaaatat  29040
tttccgcatc agccagcgca gaaatatttc cagcaaattc attctgcaat cggcttgcat  29100
aacgctgacc acgttcataa gcacttgttg ggcgataatc gttacccaat ctggataatg  29160
cagccatctg ctcatcatcc agctcgccaa ccagaacacg ataatcactt tcggtaagtg  29220
cagcagcttt acgacggcga ctcccatcgg caatttctat gacaccagat actcttcgac  29280
cgaacgccgg tgtctgttga ccagtcagta gaaaagaagg gatgagatca tccagtgcgt  29340
cctcagtaag cagctcctgg tcacgttcat tacctgacca tacccgagag gtcttctcaa  29400
cactatcacc ccggagcact tcaagagtaa acttcacatc ccgaccacat acaggcaaag  29460
taatggcatt accgcgagcc attactccta cgcgcgcaat taacgaatcc accatcgggg  29520
cagctggtgt cgataacgaa gtatcttcaa ccggttgagt attgagcgta tgttttggaa  29580
taacaggcgc acgcttcatt atctaatctc ccagcgtggt ttaatcagac gatcgaaaat  29640
ttcattgcag acaggttccc aaatagaaag agcatttctc caggcaccag ttgaagagcg  29700
ttgatcaatg gcctgttcaa aaacagttct catccggatc tgacctttac caacttcatc  29760
cgtttcacgt acaacatttt ttagaaccat gcttccccag gcatcccgaa tttgctcctc  29820
catccacggg gactgagagc cattactatt gctgtatttg gtaagcaaaa tacgtacatc  29880
aggctcgaac cctttaagat caacgttctt gagcagatca cgaagcatat cgaaaaactg  29940
cagtgcggag gtgtagtcaa acaactcagc aggcgtggga acaatcagca catcagcagc  30000
acatacgaca ttaatcgtgc cgatacccag gttaggcgcg ctgtcaataa ctatgacatc  30060
atagtcatga gcaacagttt caatggccag tcggagcatc aggtgtggat cggtgggcag  30120
tttaccttca tcaaatttgc ccattaactc agtttcaata cggtgcagag ccagacagga  30180
```

-continued

```
aggaataatg tcaagccccg gccagcaagt gggctttatt gcataagtga catcgtcctt  30240
ttccccaaga tagaaaggca ggagagtgtc ttctgcatga atatgaagat ctggtaccca  30300
tccgtgatac attgaggctg ttccctgggg gtcgttacct tccacgagca aaacacgtag  30360
ccccttcaga gccagatcct gagcaagatg aacagaaact gaggttttgt aaacgccacc  30420
tttatgggca gcaaccccga tcaccggtgg aaatacgtct tcagcacgtc gcaatcgcgt  30480
accaaacaca tcacgcatat gattaatttg ttcaattgta taaccaacac gttgctcaac  30540
ccgtcctcga atttccatat ccgggtgcgg tagtcgccct gctttctcgg catctctgat  30600
agcctgagaa gaaaccccaa ctaaatccgc tgcttcacct attctccagc gccgggttat  30660
tttcctcgct tccgggctgt catcattaaa ctgtgcaatg gcgatagcct tcgtcatttc  30720
atgaccagcg tttatgcact ggttaagtgt ttccatgagt ttcattctga acatccttta  30780
atcattgctt tgcgtttttt tattaaatct tgcaatttac tgcaaagcaa caacaaaatc  30840
gcaaagtcat caaaaaaccg caaagttgtt taaaataaga gcaacactac aaaaggagat  30900
aagaagagca catacctcag tcacttatta tcactagcgc tcgccgcagc cgtgtaaccg  30960
agcatagcga gcgaactggc gaggaagcaa agaagaactg ttctgtcaga tagctcttac  31020
gctcagcgca agaagaaata tccaccgtgg gaaaaactcc aggtagaggt acacacgcgg  31080
atagccaatt cagagtaata aactgtgata atcaaccctc atcaatgatg acgaactaac  31140
ccccgatatc aggtcacatg acgaagggaa agagaaggaa atcaactgtg acaaactgcc  31200
ctcaaatttg gcttccttaa aaattacagt tcaaaaagta tgagaaaatc catgcaggct  31260
gaaggaaaca gcaaaactgt gacaaattac cctcagtagg tcagaacaaa tgtgacgaac  31320
caccctcaaa tctgtgacag ataaccctca gactatcctg tcgtcatgga agtgatatcg  31380
cggaaggaaa atacgatatg agtcgtctgg cggcctttct ttttctcaat gtatgagagg  31440
cgcattggag ttctgctgtt gatctcatta acacagacct gcaggaagcg gcggcggaag  31500
tcaggcatac gctggtaact ttgaggcagc tggtaacgct ctatgatcca gtcgattttc  31560
agagagacga tgcctgagcc atccggctta cgatactgac acagggattc gtataaacgc  31620
atggcatacg gattggtgat ttcttttgtt tcactaagcc gaaactgcgt aaaccggttc  31680
tgtaacccga taaagaaggg aatgagatat gggttgatat gtacactgta aagccctctg  31740
gatggactgt gcgcacgttt gataaaccaa ggaaaagatt catagccttt ttcatcgccg  31800
gcatcctctt cagggcgata aaaaaccact tccttccccg cgaaactctt caatgcctgc  31860
cgtatatcct tactggcttc cgcagaggtc aatccgaata tttcagcata tttagcaaca  31920
tggatctcgc agataccgtc atgttcctgt agggtgccat cagattttct gatctggtca  31980
acgaacagat acagcatacg tttttgatcc cgggagagac tatatgccgc ctcagtgagg  32040
tcgtttgact ggacgattcg cgggctattt ttacgtttct tgtgattgat aaccgctgtt  32100
tccgccatga cagatccatg tgaagtgtga caagttttta gattgtcaca ctaaataaaa  32160
aagagtcaat aagcagggat aactttgtga aaaaacagct tcttctgagg gcaatttgtc  32220
acagggttaa gggcaatttg tcacagacag gactgtcatt tgagggtgat ttgtcacact  32280
gaaagggcaa tttgtcacaa caccttctct agaaccagca tggataaagg cctacaaggc  32340
gctctaaaaa agaagatcta aaaactataa aaaaaataat tataaaaata tccccgtgga  32400
taagtggata accccaaggg aagttttttc aggcatcgtg tgtaagcaga atatataagt  32460
gctgttccct ggtgcttcct cgctcactcg agggcttcgc cctgtcgctc gactgcggcg  32520
agcactactg gctgtaaaag gacagaccac atcatggttc tgtgttcatt aggttgttct  32580
```

-continued

```
gtccattgct gacataatcc gctccacttc aacgtaacac cgcacgaaga tttctattgt  32640
tcctgaaggc atattcaaat cgttttcgtt accgcttgca ggcatcatga cagaacacta  32700
cttcctataa acgctacaca ggctcctgag attaataatg cggatctcta cgataatggg  32760
agattttccc gactgtttcg ttcgcttctc agtggataac agccagcttc tctgtttaac  32820
agacaaaaac agcatatcca ctcagttcca catttccata taaaggccaa ggcatttatt  32880
ctcaggataa ttgtttcagc atcgcaaccg catcagactc cggcatcgca aactgcaccc  32940
ggtgccgggc agccacatcc agcgcaaaaa ccttcgtgta gacttccgtt gaactgatgg  33000
acttatgtcc catcaggctt tgcagaactt tcagcggtat accggcatac agcatgtgca  33060
tcgcatagga atggcggaac gtatgtggtg tgaccggaac agagaacgtc acaccgtcag  33120
cagcagcggc ggcaaccgcc tccccaatcc aggtcctgac cgttctgtcc gtcacttccc  33180
agatccgcgc tttctctgtc cttcctgtgc gacggttacg ccgctccatg agcttatcgc  33240
gaataaatac ctgtgacgga agatcacttc gcagaataaa taaatcctgg tgtccctgtt  33300
gataccggga agccctgggc caacttttgg cgaaaatgag acgttgatcg gcacgtaaga  33360
ggttccaact ttcaccataa tgaaataaga tcactaccgg gcgtattttt tgagttatcg  33420
agattttcag gagctaagga agctaaaatg gagaaaaaaa tcactggata taccaccgtt  33480
gatatatccc aatggcatcg taaagaacat tttgaggcat ttcagtcagt tgctcaatgt  33540
acctataacc agaccgttca gctggatatt acggcctttt taaagaccgt aaagaaaaat  33600
aagcacaagt tttatccggc ctttattcac attcttgccc gcctgatgaa tgctcatccg  33660
gaatttacat ctggaattac gtatggcaat gaaagacggt gagctggtga tatgggatag  33720
tgttcaccct tgttacaccg ttttccatga gcaaactgaa acgttttcat cgctctggag  33780
tgaataccac gacgatttcc ggcagtttct acacatatat tcgcaagatg tggcgtgtta  33840
cggtgaaaac ctggcctatt tccctaaagg gtttattgag aatatgtttt tcgtctcagc  33900
caatccctgg gtgagtttca ccagttttga tttaaacgtg gccaatatgg acaacttctt  33960
cgcccccgtt ttcaccatgg gcaaatatta tacgcaaggc gacaaggtgc tgatgccgct  34020
ggcgattcag gttcatcatg ccgtttgtga tggcttccat gtcggcagaa tgcttaatga  34080
attacaacag tactgcgatg agtggcaggg cggggcgtaa ttttttttaag gcagttattg  34140
gtgcccttaa acgcctggtt gctacgcctg aataagtgat aataagcgga tgaatggcag  34200
aaattcgatg ataagctgtc aaacatgaga attggtcgac ggcccgggcg gccgcaaggg  34260
gttcgcgttg gccgattcat taatgcagct ggcacgacag gtttcccgac tggaaagcgg  34320
gcagtgagcg caacgcaatt aatgtgagtt agctcactca ttaggcaccc caggctttac  34380
actttatgct tccggctcgt atgttgtgtg gaattgtgag cggataacaa tttcacacag  34440
gaaacagcta tgaccatgat tacgccaagc tatttaggtg acactataga atactcaagc  34500
tttgtgcttt ctgcctgaat aaaagaaacc tgaactctgt tcacccagtc cctgtcaggc  34560
aattactgac agagcaccta tggtctgtgt ttggccagaa cataggctaa ggaagatacc  34620
tcctgtttat aaagcacgcc tttggcatct ggcaagtaat tagtgatggc gcatgagagc  34680
tctgactagg gcagggtgtg ggacaggctg gctctaattg tgccctgttt atcttgttga  34740
tgcacacggc tggtttcttt cacccacagc tgtctctcta gacaacatac ctttatggag  34800
aggaacgtgt cttttccaat cttgggtttt cattcagaat tggagtgaac tggtctccat  34860
cagatagcat tggctgcggt gatttattct tttacacttc ctagttaagc aggataactc  34920
```

-continued

```
tctggctctg ctgtgtctag gcaatttaaa tgatttataa agcatagctg ttttaaggaa  34980
atcttttttt aaacatttga cttgccaatg tgtggtccta aaggcagaag gactgttcca  35040
gagtgtcagg cagagaccta ccctggattt cgttgttcag ctacccattc agtgtggctt  35100
ttggcaagga attctctgga cctgacttcc ctacctgcag agctgggata agctatcaaa  35160
ccatctcctc cacacactgt gagggtggga aaaaaaccca aacccttaaa agtgctgtat  35220
aaaggcgcct taaggctcag tatagcatgt gtgctgctga tgccccagac ctgtttgcgg  35280
gtcctgaagg tcataggaga actgctcaga agagacagaa atgcttaaga aggttttact  35340
acaaaagtct tgtgatgtta acacataata tcacattgtg cagaaggtac aaatgccccc  35400
tcctatccct gcacacctgg aagctcaagg tatggaaggg tttgttgtct gcagcctctt  35460
cgctgccctc tgctttttaa gatcctgggt agtgtgctca gtgtgtgccc tcagcagttt  35520
gggaaacgga catcttcatg caaaattaag caaggaagtg ttgcttttat actcagagta  35580
gaatctaagt tcttcaggca ggctcttgtg tgccgcctct attagaaata aaactccccc  35640
ggatcagaag atgaatgtgc tcagctaaga acacagattt atttgcttta caatgcgtgc  35700
tatggtttaa gaaaaacaca tcaggcaaac aatttatggt ttgccactga gttgtgcctg  35760
aaggaaacac aactgttaga gatgtaattg attgggcggt gacgctgtgt ggattcatgg  35820
gagatgcatc ttggtcagca tgtctgtgtg aaaccacatt tctggtgctg ctgcaggacg  35880
agtgccggga gttccgggat ctgttcaaga atgggaagct ttcctgcacg agggagaatg  35940
atcccgtccg ggattcctcg gggaagcagc acagcaataa gtgcatcatg tgtgcggaga  36000
agttgtgagt agaggaagcc aatgtttgtt atcgagagtg gcaatggggc cggggtgggc  36060
tcctacagca atgttctcct cactttctca tccttctctt tcagcaaaag ggagaatgag  36120
cagaaggcga cctcaaccag agggaaacaa aaggtgaggt taaagtattg ggttcatata  36180
caagtctata ggattcttac ccaatattac cacacttgat ttctttgtca ctctggggat  36240
ccatgtggct tttcctgctt gtatctcgtt gatgctcttt catgccctga gagaatagtt  36300
tgtctgaacg ctgcagtcta tcccactgac cgcagtgaca tgggagcaaa ccccatcgca  36360
ataagaagct gagcagaact gccctgacat ctggcacaag ggcaagaagg cactgctgct  36420
gagagcgcta atgaggttga aaagaaaatc tgggtgagaa gctttaaatg tgagctctga  36480
gatgctcaaa agttcattat gtcgtgggag gagagttcag ccctgtgctg tccctggggt  36540
ggctcggttt cagctttccc tgattggaaa cctcactctc atgatgcagc tgctgtgccc  36600
ttgtgcaccg atacttctct ggtgagagca attcagcaag gggaaggaaa aagaagcact  36660
aagtaaatct tgccatttct gtcttgcgag gaactggtac ggtcccctta agcctcattc  36720
ttggggataa tcctgtttca gtgcttttcc taatgacagt ggcacaaaaa aaatggaagc  36780
gttaatgaaa cttgctgatg gcaaagctgg gagggaggat cagcagatca ctcaggacta  36840
attggatagc actgaggcct ggagtaatag aaacaagata aaatgtaata acagagagtg  36900
caagatcaca caggcagtga ttaacgagaa ttcctgctca tcaattagaa atgacaaagg  36960
ataagaaagc tctgcattta ttagtgggtc acggatgcgg caggcctgag aaggaggcaa  37020
atgcacatct cagcaaggtc tgtgcagcag aggtcgggct ggcagcaaat ctccagaaat  37080
actgctttga agagagaggg tttgagagac gctgttaggg agaagcagct ctgccacagc  37140
aggtctgggg ttcacctggg gtttggctca ttgcctccct gtgtccctcc tccacgctgc  37200
cagtgctgca ctgggaaggt gtgggtaaga agcaatggct aagggatctg gttatacacc  37260
tcctgtatct gctatttggg attggctact gcagggcctc aggtccctga cttaaaagtg  37320
```

-continued

```
gggacttcga agcatgtttg cattgtgctg tcgtgcctta gatgttgctg ctgggtcctc  37380
aaagtcctgt tggttgtggg gtggggggga cttcttgctt cctatgtgaa gttttctgag  37440
ctgcaacttc agcaacagct gtaagagtgc attaagggca gtgggagaag tgggagggac  37500
cccattacct catcgggtat cgctggcatg ctttggatag ccccacgtgg agcgtgacaa  37560
ttagagcacg gcagagagct cccaacacgt gccatgcagg cagaggcacc cgccgctctt  37620
ctgactcact ctgtttgtag ccatgaggct gtgccacgtg ccctcttctc tctctcacac  37680
ctgggctctc ctggggcgcg tttgggaagc ctctggagga tcggagggat gtggcagggt  37740
gccctgactg ctgctccttc cgcaggatga ctgcagtgag taccgctccc agtttgaggc  37800
tggcggacgc ctgtcctgca cgcgggagaa cgaccccgtc agggattcct ctggcaagca  37860
gcacaccaac aagtgcctca tgtgtgccga gaagctgtga gtacagttcc tggcaacagc  37920
aaagagggaa acctcacatt gcgaaactgc agcttctgcc tgtgtggctg cgcctggggg  37980
agtcccgagt cccagcggcc ccccaggagc tgctcctgct gtagggctgt ggctactgcc  38040
cctcttccca cctccccct aacccctcag ggagcagagg agaagcaggg ttgatagaga  38100
gcagcccttt ccttggggca gctcccaagg aaagtttccc acgcgtgtac tttgccttcc  38160
agatgctctc tctactccca tagagcatat gcagaagcag ccctgatatg aaagcagcca  38220
cctggagccg ggatgtagca tacagtggga atggtgagga gaagggagaa ggcttagggg  38280
tgggaattag gtgcagggcc accagggatg gggaggctgg tgcctaatga catgatgctg  38340
gcttgcaggg cagccccagg tcctggcagc gttcgcactg ccatagtgct cctttctttc  38400
tcctctccct tttttccagc aaaaaagaag ctcaaagagg aggtcagtct ggtggaactg  38460
cccagcgcaa caagcagtcc actgcagagt gtgcaaacca ggtgagactg agctcagagc  38520
ctcaccaggc ttgggaaaag gggttggtgg atctggggac cccgatggtc aagggctgcc  38580
tgtggtcctg gtgtttgggg tgcaggagcc tgctggtgat ggcagagagg caggttgcat  38640
tgcaagccct gctagttcat gggatgggtt tgtgtatgag cgtgcatagt gggcagttct  38700
ggactcctct atggggcacg catcagagct atttcttcag aaagagcccc atggttccta  38760
gggtccaggg ggatgagagg gaaggacagg agctgcttta atctcactgc tttactgctt  38820
ggttgtcaaa cacgatcctg ccccttttcc agaagagctg cagtggctca gggttacagc  38880
ggggtgtaaa tgagagacgg ccgttctcca caaacagagg gtgagtacag cagcactggg  38940
atcccagcct ggccccacaa gtcctggggt cttgacactg agaagaaaca cataaaatag  39000
ggcatataca accctttctc ctttccaaag acattcttgc ttcccctgca cacgaagcac  39060
tggtgactgc tacactcaaa atccctcccc agccttgccc cctgaatcct gcctcctggc  39120
aggcacacac ttgtcctgct gcctggtcca gcgcatcctc atctgctgac ctgaggcagt  39180
gctgtgtgtg caccatgtgc tgtctgggca ctgagcgact cctctgggtt tttagggctg  39240
ccaggctctg gcagggtgca gatgctgtgt tatctaagcc ttgaggaact ctcttagtct  39300
tcctgttttt gttggtgagg cccattcatc tgcccccagt cagcactgcc agcagacaaa  39360
cagtgcacag ctctccatgg cagcaatggc tgtagcatat gtaggggcca ggtttctggg  39420
atcatctctg tgacggacat ctcttgctga ccgcccataa ggactcaaaa gtcccgttgc  39480
agggagtgcc tccatcccat ggcaagccaa gtgccctgtt gaaaaaacaa ggtgcagaat  39540
aatggcaatg gaccttagtg cagtttaatt ccaccctggg gtgatgatgt ggctgagtgg  39600
gtctgcatac ccttggctgt gccatgagct ctgtgctttc tctccctgcc agcccacaag  39660
```

-continued

```
gagacttggc tcaggactgc agcccggcac ctggccgcca gggacagagc ggaggcacca  39720
acacctacca gccggtatgc ccagctcatg tgggtcaggc acagcctttc ccagcagctg  39780
ccccagtttc cattgtcaac ctaaagcctc acaatgggac ctgtatcctt ggaggggttt  39840
aaatgggtgg tagagtccgt accctgatgc tgtcccctgg cctcaaagag gagtgaggct  39900
gcacacgtcc aaacgggagt cactgaagcc agtgctgctg ctggtgttgg ctcactgtag  39960
aagtatgtca ggtatgagag agcatcctcc aggaggtgat ggtggtgtcc cttcctgcat  40020
gctgagatgt tgggttgaag actgtggcca gagcagggtg ctggggctga gcgggggata  40080
aggacaaggc tgataagagg aggggagagg gagtagtggg ggaggacacg gtgagcaata  40140
gataacgact gtttgtggaa tcatgtggga gggagaagag ggtgtatgct ctctccatct  40200
ccacaaaaag aaaatttgtt attttcaacc aagctaaagc agaaattatg aaactaatag  40260
gagaaaataa gttactataa aaaggatgac taacctgtgg atcttgctgt cacggggtgt  40320
tgccaagagc tacagtgatt aaaaaaaatg acttgccact tatagtccat acagcaattt  40380
aggtaacatt ttggaaggga taggaaatgc ctttctgtgg ggctggaggg acctgagtgc  40440
agactgcctt aactctctct gaagtctctg tcactgactg cccttagaaa aatgatatta  40500
gaatagaaaa accagggagg cggttcaggt atggcagttt taatgcattc cagaggaagc  40560
attaggcata ataatgccag tctgcttcag ggcttagtgg tatttcctgg tagctccggt  40620
gaaggagtgg atgctgatca gcctgactga cgaggggtga ttcagagagc agatctgtgt  40680
ctctcctcgc tgcagggcca cccgtgggct ctgtcccagg gagatgctgt cctgaaggag  40740
aggtggcagt cactgtgagg actgtggggg actgttggtg tggcggcggt tgcacacgcg  40800
tgggtcacac cgtgggcagt ggtgtctggt gtgtgggaag gcatctggca gggaactgca  40860
aaggtcagcg ctgtctgtct ttgtgtcatc gttaattacc caggtgaggg aggaagcagc  40920
acattaatga aattagcaag tgatgtttaa acagagggtg ttactgcagc aacctgtgcc  40980
actgaacccc ctgcattgcc cagctgggaa acctttcttc tccatggtgc tttcaacccc  41040
atagtgctgc tgaccccagc aaagcaatga gccattgctt agtgctgaat ggggtttttt  41100
ttctccaagt gggacaggag gtgagatgtc cttcctgcag ctcttctcca attgcaccat  41160
ttgcagtcat tgcaacattt tttataggac ctggagaagg ggatgggaac agagaattca  41220
ctccttttgt ctctgcatct tttttttttt ggcctttggt gcagaggtgg gcagtgaggc  41280
tgaggaagag agggggctgt aggatctctg acctctgctg tctgaaactt gccatgattc  41340
tgcaggcacc tgtgccagaa tgctcatggg ctgataatct aatcatgagg agtcttgttc  41400
ctcctgctcc gagctctttc tagctgtgcc acgtctgctt tgtaggaaat tcgatgccta  41460
gatgctcctg ctgttatgct ggagaataaa acgagagggc acgcttaatt agtcagagct  41520
tttcatacat gtttgcatct cttcattccg tgggtgtcaa gttgtgctgt gtgtcgggct  41580
gcccttgggc agctggactc aattgtcaag gttttccctt tgtttctgcc aagtggcttg  41640
cagaagcaac aggtgtgaaa gctctgataa aggacaaagg acaggtagca gaagtttatt  41700
gtattctcgt ggatttgcag ggagaagtaa aagtgccctg gactgagatg tcagggtgga  41760
tcagatgagt gtatccatgc ctggcaatgg ggtcagggca gctttgtccc cacatcgtgg  41820
ctggttggcc caataggagg cgttacctct ttgctgaagg tgtgatggag ctcagggcaa  41880
cgcctggttt gtgagtgctt tgagcggtgc gcaggagggt cttgcaagag aaccagcacc  41940
aaatgtgatt tctttctctc ttcagctgga ctgtgatcga attctgcacg gggtaaaggg  42000
tggaaggatt ttctgcagcg aatcctcaca acccgtctgt ggcactgatg ggaaaacata  42060
```

-continued

```
cagaaatgaa tgtgacttgt gttcagctgc catgtgagta ggcggagaga tttcagtaat  42120
acagggccat ccaccattcc cgagtgtctt ttgcagcaca gtgtttgttt tgatatacca  42180
tgactcacta tcaagtgtgt ccttggtgcc tcgctgttaa gcaaacatag atcaaatgtc  42240
tgagattaat atgatgacag ctaattaaga tacacaactt tccagagtcc cttattccct  42300
ttctgctcaa tcataggatt gtttggggag taataaatgc catcaaattg gaagtagcat  42360
caaaggttta aggagcccac agaggaccac cgtgacgatg tcagggagct gtggcactgg  42420
aagtgaataa gcaatgtctt gttctccctt tgcaggagag catcagttta catcacggta  42480
aactaccgag gtgaatgccg aaagactgtc cctgaaatgg taagtgcctc cctgctgtgg  42540
catcccattt cttgttctgg gtgtgtgctg gagacccagc ctggatcccg tatctgtggt  42600
gggatcatca gagccctgtt agcagggtgc ttgtggttca catgcgtaaa tacacttcag  42660
gcttggattt aaggcatttt gaggcataat ctccacgttt tttccaggct gtgtggtagg  42720
ggagtgacat gtctgggaaa acatgtggct ttcctcctgg gattttggtg aggccaagaa  42780
aagattgcaa tcgcacaaac cataagggcc taatttccca aatgatatcc aggcagttgg  42840
ttgggaagga aatatattcc ctaagtggta tccttttggg aaaggtcttg aatcttgtgt  42900
gattgccttg tagtagatga gtcaaagatt tgttagtggt gctttgtctt cccgctcgtg  42960
gcagctcagc ggcattcaga gctttggttt ggagccaggg tgtcccagtt tgtgtgtctt  43020
gagtgtatgg gactgacctt agtgttggca tggactgttg gaaagctgag tattcatttc  43080
cccagggaaa caccgacatc tatccccatt ccaaacttgg aatgaatcaa aatatcaaat  43140
cagccaaatg gagaagttgt gcaagttttt tttgcaatga gagagatggc ttctgaatat  43200
gaatttgctg acagtttgta ggtaaaacag tattgcccgt tgaaaagctt tagagcaaaa  43260
ttaccatcat agggctttta ctctcctctg cttattgaca ggatgcccac ccatccccac  43320
aacattagaa atgaggcatc cccattcctc ttcctctctt ctgtgaagta ccagagtgct  43380
ctcaacgctg tttaaagctg aagaaaaaat gcagagaaag agttttgctt gtgatcgtgc  43440
tggaggtctt tgtgtctcgc cctttggtgc gatggagcca ttgctggttt gtgtatgctg  43500
ggagtggagg cactatgcat acctgctggt ggctgtgcta atgatgctgg agacagacaa  43560
ggttgggtgt accacggcaa ctgaaaacca gagaggactc cctcagagtt gtgcctggct  43620
gggattcctc accattttgt gttttaccaa gacgttttac cagctctcca gtctttgcag  43680
ttagaggaat atgccataca ctaaaagtca gacaatttgt agctattcca aggagagctg  43740
gaagcaatta aagggaaagt gataaggttt ttccactggg gaaaatcccc cacaaaaaac  43800
acccctccaa acaaagactt attatttcgt tctttatgta tattgtgtca cctgaagaat  43860
cagattggaa atttatggaa gcccatttcc ttagcaaacc ccttgtgtcc atcaaagact  43920
tcccttttt ttctcagttg gaagcttatg aacaatgtac tgaccagtgt tattttatgc  43980
ctctgaaatt catgctaaca ttcagcttaa tgcatccttc tgaaggccca ggcactcgct  44040
gtgtgaagga gatcacagtg cctttggcgt cagaaatgat ttcaggctgt tgcaatacgc  44100
agcacgaaga tgcaaaggcc caaagacttg agccttggaa aaagatagga gattgctgcc  44160
cgaaaatgta gtttgtcctt gagttgtgtt ttgaaattag ccacggtaat gctgtgttgc  44220
ctgccaaaat gtgtgtccaa gctcagagcc tgcagccatt cctgctagca aagcccctcc  44280
tggatttcca gcagtttgtg gcagtccttc cctagcagtg gctggattgc catcagggag  44340
ggatggctgt aggaagggac aggagaaatg tggttggaga gagatctgac attaaagggt  44400
```

-continued

```
gcatccggac agcctgcact gatgtggtgg aaaaccttcc tgcagagaga gccctggggc  44460
tggctggcag ctgggcccct gctgcctgtg tgagctctgt gccacaacca gcctcctctg  44520
atcctgttct gctttactgc agatgaatgt agctgagtct agggtttaga tttctatgtt  44580
tatttttaac aaggcagctg gcctctgcgt cctccatgct gtgacataca gctgtattaa  44640
tggtgggtct ttccagaatg tttcactttc aatgctgtat ttttttttat tttgcagttt  44700
ctctttttgt tcagatgctt tttcacacat ctcccatgtg acagatacca gtctgtccat  44760
gttagttgac aggtcaggca aaaaaaaaaa agggatatcc agtttctcct ttttaatctg  44820
ttttctaaag aacaaagaac tcccagcttt ctaatgggca aggccatttt cttacagtgc  44880
tctttttgtc ataccttttct taagaatgta gtagaaggga aaagaaacaa acaaaaaacc  44940
caggaccttt tccagcttga tattggtttt ggaaagcaca cagatccagg ctgaaatctg  45000
tttgttttct gagtctggca gtgacccatc cactgcccca tcccacctgg ttcctgtggc  45060
cactgagctg cccaaagggg ctgtcatgta gcccctaatg ctctgccagc gtaacagcag  45120
tggatgtact tgtggatcca cttatatttt gctctttctt tccagaaata atggagttca  45180
gactgccagc aaataccagg gatcagctgt gaccaaaggt acagtggtgc ggtgatttgc  45240
tccctcttgg acaacttgtc cgcatttcac aagggtttgg gtgtcagacc ttgcctgggc  45300
aggctgctgg gtatgtctgg ggcaaagggc tctgcaacac acccttccct attgccacag  45360
cacaagaatg aggcgtgtgt cttttgcaga agtagcaagg tgatgggaag cccctgccaa  45420
gggggctgag ccctttgggg tgtgcaaact tcatgaggac ctcctcatct ctcaggggtg  45480
ggccttgccc gttccttttc cctcagatat ccctgcagag ggggaaggat gctggcagag  45540
cagagtactg cagtccctcc tcacaaggag gtggaggtgg cccaaagcaa cctggctttg  45600
agctttcctt gtggttcttc tgtgtccctt gccttttgga gccatagtaa taaacccgtc  45660
tgccccctgt ttctctagga caagtaaagg aagatctgat gtcaggcacc agggaagctg  45720
ctgagttccc cagtgctgtt ggatccacct tcatctcctt ctgcagccaa cgggcctgtc  45780
cttgctcagg tggagggtga agggctgtgg ggacccagtg gtggcttccc acgttggccc  45840
cacgcatgtt gttgtagtcg ctgctcggct cgggctctgc cgcctcgctg tgtcttagca  45900
tgtttctaca ataaagataa ctccacagcg tcctgtcgct tttcttcact gagcctcacg  45960
ggagggacgt gtgagtcccc gctccggctg ctcgccacgc gtcccttgag ctctaaagca  46020
ccaaacccaa gcggagatgt cagacgcaga gaagaagaac gtggtctggg ttctgttagc  46080
agggaccagc agttgggttc tctgactcgc tgtgtagggc tttgggtgta tctctttgtc  46140
tcccttcagc ccttttctct tgcctgtaaa aacggacatt aaaggatgct tacctacctc  46200
agagggttgt ttggagattt taattggttt acgttagaga gcccacgggt ggaattctgt  46260
tcctatgtgc caatgctggt gtgcaggagg tttaactgtt gcagtcatgg cctcttccag  46320
ccaacacccg atgggccgta tgtatttcct gttctttcgt ttatggctgt tacttaaagc  46380
aaatatgttc ttatttgtat aaactttatt gcaggacatt tccagaagac cttgagtgaa  46440
cgtacagtgt ttgagtccac tttagctgtg acctgatctg caaatacact ctgctgtaga  46500
taaggctgga gtaactttca gattttggca gggtttcgct caatgccaat taatttggct  46560
ccctccacag atattgattt ttttttttct tttcaattaa gttatcgaga tcttttttttc  46620
ttaatgcagc taatgaaaat cgatttttac tctcataaag tacttccgca tgtgtcacat  46680
tgatctgtct atggcttgat tatcggcagg ctttgacatg aggttaatat tttgtgtgct  46740
ggtttttttt caccgtgtgc aaacactgtg gtttagaaat atgttaccgc tgcttatttc  46800
```

-continued tacgtggaaa atcccacggc gtggttatgc atggcagaag tcaccagttt gatccaattt 46860
agctgtttct agggatgcaa gattcctctg cctttgagcg ggtgaatcct cgggtgttat 46920
ttatacattc tgagaaggat gaacagaaga cggtaaaaac gtttgctaat gatgtctgct 46980
ggctgattcc ggctaaaatc gtgtgcaggg acctcgacgt gatttttata aaggcagctc 47040
acaatttgag gcttaaagta agttcttgca aatgaaaatg ggcgcacttg agcgcgctat 47100
tataacttgt agtgatttca agcacttaga ttttgaaata atcgcccata aaaacctgca 47160
ttaattgtgc tccaaaacca atgagctgat gaggagggtg ccctggtagc ctcttttgct 47220
ggatttgagc accttctgaa tttctcctgc caccagcaga aattagccac agaaatcata 47280
gctgctataa gggtttatta atcagattac gaaactgcta agaaggcaca caacagtgac 47340
ttgctgaagc tgcctgtgct gctgttagcg agcctcccgt aggtagcaat gctaactcct 47400
tcctttttagc agtttaccca ctgcttcctt ccatcactcc ttccttttgt agggcctact 47460
tttgcagttt gatccagtgg cttgcaggca atatctgtcc ccagcggtgc tctatgcagc 47520
tgacctccag gtagggctcc atgtgagcga tgcaatgtgt tatttccatg gggttcctaa 47580
gaaggaggaa gcaaaaagct caggaggtgc tccaaatata ttatcctgtc ctctgttttg 47640
ctctttgtgg tgccctttaa cactgtaaag agaccatagg agtcctctat gaacctggaa 47700
aggtaccagc actatgggag gtcttcagtt tgctgtaaat tatgctttat tagaggtatt 47760
tcttctgcca agacccactg accccatgcg gctcacagtg ttttctaagg ctttgcagga 47820
ctggtgttac gaattggcac cctccaggcc tctcacaaat ctcctgcttc tcacagcgtt 47880
tcttcaagtt ctcccaagca cagctgagtt ttgagctcaa ctgctccctg caggggcctt 47940
gagcctcctg ccttttttgca taaaaggtgt caggtactta tgcaatcctt agaggcatgc 48000
aaatgctgct ctggttatat actgaggact gttgattctg gcagaaccct ttgcagacct 48060
tgtactccct tgctatttcc caatccctgc agcctagcag ctctgcctaa caactgccat 48120
agccaacaca gcagcaggct gtgcatggtg caaggtgatg tggaaaggga tgattgtatg 48180
aaagcgtgat gctgtggtac tgcctctgca ggagactcgc actatttgtg taagaggacc 48240
ttatttgtct gctgcagagc tgtttcaagg ctgtccatac acccctgtga tgctgagccc 48300
ctccaagcaa tgcactggga aaaggaggct gggggggagac cttattgctc tcctccaata 48360
tttgaaaggt gcttacagcg agagcagggt tggtctcttc tcactggtga caggatgagg 48420
ggaaatggcc tcaagttgca ccagggtatg tttagattgg atatcaggaa acacttattt 48480
actaaaaggt tgttaagcac tggaatcagc tccccaggga ggtggttgag tcaccatccc 48540
tggatgtgtt taaaaactgt ttggatatgg tgctcaggga catgatttag cggagggttg 48600
ttagttaggg tagtgtggtt aggttgtggt tcactcgatg gtctttaagg tcttttccaa 48660
cctgagcaat tctatgatat ggatccctgg ggctttcagt cttatctccc tggattatca 48720
caggttcagc tctatggccc atttgattta taccggggtc tgatgaacag gtttttctct 48780
tggctcttca gggatcctat ttagcacttt ttggtacatt cccctgccct acaagtctcc 48840
ctgatacaca gagctcttat ccaagacttg ggaccttccc tactccagcc ctctgcagga 48900
ggtttcttgc taaccagtcc tccaaccagg actgcagtac acgacaaaga gctggaagag 48960
gtctgcaata cttccccagc atgaaggtat gagcactcct tttgagtagg ttactgaaag 49020
tagtaagatg tcaatacaac caactgcaag atacaaaacc gcatgaaaat tcagtttact 49080
ttgatgctga agggctgaaa agaaatgctg tggtgttagc acagatgcac tgctggcaaa 49140

-continued gtgaaaatga gcaaagagga tgagatggat ggacagctga tggaaaaact cttcctaatt 49200
gctccacaga gcagcttgct cgcctgcagg gctgcagcat ggagctgctt gtgcataatg 49260
cagacacccc aagaccagtg ctgtttgtct tagccaagac acagttgcag ctgcagcaat 49320
tttttctaga tgtcagttcc ttccctatgt tgctgacagg tgtttgctgt tctgtccctt 49380
taatctgtat cctacagcaa acattccttg aatttaataa cttagctgga agacaattgc 49440
tgtgatcttg atagaacatg ctgagccaat ctattttaac tgcagattta gtttgcaaat 49500
actgtctcct tgccgataag attcaggtgt catctttgtg gacattggca ggaattttct 49560
tgaccgtgac aggttttaca gagtctggca attaagctgt caagacacat tttcctctgc 49620
caggaagcat taattgatga tagtcttggc tgcaataggc acagagagat ggatattgta 49680
atcagaatga atagaggtcc ttgtagttga gagctacgtt ggtccaaagt tttgtagtcg 49740
ttgacgtttg gtgatactga gataaggaac aaggcacgag atattagagc taaatatcag 49800
gcacagcatg agaataaaga cctctctagc tggaactgtt ggtatctggg gagattttaa 49860
ctttctggat gcatactgca aagtactaat attagtagag ctactggatg cgagagcaaa 49920
tagttttcca ttaagtaatc ccaaaaatca tgttgttgtt ggtttgcttt tcaagtgcga 49980
ggggtgttgg agatgtattt ccctcagaaa ataaacctga tatgattcaa cctgagctct 50040
ctctgtttaa atcacactga aaatagatct gcaaatgggg attttgatta ccgagtacag 50100
aatatgaaag attaaaactt gggaaagtta gggttctgat tgagaaaact tttgtttttg 50160
tggccgaccc ttgcagctta caaaaatctg cctaaataaa ggagaaaacc acatttagaa 50220
cccatccaag ctatgctact tcagtactgg gcaaaacttc aggagacgtt tgaagaaaac 50280
tgaagacgtg aagtataaag gaatgattga tgtgcacagt aaactttctt ggaaggtaat 50340
cacgcatggg ctaatatcaa tctttacaaa gttggctgac ttcctagata aaggaagtac 50400
agtagatcta gtctacccag gcagcaaaaa tgtttgacct gttgccctgt ggggtggtgt 50460
cacctgggct tggggagggg ggtcaggatg aggttacagg ggatgtggaa gcatactgtg 50520
gaggagcagg tggggcaccc acaggagtta gcagtgagca gacagaaagg tggatctgag 50580
gaccgaactt cgtatttttg ttccttgcat taatacacaa aaagcagaca cacacacaga 50640
gcagattgct gctggttttt gttttctttt ttaaacagca gaagagcagg atttttccca 50700
cagagaatgg ggtgaccttc taggctgtga ttgcctgggc tcaagctgag atgaaacgca 50760
gtgatgagga gcacaaaacc gtgctctgag gttaaataat gagggcttcg gctatcagtt 50820
cagagctcag taaaaactgc agaggaggag gaagacctaa ttgcatgtag ccagccacag 50880
ggcaaatgag agctgcagcg tgctggggca gatccgggag cagaggggcc gtggcacgct 50940
ccctgttcac tggctcccct ggagccacac aaaaggcccc ttcctggcaa ttgtgcccac 51000
atcaatcatt agctagaaac ccagagctgg gtaaatacgt tttggcttcc cgtcttgatg 51060
acagattggg tgttacatca caaggtggga ccacttgata tgacaacacg ctatatattc 51120
ccgctgctac ctctgccctt cctcccccac tctgagagca agcgggctgt gtgtgcaccg 51180
aggtgctctg ccatgaggac tgccaggcag tttgtacagg tggctctggc cctctgctgc 51240
tttgcaggtg agtgtttcct gctatacccc gtaggtgact atagctagac cagagactag 51300
gctatctgtg agagtatctg ggtattgtaa tgtgttagag agccttgttc catgaaggaa 51360
tgctctttct gacagtgtag caaaacacca gactgcaaga tccaggtttc agcaaacctc 51420
atacagacga ctgttttcgt cgtggtttat aggagcaaat tgctgaggga gcagtgctag 51480
tgcagggcag gagcttgcac gtgcaagcac tgagtataac ggcaaagcaa agctatgtga 51540

-continued aatggctcct gtgtccatgt aagcaataca aacactgcat cttgtatcat ctataaattt 51600
tctgtgctgt tcctggcagc tgagaagttt gttgtgggaa gaacagtgct agtggtcaac 51660
agccacctga aacgtgcatg tctgagctcc tgcaagtcaa atacagagtc ttgcagaaga 51720
gtttaaactc agtgcaggct tgaaaatacc tacatttctt ccctggggca tcttaggaac 51780
tggctaacac atgtggcctc ctactgaaag tgcagtgaaa cttcatttaa taacctctga 51840
ttcattttat ggacgtacat cactggcata atgtaaaatt gcattttcct aaacccaata 51900
agccaatcaa caacggtatc taaatgtaac tgtttcatcg aaagatttgc atatgtcatc 51960
tctgcatatt aataatatgt atttattttc tgtctctact tttcttttag atattgcctt 52020
tggaattgag gtgagttaca gatttttttt cccatttatt cttttctatt ccaggcttct 52080
ggtcaaataa gagcagtata taattacctg atgagcaagt ggattaatct aatgaaagcc 52140
tggttgctca aataatactt gccagtgcat gattgaatga tattgccaag tcacgaaaaa 52200
gtaaaacaca ccccgtttat actattttcc attcatgcaa taaaatgaag aaaggaagaa 52260
ttgtacgatc ctattatgtt aacttttgga tataactgcg ttagtccaag tcaaggggtg 52320
gtagttacct cctcgagagg aaagctgtct taagatgata agctccaaag catcaaagac 52380
agtgattctg gtatcttttt ctatacagta agacacacac tacagtgttc ctgcctatac 52440
ccatatcaaa gcgaggaaag cagcagggtc tgtgcagtgc atttgtctgc aggttcttcc 52500
cacgcagtta tgagattcct gcaaatcacc agagactgca gcgtgattgg aaacgatcag 52560
attttgagtt gagcggctgt ggagcatggc caggctccca attaccagct gccttcgtta 52620
ggcgctgtct cacccacagc tctccttcct ccatgtcatg cttcccccag tcccccgcag 52680
gaaagcgtga tcagaagaag attcccacct cctgactgcc tgagcagatt ccaaatgata 52740
cctcaggtgt ttgtcccggc tggagctgtg ggtggcagga ggtttccata ctgtcttttg 52800
ttgtggaaac tgaccccagg gctgatgttg tgctgcttcc ataggttaat tgcagcctgt 52860
atgccagcgg catcggcaag gatgggacga gttgggtagc ctgcccgagg aacttgaagc 52920
ctgtctgtgg cacagatggc tccacataca gcaatgagtg cgggatctgc ctctacaaca 52980
ggtgagctta tgtggaagcc caggggagct gcagggcagg agactcgagg tgagggcggc 53040
agctctgtcc ccaaaatatg gtctgtgtgg aggagtatgt gagttagtac caggatgctg 53100
acctccagcc tgggggtggt ggctgctctc tgccatctct gacacagatc tgcgttcttc 53160
cagggagcac ggggcaaacg tggagaagga atatgatgga gagtgcaggc caaagcacgt 53220
tacggtaagt ccaacagtaa gatgaagtct tgctctgttg gtgcccataa agacttattt 53280
ttatttcata gaatcattga acagcttagg ttggaaggga ccttaaagat cattgggctc 53340
taaccccccct ggcctggccg ggctgccttc aaccaaatca gtttgcccag tcaaatgggc 53400
cttgggcacc tccagggatg gggcacctgc tctgctcagc ctgttactta tttacttgtt 53460
tttttcccat tcctgctatc cttacagatt gattgctctc cgtacctcca agttgtaaga 53520
gatggtaaca ccatggtagc ctgcccaagg attctgaaac cagtctgtgg ctcagatagc 53580
ttcacttatg acaacgaatg tgggatttgc gcctacaacg cgtaagtctt ttctgtggag 53640
catccttctg ggtaattaga gatggctaag tcccttggaa acgcttacat aaaacacttt 53700
ctaagccttt cttagggtag atgtttctgt gggactcttt gaagctggct acttgtgatt 53760
ctccagccag ctgcagattt cttccccatc ctctgtctgt gctcatgaag ggaatcacaa 53820
aaaagacaga ggacaaccca cagcagaggc atgaatagat caaagtgttg ctcagtgctg 53880

-continued

```
tgtgatatgg aaataccatg cattttctgc tcacaagtgg ttgctaccac ctgtgggctg  53940
catccagacc actcagcagt tccttacgtg aagggtggga ccttgctttc ttgccccagt  54000
atctaaggct tttcacgagg ctctctaact aaaacagctc tttctttcag agaacatcac  54060
accaacattt ccaaactgca cgatggagaa tgcaagctgg agatcggctc ggtaagtgta  54120
acagaaataa aaatccatct cctagggctg ttaacggaga gaatcccatt gattttccta  54180
agaaaatgta tgaccgggct gatcgggggt cccggtccac gctctgcttc ctgcctggtg  54240
agggtggctt ctgaaacaaa gcggtaaagg aagaggcccc agattttcct tgcattgtgc  54300
tgtgcagatt ggcaggtttc tctctggagg cgacaagcat ttccaccctt tgtaacaagc  54360
attcaaaatt ctagtgctgg tagcttggtt agatatagtg agattcataa gagcaccaag  54420
catacatatt tatagggtat agcttattgt atatttatac tggggtaaga gtccagtgcc  54480
tcaggaagaa aagcttatat atttcagcac aaaaattctg ggatgcaggg agtccgttct  54540
ccaacagacg gattcctcct ttatcacttc aactcccgtg cttaactgca gggaatctga  54600
attattaagc aatcacagca ctggggaagg aaggagaaaa accaacacaa accaaaacaa  54660
tgttaatcag atttccagct gttggaaaat atttcccact taattcaagg ctgttgtgtc  54720
gatgagaaga gggctgaaaa ggctgttttc agttcctctg cctgaaggtt tcattctcta  54780
agagaggtcc cttttcttgt ctcctagaga atgagggtag tgttctgaaa gcctatttct  54840
gatagacagt ttagttaagt gtagcagggc tttgtcctgt cacaaaaact aggaagccgg  54900
gaatacagga tgaaaaggtg ttacattgac ttctcccgtg tagcacaggc tccgggaggg  54960
cttattctcc ttattttggc aggttgactg cagtaagtac ccatccacag tctctaagga  55020
tggcaggact ttggtagcct gcccaaggat cctgagcccg gtttgcggca ccgatggttt  55080
cacctatgac aacgaatgcg ggatctgcgc ccacaatgcg taagtgctgc tcatctccca  55140
ctcctccaaa gtagccagca atgctttgcc gtgctgggag ccttccttct acgttgctgc  55200
ttatgcctgt ttcttcaagc ctcttagaaa ctgcattttt tttgttgttg ttcttactga  55260
gttttcttct gatgccttct ttgtgatcac gaggggaaat ctgcaagact cagaacacag  55320
ctccttggat tagtctgtgg gctgggcagt gactgagcag agaaaggaat agttcagaat  55380
cttgctttaa ataacacgag aagacgtgat gagcttgtta acgagcagag taatgtagct  55440
atatcaatac aatcgtgcag agaggctgaa gccctacttt gttaggtacc tgctttaggc  55500
tacgtctggt tcattctgca tgcaagtgtt taaaccaaga gttaaagcat ctccttactc  55560
actttgtctc cctctttcag agagcagagg acccatgtca gcaagaagca tgatggaaaa  55620
tgcaggcagg agattcctga agtgagtata caacgtaagg tgtatttctc cccttgcctc  55680
tgcccactga gctatttgct gaggccacgt ctactctgaa agtgagctgg cttgaagcct  55740
ggctctctgc acgtgtcctt tgggatgtgc caacgtgtat ccaacacaca aacagtgtgg  55800
aagttgggca gggggaactt aggtctttta aggatgatca ctaaatgcat tgccagcaaa  55860
gtccttttgt gccagtgaag tcctattatg tttgccttct tttgtttcat tctatagtgc  55920
agagagaaaa ggagatgata tatctttgtt ggtttttttt ttgtttgttt gttttgcttt  55980
tctgccatat ctagcaaact gtttcagtag gttgtgaccc ctttggatca caagtgaagc  56040
tcagtggcat ttgggattga ctgagctgtc tgccctggtg atttggcatc tcacagatta  56100
cacagcgcca tgtagctcct cctgggcatg agagagtttc tgcagagctg actcaggctg  56160
gctttgagag aactgaagtg tagcaccagc gttgtttcag catcccagcg taaaagacat  56220
ggattgcagc aggaggcaat gctagggttt gtctttgaga gcaagggctt tttcagggct  56280
```

-continued gacgctccta ctttttgcag attgactgtg atcaataccc aacaagaaaa accactggtg 56340
gcaaactcct ggtgcgctgc ccaaggattc tgctcccagt ctgtggcaca gacggattta 56400
cttatgacaa cgagtgtggc atttgtgccc ataatgcgta agtactgcaa acaggacttc 56460
cttttgtagc gactagccac gttagtactg cagatggctt cccctccacc cttcatcttc 56520
ttctttcttt cttttttttt gatagcagta tgtctatatg tctcctgttc ttccttcaac 56580
ctcctgaagc tctgtcgcct cggtttcctt tcctgatgtg ctcctcaggg agctgtggga 56640
gagccagcta acagctgagt gtcctatgag ggctgtggca tttgtgcaga ggaaaaagag 56700
aatgggtctg ctacaagtag acctgagaag cctgtaactt cttaggatca tgatccctaa 56760
tggcagcctt tccctttcag acaacatggg actgaggtta agaagagcca cgatggaaga 56820
tgcaaggagc ggagcacccc ggtaagtggg gatggatgtc agatgagcgc cagctcctgt 56880
acgtgccttg tggctgcaga ggttgctaac cagggtctgt ccattcaggc agcagagaag 56940
gggaatgggc caggatttag gtaacaaaat gtcccaatac tgcaggtctc tggagggaaa 57000
catcagaggc agcccagaac agcacagcct gttttagcac agtaggagag gaagagcaga 57060
agctgtgtta gatgcctgtg tagtcattca gtgctaggat ttccattgca gcagacaggt 57120
taaaaaatct ctgtaccgtg gtcagccaag aaaaggctgc ttgcaggaat gcacgcagaa 57180
atagctctat aaacatgcac ggtaacaata tgtgctgata atatctcagc acatttattc 57240
tgcttatgca gagcagctct aaaacactga aaataacttt gtgcatctca agggattgct 57300
gtatcttttc tgtagtaaag acacactgtt atggtgctgt ctttgctata atttgctctt 57360
ggactgtgtg gggaaatatg ggtaataaga gctactacac aggggaaggt atgcaaaacg 57420
attgtgaagt gtcagaagct tagccagtgt agactgactt ccagtgccat cagtagatac 57480
ttgcttattt atcctcaaat attggaactg tttttaagta ctgtgaggat ttctgcagca 57540
gcagctgatg agctgatgga acagtttctt cttgccgttt tgaaaacgtg gaaacaaaat 57600
ctaaggctta gctaagtcag gcatgaccta atgtcaaact ggacataaca tcaaactcct 57660
tatatcaaat tcctttgaat aatgcttgtt ttgaaacttg gacatacgct gcataaggaa 57720
gatgatcttt ctggtctgct attcctttgc gttccctttg ttagtgagca atatcaaacc 57780
caaccacaat tagttcattt ataatgggag actaaactga aatcaaccct gatttttcct 57840
atggctcgag gcagtctgtc cccagctcc cagcacctga ctcagcatcc ttactgtttt 57900
ctccccagct tgactgcacc caatacctga gcaataccca aaacggtgaa gccattaccg 57960
cctgcccctt catcctgcag gaggtctgtg gcactgacgg cgtcacctac agcaacgact 58020
gttctctgtg tgcccacaac atgtaagccc tgcaggtcac ccactcgtgt gtcaccgcag 58080
ctgcttgttg agctttgtca actctgtttt ctctctcttc cagtgaattg ggaaccagcg 58140
ttgccaaaaa gcacgatggg aggtgcagag aggaggttcc tgaggtaagc gataaagaaa 58200
acaagagctt gaggtggtgc ttattgccta acaagtacaa cgctggctgg ttttggtgat 58260
gctgggtcat gccctcctgc tgccatcctt cctgcaggta aacatcaacc ctggcagcag 58320
ggatgctgtg cattttctgc atgtagtcag ggaaagaaag agaagaggac gggtgaggaa 58380
tgagttatga tgcaggtagc ataaatgatt taaggcgtta cgaagaaatc tctttcccac 58440
agcagtctat catacctgcc gtgggagtgt agctgtctgt tctggcaata tgggaaaggg 58500
acacagagca cccgcaggta cctggtgcct tctggatacc tgtgctgtgc aaaaggatgt 58560
tgtgcaaaga tcagaaaact acctgcattt tgaatgcttt tacctaatgt accagaggat 58620

-continued

```
tcaaacacct ctctcttcct attgtaaatg cgatataatg taatgtatac caacaatgaa  58680
tcttgtaaaa ataccagata aactatattt ggccagctct aaactattta cgctcactgg  58740
ggaatagaaa aacaaagcca tctcattatc ttgtgtttga aagagtcaac gtcgtgagtc  58800
agatatttca tttctatgca aacagactat gaaatgtcat tgctttgttt cctgcgtatg  58860
ctctgtgctc agaccaagtc agatgcataa atcagtgagg aagagctcac actggagaaa  58920
ctgggatagc tgaaactcaa ggccagttct tcaaatggca taaatcattt tgaactgctg  58980
ttggtccttc tgtccgattg caacacacag aaccagcccc tcgcaacaaa aggcatgtca  59040
gcacatctcc tcagttcttg tgggccgtga cacactcctt ggccacactg agcttctctt  59100
gcaggaattg cataaatcac gccagtttga tttgcagatt atttatgagc tgcgttttgc  59160
agcgtcccag caagtggttc agcaagctct aagggcatcg tgataaatgc agggctgaat  59220
gagtgatacg cgccttcaag ctttgattca gtcttctcca gtataaggct gtgacagaaa  59280
attgatagtt ttcaatgaag aatgagtcaa tgcataacca taatccatcc tgtggcagat  59340
cttgaaaggc agaggcgtaa ggaagggggt tgtgtctgag caccccttaca cagagcattt  59400
gctgcctttg tttcctagct tgactgcagc aagtacaaaa cctccacgct gaaggatggc  59460
agacaggtgg tggcctgcac catgatctac gatcccgtct gtgctaccaa tggtgtcacc  59520
tatgccagcg aatgcacgct gtgcgctcac aacctgtaag tactcattca tctccagggg  59580
gacccaccgt ggctgtgact ggacacatct ttgagtgctg aataacatgc aagggctctg  59640
tctaaaatct cgtgctgcat gggtcctgtc tgcctatccc cgtttccctg gttgccatgg  59700
ttggtgtttg agatgggcat ttagcaaggc ccactgcccc cagtgaccca gaaaaagggt  59760
tcactgcctg ggaaagcatt attccaaaag acacatccct agtccttaag ggcatgttct  59820
tgctaatgct tctcaggcaa tgcttagcta atttatctga aattgtcctg tgtaccacat  59880
gggaacgagg ttgtgctctt gtactacggt tgtaaatggg aagggtttct gctaatatcc  59940
atctctcctt cctccaggga gcagcggacc aatcttggca agagaaagaa tggaagatgt  60000
gaagaggata taacaaaggt gagtgtgaaa ggatgggcac aaagagttac agtcgtaggg  60060
gaccgtcctc tgctccacat caaaaactgg gggagcggtg tgcagccctg gcgaggtcgc  60120
ttgggaatgt catactggtt atagaatagc tgccatccat cccatgggaa tggacatggc  60180
agtgaacagg aacagtgtga ggtcacatcc ctcaccagga ggaactgagc tgattactgc  60240
cgtaattttc cagtttcact ctttgtgctg ggggaatact gtttgctccc aggcagagac  60300
tcacatcttc cttgtgtgtg caggaacatt gccgtgagtt ccagaaagtc tctcccatct  60360
gcaccatgga atacgtaccc cactgtggct ctgatggcgt aacatacagc aacagatgtt  60420
tcttctgcaa cgcatatgtg taagtatagg agtgaaaccc ttcctgtaac tgctacaaac  60480
gcagagttga ttttataagg agttctttac taacacttta tgggtgtgtg ctagacattt  60540
cggatgcacc gtgacgtgca aggaggtgct tttttgcttt ttaagaaaaa atgcaaagca  60600
cccacatctg cccatgtgta tgtggcttcc tgttttattt agtttcaaag acattttgct  60660
aattttcacc agcatagttt gtcccacaag ctcatcaggg tatggggaaa gtacttcacc  60720
aaactacctg gagcgtttca agtgtgtgaa acctgtcatc tttcctttaa ttttcataat  60780
gaaaggaagt ggttggcctt ctgagactgt tctttatctt ctgccaacat tatcaacatt  60840
tgggctggta aggagaggaa caaggctgca gcacaaattc tattgtgttt aatcctttct  60900
tctcttttca ttaggcagag caataggact ctcaacctcg tgagtatggc agcgtgttaa  60960
ctctgcactg gagtccatcg tgggaaacaa tctgccttgc acatgagtct tcgtgggcca  61020
```

-continued atattcccca acggttttcc ttcagcttgt cttgtctccc aagctctcaa aacacctttt 61080
tggtgaataa actcacttgg caacgtttat ctgtcttacc ttagtgtcac gtttcatccc 61140
tattcccctt tctcctcctc cgtgtggtac acagtggtgc acactggttc ttctgttgat 61200
gttctgctct gacagccaat gtgggtaaag ttcttcctgc catgtgtctg tgttgttttc 61260
acttcaaaaa gggccctggg ctccccttgg agctctcagg catttcctta atcatcacag 61320
tcacgctggc aggattagtc tctcctaaac cttagaatga cctgaacgtg tgctccctct 61380
ttgtagtcag tgcagggaga cgtttgcctc aagatcaggg tccatctcac ccacagggca 61440
attcccaaga tgaggtggat ggtttactct cacaaaaagt tttcttacgt tttgctagaa 61500
aggagagctc actgcctacc tgtgaattcc cctagtcctg gttctgctgc caccgctgcc 61560
tgtgcagcct gtcccatgga gggggcagca actgctgtca caaaggtgat cccaccctgt 61620
ctccactgaa atgacctcag tgccacgtgt tgtataggat ataaagtacg ggaggggaat 61680
gcccggctcc cttcagggtt gcagggcaga agtgtctgtg tatagagtgt gtgtcttaat 61740
ctattaatgc aacagaacaa cttcagtcct ggtgttttgt gggctggaat tgcccatgtg 61800
gtagggacag gcctgctaaa tcactgcaat cgcctatgtt ctgaaggtat ttgggaaaga 61860
aagggatttg gggattgcc tgtgattggc tttaattgaa tggcaaatca caggaaagca 61920
gttctgctca acagttggtt gtttcagcca attcttgcag ccaaagagcc gggtgcccag 61980
cgatataata gttgtcactt gtgtctgtat ggatgacagg gaggtagggt gacctgagga 62040
ccaccctcca gcttctgcca gcgtaggtac agtcaccacc tccagctcca cacgagtccc 62100
atcgtggttt accaaagaaa cacaattatt tggaccagtt tggaaagtca cccggtgtat 62160
tgtgaggcta gattaatagg ctgaaggcaa atgttcccaa cttggagata ctgttggtat 62220
tgtatcaggg aacagggcca tagcacctcc atgctattag attccggctg gcatgtactt 62280
ttcaagatga tttgtaacta acaatggctt attgtgcttg tcttaagtct gtgtcctaat 62340
gtaaatgttc ctttggttta tataaccttc ttgccgtttg ctcttcaggt gttcttgcag 62400
aacactggct gctttaatct agtttaactg ttgcttgatt attcttaggg ataagatctg 62460
aataaacttt ttgtggcttt ggcagacttt agcttgggct tagctcccac attagctttt 62520
gcagcctttt ctgtgaagct atcaagatcc tactcagtga cattagctgg gtgcaggtgt 62580
accaaatcct gctctgtgga acacattgtc tgatgatacc gaaggcaaac gtgaactcaa 62640
agaggcacag agttaagaag aagtctgtgc aattcagagg aaaagccaaa gtggccatta 62700
gacacacttt ccatgcagta tttgccagta ggtttcatat aaaactacaa aatggaataa 62760
accactacaa atgggaaaaa cctgatactg gaatttaaat attcacccag gctcaagggg 62820
tgtttcatgg agtaacatca ctctataaaa gtagggcagc caattattca cagacaaagc 62880
tttttttttt ttctgtgctg cagtgctgtt tttcggctga tccagggtta cttattgtgg 62940
gtctgagagc tgaatgattt ctccttgtgt catgttggtg aaggagatat ggccaggggg 63000
agatgagcat gttcgagagg aaacgttgca ttttggtggc ttgggagaaa ggtagaacga 63060
tatcaggtct acagtgtcac taagggatct gaaggatggt tttacagaac agttgacttg 63120
gctgggtgca ggcttggctg taaatggatg gaaggatgga cagatgggtg gacagagatt 63180
tctgtgcagg agatcatctc ctgagctcgg tgcttgacag actgcagatc catcccataa 63240
ccttctccag catgagagcg cggggagctt tggtactgtt cagtctgctg cttgttgctt 63300
cctgggtgca cagtggtgat tttcttactc acacagggca aaaacctgag cagcttcaaa 63360

-continued

```
gtgaacaggt tgctctcata ggccattcag ttgtcaagat gaggtttttg gtttcttgtt  63420
ttgtaaggtg ggaagaagca ctgaaggatc ggttgcgagg gcaggggttt agcactgttc  63480
agagaagtct tattttaact cctctcatga acaaaaagag atgcaggtgc agattctggc  63540
aaggatgcag tgaaggagaa agccctgaat ttctgatata tgtgcaatgt tgggcaccta  63600
acattccctg ctgaagcaca gcagctccag ctccatgcag tactcacagc tggtgcagcc  63660
ctcggctcca gggtctgagc agtgctggga ctcatgaggt tccatgtctt tcacactgat  63720
aatggtccaa tttctggaat gggtgcccat ccttggaggt ccccaaggcc aggctggctg  63780
cgtctccgag cagcccgatc tggtggtgag tagccagccc atggcaggag ttagagcctg  63840
atggtcttta aggtcccttc caacctaagc catcctacga ttctaggaat catgacttgt  63900
gagtgtgtat tgcagaggca atattttaaa gttataaatg ttttctcccc ttccttgttt  63960
gtcaaagtta tcttgatcgc cttatcaatg cttttggagt ctccagtcat ttttcttaca  64020
acaaaaagag gaggaagaat gaagagaatc atttaatttc ttgattgaat agtaggattc  64080
agaaagctgt acgtaatgcc gtctctttgt atcgagctgt aaggtttctc atcatttatc  64140
agcgtggtac atatcagcac ttttccatct gatgtggaaa aaaaaatcct tatcatctac  64200
agtctctgta cctaaacatc gctcagactc tttaccaaaa aagctatagg ttttaaaact  64260
acatctgctg ataatttgcc ttgttttagc tcttcttcca tatgctgcgt ttgtgagagg  64320
tgcgtggatg ggcctaaact ctcagttgct gagcttgatg ggtgcttaag aatgaagcac  64380
tcactgctga aactgttttc atttcacagg aatgttttag tggcattgtt tttataacta  64440
catattcctc agataaatga aatccagaaa taattatgca aactcactgc atccgttgca  64500
caggtcttta tctgctagca aaggaaataa tttggggatg gcaaaaacat tccttcagac  64560
atctatattt aaaggaatat aatcctggta cccacccact tcatccctca ttatgttcac  64620
actcagagat actcattctc ttgttgttat catttgatag cgttttcttt ggttctttgc  64680
cacgctctgg gctatggctg cacgctctgc actgatcagc aagtagatgc gagggaagca  64740
gcagtgagag gggctgccct cagctggcac ccagccgctc agcctaggag gggaccttgc  64800
ctttccacca gctgaggtgc agccctacaa gcttacacgt gctgcgagca ggtgagcaaa  64860
gggagtcctc atggtgtgtt tcttgctgcc cggaagcaaa actttacttt cattcattcc  64920
ccttgaagaa tgaggaatgt ttggaaacgg actgctttac gttcaatttc tctcttccct  64980
ttaaggctca gccaggggcc attgctgagg acggcatcgg ggccccctgg accaaatctg  65040
tggcacagat ggtttcactt acatcagtgg atgtgggatc tgcgcctgta atgtgtcctt  65100
ctgaaggaag gaacgtgcct tccaagtgcc agccccacag cccccagccc ctccctgtgc  65160
tgctccaatt catctcctct tcctccttct ccctttgctg tttgtgctcg ggtagaaatc  65220
atgaagattt agaagagaaa acaaaataac tggagtggaa acccaggtga tgcagttcat  65280
tcagctgtca taggtttgtc attgctatag gtctgtatca gagatgctaa caccactttg  65340
ctgtcggtgc ttaactcggg tgaactctcc ttcactcgca tcatttgcgg gccttattta  65400
catccccagc atccatcacc ctctgggaaa atgggcacac tggatctcta atggaagact  65460
ttccctcttt cagagcctgt gggatgtgca gtgacaagaa acgtggaggg gctgagcagc  65520
agcactgccc ccagggagca ggagcggatg ccatcggtgg cagcatccca aatgatgtca  65580
gcggatgctg agcaggcagc ggacgaacag acagaagcga tgcgtacacc ttctgttgac  65640
atggcatttg gcagcgattt aacactcgct tcctagtcct gctattctcc acaggctgca  65700
ttcaaatgaa cgaagggaag ggaggcaaaa agatgcaaaa tccgagacaa gcagcagaaa  65760
```

-continued

```
tatttcttcg ctacggaagc gtgcgcaaac aaccttctcc aacagcacca gaagagcaca  65820
gcgtaacctt tttcaagacc agaaaaggaa attcacaaag cctctgtgga taccagcgcg  65880
ttcagctctc ctgatagcag atttcttgtc aggttgcaaa tggggtatgg tgccaggagg  65940
tgcagggacc atatgatcat atacagcaca gcagtcattg tgcatgtatt aatatatatt  66000
gagtagcagt gttactttgc caaagcaata gttcagagat gagtcctgct gcatacctct  66060
atcttaaaac taacttataa atagtaaaac cttctcagtt cagccacgtg ctcctctctg  66120
tcagcaccaa tggtgcttcg cctgcaccca gctgcaagga atcagcccgt gatctcatta  66180
acactcagct ctgcaggata aattagattg ttccactctc ttttgttgtt aattacgacg  66240
gaacaattgt tcagtgctga tggtcctaat tgtcagctac agaaaacgtc tccatgcagt  66300
tccttctgct ccagcaaact gtccaggcta tagcaccgtg atgcatgcta cctctcactc  66360
catccttctt ctctttccca ccagggagag ctgtgtgttt tcactctcag ccgctctgaa  66420
caataccaaa ctgctacgca ctgcctccct cggaaagaga atccccttgt tgctttttta  66480
tttacaggat ccttcttaaa aagcagacca tcattcactg caaacccaga gcttcctgcc  66540
tctccttcca caaccgaaaa cagccggctt catttgtctt ttttaaatgc tgttttccag  66600
gtgaattttg gccagcgtgt tggctgagat ccaggagcac gtgtcagctt tctgctctca  66660
ttgctcctgt tctgcattgc ctctttctgg ggcttccaag aggggggggag actttgcacg  66720
gggatgagat aatgcccctt ttcttagggt ggctgctggg cagcagagtg gctctgggtc  66780
actgtggcac caatgggagg caccagtggg ggtgtgtttt gtgcagggag gaagcattca  66840
cagaatgggg ctgatcctga agcttgcagt ccaaggcttt gtctgtgtac ccagtgaaat  66900
ccttcctctg ttacataaag cccagatagg actcagaaat gtagtcattc cagccccccct  66960
cttcctcaga tctggagcag cacttgtttg cagccagtcc tccccaaaat gcacagacct  67020
cgccgagtgg agggagatgt aaacagcgaa ggttaattac ctccttgtca aaaacacttt  67080
gtggtccata gatgtttctg tcaatcttac aaaacagaac cgagggcagc gagcactgaa  67140
ggcgtgttcc catgctgagt taatgagact tggcagctcg ctgtgcagag atgatccctg  67200
tgcttcatgg gaggctgtaa cctgtctccc catcgccttc acaccgcagt gctgtcctgg  67260
acacctcacc ctccataagc tgtaggatgc agctgcccag ggatcaagag acttttccta  67320
aggctcttag gactcatctt tgccgctcag tagcgtgcag caattactca tcccaactat  67380
actgaatggg tttctgccag ctctgcttgt ttgtcaataa gcatttttttc attttgcctc  67440
taagtttctc tcagcagcac cgctttgggt gacttcagtg gccgcctgga acccgagggg  67500
cacagccacc acctccctgt tgctgctgct ccggggactc acgtgctgct ggatgggggg  67560
aagcatgaag ttcctcaccc agacacctgg gttgcaatgg ttgcagtgtg ctcttcttgg  67620
tatgcagatt gtttctagcc attacttgta gaaatgtgct gtggaagccc tttgtatctc  67680
tttctgtggc ccttcagcaa aagctgtggg aaagctctga ggctgctttc ttgggtcgtg  67740
gaggaattgt atgttccttc tttaacaaaa attatcctta ggagagagca ctgtgcaagc  67800
attgtgcaca taaaacaatt caggttgaaa gggctctctg gaggtttcca gcctgactac  67860
tgctcgaagc aaggccaggt tcaaagatgg ctcaggatgc tgtgtgcctt cctgattatc  67920
tgtgccacca atggaggaga ttcacagcca ctctgcttcc cgtgccactc atggagagga  67980
atattccctt atattcagat agaatgtcat cctttagctc agccttccct ataaccccat  68040
gagggagctg cagatcccca tactctcctc ttctctgggg tgaaggccgt gtcctccagc  68100
```

-continued cccccttccc accctgtgcc ctgagcagcc cgctggcctc tgctggatgt gtgcccatat 68160
gtcaatgcct gtccttgcag tccagcctgg aacatttaat tcatcaccag ggtaatgtgg 68220
aactgtgtca tcttcccctg cagggtacaa agttctgcac ggggtccttt cggttcagga 68280
aaaccttcgc tggtgctacc tgaatcaagc tctatttaat aagttcataa gcacatggat 68340
gtgttttcct agagatacgt tttaatggta tcagtgattt ttatttgctt tgttgcttac 68400
ttcaaacagt gcctttgggc aggaggtgag ggacgggtct gccgttggct ctgcagtgat 68460
ttctccaggc gtgtggctca ggtcagatag tggtcactct gtggccagaa gaaggacaaa 68520
gatggaaatt gcagattgag tcatgttaag caggcatctt ggagtgattt gaggcagttt 68580
catgaaagag ctacgaccac ttattgttgt tttccccttt tacaacagaa gttttcatca 68640
aaataacgtg gcaaagccca ggaatgtttg ggaaaagtgt agttaaatgt tttgtaattc 68700
atttgtcgga gtgttaccag ctaagaaaaa agtcctacct ttggtatggt agtcctgcag 68760
agaatacgac atcaatatta gtttggaaaa aaacaccacc accaccagaa actgtaatgg 68820
aaaatgtaaa ccaagaaatt ccttgggtaa gagagaaagg atgtcgtata ctggccaagt 68880
cctgcccagc tgtcagcctg ctgaccctct gcagctcagg accatgaaac gtggcactgt 68940
aagacgtgtc cctgcctttg cttgctcaca gatctctgcc ctcgtgctga ctcctgcaca 69000
caagagcatt tccctgtagc caaacagcga ttagccataa gctgcacctg actttgagga 69060
ttaagagttt gcaattaagt ggattgcagc aggagatcag tggcagggtt gcagatgaaa 69120
tcctttctag gggtagctaa gggctgagca acctgtccta cagcacaagc caaaccagcc 69180
aagggttttc ctgtgctgtt cacagaggca gggccagctg gagctggagg aggttgtgct 69240
gggactcttc tccctgtgct gagaatggag tgatttctgg gtgctgttcc tgtggcttgc 69300
actgagcagc tcaagggaga tcggtgctcc tcatgcagtg ccaaaactcg tgtttgatgc 69360
agaaagatgg atgtgcacct ccctcctgct aatgcagccg tgagcttatg aaggcaatga 69420
gccctcagtg cagcaggagc tgtagtgcac tcctgtaggt gctagggaaa atctctggtt 69480
cccagggatg cattcataag gacaatatat cttgaggctg tgccaaatct ttctgaaata 69540
ttcatgcatg ttcccttaat ttatagaaac aaacacagca gaataattat tccaatgcct 69600
cccctcgaag gaaacccata tttccatgta gaaatgtaac ctatatacac acagccatgc 69660
tgcatccttc agaacatgcc agtgctcatc tcccatggca aaatactaca ggtattctca 69720
ctatgttgga cctgtgaaag gaaccatggt aagaaactca ggttaaaggt atggctgcaa 69780
aactactcat accaaaacag cagagctcca gacctcctct taggaaagag ccacttggag 69840
agggatggtg tgaaggctgg aggtgagaga cagagcctgt cccagttttc ctgtctctat 69900
tttctgaaat gtctgcagga ggaaaggaca actgtacttt caggcatagc tggtgccctc 69960
acgtaaataa gttccccgaa cttctgtgtc atttgttctt aagatgcttt ggcagaacac 70020
tttgagtcaa ttcgcttaac tgtgactagg tctgtaaata agtgctccct gctgataagg 70080
ttcaagtgac atttttagtg gtatttgaca gcatttacct tgctttcaag tcttctacca 70140
agctcttcta tacttaagca gtgaaaccgc caagaaaccc ttccttttat caagctagtg 70200
ctaaatacca ttaacttcat aggttagata cggtgctgcc agcttcacct ggcagtggtt 70260
ggtcagttct gctggtgaca aagcctccct ggcctgtgct tttacctaga ggtgaatatc 70320
caagaatgca gaactgcatg gaaagcagag ctgcaggcac gatggtgctg agccttagct 70380
gcttcctgct gggagatgtg gatgcagaga cgaatgaagg acctgtccct tactcccctc 70440
agcgttctgt gctatttagg gttctaccag agtccttaag aggttttttt tttttttggg 70500

-continued

```
tccaaaagtc tgtttgtttg gttttgacca ctgagagcat gtgacacttg tctcaagcta  70560
ttaaccaagt gtccagccaa aatcaattgc ctgggagacg cagaccatta cctggaggtc  70620
aggacctcaa taaatattac cagcctcatt gtgccgctga cagattcagc tggctgctct  70680
gtgttccagt ccaacagttc ggacgccacg tttgtatata tttgcaggca gcctcggggg  70740
gaccatctca ggagcagagc accggcagcc gcctgcagag ccgggcagta cctcaccatg  70800
gccatggcag gcgtcttcgt gctgttctct ttcgtgcttt gtggcttcct cccaggtgag  70860
taactcccag agtgctgcag aagctttgtg cctgccagtc ctggctctcc ttagcagaac  70920
atggtggtga ccatcagaga gagactcccc tacaaagtgc ctgcaaaggc tgcctcagta  70980
catcagtatt aaacggatta ctgttgtgct gggtgtctgt tgggttctgt gctcccaaca  71040
catttcttac gctctcagct ctgttacact gcttgcattt gctgcacagt tgcatagaat  71100
ggataaatgc ttgaaacaag gccataacga ggtggtcaga cctccaggaa ctagttaggg  71160
aaatattgtc atggcccaag caagctctgt gcaggaacct ggcagctttc ctgcaatgct  71220
tttgctgcta atggagaaac aagagatgca aacaagccag gatctgatgt tctccttctg  71280
tatttacatc tcatgaaatt acaaagtcaa agacaagcgt ggtttatttc ttacactcag  71340
cttctttaaa atgtatatcc ctgacaacag atgctgtgta tgtttgctta tcctgtatgt  71400
gactatttgc atttgcattt atctctattg actcaggttt cttttcagat atgtgataga  71460
tgttttctag ggacaaaacg gatgtgtgaa tagataagga aggaaaagat attcattttt  71520
caattaataa atctacctat ctcttaactt tttttttttt ttaagaacag agctattcaa  71580
gaactcgttt catcagccag caataagaag ctaaattatg tttatcagca ttaaacaaaa  71640
atcatatata gtttgcttag ttcaagaatc gaatcggtgg aaatcactca gtttggttct  71700
ctgtgctgga gttttgcaca cacatttcag ctagctgtgg tctcactgat cagactgcct  71760
ttgtttccca tttttgtccc cttttttttcc ccagatgctg cctttggggc tgaggtgagt  71820
aagagagttc ttcttgtcca cttttctctt ttctcttttc tctctctctc ttttttttccc  71880
cccgtcttaa ttagtatcac tataatcaga tcccagagtg taaaatgtta aattatgcag  71940
ttctgagctc tacatctatg ctgcatgtaa gtaatgtagc agtgatataa aactgttaga  72000
tgaattaatt tctgaccaac tctgaactgg tctaagcttt aagttgatca tatgttctac  72060
taaataatac agtggtttgg gttggaaggg tcctttaaga tcatctactt ccaacccctc  72120
tgctataggc agggacaact cccactagac aagattgctc aaagctccat ccatatgatc  72180
agctgtagac tgatggctgt agactatagc attaaaaact accccaaagc agcctactga  72240
aagaagaaag tactgtgagg tgctacagct tccaaatccc atgttgttag acctgttctt  72300
ttgaataaac gtgtttgtac gttgagaatg aatgagtaac aatggcagaa cactggaggg  72360
gccaactctc aggctttgca aaatggtgcc tggggggcat gatagatccc tgctggttta  72420
tcacatgggg agctgcatgg ctataacccc attgcccagt tctctcccac tgcatggaga  72480
gaaggctgga tctggtcgct gccctgctga aaatggcaga tgtaactaca aaatgtcact  72540
ttgtcctgtt actgtgtgtt tctttgtcag gtggactgca gtaggtttcc caacgctaca  72600
gacaaggaag gcaaagatgt attggtttgc aacaaggacc tccgccccat ctgtggtacc  72660
gatggagtca cttacaccaa cgattgcttg ctgtgtgcct acagcatgtg tgtactgcag  72720
agagagctca tactgcaagc aagcagctgt gcttagggct cctgacagca cccctttcca  72780
acaaacagtg atctgtcaca tgtcacttat gtcaactctt tcagggaaag cttgagtatc  72840
```

-continued

```
actgcgtgac actcggttgc ctagacatca ctttggttac tgtgtctttt ttgttgatgt  72900
aatttattca ggtttttctc ctccatctcg gggatgaggc agatgacagc ccctagggca  72960
tatttcatcc cagcaaaaaa ggagcaaaag gatggagagg tgctccagtc tgaatggtcc  73020
aaaacagtcc taaagatttc agagtcttta gatccctgcc agccactcag tatggcacta  73080
ccctctccaa tacaaatata tatatataca aagatgactt agccagactc agcctcattg  73140
cattaggtac atattcccaa taacgagaag ctgagcttcc taatacctgt tttccctctt  73200
cagagaattt ggaaccaata tcagcaaaga gcacgatgga gaatgcaagg aaactgttcc  73260
tgtaagtgaa accaagttca tcctttgtgc agccaaaact gcttattgac ttgcccaata  73320
aataatgtaa atgctgacta agaggccatg tgagatgtca gaatcttgta ttgatcatct  73380
tcaggtgaag tttcatcaca ataacacaaa aaaagacttt atttcctgct gaggtggcat  73440
tttaggagac ccaacgcacg cgctccgctg gtctacgtgg tccctgtaag ccctcaccag  73500
cgctttgctg tgtgctcctt ccacagatga actgcagtag ttatgccaac acgacaagcg  73560
aggacggaaa agtgatggtc ctctgcaaca gggccttcaa ccccgtctgt ggtactgatg  73620
gagtcaccta cgacaatgag tgtctgctgt gtgcccacaa agtgtaagta ccgagctgtg  73680
ctcccttggc aggaatgggt cctgcgctcc tggcagccac tctttgagca ctgggatttc  73740
caatgaggct ttttctgtat ggctcttgga ctccgtccct cctctccctg ataacctcat  73800
gctgttttcc tttgtgatta gaaagagaac tgtggctttg atcttgagag agaagcagag  73860
agctgggtgg ggacttaaga gaagcactct gttctgtgtt aactaagtta aaagggtctg  73920
tgtggcacac actgccttgc agaggacagc agtgaacctc tgctgcacct atattgtaaa  73980
acaacctagc tcctaggcca tgacagcctg tcacctctcc tcctttgcat catgcaatac  74040
tgcaacactg tggcacatag taccacctcc cataaggact gatatgttga accagtgtgt  74100
cagagaccag tagcatctct gtcttcagga tcatcaggta gcattctata tacagggtgt  74160
tgcccaggac tccgagtccc atgaagtatg gcaggggttt tggaactgga tgaccttcga  74220
ggtcacttcc aacccaagcc attctattat tctgtgaaag ccagggaggt gggggtgctt  74280
gcagggctgg tatcttgagc agtgtgggca caaactaggc tgggcatctg cagcccatca  74340
gcactgcggg gatgtggagt tcagcacagc aggatgcagg cacagctccc taacatggat  74400
ttttttcctt tcagagagca gggggccagc gttgacaaga ggcatgatgg tggatgtagg  74460
aaggaacttg ctgctgtgag tgtgagtagc acaatgaagg agcaggttct ggtcccactg  74520
atgtcaaggg aaacatggcc agcatcttta gtagcctcag gagcatcagt tgtgcttcag  74580
cacagagaag attttacttt ctacacacgt aatacacatt atccacagta atgtcaggaa  74640
gggaagagga tgactgcaca ggcagggatc agtaaaagac cataagcaga aataacccat  74700
gagggcagaa ctgagaataa gaactgagac tagatccagg gggtcagacc aatgggccat  74760
caaacccatg atggtttgat gcagagtcca ctctttcagc attcataaga attgagtagg  74820
ggggagtaag ggtggggtga gtacgtacgg atcttcccaa acacccttcc aacctacagc  74880
tatgcacctc agccaggtgt gatttctgtg tagttcacaa gcctcagtgg atttctctcc  74940
catgggattc tccagcctct ttctggacct gtatacacgg tagttgggtt ggtttttttt  75000
ttctgtctct cttttttttcc ccccactaca atgtccctca gcaaacatag tcctcatctc  75060
tcaaacaaac aaatctcatt ctctaagtac ccagataaga gctgattttt gctttaagcc  75120
tgtgggggag atgctggact attataaagg tatcagtgct gcctcttctc cagacaccaa  75180
tgttttttcc atttaatttc ctgaacaggt caggaacacg gtgcaacatg attgtaagca  75240
```

-continued

```
cagcacgttc atggagcgag ctgctgctgc agctcagaaa tgcagcagtc agattgtgat  75300
atgcatctct tacacaggaa attatgctct atttttatat tattaaatct agcatacgag  75360
aaaggacatc cagtttatat cagatcgtgc aaggaagtta attattttta gtttgatcat  75420
tatcatcggc actgcagctg tagctaggga ggggttgaag ctcttcagct atcgactcct  75480
tcatatcctc cacgttacaa ttgtgttttt gcaggttgac tgcagcgagt accctaagcc  75540
tgactgcacg gcagaagaca gacctctctg tggctccgac aacaaaacat atggcaacaa  75600
gtgcaacttc tgcaatgcag tcgtgtacgt acagccctga ttgcattcac gttgtcggct  75660
gcctcctaca ggcaccagct tgcacagttc ctgctttcgt tgctgattgc tgaccaggat  75720
ctgggggcag aaaagaacac cgggcatcac gccagccatt catttgattt ttcaccagag  75780
cttgtctggt ttgttaggat ggatgttttg aacgccatta accttaaggg aagttttcct  75840
tgctgcgaag aaaatcagat ttggtgtttc attatagttt tcagaagggg ttaaacgatt  75900
tcactcatct cctaataatc aggtagctga ggagatgctg agtctgccag ttcttgggct  75960
ctgggcagga tcccatctcc tgccttctct aggacagagc tcagcaggca gggctctgtg  76020
gctctgtgtc taacccactt cttcctctcc tcgctttcag ggaaagcaac gggactctca  76080
ctttaagcca ttttggaaaa tgctgaatat cagagctgag agaattccgc ccctctccct  76140
cccccccccc taacgttact ggccgaagcc gcttggaata aggccggtgt gcgtttgtct  76200
atatgttatt ttccaccata ttgccgtctt ttggcaatgt gagggcccgg aaacctggcc  76260
ctgtcttctt gacgagcatt cctaggggtc tttcccctct cgccaaagga atgcaaggtc  76320
tgttgaatgt cgtgaaggaa gcagttcctc tggaagcttc ttgaagacaa acaacgtctg  76380
tagcgaccct ttgcaggcag cggaaccccc cacctggcga caggtgcctc tgcggccaaa  76440
agccacgtgt ataagataca cctgcaaagg cggcacaacc ccagtgccac gttgtgagtt  76500
ggatagttgt ggaaagagtc aaatggctct cctcaagcgt attcaacaag gggctgaagg  76560
atgcccagaa ggtaccccat tgtatgggat ctgatctggg gcctcggtgc acatgcttta  76620
catgtgttta gtcgaggtta aaaaaacgtc taggcccccc gaaccacggg gacgtggttt  76680
tcctttgaaa aacacgatga taagcttgcc acaaccatgg gtgtactgct cacacagagg  76740
acgctgctca gtctggtcct tgcactcctg tttccaagca tggcgagcat ggcaatgcac  76800
gtggcccagc ctgctgtggt actggccagc agccgaggca tcgccagctt tgtgtgtgag  76860
tatgcatctc caggcaaagc cactgaggtc cgggtgacag tgcttcggca ggctgacagc  76920
caggtgactg aagtctgtgc ggcaacctac atgatgggga atgagttgac cttcctagat  76980
gattccatct gcacgggcac ctccagtgga aatcaagtga acctcactat ccaaggactg  77040
agggccatgg acacgggact ctacatctgc aaggtggagc tcatgtaccc accgccatac  77100
tacctgggca taggcaacgg aacccagatt tatgtaattg atccagatac cgtgcccaga  77160
ttctgatcag gagcccaaat cttctgacaa aactcacaca tccccaccgt ccccagcacc  77220
tgaactcctg ggtggatcgt cagtcttcct cttcccccca aaacccaagg acaccctcat  77280
gatctcccgg acccctgagg tcacatgcgt ggtggtggac gtgagccacg aagaccctga  77340
ggtcaagttc aactggtacg tggacggcgt ggaggtgcat aatgccaaga caaagccgcg  77400
ggaggagcag tacaacagca cgtaccgggt ggtcagcgtc ctcaccgtcc tgcaccagga  77460
ctggctgaat ggcaaggagt acaagtgcaa ggtctccaac aaagccctcc cagcccccat  77520
cgagaaaacc atctccaaag ccaaagggca gccccgagaa ccacaggtgt acaccctgcc  77580
```

-continued

```
cccatcccgg gatgagctga ccaagaacca ggtcagcctg acctgcctgg tcaaaggctt  77640

ctatcccagc gacatcgccg tggagtggga gagcaatggg cagccggaga acaactacaa  77700

gaccacgcct cccgtgctgg actccgacgg ctccttcttc ctctacagca agctcaccgt  77760

ggacaagagc aggtggcagc aggggaacgt cttctcatgc tccgtgatgc atgaggctct  77820

gcacaaccac tacacgcaga agagcctctc cctgtctccg ggtaaatgag ga          77872
```

<210> SEQ ID NO 45
<211> LENGTH: 780
<212> TYPE: DNA
<213> ORGANISM: SV40

<400> SEQUENCE: 45

```
cccagagctg tgcagttggg atcctaacac catgcagatg ctccaggacc tgcaccgagc     60

cccagcactg gcactcatct cttctttcca cccctctgag agcaacaagt ggctctgcaa    120

tggcaatgta agtgaaaccg ggcgggtatc ttagagcacc tggaagcttg catgcctgca    180

ggtcgactct agaggatccc cgggtaccga gctcgaattc caggtaccgt cgacgatgta    240

ggtcacggtc tcgaagccgc ggtgcgggtg ccagggcgtg cccttgggct ccccgggcgc    300

gtactccacc tcacccatct ggtccatcat gatgaacggg tcgaggtggc ggtagttgat    360

cccggcgaac gcgcggcgca ccgggaagcc ctcgccctcg aaaccgctgg gcgcggtggt    420

cacggtgagc acgggacgtg cgacggcgtc ggcgggtgcg gatacgcggg gcagcgtcag    480

cgggttctcg acggtcacgg cgggcatgtc gacagccaag ccgaattcgc cctatagtga    540

gtcgtattac aattcactgg ccgtcgtttt acaacgtcgt gactgggaaa accctggcgt    600

tacccaactt aatcgccttg cagcacatcc ccctttcgcc agctggcgta atagcgaaga    660

ggcccgcacc gatcgccctt cccaacagtt gcgcagcctg aatggcgaat ggcgcctgat    720

gcggtatttt ctccttacgc atctgtgcgg tatttcacac cgcatatggt gcactctcag    780
```

<210> SEQ ID NO 46
<211> LENGTH: 1957
<212> TYPE: DNA
<213> ORGANISM: human

<400> SEQUENCE: 46

```
ataatcaggt agctgaggag atgctgagtc tgccagttct tgggctctgg gcaggatccc     60

atctcctgcc ttctctagga cagagctcag caggcagggc tctgtggctc tgtgtctaac    120

ccacttcttc ctctcctcgc tttcagggaa agcaacggga ctctcacttt aagccatttt    180

ggaaaatgct gaatatcaga gctgagagaa ttccgcccct ctccctcccc ccccccctaac    240

gttactggcc gaagccgctt ggaataaggc cggtgtgcgt ttgtctatat gttattttcc    300

accatattgc cgtcttttgg caatgtgagg gcccggaaac ctggccctgt cttcttgacg    360

agcattccta ggggtctttc ccctctcgcc aaaggaatgc aaggtctgtt gaatgtcgtg    420

aaggaagcag ttcctctgga agcttcttga agacaaacaa cgtctgtagc gaccctttgc    480

aggcagcgga acccccccacc tggcgacagg tgcctctgcg gccaaaagcc acgtgtataa    540

gatacacctg caaaggcggc acaaccccag tgccacgttg tgagttggat agttgtggaa    600

agagtcaaat ggctctcctc aagcgtattc aacaaggggc tgaaggatgc ccagaaggta    660

ccccattgta tgggatctga tctggggcct cggtgcacat gctttacatg tgtttagtcg    720

aggttaaaaa aacgtctagg ccccccgaac cacggggacg tggttttcct ttgaaaaaca    780

cgatgataag cttgccacaa ccatgggtgt actgctcaca cagaggacgc tgctcagtct    840
```

-continued

```
ggtccttgca ctcctgtttc caagcatggc gagcatggca atgcacgtgg cccagcctgc    900
tgtggtactg gccagcagcc gaggcatcgc cagctttgtg tgtgagtatg catctccagg    960
caaagccact gaggtccggg tgacagtgct tcggcaggct gacagccagg tgactgaagt   1020
ctgtgcggca acctacatga tggggaatga gttgaccttc ctagatgatt ccatctgcac   1080
gggcacctcc agtggaaatc aagtgaacct cactatccaa ggactgaggg ccatggacac   1140
gggactctac atctgcaagg tggagctcat gtacccaccg ccatactacc tgggcatagg   1200
caacggaacc cagatttatg taattgatcc agataccgtg cccagattct gatcaggagc   1260
ccaaatcttc tgacaaaact cacacatccc caccgtcccc agcacctgaa ctcctgggtg   1320
gatcgtcagt cttcctcttc cccccaaaac ccaaggacac cctcatgatc tcccggaccc   1380
ctgaggtcac atgcgtggtg gtggacgtga gccacgaaga ccctgaggtc aagttcaact   1440
ggtacgtgga cggcgtggag gtgcataatg ccaagacaaa gccgcgggag gagcagtaca   1500
acagcacgta ccgggtggtc agcgtcctca ccgtcctgca ccaggactgg ctgaatggca   1560
aggagtacaa gtgcaaggtc tccaacaaag ccctcccagc ccccatcgag aaaaccatct   1620
ccaaagccaa agggcagccc cgagaaccac aggtgtacac cctgccccca tcccgggatg   1680
agctgaccaa gaaccaggtc agcctgacct gcctggtcaa aggcttctat cccagcgaca   1740
tcgccgtgga gtgggagagc aatgggcagc cggagaacaa ctacaagacc acgcctcccg   1800
tgctggactc cgacggctcc ttcttcctct acagcaagct caccgtggac aagagcaggt   1860
ggcagcaggg gaacgtcttc tcatgctccg tgatgcatga ggctctgcac aaccactaca   1920
cgcagaagag cctctccctg tctccgggta aatgagg                            1957
```